US012669427B2

(12) United States Patent
Zhang et al.

(10) Patent No.: US 12,669,427 B2
(45) **Date of Patent: *Jun. 30, 2026**

(54) SIZE-TUNABLE SYNTHETIC PARTICLES WITH TUNABLE OPTICAL PROPERTIES AND METHODS FOR USING THE SAME FOR IMMUNE CELL ACTIVATION

(71) Applicant: Slingshot Biosciences, Inc., Emeryville, CA (US)

(72) Inventors: Daixuan Zhang, Fremont, CA (US); Solomon Stonebloom, Emeryville, CA (US); Juan Armas, Emeryville, CA (US); Harini Kethar, Danville, CA (US); Sunil Thomas, San Bruno, CA (US); Martina De Geus, Berkeley, CA (US)

(73) Assignee: Slingshot Biosciences, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/966,771

(22) Filed: Dec. 3, 2024

(65) Prior Publication Data

US 2025/0093251 A1     Mar. 20, 2025

Related U.S. Application Data

(63) Continuation of application No. 18/735,500, filed on Jun. 6, 2024, now Pat. No. 12,196,661, which is a
(Continued)

(51) Int. Cl.
G01N 15/08     (2006.01)
G01N 15/10     (2024.01)
(Continued)

(52) U.S. Cl.
CPC ..... *G01N 15/0893* (2013.01); *G01N 15/1012* (2013.01); *G01N 15/1468* (2013.01); *G01N 33/563* (2013.01); *G01N 2015/1006* (2013.01)

(58) Field of Classification Search
CPC ........... G01N 15/1012; G01N 15/1468; G01N 2015/1014; G01N 15/0893;
(Continued)

(56) References Cited

U.S. PATENT DOCUMENTS

| | | | |
|---|---|---|---|
| 3,822,095 A | 7/1974 | Hirschfeld |
| 3,872,312 A | 3/1975 | Hirschfeld |

(Continued)

FOREIGN PATENT DOCUMENTS

| | | | |
|---|---|---|---|
| CN | 101214217 A | 7/2008 |
| CN | 101245368 A | 8/2008 |

(Continued)

OTHER PUBLICATIONS

Atkin-Smith et al., "Isolation of cell type-specific apoptotic bodies by fluorescence-activated cell sorting," Scientific Reports, vol. 7, No. 1, Feb. 1, 2017, pp. 1-7.
(Continued)

*Primary Examiner* — Paul M. West
(74) *Attorney, Agent, or Firm* — Sheppard, Mullin, Richter & Hampton LLP; Jaime D. Choi

(57) ABSTRACT

A hydrogel particle, comprising a matrix comprising a polymerized monomer, said matrix comprising a plurality of micropores and a plurality of macropores, and one or more immunostimulatory biomolecules selected from the group consisting of an anti-CD3 antibody or antigen-binding fragment thereof, an anti-CD28 antibody or antigen-binding fragment thereof, and combinations thereof.

78 Claims, 30 Drawing Sheets

Related U.S. Application Data continuation of application No. PCT/US2023/077961, filed on Oct. 26, 2023.

(60) Provisional application No. 63/419,580, filed on Oct. 26, 2022, provisional application No. 63/488,949, filed on Mar. 7, 2023.

(51) Int. Cl.
*G01N 15/14* (2024.01)
*G01N 33/563* (2006.01)

(58) Field of Classification Search
CPC ......... G01N 2015/1006; G01N 15/147; G01N 2015/1472; G01N 33/563
See application file for complete search history.

(56) References Cited

U.S. PATENT DOCUMENTS

| | | | |
|---|---|---|---|
| 3,916,205 | A | 10/1975 | Kleinerman |
| 3,937,799 | A | 2/1976 | Lewin et al. |
| 3,947,564 | A | 3/1976 | Shannon et al. |
| 3,975,084 | A | 8/1976 | Block |
| 4,271,123 | A | 6/1981 | Curry et al. |
| 4,295,199 | A | 10/1981 | Curry et al. |
| 4,389,491 | A | 6/1983 | Hanamoto et al. |
| 4,409,335 | A | 10/1983 | Hanamoto et al. |
| 4,448,888 | A | 5/1984 | Bleile et al. |
| 4,511,662 | A | 4/1985 | Baran et al. |
| 4,704,891 | A | 11/1987 | Recktenwald et al. |
| 4,774,189 | A | 9/1988 | Schwartz |
| 4,857,451 | A | 8/1989 | Schwartz |
| 5,093,234 | A | 3/1992 | Schwartz |
| 5,244,799 | A | 9/1993 | Anderson |
| 5,283,079 | A | 2/1994 | Wang et al. |
| 5,395,688 | A | 3/1995 | Wang et al. |
| 5,820,879 | A | 10/1998 | Fernandez et al. |
| 5,841,139 | A | 11/1998 | Sostek et al. |
| 5,871,722 | A | 2/1999 | Nacht et al. |
| 5,888,823 | A | 3/1999 | Matsumoto et al. |
| 6,043,506 | A | 3/2000 | Heffelfinger et al. |
| 6,107,365 | A | 8/2000 | Bertozzi et al. |
| 6,108,082 | A | 8/2000 | Pettipiece et al. |
| 6,214,539 | B1 | 4/2001 | Cosand |
| 6,280,618 | B2 | 8/2001 | Watkins et al. |
| 6,372,813 | B1 | 4/2002 | Johnson et al. |
| 6,516,537 | B1 | 2/2003 | Teich et al. |
| 6,586,176 | B1 | 7/2003 | Trnovsky et al. |
| 6,657,030 | B2 | 12/2003 | Vanderbilt |
| 6,762,055 | B2 | 7/2004 | Carver et al. |
| 6,806,058 | B2 | 10/2004 | Jesperson et al. |
| 6,872,578 | B2 | 3/2005 | Watkins et al. |
| 6,897,072 | B1 | 5/2005 | Rich et al. |
| 7,045,366 | B2 | 5/2006 | Huang et al. |
| RE39,542 | E | 4/2007 | Jain et al. |
| 7,205,156 | B2 | 4/2007 | Rich et al. |
| 7,294,503 | B2 | 11/2007 | Quake et al. |
| 7,314,584 | B2 | 1/2008 | Tsutsui et al. |
| 7,465,538 | B2 | 12/2008 | Watkins et al. |
| 7,479,631 | B2 | 1/2009 | Rich et al. |
| 7,482,161 | B2 | 1/2009 | Carver et al. |
| 7,482,167 | B2 | 1/2009 | Sammak et al. |
| 7,531,357 | B2 | 5/2009 | Carver et al. |
| 7,569,399 | B2 | 8/2009 | Watkins et al. |
| 7,588,942 | B2 | 9/2009 | Ho et al. |
| 7,601,539 | B2 | 10/2009 | Kawate |
| 7,776,927 | B2 | 8/2010 | Chu et al. |
| 7,842,498 | B2 | 11/2010 | Um et al. |
| 8,030,095 | B2 | 10/2011 | Harriman |
| 8,105,845 | B2 | 1/2012 | Notcovich et al. |
| 8,114,580 | B2 | 2/2012 | Carver et al. |
| 8,187,885 | B2 | 5/2012 | Purvis, Jr. |
| 8,415,161 | B2 | 4/2013 | Yan et al. |
| 8,415,173 | B2 | 4/2013 | Harriman |
| 8,451,450 | B2 | 5/2013 | Heng |
| 8,580,530 | B2 | 11/2013 | Buffiere et al. |
| 8,580,531 | B2 | 11/2013 | Buffiere et al. |
| 8,603,828 | B2 | 12/2013 | Walker et al. |
| 8,609,363 | B2 | 12/2013 | Heng et al. |
| 8,704,158 | B2 | 4/2014 | Haberstroh et al. |
| 8,748,183 | B2 | 6/2014 | Durack et al. |
| 9,012,167 | B2 | 4/2015 | Dallenne et al. |
| 9,110,050 | B2 | 8/2015 | Likuski et al. |
| 9,175,421 | B2 | 11/2015 | Notcovich et al. |
| 9,176,154 | B2 | 11/2015 | Darmstadt et al. |
| 9,213,034 | B2 | 12/2015 | Walker et al. |
| 9,217,175 | B2 | 12/2015 | Regan et al. |
| 9,228,898 | B2 | 1/2016 | Kiani et al. |
| 9,417,190 | B2 | 8/2016 | Hindson et al. |
| 9,476,101 | B2 | 10/2016 | Pregibon et al. |
| 9,658,220 | B2 | 5/2017 | King et al. |
| 9,696,257 | B2 | 7/2017 | Fox et al. |
| 9,714,897 | B2 | 7/2017 | Kim et al. |
| 9,804,149 | B2 | 10/2017 | Darmstadt et al. |
| 9,816,931 | B2 | 11/2017 | Abate et al. |
| 9,915,598 | B2 | 3/2018 | Kim et al. |
| 10,067,135 | B2 | 9/2018 | Kaul et al. |
| 10,180,385 | B2 | 1/2019 | Fox et al. |
| 10,191,039 | B2 | 1/2019 | King et al. |
| 10,343,167 | B2 | 7/2019 | Esmail et al. |
| 10,344,100 | B1 | 7/2019 | Vashist et al. |
| 10,392,557 | B2 | 8/2019 | Chan |
| 10,416,070 | B1 | 9/2019 | Handique |
| 10,429,291 | B2 | 10/2019 | Fox et al. |
| 10,481,068 | B2 | 11/2019 | Kim et al. |
| 10,508,990 | B2 | 12/2019 | Fox et al. |
| 10,732,189 | B2 | 8/2020 | Buffiere et al. |
| 10,753,846 | B2 | 8/2020 | Kim et al. |
| 10,942,109 | B2 | 3/2021 | Kim et al. |
| 11,047,845 | B1 | 6/2021 | Barry, Jr. et al. |
| 11,085,036 | B2 | 8/2021 | Norberg et al. |
| 11,118,217 | B2 | 9/2021 | Xue et al. |
| 11,155,809 | B2 | 10/2021 | Lebofsky |
| 11,180,752 | B2 | 11/2021 | Wu et al. |
| 11,186,862 | B2 | 11/2021 | Lebofsky et al. |
| 11,213,490 | B2 | 1/2022 | Shoichet et al. |
| 11,231,355 | B2 | 1/2022 | Handique |
| 11,274,337 | B2 | 3/2022 | Xue et al. |
| 11,300,496 | B2 | 4/2022 | Handique |
| 11,313,782 | B2 | 4/2022 | Kim et al. |
| 11,479,816 | B2 | 10/2022 | Lebofsky et al. |
| 11,506,655 | B2 | 11/2022 | Hunsley et al. |
| 11,598,768 | B2 | 3/2023 | Kim |
| 11,603,556 | B2 | 3/2023 | Lebofsky |
| 11,663,717 | B2 | 5/2023 | Barnes et al. |
| 11,686,661 | B2 | 6/2023 | Kim et al. |
| 11,726,023 | B2 | 8/2023 | Kim et al. |
| 11,747,261 | B2 | 9/2023 | Kim et al. |
| 11,761,877 | B2 | 9/2023 | Kim et al. |
| 11,927,519 | B2 | 3/2024 | Kim et al. |
| 12,066,369 | B2 | 8/2024 | Kim et al. |
| 12,134,779 | B2 | 11/2024 | Nguyen et al. |
| 12,196,661 | B2 * | 1/2025 | Zhang ............... G01N 15/1459 |
| 2001/0008217 | A1 | 7/2001 | Watkins et al. |
| 2001/0054580 | A1 | 12/2001 | Watkins et al. |
| 2002/0106730 | A1 | 8/2002 | Coyle et al. |
| 2002/0115116 | A1 | 8/2002 | Song et al. |
| 2003/0013116 | A1 | 1/2003 | Song et al. |
| 2003/0064403 | A1 | 4/2003 | Song et al. |
| 2003/0124371 | A1 | 7/2003 | Um et al. |
| 2003/0132538 | A1 | 7/2003 | Chandler |
| 2003/0218130 | A1 | 11/2003 | Boschetti et al. |
| 2003/0232323 | A1 | 12/2003 | Freeman et al. |
| 2004/0126904 | A1 | 7/2004 | Watkins et al. |
| 2004/0137577 | A1 | 7/2004 | Coyle et al. |
| 2005/0059086 | A1 | 3/2005 | Huang et al. |
| 2005/0090016 | A1 | 4/2005 | Rich et al. |
| 2005/0112650 | A1 | 5/2005 | Chang et al. |
| 2005/0118230 | A1 | 6/2005 | Hill et al. |
| 2005/0172476 | A1 | 8/2005 | Stone et al. |
| 2005/0176056 | A1 | 8/2005 | Sammak et al. |
| 2005/0208573 | A1 | 9/2005 | Bell et al. |
| 2006/0163385 | A1 | 7/2006 | Link et al. |
| 2006/0223187 | A1 | 10/2006 | Carver et al. |

(56) References Cited

U.S. PATENT DOCUMENTS

| | | |
|---|---|---|
| 2006/0240560 A1 | 10/2006 | Bakker et al. |
| 2006/0250616 A1 | 11/2006 | Pettipiece et al. |
| 2006/0269962 A1 | 11/2006 | Watkins et al. |
| 2006/0275820 A1 | 12/2006 | Watkins et al. |
| 2007/0000342 A1 | 1/2007 | Kazuno |
| 2007/0003442 A1 | 1/2007 | Link et al. |
| 2007/0054119 A1 | 3/2007 | Garstecki et al. |
| 2007/0082019 A1 | 4/2007 | Huang et al. |
| 2007/0087348 A1 | 4/2007 | Notcovich et al. |
| 2007/0158547 A1 | 7/2007 | Rich et al. |
| 2007/0178168 A1 | 8/2007 | Ho et al. |
| 2007/0254378 A1 | 11/2007 | Zhang et al. |
| 2007/0259415 A1 | 11/2007 | Zigova et al. |
| 2008/0014589 A1 | 1/2008 | Link et al. |
| 2008/0019921 A1 | 1/2008 | Zhang |
| 2008/0023630 A1 | 1/2008 | Boschetti et al. |
| 2008/0026468 A1 | 1/2008 | Carver et al. |
| 2008/0032405 A1 | 2/2008 | Ho et al. |
| 2008/0044472 A1 | 2/2008 | Garcia et al. |
| 2008/0090737 A1 | 4/2008 | Boschetti |
| 2008/0241262 A1 | 10/2008 | Lee et al. |
| 2009/0148961 A1 | 6/2009 | Luchini et al. |
| 2010/0029794 A1 | 2/2010 | Yilmaz et al. |
| 2010/0120059 A1 | 5/2010 | Yan et al. |
| 2010/0178647 A1 | 7/2010 | Carver et al. |
| 2010/0178656 A1 | 7/2010 | Buffiere et al. |
| 2010/0184101 A1 | 7/2010 | Buffiere et al. |
| 2010/0187441 A1 | 7/2010 | Waldbeser et al. |
| 2010/0234252 A1 | 9/2010 | Moradi-Araghi et al. |
| 2010/0285594 A1 | 11/2010 | Purvis, Jr. |
| 2010/0303811 A1 | 12/2010 | Ochi |
| 2011/0117670 A1 | 5/2011 | Walker et al. |
| 2011/0212179 A1 | 9/2011 | Liu |
| 2011/0218123 A1 | 9/2011 | Weitz et al. |
| 2011/0222068 A1 | 9/2011 | Heng |
| 2011/0318820 A1 | 12/2011 | Hinz et al. |
| 2012/0129723 A1 | 5/2012 | Notcovich et al. |
| 2012/0295300 A1 | 11/2012 | Heng et al. |
| 2012/0309651 A1 | 12/2012 | Pregibon et al. |
| 2013/0089883 A1 | 4/2013 | Dallenne et al. |
| 2013/0177973 A1 | 7/2013 | Kondo |
| 2013/0274125 A1 | 10/2013 | Binder et al. |
| 2014/0073532 A1 | 3/2014 | Walker et al. |
| 2014/0100791 A1 | 4/2014 | Darmstadt et al. |
| 2014/0142039 A1 | 5/2014 | Little et al. |
| 2014/0157859 A1 | 6/2014 | Darmstadt et al. |
| 2014/0179808 A1 | 6/2014 | Flanagan |
| 2014/0198313 A1 | 7/2014 | Tracy et al. |
| 2014/0221238 A1 | 8/2014 | Regan et al. |
| 2014/0271677 A1 | 9/2014 | Palese et al. |
| 2014/0377334 A1 | 12/2014 | Irvine et al. |
| 2015/0027207 A1 | 1/2015 | Likuski et al. |
| 2015/0094232 A1 | 4/2015 | Abate et al. |
| 2015/0177115 A1 | 6/2015 | Kim et al. |
| 2015/0211044 A1 | 7/2015 | Dallenne et al. |
| 2015/0267196 A1 | 9/2015 | Alsberg et al. |
| 2016/0258856 A1 | 9/2016 | Kim et al. |
| 2017/0045436 A1 | 2/2017 | Fox et al. |
| 2017/0081636 A1 | 3/2017 | Kevlahan et al. |
| 2017/0159132 A1 | 6/2017 | Okino et al. |
| 2017/0268998 A1 | 9/2017 | Fox et al. |
| 2017/0361322 A1 | 12/2017 | Esmail et al. |
| 2017/0370951 A1 | 12/2017 | Buffiere et al. |
| 2018/0172687 A1 | 6/2018 | Kaul et al. |
| 2018/0216171 A1 | 8/2018 | Xue et al. |
| 2018/0275040 A1 | 9/2018 | Kim et al. |
| 2018/0282423 A1 | 10/2018 | Wang et al. |
| 2018/0371525 A1 | 12/2018 | Lebofsky et al. |
| 2019/0145881 A1 | 5/2019 | Fox et al. |
| 2019/0154707 A1 | 5/2019 | Flamini et al. |
| 2019/0169572 A1 | 6/2019 | Shi et al. |
| 2019/0249171 A1 | 8/2019 | Wu et al. |
| 2019/0293546 A1 | 9/2019 | Handique |
| 2020/0056231 A1 | 2/2020 | Lebofsky et al. |
| 2020/0085971 A1 | 3/2020 | Kevlahan et al. |
| 2020/0115675 A1 | 4/2020 | Pathak et al. |
| 2020/0150020 A1 | 5/2020 | Kim et al. |
| 2020/0206145 A1 | 7/2020 | Shi et al. |
| 2020/0209064 A1 | 7/2020 | Owsley et al. |
| 2020/0232979 A1 | 7/2020 | Revzin et al. |
| 2020/0249242 A1 | 8/2020 | Batxelli-Molina et al. |
| 2020/0268845 A1 | 8/2020 | Peled et al. |
| 2020/0332354 A1 | 10/2020 | Xue et al. |
| 2020/0363434 A1 | 11/2020 | Buffiere et al. |
| 2020/0399428 A1 | 12/2020 | Kleine-Brüggeney et al. |
| 2020/0400546 A1 | 12/2020 | Kim et al. |
| 2020/0408747 A1 | 12/2020 | Zur Megede et al. |
| 2021/0032297 A1 | 2/2021 | Schmidt et al. |
| 2021/0040567 A1 | 2/2021 | Handique et al. |
| 2021/0130880 A1 | 5/2021 | Lebofsky |
| 2021/0190740 A1 | 6/2021 | Scolari et al. |
| 2021/0231552 A1 | 7/2021 | Kim et al. |
| 2021/0247294 A1 | 8/2021 | Handique |
| 2021/0341469 A1 | 11/2021 | Kim et al. |
| 2022/0042077 A1 | 2/2022 | Lebofsky et al. |
| 2022/0065878 A1 | 3/2022 | Lee |
| 2022/0152150 A1 | 5/2022 | Koshy et al. |
| 2022/0154266 A1 | 5/2022 | Xue et al. |
| 2022/0178810 A1 | 6/2022 | Kim et al. |
| 2022/0213530 A1 | 7/2022 | Larson et al. |
| 2022/0260476 A1 | 8/2022 | Kim et al. |
| 2022/0364976 A1 | 11/2022 | Kim et al. |
| 2023/0012786 A1 | 1/2023 | Lebofsky et al. |
| 2023/0062518 A1 | 3/2023 | Ebrahim et al. |
| 2023/0067460 A1 | 3/2023 | Nguyen et al. |
| 2023/0152202 A1 | 5/2023 | Kim et al. |
| 2023/0176042 A1 | 6/2023 | Kim et al. |
| 2023/0266223 A1 | 8/2023 | Kim et al. |
| 2024/0053248 A1 | 2/2024 | Kim et al. |
| 2024/0060038 A1 | 2/2024 | Nguyen et al. |
| 2024/0269185 A1 | 8/2024 | Nguyen et al. |
| 2024/0353305 A1 | 10/2024 | Zhang et al. |

FOREIGN PATENT DOCUMENTS

| | | |
|---|---|---|
| CN | 103744185 A | 4/2014 |
| CN | 104641217 A | 5/2015 |
| EP | 3585364 A1 | 1/2020 |
| JP | H07196916 A | 8/1995 |
| JP | 2002510541 A | 4/2002 |
| JP | 2005281470 A | 10/2005 |
| JP | 2007114026 A | 5/2007 |
| JP | 2012011269 A | 1/2012 |
| JP | 2013520530 A | 6/2013 |
| JP | 2013155358 A | 8/2013 |
| JP | 2014508516 A | 4/2014 |
| WO | WO-8910566 A1 | 11/1989 |
| WO | WO-1995003408 A1 | 2/1995 |
| WO | WO-0008212 A1 | 2/2000 |
| WO | WO-0132829 A2 | 5/2001 |
| WO | WO-03000014 A2 | 1/2003 |
| WO | WO-2005013896 A2 | 2/2005 |
| WO | WO-2006003423 A2 | 1/2006 |
| WO | WO-2006078841 A1 | 7/2006 |
| WO | WO-2006096571 A2 | 9/2006 |
| WO | WO-2007101130 A2 | 9/2007 |
| WO | WO-2008115653 A2 | 9/2008 |
| WO | WO-2008121342 A2 | 10/2008 |
| WO | WO-2010025190 A1 | 3/2010 |
| WO | WO-2010025988 A1 | 3/2010 |
| WO | WO-2011098407 A1 | 8/2011 |
| WO | WO-2012033811 A1 | 3/2012 |
| WO | WO-2013113670 A1 | 8/2013 |
| WO | WO-2014089009 A1 | 6/2014 |
| WO | WO-2018108341 A1 | 6/2018 |
| WO | WO-2019018727 A1 | 1/2019 |
| WO | WO-2020037214 A1 | 2/2020 |
| WO | WO-2021113065 A1 | 6/2021 |
| WO | WO-2021154900 A1 | 8/2021 |

(56) References Cited

FOREIGN PATENT DOCUMENTS

WO    WO-2023215886 A1    11/2023
WO    WO-2024092161 A2    5/2024

OTHER PUBLICATIONS

Bele, Marjan, Olavi Siiman and Egon Matjevic, "Preparation and flow cytometry of uniform silica-fluorescent dye microspheres." Journal of colloid and interface science 254(2):274-282 (2002).
Chen et al., "Molecular mechanisms of T cell co-stimulation and co-inhibition," Nature reviews Immunology, 13:227-242 (2013).
Chen, M., et al., "Initiator caspases in apoptosis signaling pathways", Apoptosis (London), Aug. 1, 2002, pp. 313-319, DOI: 10.1023/A:1016167228059.
Claus et al., "The emerging landscape of novel 4-1BB (CD137) agonistic drugs for cancer immunotherapy," MAbs 15(1):2167189, pp. 1-22 (Jan.-Dec. 2023).
Elbert, "Liquid-liquid two-phase systems for the production of porous hydrogels and hydrogel microspheres for biomedical applications: A tutorial review," Acta Biomater. 7(1):31-56 (Jan. 2011). Epub Jul. 24, 2010.
Extended European Search Report for European Application No. EP21744765.5 dated Jan. 29, 2024, 8 pages.
Extended European Search Report issued by the European Patent Office for Application No. 16749674.4, dated Sep. 6, 2018, 12 pages.
Hasegawa, Urara et al. "Nanogel-quantum dot hybrid nanoparticles for live cell imaging." Biochemical and biophysical research communications 331(4):917-921 (2005).
Hegelson et al., "Hydrogel microparticles from lithographic processes: novel materials for fundamental and applied colloid science," Curr. Opin. Colloid. Interface Sci. 16(2):106-117 (Apr. 1, 2011).
Heller et al., "inylcarbonates and vinylcarbamates: Biocompatible monomers for radical photopolymerization," Journal of Polymer Science Part A: Polymer Chemistry 49, pp. 650-661 (Dec. 2, 2010).
Hermenegildo et al., "Hydrogel-based Magnetoelectric Microenvironments for Tissue Stimulation," Colloids and Surfaces B: Biointerfaces 181 1041-1047 2019.
Higuchi, A., et al., "Design of polymeric materials for culturing human pluripotent stem cells: Progress toward feeder-free and xeno-free culturing," Progress in Polymer Science, Jul. 2014, vol. 39 (7), pp. 1348-1374.
Hu and Messersmith, "Rational design of transglutaminase substrate peptides for rapid enzymatic formation of hydrogels," . J Am. Chem. Soc. 125, 14298-14299 (Oct. 31, 2003).
International Search Report and Written Opinion for International Application No. PCT/US2022/048283 dated Feb. 14, 2023, 14 pages.
International Search Report and Written Opinion for International Application No. PCT/US2023/075041 dated Mar. 8, 2024, 11 pages.
International Search Report and Written Opinion for International Patent Application No. PCT/US2016/017029, mailed May 19, 2016, 8 pages.
International Search Report and Written Opinion for International Patent Application No. PCT/US21/014538, dated Apr. 8, 2021, 19 pages.
International Search Report and Written Opinion for International Patent Application No. PCT/US21/030590, dated Jul. 26, 2021, 13 pages.
International Search Report and Written Opinion for PCT Application No. PCT/US2023/066684 dated Aug. 7, 2023, 15 pages.
International Search Report and Written Opinion for PCT Application No. PCT/US2023/067893 dated Oct. 10, 2023, 22 pages.
Jain et al. Zwitterionic Hydrogels Based on a Degradable Disulfide Carboxybetaine Cross-Linker, Langmuir 2019, 35, 1864-1871 (Year: 2019).

Jin et al., "Overview of cell death signaling pathways" , Cancer Biology & Therapy, vol. 4, No. 2, Feb. 2, 2005, pp. 147-171, DOI: 10.4161/cbt.4.2.1508.
Kim, Jin-Woong et al., "Fabrication of Monodisperse Gel Shells and Functional Microgels in Microfluidic Devices," Angew. Chem. Int. Ed. 46:819-1822 (2007).
Lee, Ki-Chang and Lee, Sang-Yun, "Preparation of Highly Cross-Linked, Monodisperse Poly (methyl methacrylate) Microspheres by Dispersion Polymerization; Part II. Semi-continuation Processes," Macromolecular Research 6(4):293-302 (2008).
Liu, A.L., et al., "Methods for Generating Hydrogel Particles for Protein Delivery," Annals of Biomedical Engineering, Jun. 2016, vol. 44 (6), pp. 1946-1958.
Liu, Z et al., Recent Advances on Magnetic Sensitive Hydrogels in Tissue Engineering, Frontiers in Chemistry, vol. 8 , Article 124, pp. 1-17, (Mar. 2020).
Luchini, Alessandra et al. "Smart hydrogel particles: biomarker harvesting: one-step affinity purification, size exclusion, and protection against degradation." Nano letters 8(1): 350-361 (2008).
Lutolf et al., "Synthetic matrix metalloproteinase-sensitive hydrogels for the conduction of tissue regeneration: engineering cell-invasion characteristics," Proc Natl Acad Sci U S A 100(9):5413-8. (Apr. 29, 2003). Epub Apr. 9, 2003.
Martin, et al., "Elucidating the Structure of Membrane Proteins, "BioTechniques, 2019, vol. 66 (4), pp. 167-170.
Martino et al., "Controlling integrin specificity and stem cell differentiation in 2D and 3D environments through regulation of fibronectin domain stability," Biomaterials 30(6): 1089-97 (Feb. 2009). Epub Nov. 22, 2008.
Martino et al., "Engineering the growth factor microenvironment with fibronectin domains to Promote Wound and Bone Tissue Healing," Sci. Trans. Med. 3(100); 100ra89, 10 pages (Sep. 14, 2011).
McDonald et al., "Fabrication of microfluidic systems in poly(dimethylsiloxane), "Electrophoresis 21 :27-40 (Jan. 1, 2000). First published: Dec. 29, 1999.
Pastor et al., "CD28 aptamers as powerful immune response modulators," Mol Ther Nucleic Acids 2:e98, 9 pages (Jun. 11, 2013).
Patanarut, Alexis et al., "Synthesis and characterization of hydrogel particles containing Cibacron Blue F3G-A." Colloids and Surfaces A: Physicochemical and Engineering Aspects 362(1):8-19 (2010).
Perez-Luna, V.H., et al., "Encapsulation of Biological Agents in Hydrogels for Therapeutic Applications," Gels, vol. 4(61), pp. 1-30, (Jul. 11, 2018).
Petka et al., "Reversible hydrogels from self-assembling artificial proteins," Science 281(5375):389-392 (Jul. 1998).
Poirier et al., "CD28-specific immunomodulating antibodies: what can be learned from experimental models?" American Journal of Transplantation 12(7): 1682-1690 (Jul. 2012). Epub Apr. 4, 2012.
Porto, "Polymer Biocompatibility," Polymerization, Dr. Ailton De Souza Gomes (Ed.), 17 pages (2012).
Proll, Guenther et al. "Potential of label-free detection in high-content-screening applications." Journal of Chromatography A 1116(1):2-8 (2007).
Qui et al., "Apoptosis of multiple myeloma cells induced by agonist monoclonal antibody against human CD28," Cell Immunol. 236(1-2): 154-60 (Jul.-Aug. 2005). Epub 2005 Sep. 26, 2005.
Riley et al., Human T regulatory cell therapy: take a billion or so and call me in the morning,' Immunity 30(5):656-65. (May 2009).
Shastri, V.P., et al., "Non-Degradable Biocompatible Polymers in Medicine: Past, Present and Future", Current Pharmaceutical Biotechnology, Bentham Science Publishers, NL, vol. 4, No. 5, Jan. 1, 2003, pp. 331-337.
Simpson, et al., "Protein Folding and Assembly in Confined Environments: Implications for Protein Aggregation in Hydrogels and Tissues," Biotechnology Advances, 2020, vol. 42, pp. 1-11.
Sugiura et al., "Effect of Channel Structure on Microchannel Emulsification," Languimir 18(15): 5708-5712 (Jun. 22, 2002).
Tomczak, Nikodem et al., "Designer polymer-quantum dot architectures." Progress in Polymer Science 34:393-430 (2009).

(56) References Cited

OTHER PUBLICATIONS

Ugelstad, J. and Mork, P.C., "Swelling of Oligomer-Polymer Particles. New Methods of Preparation of Emulsions and Polymer Dispersions," Advances in Colloid and Interface Sciences, 13:101-140 (1980).

Wallberg et al., "Analysis of Apoptosis and Necroptosis by Fluorescence-Activated Cell Sorting," Cold Spring Harbor Protocol, vol. 2016, No. 4, Apr. 1, 2016, 7 pages.

Weinkove et al., "Selecting costimulatory domains for chimeric antigen receptors: functional and clinical considerations," Clin Transl Immunology 8(5): el049, p. 1-14 (May 11, 2019).

Xu et al., "Hyaluronic Acid-Based Hydrogels: From a Natural Polysaccharide to Complex Networks," Soft Matter. 8(12):3280-3294 (Mar. 2012).

Yadav and Redmond, "Current Clinical Trial Landscape of OX40 Agonists," Curr Oncol Rep. 24(7):951-960 (Jul. 2022).

Yang et al., "IDBD: Infectious Disease Biomarker Database," Nucleic Acid Res. 36:D455-D460 (Jan. 2008). Published online Nov. 3, 2007.

Zhang et al., "Protein engineering with unnatural amino acids," Current Opinion in Structural Biology 23(4):581-587 (Aug. 2013),.

* cited by examiner

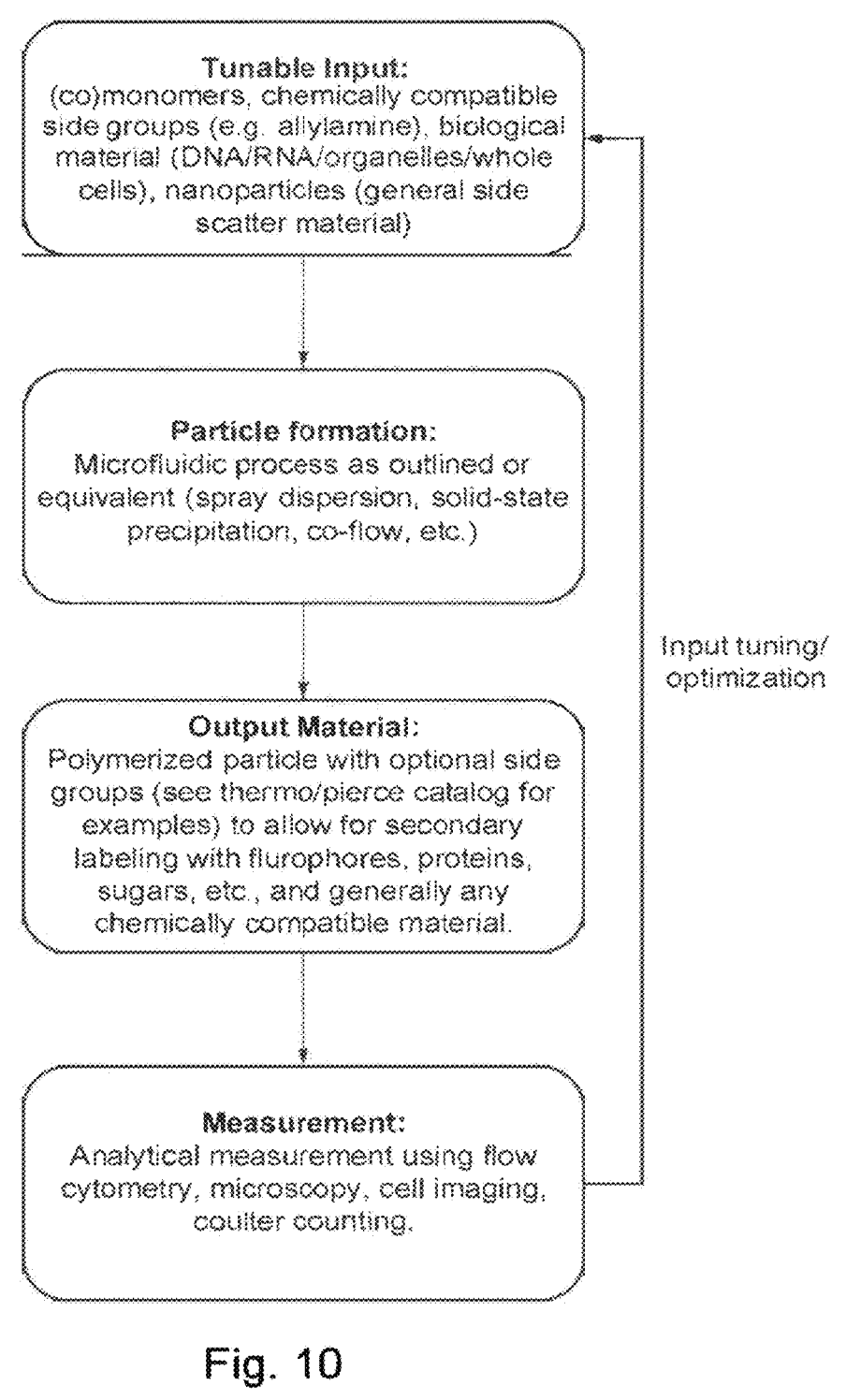

Tunable Input:
(co)monomers, chemically compatible side groups (e.g. allylamine), biological material (DNA/RNA/organelles/whole cells), nanoparticles (general side scatter material)

Particle formation:
Microfluidic process as outlined or equivalent (spray dispersion, solid-state precipitation, co-flow, etc.)

Output Material:
Polymerized particle with optional side groups (see thermo/pierce catalog for examples) to allow for secondary labeling with flurophores, proteins, sugars, etc., and generally any chemically compatible material.

Measurement:
Analytical measurement using flow cytometry, microscopy, cell imaging, coulter counting.

Input tuning/ optimization

Fig. 10

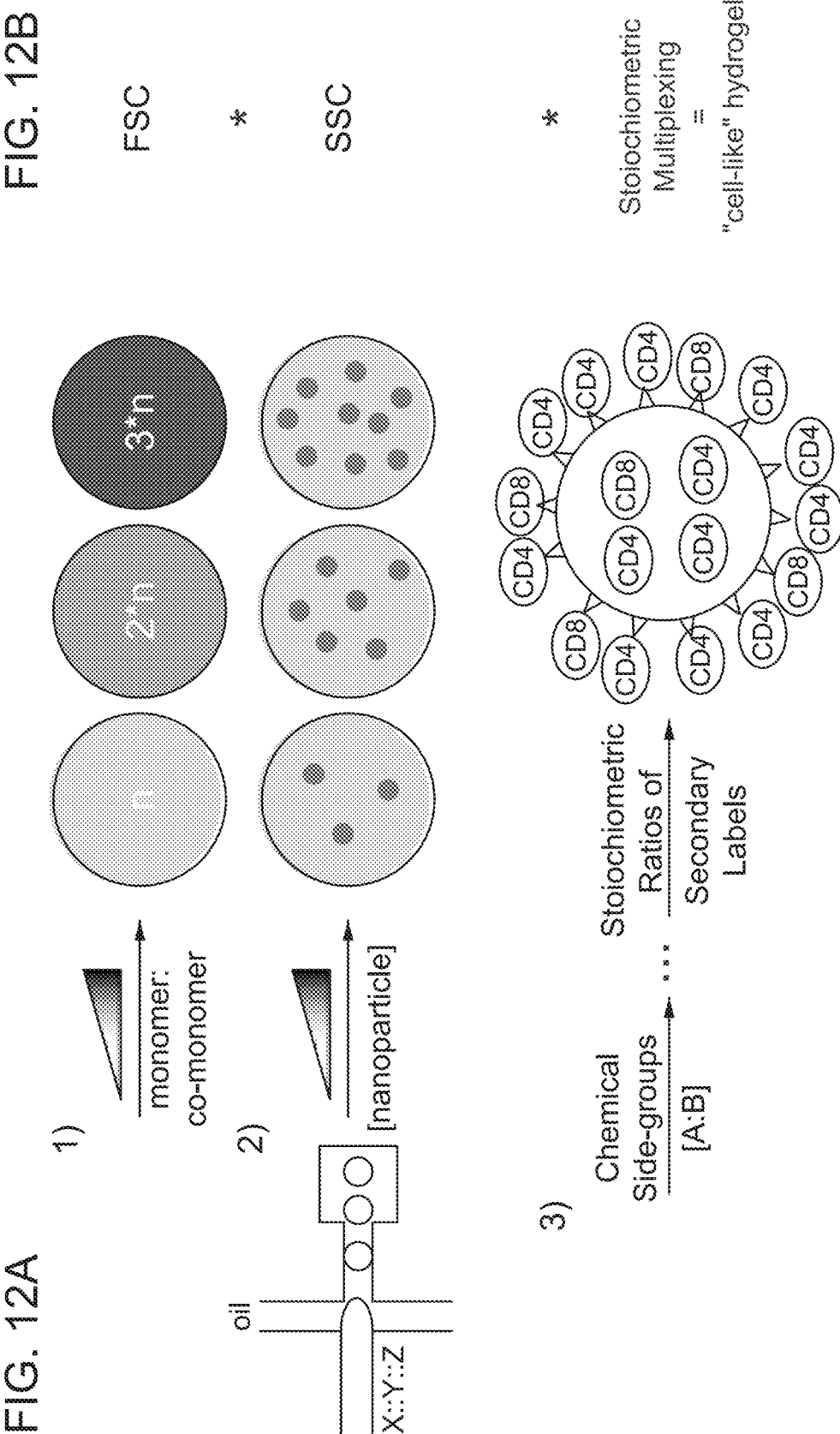

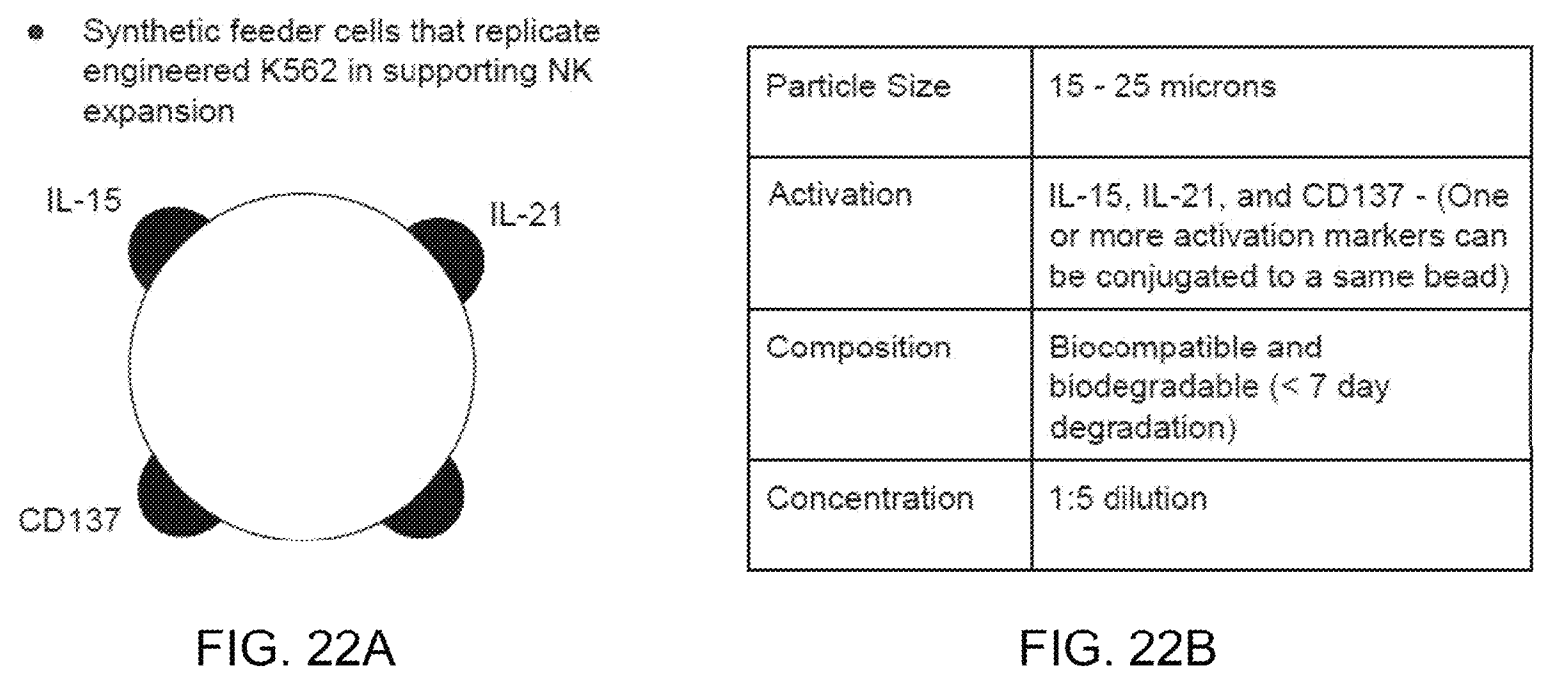

| Particle Size | 15 - 25 microns |
| Activation | IL-15, IL-21, and CD137 - (One or more activation markers can be conjugated to a same bead) |
| Composition | Biocompatible and biodegradable (< 7 day degradation) |
| Concentration | 1:5 dilution |

FIG. 22B

- Synthetic feeder cells that replicate engineered K562 in supporting NK expansion

| Particle Size | 10 - 20 micron |
|---|---|
| Cell activation | anti-CD3 (clone OKT3) anti-CD28 (clone 15E8) |
| Composition | • Biocompatible and biodegradable (< 3 day degradation)<br>• Customize hydrogel elasticity to mimic cell-to-cell interaction |
| Concentration | 1:100 dilution |

FIG. 23B

• Biocompatible and biodegradable hydrogel
• Elasticity to more accurately mimic cell-to-cell synapse (ligand-receptor) interaction

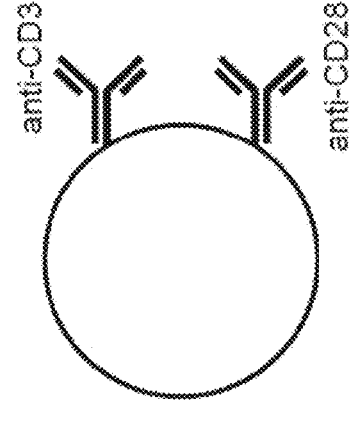

anti-CD3 anti-CD28

FIG. 23A

SIZE-TUNABLE SYNTHETIC PARTICLES WITH TUNABLE OPTICAL PROPERTIES AND METHODS FOR USING THE SAME FOR IMMUNE CELL ACTIVATION

CROSS-REFERENCE TO RELATED APPLICATIONS

This application is a continuation of U.S. application Ser. No. 18/735,500, filed on Jun. 6, 2024, which is a continuation of International Application No. PCT/US2023/077961, filed on Oct. 26, 2023, which claims the benefit of U.S. Provisional Patent Application No. 63/419,580, filed on Oct. 26, 2022, and U.S. Provisional Patent Application No. 63/488,949, filed on Mar. 7, 2023, each of which is incorporated by reference herein in its entirety for all purposes.

BACKGROUND OF THE INVENTION

Flow cytometry is a technique that allows for the rapid separation, counting, and characterization of individual cells and is routinely used in clinical and laboratory settings for a variety of applications. The technology relies on directing a beam of light onto a hydrodynamically-focused stream of liquid. A number of detectors are then aimed at the point where the stream passes through the light beam: one in line with the light beam (forward scatter or FSC) and several perpendicular to it (side scatter or SSC). FSC correlates with the cell volume and SSC depends on the inner complexity of the particle (e.g., shape of the nucleus, the amount and type of cytoplasmic granules or the membrane roughness). As a result of these correlations, different specific cell types exhibit different FSC and SSC, allowing cell types to be distinguished in flow cytometry. The ability to identify specific cell types, however, relies on proper calibration of the instrument, a process that has relied on the use of purified cells of the cell type of interest. Obtaining these purified cells can require costly, laborious procedures that are prone to batch-to-batch variation. Therefore, there is a need in the art for synthetic compositions with tunable optical properties that can mimic specific cell types in devices such as flow cytometers.

To this end, hydrogel particles for immunotherapy are also desired. Immunotherapy involving priming and expansion of immune cells, including T lymphocytes (T cells), is a promising treatment for the treatment of cancer and infectious disease. Current standards for in vitro T cell activation are magnetic microbeads containing αCD3 and αCD28 antibodies and having a subcellular sized diameter. However, these microbeads, which may be monodisperse polystyrene beads, are superparamagnetic, thus requiring an additional isolation step after beads have been in culture. Other methods to stimulate e.g., T cells in vitro include a plate-bound method where αCD3 and αCD28 antibodies are directly added to T cell culture and are washed off after 24 h of stimulation. Still other methods rely on T cells stimulated in vitro on autologous dendritic cells, virally infected B cells, and/or allogenic feeder cells cloned and injected with expanded T cells. However, these methods require billions of cells, and co-culturing e.g., T cells with other cell types may induce undesirable immune reactions or the introduction of viruses when the expanded T cells are administered to a patient. Accordingly, an improved method for immune cell activation is needed.

SUMMARY OF THE INVENTION

In an embodiment, the present disclosure relates to a hydrogel particle comprising a polymerized monomer and having at least one surface is provided. The hydrogel particle has at least one optical property that is substantially similar to the at least one optical property of a target cell. The optical property in one embodiment, is a side scatter profile (SSC), forward scatter profile (FSC), a fluorescence emission profile, or a combination thereof. The target cell can be any target cell that the user specifies. For example, in one embodiment, the target cell is an immune cell, stem cell or cancer cell.

In an embodiment, the present disclosure relates to a method for calibrating a cytometric device for analysis of a target cell, is provided. In one embodiment, the method comprises inserting into the device a hydrogel particle having at least one optical property substantially similar to a target cell, wherein the hydrogel particle comprises a polymerized monomer and has at least one surface. The method further comprises measuring the at least one optical property of the hydrogel particle using the cytometric device. The at least one optical property in one embodiment, is used as a reference to detect a target cell in a sample.

In an embodiment, the present disclosure relates to a method for detecting a target cell in a sample is provided. The method comprises inserting into the device a hydrogel particle having at least one optical property substantially similar to a target cell, wherein the hydrogel particle comprises a polymerized monomer. The method further comprises measuring the at least one optical property of the hydrogel particle using the cytometric device. A sample comprising a plurality of cells is inserted into the cytometric device, and the at least one optical property of individual cells of the plurality are measured. Finally, a determination is made, based on the optical property measurement, whether the target cell or plurality thereof is present in the sample.

In an embodiment of the methods provided herein, the hydrogel particle comprises a biodegradable monomer. In a further embodiment, the biodegradable monomer is a monosaccharide, disaccharide, polysaccharide, peptide, protein, or protein domain. In even a further embodiment, the biodegradable monomer is functionalized with acrylamide or acrylate.

In an embodiment, the methods herein can be used on any appropriate detection or analysis platform, including, without limitation, imaging (e.g., a microscope, a scanner, or the like), flow cytometry, or other immunodetection methods (e.g., an ELISA assay), electrophoresis, omic analysis (genomics, glycomics, proteomics, lipidomics analysis), molecular analysis (q-PCR etc.), or the like. Analysis, such as imaging or detecting, can be performed in fluorescence, bright field, dark field, or immunohistochemical (e.g. chromogenic stains).

In an embodiment, the present disclosure relates to particles for immune cell activation.

BRIEF DESCRIPTION OF THE FIGURES

FIG. 10 shows one embodiment of hydrogel parameter tuning to match and/or mimic desired cell population metrics.

FIGS. 11A-11D and 12A-B are diagrams showing embodiments of how to adjust the forward scatter, side scatter and surface properties of a hydrogel particle.

As shown in FIG. 15, the porogen may be polyethylene glycol 8000 at concentrations of 2.25%, 3.4%, 4.5%, 6.3%, and 9% w/v. By visual observation, the porosity of the porous particles increases with increasing content of polyethylene glycol 8000 in the water phase formulations. Each image of the porogen concentrations can be evaluated in view of the 50 µm scale bar in the 9% porogen image. Increased porosity can be used as a factor for increase SSC optical match of particles. Porosity can also help replicate visual morphologies of target cells. Further conjugation of biomolecules on particles can provide additional functionality, including immune response activation functions.

FIG. 22A and FIG. 22B relate to particles as feeder cells, according to embodiments of the present disclosure.

FIG. 23A and FIG. 23B relate to synthetic biomolecule presenting particles, according to embodiments of the present disclosure.

FIG. 26 depicts an increased activation of Jurkat samples as indicated by upregulation of activation marker CD69 when compared with baseline Jurkats values and also when compared against cells activated by Dynabeads™.

DETAILED DESCRIPTION OF THE INVENTION

Definitions

Figure 1A:
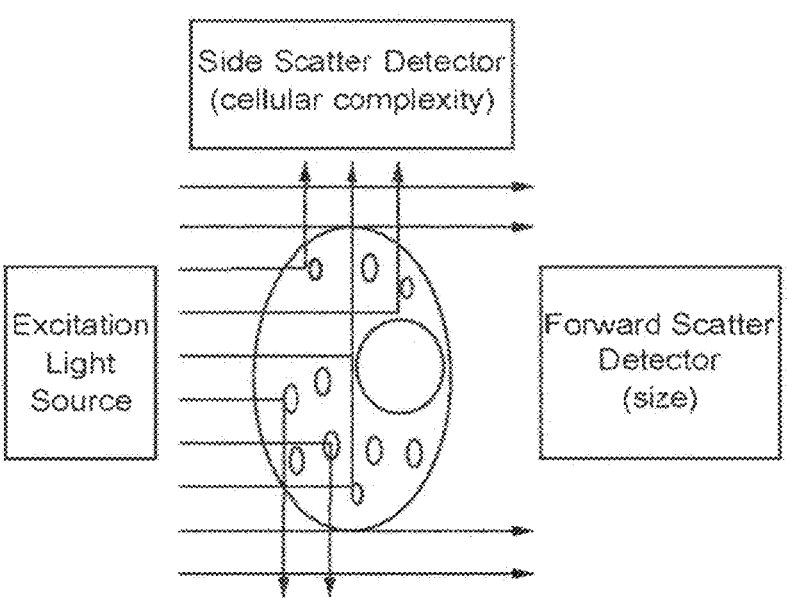
FIG. 1A-B illustrates the optical properties of disclosed hydrogel particles compared to polystyrene beads.

The indefinite articles "a" and "an" and the definite article "the" are intended to include both the singular and the plural, unless the context in which they are used clearly indicates otherwise.

"At least one" and "one or more" are used interchangeably to mean that the article may include one or more than one of the listed elements.

Throughout this application, the term "about" is used to indicate that a value includes the inherent variation of error for the device or the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents.

"Substantially similar," as may be used herein, denotes at least 40% similar, at least 50% similar, at least 60% similar, at least 70% similar, at least 80% similar, at least 90% similar, at least 95% similar, at least 96% similar, at least 97% similar, at least 98% similar or at least 99% similar.

As referred to herein, "porosity" may be used to refer to the percentage of void space within the hydrogel particle. When porogens are used, the porosity is the percentage of void space within the hydrogel particle after removal of the porogens. In such a case, the porosity may comprise a plurality of micropores and a plurality of macropores, as will be described below.

Unless otherwise indicated, it is to be understood that all numbers expressing quantities, ratios, and numerical properties of ingredients, reaction conditions, and so forth, used in the specification are contemplated to be able to be modified in all instances by the term "about".

As may be used herein, the term "contacting" (i.e., contacting a cell e.g., a differentiable cell, with a compound) is intended to include incubating the item/compound and the cell together in vitro (e.g., adding the compound/particles to cells in culture). It is understood that the cells contacted with the defined medium (e.g., particles) can be further treated with a cell differentiation environment to stabilize the cells, or to differentiate the cells.

As may be used herein, the term "stabilize," when used in reference to the differentiation state of a cell or culture of cells, indicates that the cells will continue to proliferate over multiple passages in culture, and preferably indefinitely in culture, where most, if not all, of the cells in the culture are of the same differentiation state. In addition, when the stabilized cells divide, the division typically yields cells of the same cell type or yields cells of the same differentiation state. A stabilized cell or cell population in general, does not further differentiate or de-differentiate if the cell culture conditions are not altered and the cells continue to be passaged and are not overgrown. In one embodiment, the cell that is stabilized is capable of proliferation in the stable state indefinitely, or for at least more than 2 passages. In a more specific embodiment, the cells are stable for more than 3 passages, 4 passages, 5 passages, 6 passages, 7 passages, 8 passages, 9 passages, more than 10 passages, more than 15 passages, more than 20 passages, more than 25 passages, or more than 30 passages. In one embodiment, the cell is stable for greater than approximately 1 month, 2 months, 3 months, 4 months, 5 months, 6 months, 7 months, 8 months, 9 months, 10 months, or 11 months of continuous passaging. In another embodiment, the cell is stable for greater than approximately 1 year of continuous passaging. In one embodiment, stem cells are maintained in culture in a pluripotent state by routine passage in the defined medium until it is desired that they be differentiated. As used herein, the term "proliferate" refers to an increase in the number of cells in a cell culture.

Hence, as may be used herein, the term "growth environment" is an environment in which stem cells (e.g., primate embryonic stem cells) will proliferate in vitro. Features of the environment include the medium in which the cells are cultured, and a supporting structure (such as a substrate on a solid surface) if present.

As may be used herein, a "defined" medium refers to a biochemically defined formulation comprised solely of the biochemically-defined constituents. A defined medium may include solely constituents having known chemical compositions. A defined medium may also include constituents that are derived from known sources. For example, a defined medium may also include factors and other compositions secreted from known tissues or cells; however, the defined medium will not include the conditioned medium from a culture of such cells. Thus, a "defined medium" may, if indicated, include particular compounds added to form the culture medium.

As may be used herein, the term "basal medium" refers to a solution of amino acids, vitamins, salts, and nutrients that is effective to support the growth of cells in culture, although normally these compounds will not support cell growth unless supplemented with additional compounds. The nutrients include a carbon source (e.g., a sugar such as glucose) that can be metabolized by the cells, as well as other compounds necessary for the cells' survival. These are compounds that the cells themselves cannot synthesize, due to the absence of one or more of the gene(s) that encode the protein(s) necessary to synthesize the compound (e.g., essential amino acids) or, with respect to compounds which the cells can synthesize, because of their particular developmental state the gene(s) encoding the necessary biosynthetic proteins are not being expressed as sufficient levels. A number of base media are known in the art of mammalian cell culture, such as Dulbecco's Modified Eagle Media (DMEM), Knockout-DMEM (KO-DMEM), and DMEM/F12, although any base medium that supports the growth of primate embryonic stem cells in a substantially undifferentiated state can be employed. A "basal medium" as described herein also refers to the basal medium described in PCT/US2007/062755, filed Jun. 13, 2007, which is herein incorporated in its entirety.

Several critical calibration measurements for flow cytometers require precise time resolution, such as setting the offset time between lasers, and calculating the delay time between detection and sorting of an object. Due to the fluidic conditions within the instrument, precise setting of these timing parameters requires the use of calibration particles that are the same size as the cells to be analyzed. Timing calibrations are typically performed using polystyrene beads with variable fluorescent intensities to calibrate the response of an excitation source and to set the inter-laser timing delay and sorting delay. Flow cytometers can also be calibrated using forward and side scatter signals which are general measures of size and granularity or complexity of the target sample. These calibrations are crucial for the accurate performance of the cytometer and for any downstream analysis or sorting of cell populations. The disclosed hydrogel particles exhibit tuned scatter properties and are suitable for use as calibration reagents for a range of mammalian or bacterial cell types. Scattering is a standard metric for distinguishing cell types in heterogeneous mixtures for clinical, food safety, and research purposes.

Figure 1B:
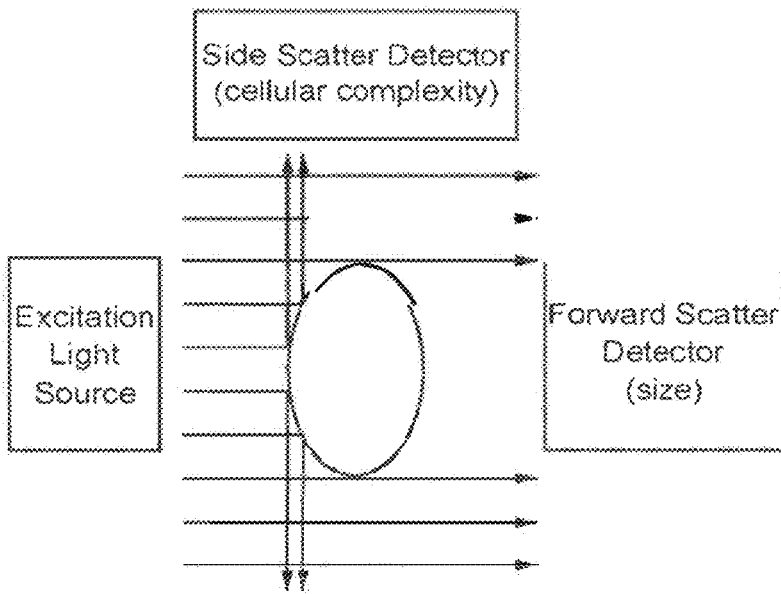

Although polystyrene particles can be used to set inter-laser and sorting delays for some applications, many eukaryotic cell types fall outside of the size range of commercially available polystyrene particles (1-20 μm) making it nearly impossible to accurately calibrate a flow cytometer for these targets. Also, as shown in FIG. 1, polystyrene particles are fundamentally limited in the optical properties that can possess such as side scattering, which is a general measure of cellular complexity. Polystyrene particles are therefore limited in the two most important passive optical measurements used in flow cytometry: FSC (forward scattering), and SSC (side scattering) which measure the size and complexity of the target respectively. Due to these limitations of polystyrene, users must rely on purified cell lines to calibrate fluorescent intensity, inter-laser delay, sort delays, size and cellular complexity for experiments. This is a lengthy and labor-intensive process that increases the cost of flow cytometry validation and research pipelines significantly. More importantly, these calibration cell lines introduce biological variation, causing disparities in the interpretation of data.

Moreover, quality control (QC) for calibration of flow cytometers is also a crucial consideration when these instruments are used for clinical applications, for example, to isolate human T-regulatory cells or stem cells for downstream cellular therapies. The FDA mandates that the sterility, identity, purity, and potency of a cell therapy product be demonstrated before administration to patients (Riley et al. (2009). Immunity 30, pp. 656-665). Contamination of a cellular population with polystyrene QC particles could therefore be problematic, as polystyrene has been implicated in certain cancers. Additionally, a cellular population that is contaminated with a QC standard that is enzymatically degraded or digested internally after administration to a patient potentially overcomes contamination issues, should they arise.

The present invention addresses these and other needs, as discussed below.

In one aspect, a composition comprising a plurality of hydrogel particles is provided, wherein the individual hydrogel particles of the plurality each has one or more optical properties substantially similar to one or more optical properties of a target cell. Each of the individual hydrogel particles of the plurality independently comprises a hydrogel which is synthesized by polymerizing one or more monomers, i.e., to form a homopolymer or copolymer. As discussed further below, the use of bifunctional monomers allows for the further derivatization of hydrogels, e.g., with fluorescent dyes, biomolecules, such as cell surface markers or epitope binding fragments thereof, and immunostimulatory biomolecules, including CD markers and antibodies or antigen-binding fragments thereof, as well as a combination thereof. An example of hydrogel parameter tuning to meet/match desired cell subpopulation metrics is provided at FIG. 10. Methods for tuning the properties of a hydrogel are described herein. The ability to adjust a range of parameters including hydrogel components and concentration of the same allows for the ability to tune a particle to mimic a wide range of cells, for example one of the cell types described herein.

As provided above, in one aspect, the present invention provides individual hydrogel particles each having one or more optical properties substantially similar to one or more optical properties of a target cell. In one embodiment, the one or more optical properties, is a side scatter profile, a forward scatter profile or a secondary marker profile, such as a fluorescence marker profile, for example a fluorescence marker profile of a fluorescently-labeled antibody that binds to the surface of the hydrogel particle. "Substantially similar," as used herein, denotes at least 40% similar, at least 50% similar, at least 60% similar, at least 70% similar, at least 80% similar, at least 90% similar, at least 95% similar, at least 96% similar, at least 97% similar, at least 98% similar or at least 99% similar.

The present invention is based in part on the unexpected discovery that one or more optical properties of a hydrogel particle can be independently modulated by altering the composition of the hydrogel particle, for example, by altering the amount of initial monomer (or co-monomer) in the composition, by altering the surface functionalization, by altering the amount of a polymerization initiator or by altering the amount of crosslinker. For example, side scattering (SSC) can be modulated without substantially affecting forward scattering (FSC), and vice versa. Furthermore, the optical properties (e.g. refractive index) of hydrogel particles can be tuned without having a substantial effect on density of the particle. This is a surprising and useful feature, as hydrogel particles that serve as surrogates for cells in cytometric methods such as flow cytometry or (fluorescence-activated cell sorting) FACS require a minimal density in order to function in those assays.

In another aspect, a method for producing a hydrogel particle is provided, wherein the hydrogel particle has one or more optical properties substantially similar to the optical properties of one or more target cells. In one embodiment, the hydrogel particle has pre-determined optical properties. The optical property, in one embodiment, is SSC, FSC, fluorescence emission, or a combination thereof.

In yet another aspect, a method of calibrating a cytometric device for analysis of a target cell is provided. In one embodiment, the method comprises (a) inserting into the device a hydrogel particle having optical properties substantially similar to the optical properties of the target cell; b) measuring the optical properties of the hydrogel particle using the cytometric device, thereby calibrating the cytometric device for analysis of the target cell. Cytometric devices are known in the art, and include commercially available devices for performing flow cytometry and FACS.

As provided above, in one aspect of the invention, compositions comprising a plurality of hydrogel particles are provided. A hydrogel is a material comprising a macromolecular three-dimensional network that allows it to swell when in the presence of water, to shrink in the absence of (or by reduction of the amount of) water, but not dissolve in water. The swelling, i.e., the absorption of water, is a consequence of the presence of hydrophilic functional groups attached to or dispersed within the macromolecular network. Crosslinks between adjacent macromolecules result in the aqueous insolubility of these hydrogels. The cross-links may be due to chemical (i.e., covalent) or physical (i.e., Van Der Waal forces, hydrogen-bonding, ionic forces, etc.) bonds. Synthetically prepared hydrogels can be prepared by polymerizing a monomeric material to form a backbone and cross-linking the backbone with a crosslinking agent. As referred to herein, the term "hydrogel" refers to the macromolecular material whether dehydrated or in a hydrated state. A characteristic of a hydrogel that is of particular value is that the material retains the general shape, whether dehydrated or hydrated. Thus, if the hydrogel has an approximately spherical shape in the dehydrated condition, it will be spherical in the hydrated condition.

In one embodiment, a hydrogel particle disclosed herein comprises greater than about 30%, greater than about 40%, greater than about 50%, greater than about 55%, greater than about 60%, greater than about 65%, greater than about 70%, greater than about 75%, greater than about 80%, greater than about 85%, greater than about 90%, or greater than about 95% water. In another embodiment, a hydrogel particle has a water content of about 10 percent by weight to about 95 percent by weight, or about 20 percent by weight to about 95 percent by weight, or about 30 percent by weight to about 95 percent by weight, or about 40 percent by weight to about 95 percent by weight, or about 50 percent by weight to about 95 percent by weight, or about 60 percent by weight to about 95 percent by weight, or about 70 percent by weight to about 95 percent by weight, or about 80 percent by weight to about 95 percent by weight.

The hydrogels provided herein, in the form of particles, are synthesized by polymerizing one or more of the monomers provided herein. The synthesis is carried out to form individual hydrogel particles. The monomeric material (monomer) in one embodiment is polymerized to form a homopolymer. However, in another embodiment copolymers of different monomeric units (i.e., co-monomers) are synthesized and used in the methods provided herein. The monomer or co-monomers used in the methods and compositions described herein, in one embodiment, is a bifunctional monomer or includes a bifunctional monomer (where co-monomers are employed). In one embodiment, the hydrogel is synthesized in the presence of a crosslinker. In a further embodiment, embodiment, the hydrogel is synthesized in the presence of a polymerization initiator.

The amount of monomer can be varied by the user of the invention, for example to obtain a particular optical property that is substantially similar to that of a target cell. In one embodiment, the monomeric component(s) (i.e., monomer, co-monomer, bifunctional monomer, or a combination thereof, for example, bis/acrylamide in various crosslinking ratios, allyl amine or other co-monomers which provide chemical functionality for secondary labeling/conjugation or alginate is present at about 10 percent by weight to about 95 percent weight of the hydrogel. In a further embodiment, the monomeric component(s) is present at about 15 percent by weight to about 90 percent weight of the hydrogel, or about 20 percent by weight to about 90 percent weight of the hydrogel.

Examples of various monomers and cross-linking chemistries available for use with the present invention are provided in the Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf, the disclosure of which is incorporated by reference in its entirety for all purposes. For example, hydrazine (e.g., with an NHS ester compound) or EDC coupling reactions (e.g., with a maleimide compound) can be used to construct the hydrogels of the invention.

In one embodiment, a monomer for use with the hydrogels provided herein is lactic acid, glycolic acid, acrylic acid, 1-hydroxyethyl methacrylate, ethyl methacrylate, 2-hydroxyethyl methacrylate (HEMA), propylene glycol methacrylate, acrylamide, N-vinylpyrrolidone (NVP), methyl methacrylate, glycidyl methacrylate, glycerol methacrylate (GMA), glycol methacrylate, ethylene glycol, fumaric acid, a derivatized version thereof, or a combination thereof. In an embodiment, the polymer may be degradable. For instance, the polymer may be a polyester based on polylactide (PLA), polyglycolide (PGA), polycaprolactone, poly(lactic-co-glycolic) acid (PLGA), and their copolymers. Other biodegradable polymers may be used.

In one embodiment, one or more of the following monomers is used herein to form a hydrogel of the present invention: 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxy-poly(ethylene glycol) methacrylate, methacrylic acid, sodium methacrylate, glycerol methacrylate, hydroxypropyl methacrylate, hydroxybutyl methacrylate or a combination thereof.

In another embodiment, one or more of the following monomers is used herein to form a tunable hydrogel: phenyl acrylate, phenyl methacrylate, benzyl acrylate, benzyl methacrylate, 2-phenylethyl acrylate, 2-phenylethyl methacrylate, 2-phenoxyethyl acrylate, 2-phenoxyethyl methacrylate, phenylthioethyl acrylate, phenylthioethyl methacrylate, 2,4,6-tribromophenyl acrylate, 2,4,6-tribromophenyl methacrylate, pentabromophenyl acrylate, pentabromophenyl methacrylate, pentachlorophenyl acrylate, pentachlorophenyl methacrylate, 2,3-dibromopropyl acrylate, 2,3-dibromopropyl methacrylate, 2-naphthyl acrylate, 2-naphthyl methacrylate, 4-methoxybenzyl acrylate, 4-methoxybenzyl methacrylate, 2-benzyloxyethyl acrylate, 2-benzyloxyethyl methacrylate, 4-chlorophenoxyethyl acrylate, 4-chlorophenoxyethyl methacrylate, 2-phenoxyethoxyethyl acrylate, 2-phenoxyethoxyethyl methacrylate, N-phenyl acrylamide, N-phenyl methacrylamide, N-benzyl acrylamide, N-benzyl methacrylamide, N,N-dibenzyl acrylamide, N,N-dibenzyl methacrylamide, N-diphenylmethyl acrylamide N-(4-methylphenyl)methyl acrylamide, N-1-naphthyl acrylamide, N-4-nitrophenyl acrylamide, N-(2-phenylethyl)acrylamide, N-triphenylmethyl acrylamide, N-(4-hydroxyphenyl)acrylamide, N,N-methylphenyl acrylamide, N,N-phenyl phenylethyl acrylamide, N-diphenylmethyl methacrylamide, N-(4-methyl phenyl)methyl methacrylamide, N-1-naphthyl methacrylamide, N-4-nitrophenyl methacrylamide, N-(2-phenylethyl)methacrylamide, N-triphenylmethyl methacrylamide, N-(4-hydroxyphenyl)methacrylamide, N,N-methylphenyl methacrylamide, N,N'-phenyl phenylethyl methacrylamide, N-vinylcarbazole, 4-vinylpyridine, 2-vinylpyridine, as described in U.S. Pat. No. 6,657,030, which is incorporated by reference in its entirety herein for all purposes.

Both synthetic monomers and bio-monomers can be used in the hydrogels provided herein, to form synthetic hydrogels, bio-hydrogels, or hybrid hydrogels that comprise a synthetic component and a bio-component (e.g., peptide, protein, monosaccharide, disaccharide, polysaccharide, primary amines sulfhydryls, carbonyls, carbohydrates, carboxylic acids present on a biomolecule). For example, proteins, peptides or carbohydrates can be used as individual monomers to form a hydrogel that includes or does not include a synthetic monomer (or polymer) and in combination with chemically compatible co-monomers and crosslinking chemistries (see for example, the Thermo Scientific Crosslinking Technical Handbook entitled "Easy molecular bonding crosslinking technology," available at tools.lifetechnologies.com/content/sfs/brochures/1602163-Crosslinking-Reagents-Handbook.pdf, the disclosure of which is incorporated by reference in its entirety for all purposes.). Compatible crosslinking chemistries include, but are not limited to, amines, carboxyls, and other reactive chemical side groups. Representative reactive groups amenable for use in the hydrogels and monomers described herein are provided in Table 1, below.

TABLE 1

| Crosslinker reactive groups amenable for bio-monomer conjugation | | |
| --- | --- | --- |
| Reactivity class | Target functional group | Reactive chemical group |
| Amine reactive | —NH$_2$ | NHS ester |
| | | Imidoester |
| | | Penafluorophenyl ester |
| | | Hydroxymethyl phosphine |
| Carboxyl-to-amine reactive | —COOH | Carbodiimide (e.g., EDC) |
| Sulfhydryl-reactive | —SH | Maeleimide |
| | | Haloacetyl (bromo-or iodo-) |
| | | Pyridylisulfide |
| | | Thiosulfonate |
| | | Vinylsulfonate |
| Aldehyde-reactive (oxidized sugars, carbonyls) | —CHO | Hydrazine |
| | | Alkoxyamine |
| Photo-reactive, i.e., nonselective, random insertion | Random | Diazirine |
| | | Aryl azide |
| Hydroxyl (nonaqueous)-reactive | —OH | Isocyanate |
| Azide-reactive | —N3 | phosphine |

In general, any form of polymerization chemistry/methods commonly known by those skilled in the art, can be employed to form polymers. In some embodiments, polymerization can be catalyzed by ultraviolet light-induced radical formation and reaction progression. In other embodiments, a hydrogel particle of the disclosure is produced by the polymerization of acrylamide or the polymerization of acrylate. For example, the acrylamide in one embodiment is a polymerizable carbohydrate derivatized acrylamide as described in U.S. Pat. No. 6,107,365, the disclosure of which is incorporated by reference in its entirety for all purposes. As described therein and known to those of ordinary skill in the art, specific attachment of acrylamide groups to sugars is readily adapted to a range of monosaccharides and higher order polysaccharides, e.g., synthetic polysaccharides or polysaccharides derived from natural sources, such as glycoproteins found in serum or tissues.

In one embodiment, an acrylate-functionalized poly(ethylene) glycol monomer is used as a hydrogel monomer. For example, the PEG in one embodiment is an acrylate or acrylamide functionalized PEG.

In some embodiments, a hydrogel particle comprises a monofunctional monomer polymerized with at least one bifunctional monomer. One example includes, but is not limited to, the formation of poly-acrylamide polymers using acrylamide and bis-acrylamide (a bifunctional monomer). In another embodiment, a hydrogel particle provided herein comprises a bifunctional monomer polymerized with a second bifunctional monomer. One example include, but is not limited to, the formation of polymers with mixed composition containing compatible chemistries such as acrylamide, bis-acrylamide, and bis-acrylamide structural congeners containing a wide range of additional chemistries. The range of chemically compatible monomers, bifunctional monomers, and mixed compositions is obvious to those skilled in the art and follows chemical reactivity principles know to those skilled in the art. (reference Thermo handbook and acrylamide polymerization handbook). See, for example, the Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf) and the Polyacrylamide Emulsions Handbook (SNF Floerger, available at snf.com.au/downloads/Emulsion_Handbook_E.pdf), the disclosure of each of which is incorporated by reference in its entirety for all purposes.

In one embodiment, a hydrogel particle provided herein comprises a polymerizable monofunctional monomer and is a monofunctional acrylic monomer. Non-limiting examples of monofunctional acrylic monomers for use herein are acrylamide; methacrylamide; N-alkylacrylamides such as N-ethylacrylamide, N-isopropylacrylamide or N-tertbutylacrylamide; N-alkylmethacrylamides such as N-ethylmethacrylamide or Nisopropylmethacrylamide; N,N-dialkylacrylamides such as N,N-dimethylacrylamide and N,N-diethylacrylamide; N-[(dialkylamino)alkyl]acrylamides such as N-[3dimethylamino) propyl]acrylamide or N-[3-(diethylamino)propyl]acrylamide; N-[(dialkylamino) alkyl]methacrylamides such as N-[3-dimethylamino)propyl]methacrylamide or N-[3-(diethylamino) propyl]methacrylamide; (dialkylamino)alkyl acrylates such as 2-(dimethylamino) ethyl acrylate, 2-(dimethylamino)propyl acrylate, or 2-(diethylamino)ethyl acrylates; and (dialkylamino) alkyl methacrylates such as 2-(dimethylamino) ethyl methacrylate.

A bifunctional monomer is any monomer that can polymerize with a monofunctional monomer of the disclosure to form a hydrogel as described herein that further contains a second functional group that can participate in a second reaction, e.g., conjugation of a fluorophore, cell surface receptor (or domain thereof), or immunostimulatory biomolecule.

In some embodiments, a bifunctional monomer is selected from the group consisting of: allyl amine, allyl alcohol, allyl isothiocyanate, allyl chloride, and allyl maleimide.

A bifunctional monomer can be a bifunctional acrylic monomer. Non-limiting examples of bifunctional acrylic monomers are N,N'-methylenebisacrylamide, N,N'methylene bismethacrylamide, N,N'-ethylene bisacrylamide, N,N'-ethylene bismethacrylamide, N,N'propylenebisacrylamide and N,N'-(1,2-dihydroxyethylene) bisacrylamide.

Higher-order branched chain and linear co-monomers can be substituted in the polymer mix to adjust the refractive index while maintaining polymer density, as described in U.S. Pat. No. 6,657,030, incorporated herein by reference in its entirety for all purposes.

In some embodiments, a hydrogel comprises a molecule that modulates the optical properties of the hydrogel. Molecules capable of altering optical properties of a hydrogel are discussed further below.

In one embodiment, an individual hydrogel particle or a plurality thereof comprises a biodegradable polymer as a hydrogel monomer. In one embodiment, the biodegradable polymer is a poly(esters) based on polylactide (PLA), polyglycolide (PGA), polycaprolactone (PCL), poly(lactic-co-glycolic) acid (PLGA), and their copolymers. In one embodiment, the biodegradable polymer is a carbohydrate or a protein, or a combination thereof. For example, in one embodiment, a monosaccharide, disaccharide or polysaccharide, (e.g., glucose, sucrose, or maltodextrin) peptide, protein (or domain thereof) is used as a hydrogel monomer. Other biodegradable polymers include poly(hydroxyalkanoate)s of the PHB-PHV class, additional poly(ester)s, and natural polymers, for example, modified poly(saccharide)s, e.g., starch, cellulose, and chitosan. In another embodiment, the biocompatible polymer is an adhesion protein, cellulose, a carbohydrate, a starch (e.g., maltodextrin, 2-hydroxyethyl starch, alginic acid), a dextran, a lignin, a polyaminoacid, an amino acid, or chitin. Such biodegradable polymers are available commercially, for example, from Sigma Aldrich (St. Louis, MO).

The protein in one embodiment comprises only natural amino acids. However, the invention is not limited thereto. For example, self-assembling artificial proteins and proteins with non-natural amino acids (e.g., those incorporated into non-ribosomal peptides or synthetically introduced via synthetic approaches, see for example, Zhang et al. (2013). Current Opinion in Structural Biology 23, pp. 581-587, the disclosure of which is incorporated by reference in its entirety for all purposes), or protein domains thereof, can also be used as hydrogel monomers. The range of non-natural (unnatural) amino acids that can be incorporated into such compositions is well known to those skilled in the art (Zhang et al. (2013). Current Opinion in Structural Biology 23, pp. 581-587; incorporated by reference in its entirety for all purposes). The biodegradable polymer in one embodiment, is used as a co-monomer, i.e., in a mixture of monomers. The biodegradable polymer in one embodiment is a bifunctional monomer.

The biomonomer, in one embodiment, is functionalized with acrylamide or acrylate. For example, in one embodiment, the polymerizable acrylamide functionalized biomolecule is an acrylamide or acrylate functionalized protein (for example, an acrylamide functionalized collagen or functionalized collagen domain), an acrylamide or acrylate functionalized peptide, or an acrylamide or acrylate functionalized monosaccharide, disaccharide or polysaccharide.

Any monosaccharide, disaccharide or polysaccharide (functionalized or otherwise) can be used as a hydrogel monomer. In one embodiment, an acrylamide or acrylate functionalized monosaccharide, disaccharide or polysaccharide is used as a polymerizable hydrogel monomer. In one embodiment, a structural polysaccharide is used as a polymerizable hydrogel monomer. In a further embodiment, the structural polysaccharide is an arabinoxylan, cellulose, chitin or a pectin. In another embodiment, alginic acid (alginate) is used as a polymerizable hydrogel monomer. In yet another embodiment, a glycosaminoglycan (GAG) is used as a polymerizable monomer in the hydrogels provided herein. In a further embodiment, the GAG is chondroitin sulfate, dermatan sulfate, keratin sulfate, heparin, heparin sulfate or hyaluronic acid (also referred to in the art as hyaluron or hyaluronate) is used as a polymerizable hydrogel monomer. The additional range of compatible biomonomers and their reactive chemistries are known be individuals skilled in the art and follow general chemical reactivity principles.

An additional range of biocompatible monomers that can be incorporated are known in the art, see, for example the non-degradable biocompatible monomers disclosed in Shastri (2003). Current Pharmaceutical Biotechnology 4, pp. 331-337, incorporated by reference herein in its entirety for all purposes. Other monomers are provided in de Moraes Porto (2012). Polymer Biocompatibility, Polymerization, Dr. Ailton De Souza Gomes (Ed.), ISBN: 978-953-51-0745-3; InTech, DOI: 10.5772/47786; Heller et al. (2010). Journal of Polymer Science Part A: Polymer Chemistry 49, pp. 650-661; Final Report for Biocompatible Materials (2004), The Board of the Biocompatible Materials and the Molecular Engineering in Polymer Science programmes, ISBN 91-631-4985-0, the disclosure of each of which are hereby incorporated by reference in their entirety.

Biocompatible monomers for use with the hydrogels described herein include in one embodiment, ethyleglycol dimethacrylate (EGDMA), 2-hydroxyethyl methacrylate (HEMA), methylmethacrylte (MMA), methacryloxymethyltrimethylsilane (TMS-MA), N-vinyl-2-pyrrolidon (N-VP), styrene, or a combination thereof.

Naturally occurring hydrogels useful in this invention include various polysaccharides available from natural sources such as plants, algae, fungi, yeasts, marine invertebrates and arthropods. Non-limiting examples include agarose, dextrans, chitin, cellulose-based compounds, starch, derivatized starch, and the like. These generally will have repeating glucose units as a major portion of the polysaccharide backbone. Cross-linking chemistries for such polysaccharides are known in the art, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf).

Hyaluronan in one embodiment is used as a hydrogel monomer (either as a single monomer or as a co-monomer). Hyaluronan in one embodiment, is functionalized, for example with acrylate or acrylamide. Hyaluronan is a high molecular weight GAG composed of disaccharide repeating units of N-acetylglucosamine and glucuronic acid linked together through alternating $\beta$-1,4 and $\beta$-1,3 glycosidic bonds. In the human body, hyaluronate is found in several soft connective tissues, including skin, umbilical cord, synovial fluid, and vitreous humor. Accordingly, in one embodiment, where one or more optical properties of a skin cell, umbilical cord cell or vitreous humor cell is desired to be mimicked, in one embodiment, hyaluronan is used as a hydrogel monomer. Methods for fabricating hydrogel particles are described in Xu et al. (2012). *Soft Matter.* 8, pp. 3280-3294, the disclosure of which is incorporated herein in its entirety for all purposes. As described therein, hyaluronan can be derivatized with various reactive handles depending on the desired cross-linking chemistry and other monomers used to form a hydrogel particle.

In yet other embodiments, chitosan, a linear polysaccharide composed of randomly distributed $\beta$-(1-4)-linked D-glucosamine (deacetylated unit) and N-acetyl-D-glucosamine (acetylated unit), is used as a hydrogel monomer (either as a single monomer or as a co-monomer).

Other polysaccharides for use as a hydrogel monomer or co-monomer include but are not limited to, agar, agarose, alginic acid, alguronic acid, alpha glucan, amylopectin, amylose, arabinoxylan, beta-glucan, callose, capsullan, carrageenan polysaccharides (e.g., kappa, iota or lambda class), cellodextrin, cellulin, cellulose, chitin, chitosan, chrysolaminarin, curdlan, cyclodextrin, alpha-cyclodextrin, dextrin, ficoll, fructan, fucoidan, galactoglucomannan, galactomannan, galactosaminoogalactan, gellan gum, glucan, glucomannan, glucorunoxylan, glycocalyx, glycogen, hemicellulose, homopolysaccharide, hypromellose, icodextrin, inulin, kefiran, laminarin, lentinan, levan polysaccharide, lichenin, mannan, mixed-linkage glucan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, or a combination thereof. As described throughout, depending on the desired cross-linking chemistry and/or additional co-monomers employed in the hydrogel, the polysaccharide can be further functionalized. For example, one or more of the polysaccharides described herein in one embodiment is functionalized with acrylate or acrylamide.

In one embodiment, an individual hydrogel particle or a plurality thereof comprises a peptide, protein, a protein domain, or a combination thereof as a hydrogel monomer or plurality thereof. In a further embodiment, the protein is a structural protein, or a domain thereof, for example, such as silk, elastin, titin or collagen, or a domain thereof. In one embodiment, the protein is an extracellular matrix (ECM) component (e.g., collagen, elastin, proteoglycan, fibrin, lysine, fibronectin). In even a further embodiment, the structural protein is collagen. In yet a further embodiment, the collagen is collagen type I, collagen type II or collagen type III or a combination thereof. In another embodiment, the hydrogel monomer comprises a proteoglycan. In a further embodiment, the proteoglycan is decorin, biglycan, testican, bikunin, fibromodulin, lumican, or a domain thereof.

In another embodiment, an acrylate-functionalized structural protein hydrogel monomer is used as a component of the hydrogel provided herein (e.g., an acrylate functionalized protein or protein domain, for example, silk, elastin, titin, collagen, proteoglycan, or a functionalized domain thereof). In a further embodiment, the acrylate functionalized structural protein hydrogel monomer comprises a proteoglycan, e.g., decorin, biglycan, testican, bikunin, fibromodulin, lumican, or a domain thereof.

In one embodiment PEG monomers and oligopeptides can be that mimic extracellular matrix proteins are used in the hydrogels provided herein, for example, with vinyl sulfone-functionalized multiarm PEG, integrin binding peptides and bis-cysteine matrix metalloproteinase peptides as described by Lutolf et al. (2003). *Proc. Natl. Acad. Sci. U.S.A.* 100, 5413-5418, incorporated by reference in its entirety for all purposes. In this particular embodiment, hydrogels are formed by a Michael-type addition reaction between the di-thiolated oligopeptides and vinyl sulfone groups on the PEG. The range of additional compatible chemistries that can be incorporated here are obvious to those skilled in the art and follow general chemical reactivity principles, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf).

Other bioactive domains in natural proteins can also be used as a hydrogel monomer or portion thereof. For example, a cell-adhesive integrin binding domain, a controlled release affinity binding domain or a transglutaminase cross-linking domain can be used in the hydrogels provided herein. Details for producing such hydrogels can be found in Martino et al. (2009). Biomaterials 30, 1089; Martino et al. (2011). *Sci. Trans. Med.* 3, 100ra89; Hu and Messersmith (2003). *J. Am. Chem. Soc.* 125, 14298, each of which is incorporated by reference in its entirety for all purposes.

In one embodiment, recombinant DNA methods are used to create proteins, designed to gel in response to changes in pH or temperature, for example, by the methods described by Petka et al. (1998). *Science* 281, pp. 389-392, incorporated by reference in its entirety for all purposes. Briefly, the proteins consist of terminal leucine zipper domains flanking a water-soluble polyelectrolyte segment. In near-neutral aqueous solutions, coiled-coil aggregates of the terminal domains form a three-dimensional hydrogel polymer network.

Common cross linking agents that can be used to cross-link the hydrogels provided herein include but are not limited to ethylene glycol dimethacrylate (EGDMA), tetraethylene glycol dimethacrylate, and N,N'-15 methylenebisacrylamide. The range of additional crosslinking chemistries which can be used are obvious to those skilled in the art and follow general chemical reactivity principles, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf).

In one embodiment, polymerization of a hydrogel is initiated by a persulfate or an equivalent initiator that catalyzes radical formation. The range of compatible initiators are known to those skilled in the art and follow general chemical reactivity principles, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf). The persulfate can be any water-soluble persulfate. Non-limiting examples of water soluble persulfates are ammonium persulfate and alkali metal persulfates. Alkali metals include lithium, sodium and potassium. In some embodiments, the persulfate is ammonium persulfate or potassium persulfate. In a further embodiment, polymerization of the hydrogel provided herein is initiated by ammonium persulfate.

Polymerization of a hydrogel can be accelerated by an accelerant which can catalyze the formation of polymerization-labile chemical side groups. The range of possible accelerants is known to those skilled in the art and follow general chemical reactivity principles see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf). The accelerant in one embodiment, is a tertiary amine. The tertiary amine can be any water-soluble tertiary amine. In one embodiment, an accelerant is used in the polymerization reaction and is N,N,N',N'tetramethylethylenediamine, 3-dimethylamino) propionitrile, or N,N,N',N'tetramethylethylenediamine (TEMED). In another embodiment, an accelerant is used in the polymerization reaction and isazobis (isobutyronitrile) (AIBN).

Figure 2:
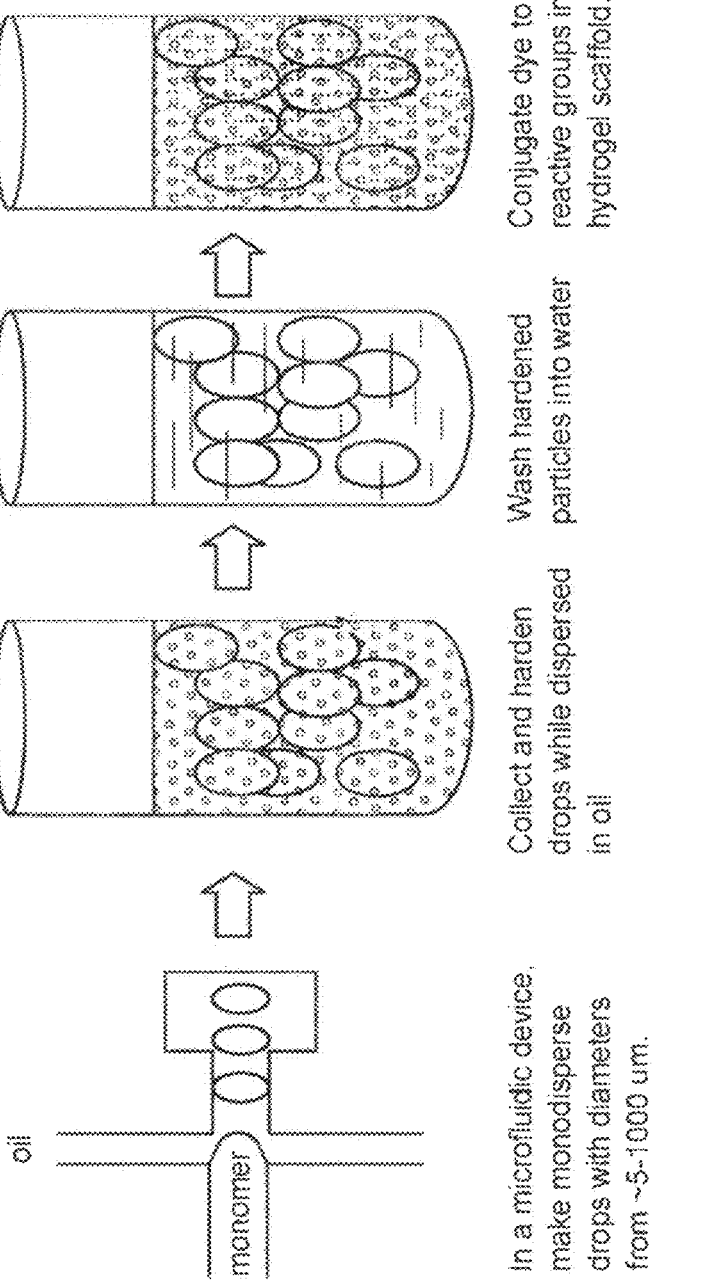
FIG. 2 depicts the process of producing labeled hydrogel particles of the disclosure, including hydrogels with attached biomolecules.

As discussed above, the hydrogel for use in the compositions and methods described herein can include any of the monomeric units and crosslinkers as described herein, and in one aspect, are produced as hydrogel particles by polymerizing droplets (see, e.g., FIG. 2). Microfluidic methods of producing a plurality of droplets, including fluidic and rigidified droplets, are known to those of ordinary skill in the art, and described in US Patent Publication No. 2011/0218123 and U.S. Pat. No. 7,294,503, each incorporated herein by reference in their entireties for all purposes. Such methods provide for a plurality of droplets containing a first fluid (e.g., dispersed phase) and being substantially surrounded by a second fluid (e.g., a continuous phase), where the first fluid and the second fluid are substantially immiscible (e.g., droplets containing an aqueous-based liquid being substantially surrounded by an oil-based liquid).

A plurality of fluidic droplets (e.g., prepared using a microfluidic device) may be polydisperse (e.g., having a range of different sizes), or in some cases, the fluidic droplets may be monodisperse or substantially monodisperse, e.g., having a homogenous distribution of diameters, for instance, such that no more than about 10%, about 5%, about 3%, about 1%, about 0.03%, or about 0.01% of the droplets have an average diameter greater than about 10%, about 5%, about 3%, about 1%, about 0.03%, or about 0.01% of the average diameter. The average diameter of a population of droplets, as used herein, refers to the arithmetic average of the diameters of the droplets. Average diameters of the particles can be measured, for example, by light scattering techniques. Average diameters of hydrogel particles in one embodiment, are tailored, for example by varying flow rates of the fluid streams of the first and second fluids within the channel(s) of a microfluidic device, or by varying the volume of the channel(s) of the microfluidic device.

Accordingly, the disclosure provides population of hydrogel particles comprising a plurality of hydrogel particles, wherein the population of hydrogel particles is substantially monodisperse.

The term microfluidic refers to a device, apparatus or system including at least one fluid channel having a cross-sectional dimension of less than 1 mm, and a ratio of length to largest cross-sectional dimension perpendicular to the channel of at least about 3:1. A micro fluidic device comprising a micro fluidic channel is especially well suited to preparing a plurality of mono disperse droplets.

Non-limiting examples of microfluidic systems that may be used with the present invention are disclosed in U.S. Patent Application Publication No. 2006/0163385; U.S. Patent Application Publication No. 2005/0172476; U.S. Patent Application Publication No. 2007/000342; International Patent Application Publication No. WO 2006/096571; U.S. Patent Application Publication No. 2007/0054119; U.S. Pat. No. 7,776,927; and International Patent Application Publication No. WO 2006/078841, each incorporated herein by reference in their entireties for all purposes.

Droplet size (e.g., volume) is related to microfluidic channel size. The micro fluidic channel may be of any size, for example, having a largest dimension perpendicular to fluid flow of less than about 5 mm or 2 mm, or less than about 1 mm, or less than about 500 μm, less than about 200 μm, less than about 100 μm, less than about 60 μm, less than about 50 μm, less than about 40 μm, less than about 30 μm, less than about 25 μm, less than about 10 μm, less than about 3 μm, less than about 1 μm, less than about 300 nm, less than about 100 nm, less than about 30 nm, or less than about 10 nm.

Droplet size can be tuned by adjusting the relative flow rates. In some embodiments, drop diameters are equivalent to the width of the channel, or within about 10%, 15%, 20%, 30%, 40%, 50%, 60%, 70%, 80%, 90%, or 100% the width of the channel.

The dimensions of a hydrogel particle of the disclosure are substantially similar to the droplet from which it was formed. Therefore, in some embodiments, a hydrogel particle has a diameter of less than about 1 μm, 2, 5, 10, 15, 20, 25, 30, 35, 40, 45, 50, 60, 70, 80, 90, 100, 120, 150, 200, 250, 300, 350, 400, 450, 500, 600, 800, or less than 1000 μm in diameter. In some embodiments, a hydrogel particle has a diameter of more than about 1 μm, 2, 5, 10, 15, 20, 25, 30, 35, 40, 45, 50, 60, 70, 80, 90, 100, 120, 150, 200, 250, 300, 350, 400, 450, 500, 600, 800, or greater than 1000 μm in diameter. In one embodiment, a hydrogel particle has a diameter in the range of 5 μm to 100 μm.

In some embodiments, a hydrogel particle of the disclosure is spherical in shape.

In some embodiments, a hydrogel particle of the disclosure does not comprise agarose.

Hydrogel particle manufacturing in one embodiment, is carried out by suspension polymerization, which is also referred to in the art as pearl, bead or granular polymerization (see Elbert (2011). *Acta Biomater.* 7, pp. 31-56, incorporated by reference herein in its entirety for all purposes). In suspension polymerization, the monomer is insoluble in the continuous phase, for example an aqueous monomer solution (dispersed phase) in a continuous oil phase (continuous phase). In suspension polymerization, polymerization initiation occurs within the monomer-rich droplets and with greater than one radical per droplet at any time. The monomer phase in one embodiment includes a monomer which can be a bifunctional monomer or a plurality of monomer species (co-monomers, which can be a plurality of bifunctional monomers. The monomer phase in one embodiment, includes an initiator and/or a crosslinking agent.

Emulsion polymerization can also be used to form the hydrogel particles described herein. In emulsion polymerization, the monomer has poor solubility in the continuous phase, similar to suspension polymerization, however, polymerization initiation occurs outside the monomer droplets (see Elbert (2011). *Acta Biomater.* 7, pp. 31-56, incorporated by reference herein in its entirety for all purposes). In emulsion polymerization embodiments, the initiator causes chain growth of the monomer (or co-monomers) dissolved in the continuous phase or monomer contained in micelles if surfactants are present.

In another embodiment, hydrogel particles are formed by precipitation polymerization, for example as described in Elbert (2011). *Acta Biomater.* 7, pp. 31-56, incorporated by reference herein in its entirety for all purposes. Precipitation polymerization is a technique that takes advantage of the differences in the solubility of monomer and polymer to produce microparticles. Specifically, it is known that larger polymer chains generally have lower solubility than smaller ones. Accordingly, above a specific molecular weight, phase separation may be favored. Precipitation polymerization initially begins as solution polymerizations in a single phase, homogenous system. Shortly after the start of the polymerization, in one embodiment, a relatively high concentration of polymer chains is present, favoring phase separation by nucleation. As polymerization proceeds, the concentration of polymer chains is low and existing particles capture the chains before nucleation of new particles can occur. Thus, nucleation of particles occurs only for a brief period of time shortly after the start of the reaction, which in one embodiment, results in a narrow size distribution of particles. Additional methods include but are not limited to lithographic particle formation (Helgeson et al. (2011). Curr. Opin. Colloid. Interface Sci. 16, pp. 106-117, incorporated by reference herein in its entirety for all purposes) membrane emulsification (e.g., by the micosieve emulsification technology techniques described by Nanomi B. V. (Netherlands)) and microchannel emulsification (Sugiura et al. (2002). Langmuir 18, pp. 5708-5712, incorporated by reference herein in its entirety) and bulk emulsification (SNF Floerger, available at snf.com.au/downloads/Emulsion-_Handbook_E.pdf, incorporated by reference herein in its entirety).

In one embodiment, hydrogel particles are formed within a microfluidic device having two oil channels that focus on a central stream of aqueous monomer solution. In this embodiment, droplets form at the interface of the two channels and central stream to break off droplets in water-in-oil emulsion. Once droplets are formed, in one embodiment, they are stabilized prior to polymerization, for example, by adding a surfactant to the oil phase. However, in another embodiment, droplets are not stabilized prior to polymerization. Polymerization of the monomer in one embodiment is triggered by adding an accelerator (e.g., N,N,N',N'tetramethylethylenediamine) to one or both of the oil channels after initial droplets are formed.

The aqueous monomer solution as provided above can include a single monomer species or a plurality of monomer species. The aqueous monomer solution can include co-monomers, a bifunctional monomer or a combination thereof. In one embodiment, the monomer or plurality of monomers can includes a bifunctional monomer, for example, one of the monomers described above. As described below, co-monomers can be used to modulate forward scatter or side scatter, for example, by adjusting the refractive index of the hydrogel particle.

In one embodiment, the central stream of aqueous monomer solution comprises a cross-linker, for example, N,N'-bisacrylamide. In a further embodiment, the central stream of aqueous monomer solution comprises a cross-linker and an accelerator, in addition to the monomer. In yet a further embodiment, the aqueous monomer solution comprises an initiator, for example an oxidizing agent such as ammonium persulfate.

Figures 11A, 11B, 11C, 11D:
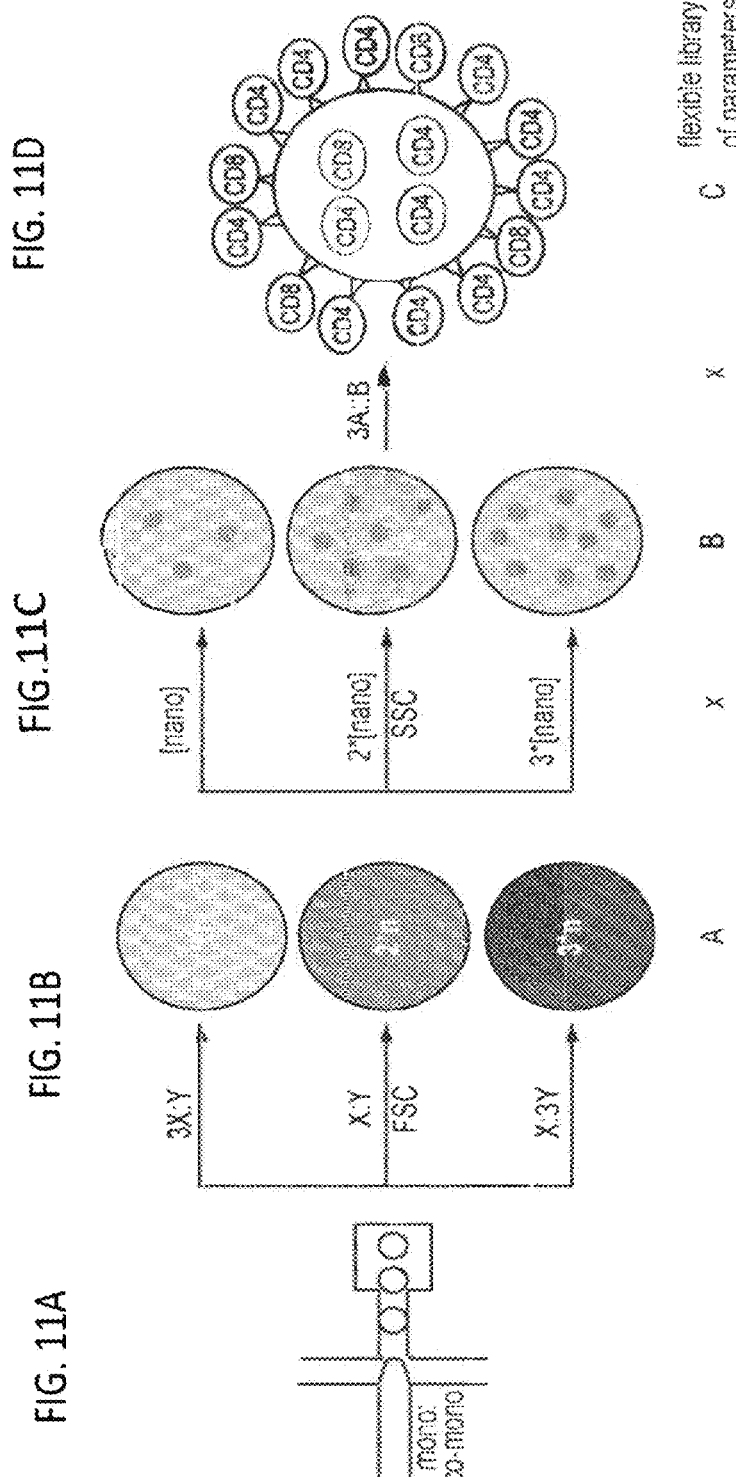

Forward scatter was modulated by adjusting the refractive index of the gel by adding co-monomers allyl acrylate and allyl methacrylate (see also FIGS. 11 and 12). Forward scatter can also be modulated with side scattering nanoparticles containing sufficient optical resolution/size/density including, but not limited to, higher density colloidal suspensions of silica and/or PMMA particles. Side scattering of the droplets was tuned by adding a colloidal suspension of silica nanoparticles and/or PMMA (poly(methyl methacrylate)) particles (~100 nm) to the central aqueous phase prior to polymerization (FIGS. 11 and 12).

In one embodiment, a bead, plurality of beads, biomolecule, or plurality of biomolecules is embedded (encapsulated) within the hydrogel particle. An encapsulated bead or biomolecule, in one embodiment, is employed to mimic one or more intracellular organelles of a target cell, or a cell after it engulfs a particle. In one embodiment, encapsulating or embedding a bead or biomolecule is accomplished at the time of hydrogel particle formation. For example, beads can be suspended in the appropriate concentration to allow for an average of one bead to be embedded/encapsulated in a single hydrogel particle. The bead suspension can be included, for example, within the aqueous solution of monomer. Similarly, a biomolecule or mixture of biomolecules can be incorporated into the aqueous solution of monomer to encapsulate the biomolecule or biomolecules.

Alternatively, once a hydrogel particle is formed, for example by the methods described above, in one embodiment, it can be further manipulated, for example, by embedding a bead, plurality of beads, biomolecule or plurality of biomolecules within the hydrogel particle.

Accordingly, in one aspect of the invention, a hydrogel comprising an embedded substance is provided.

In one embodiment, the embedded substance is an embedded molecule, for example a biomolecule. The biomolecule can be a single species or a plurality of different species. For example, a protein, peptide, carbohydrate, nucleic acid or combination thereof can be encapsulated within a hydrogel particle of the invention. Moreover, different nucleic acid molecules (e.g., of varying sequences or nucleic acid type such as genomic DNA, messenger RNA or DNA-RNA hybrids) can be encapsulated by the hydrogel particle of the invention. These can be comprised of any protein or nucleic acid as both forms of biological material contain labile chemical side-groups (or can be modified by commercial vendors (e.g., Integrated DNA Technology chemical side group modifications). Such side-groups are compatible with reaction chemistries commonly found in co-monomer compositions (e.g., acrylate chemistry, NHS-ester, primary amines, copper catalyzed click chemistry (Sharpless)). The range of possible embedded molecules which contain compatible chemistries is understood by those skilled in the art.

In some embodiments embedded molecules can also be attached on particle surfaces, including micro and/or macropore surfaces.

In one embodiment, different subpopulations of hydrogel particles are fabricated, each with a different concentration of biomolecule. In a further embodiment, the biomolecule is a nucleic acid, a protein, an intracellular ion such as calcium acid (or other biomolecule of the user's choosing, for example, calcium). In another embodiment, different subpopulations of hydrogel particles are fabricated, each with a different concentration of a drug substance. The drug substance in one embodiment is a biomolecule (i.e., a biologic, antibody or antigen-binding fragment thereof, antibody drug conjugate, protein/enzyme, peptide, non-ribosomal peptide, or related molecule) or a small molecule synthetic drug (e.g., Type I/II/III polyketide, non-ribosomal peptide with bioactive properties, or other small molecule entity as generally classified by those skilled in the art).

In this regard, the present invention is particularly useful for determining assay resolution where cells are stained for their respective nucleic acid or protein content. In one embodiment, different populations of the hydrogel particles provided herein are encapsulated with known, differing amounts of an intracellular substance, e.g., nucleic acid or protein. Individual hydrogel particles are stained for the intracellular substance and fluorescence is measured via a cytometric device for the individual hydrogels of the various populations. This allows for a generation of a standard curve to establish the sensitivity and dynamic range of the intracellular assay. Once established, a sample can be run through the cytometer to detect target cell(s) if present, and to quantify the amount of intracellular substance in the respective target cell(s). In one embodiment, the embedded substance is an infectious disease biomarker, for example one of the infectious disease biomarkers in the Infectious Disease Biomarker Database (IDBD, see Yang et al. (2008) IDBD: Infectious Disease Biomarker Database. *Nucleic Acid Res.* 36, pp. D455-D460, incorporated by reference in its entirety for all purposes). In a further embodiment, the infectious disease biomarker is a biomarker of gastrointestinal infection, respiratory infection, neurological infection, urogenital infection, viral infection, hemorrhagic fever, zoonosis, arbovirus, antibiotics resistance or bioterrorism. In a further embodiment, the viral infection is an Ebola infection.

In one embodiment, the methods provided herein are used to determine the sensitivity and/or dynamic range of a cellular nucleic acid quantification assay. In this embodiment, a sample is interrogated for cell types within the sample (if present), and amount of cellular nucleic acid within the cell.

In another embodiment, the present invention provides a means for determining the resolution and/or sensitivity of an intracellular protein quantification assay. Hydrogel particles, in one embodiment, encapsulate known amounts of protein, at various concentrations, and subsequently stained with the appropriate protein antibody. Fluorescence is measured for the various particles to determine the sensitivity and/or dynamic range of the assay. The fluorescence values can then be compared to the values obtained from cells in a sample, to determine whether a target cell is present and whether it contains the intracellular protein, and the amount of the protein.

In one embodiment, individual hydrogel particles are tuned to have at least one optical property substantially similar to a circulating tumor cell or a fetal cell, present in maternal blood. The individual particles are embedded with known quantities of a biomolecule of interest. The particles are used to generate a standard curve for a biomolecule detection assay for the particular cell type.

As provided above, in one aspect of the invention, a hydrogel comprising an embedded substance is provided. In one embodiment, the embedded substance is a bead or plurality of beads. In one embodiment, a hydrogel particle is embedded with a single bead. In another embodiment, individual hydrogels the average number of embedded beads in a plurality of hydrogel particles is one.

In the case where a bead or plurality of beads are embedded into a hydrogel particle, in one embodiment, the optical properties of the bead or plurality of beads are used in combination with the FSC and SSC properties of the hydrogel particle for quality control of a flow cytometry assay. For example, the embedded bead in one embodiment is used as a control to calibrate the flow cytometer system, including the laser source, optics, and stream flow. In another embodiment, the embedded bead is used as a means for quantitating the amount of fluorescence in a sample, e.g., a particular cell. In this regard, embedded beads of various intensities can be used to generate a standard curve of fluorescence to determine whether a cell expresses a certain marker and at what level of expression.

In one embodiment, a bead with the diameter of about 1 μm to about 3 μm, about 2 μm to about 4 μm or about 3 μm to about 7 μm is embedded in a hydrogel provided herein. For example, in one embodiment, the bead has a diameter of about 3 μm to about 3.5 μm. In a further embodiment, the bead is a fluorescent bead. In another embodiment, the bead has a diameter of about 1 μm to about 2.5 μm or about 1.5 μm to about 3 μm. In a further embodiment, the bead is a fluorescent bead and can be stained either internally or at its surface. In even a further embodiment, the fluorescent bead is stained internally. Without wishing to be bound by theory, it is thought that internal staining insulates the fluorophores from environmental interactions that could cause variable fluorescence output.

As provided above, in one embodiment, the embedded bead is a fluorescence bead and in a further embodiment, the fluorescent bead is stained internally. It is within the skill in the art to select the appropriate fluorophore for use in conjunction with an embedded bead. In one embodiment, the bead is derivatized with one or more of the following fluorescent dyes: 6-carboxy-4', 5'-dichloro-2', 7'-dimethoxyfluorescein succinimidylester; 5-(and-6)-carboxyeosin; 5-carboxyfluorescein; 6 carboxyfluorescein; 5-(and-6)-carboxyfluorescein; S-carboxyfluorescein-bis-(5-carboxymethoxy-2-nitrobenzyl)ether,-alanine-carboxamide, or succinimidyl ester; 5-carboxy fluorescein succinimidyl ester; 6-carboxyfluorescein succinimidyl ester; 5-(and-6)-carboxyfluorescein succinimidyl ester; 5-(4,6-dichlorotriazinyl) amino fluorescein; 2', 7'-difluoro fluorescein; eosin-5-isothiocyanate; erythrosin5-isothiocyanate; 6-(fluorescein-5-carboxamido) hexanoic acid or succinimidyl ester; 6-(fluorescein-5-(and-6)-carboxamido) hexanoic acid or succinimidylester; fluorescein-S-EX succinimidyl ester; fluorescein-5-isothiocyanate; fluorescein-6-isothiocyanate; OregonGreen® 488 carboxylic acid, or succinimidyl ester; Oregon Green® 488 isothiocyanate; Oregon Green® 488-X succinimidyl ester; Oregon Green® 500 carboxylic acid; Oregon Green® 500 carboxylic acid, succinimidylester or triethylammonium salt; Oregon Green® 514 carboxylic acid; Oregon Green® 514 carboxylic acid or succinimidyl ester; RhodamineGreen™ carboxylic acid, succinimidyl ester or hydrochloride; Rhodamine Green™ carboxylic acid, trifluoroacetamide or succinimidylester; Rhodamine Green™-X succinimidyl ester or hydrochloride;

RhodolGreen™ carboxylic acid, N,O-bis-(trifluoroacetyl) or succinimidylester; bis-(4-carboxypiperidinyl) sulfonerhodamine or di(succinimidylester); 5-(and-6)carboxynaphtho fluorescein, 5-(and-6)carboxynaphthofluorescein succinimidyl ester; 5-carboxyrhodamine 6G hydrochloride; 6-carboxyrhodamine6Ghydrochloride, 5-carboxyrhodamine 6G succinimidyl ester; 6-carboxyrhodamine 6G succinimidyl ester; 5-(and-6)-carboxyrhodamine6G succinimidyl ester; 5-carboxy-2',4',5',7'-tetrabromosulfonefluorescein succinimidyl esteror bis-(diisopropylethylammonium) salt; 5-carboxytetramethylrhodamine; 6-carboxytetramethylrhodamine; 5-(and-6)-carboxytetramethylrhodamine; 5-carboxytetramethylrhodamine succinimidyl ester; 6-carboxytetramethylrhodaminesuccinimidyl ester; 5-(and-6)-carboxytetramethylrhodamine succinimidyl ester; 6-carboxy-X-rhodamine; 5-carboxy-X-rhodamine succinimidyl ester; 6-carboxy-Xrhodamine succinimidyl ester; 5-(and-6)-carboxy-Xrhodaminesuccinimidyl ester; 5-carboxy-X-rhodamine triethylammonium salt; Lissamine™ rhodamine B sulfonyl chloride; malachite green; isothiocyanate; NANOGOLD® mono(sulfosuccinimidyl ester); QSY® 21carboxylic acid or succinimidyl ester; QSY® 7 carboxylic acid or succinimidyl ester; Rhodamine Red™-X succinimidyl ester; 6-(tetramethylrhodamine-5-(and-6)-carboxamido) hexanoic acid; succinimidyl ester; tetramethylrhodamine-5-isothiocyanate; tetramethylrhodamine-6-isothiocyanate; tetramethylrhodamine-5-(and-6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; and X-rhodamine-5-(and-6) isothiocyanate, BODIPY® dyes commercially available from Invitrogen, including, but not limited to BODIPY® FL; BODIPY® TMR STP ester; BODIPY® TR-X STP ester; BODIPY® 630/650-X STPester; BODIPY® 650/665-X STP ester; 6-dibromo-4,4-difluoro-5, 7-dimethyl-4-bora-3 a, 4a-diaza-s-indacene-3-propionic acid succinimidyl ester; 4,4-difluoro-4-bora-3a,4a-diaza-s-indacene-3,5-dipropionic acid; 4,4-difluoro-5,7-dimethyl-4-bora-3a,4a-diaza-s-indacene-3-pentanoicacid; 4,4-difluoro-5,7-dimethyl-4-bora3a,4a-diaza-s-indacene-3-pentanoicacid succinimidyl ester; 4,4-difluoro-5,7-dimethyl-4-bora-3 a, 4a-diaza-s-indacene-3propionicacid; 4, 4-difluoro-5, 7-dimethyl-4-bora-3 a, 4adiaza-s-indacene-3-propionicacid succinimidyl ester; 4, 4difluoro-5, 7-dimethyl-4-bora-3a,4a-diaza-s-indacene-3propionic acid; sulfosuccinimidyl ester or sodium salt; 6-((4,4-difluoro-5, 7-dimethyl-4-bora-3a,4a-diaza-s-indacene-3propionyl)amino)hexanoicacid; 6-((4,4-difluoro-5, 7 dimethyl-4-bora-3a,4a-diaza-s-indacene-3-propionyl)amino)hexanoic acid or succinimidyl ester; N-(4, 4-difluoro 5, 7-dimethyl-4-bora-3 a, 4a-diaza-s-indacene-3-propionyl) cysteic acid, succinimidyl ester or triethylammonium salt; 6-4,4-difluoro-1,3-dimethyl-5-(4-methoxyphenyl)-4-bora3a, 4a4, 4-difluoro-5, 7-diphenyl-4-bora-3a,4adiaza-sindacene-3-propionicacid; 4, 4-difluoro-5, 7-diphenyl-4-bora3 a, 4a-diaza-s-indacene-3-propionicacid succinimidyl ester; 4, 4-difluoro-5-phenyl-4-bora-3 a, 4a-diaza-s-indacene-3-propionic acid; succinimidyl ester; 6-((4, 4-difluoro-5-phenyl-4 bora-3 a, 4a-diaza-s-indacene-3-propionyl)amino) hexanoicacid or succinimidyl ester; 4,4-difluoro-5-(4-phenyl-1,3butadienyl)-4-bora-3 a, 4a-diaza-s-indacene-3-propionicacid succinimidyl ester; 4, 4-difluoro-5-(2-pyrrolyl)-4-bora-3a,4a-diaza-s-indacene-3-propionic acid succinimidyl ester; 6-(((4,4-difluoro-5-(2-pyrrolyl)-4-bora-3a,4a-diaza-s-indacene-3-yl)styryloxy)acetyl)amino-hexanoicacid or succinimidyl ester; 4,4-difluoro-5-styryl-4-bora-3a, 4a-diaza-s-indacene-3-propionic acid; 4, 4-difluoro-5-styryl-4-bora-3 a, 4a-diaza-sindacene-3-propionic acid; succinimidyl ester; 4,4-difluoro-1,3,5,7-tetram-ethyl-4-bora-3a,4adiaza-s-indacene-8-propionicacid; 4,4-di-fluoro-1,3,5,7-tetramethyl-4bora-3a,4a-diaza-sindacene-8-propionic acid succinimidyl ester; 4,4-difluoro-5-(2-thienyl)-4-bora-3a,4a-diaza-sindacene-3-propionic acid succinimidyl ester; 6-(((4-(4, 4-difluoro-5-(2-thienyl)-4-bora-3 a, 4adiazas-indacene-3-yl)phenoxy)acetyl)amino) hexanoic acid or succinimidyl ester; and 6-(((4,4-difluoro-5-(2-thienyl)-4-bora-3a,4a-diaza-s-indacene-3-yl)styryloxy) acetyl) aminohexanoic acid or succinimidyl ester, Alexa fluor dyes commercially available from Invitrogen, includ-ing but not limited to Alexa Fluor® 350 carboxylic acid;

Alexa Fluor® 430 carboxylic acid; Alexa Fluor® 488 car-boxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 64 7 carboxylic acid; Alexa Fluor® 660 carboxylic acid; and Alexa Fluor® 680 carboxylic acid, cyanine dyes commercially available from Amersham-Pharmacia Bio-tech, including, but not limited to Cy3 NHS ester; Cy 5 NHS ester; Cy5.5 NHSester; and Cy7 NHS ester.

Other Fluorophores amenable for use with the present invention are provided in Table 2 below.

TABLE 2

| ID | NAME | Alternate Names | Excitation | Emission | Vendor/Source | ACS CAS# |
|---|---|---|---|---|---|---|
| ISAC148 | 6-carboxyfluorescein | | 492 | 518 | PubChem | 3301-79-9 |
| ISAC1 | 6-JOE | | 520 | 550 | LifeTechnologies | 82855-40-1 |
| ISAC2 | 7-AAD | | 545 | 647 | LifeTechnologies | 7240-37-1 |
| ISAC3 | Acridine Orange | | 503 | 525 | LifeTechnologies | 65-61-2 |
| ISAC4 | Alexa Fluor 350 | AF350; 2H-1-Benzopyran-6-sulfonic acid, 7-amino-3-[2-[(2,5-dioxo-1-pyrrolidinyl)oxy]-2-oxoethyl]-4-methyl-2-oxo-; 200554-19-4 | 343 | 442 | LifeTechnologies | 244636-14-4 |
| ISAC6 | Alexa Fluor 405 | AF405; C46H69N5O15S3 | 401 | 425 | LifeTechnologies | 791637-08-6 |
| ISAC7 | Alexa Fluor 430 | AF430; C32H42F3N3O9S | 433 | 541 | LifeTechnologies | 467233-94-9 |
| ISAC8 | Alexa Fluor 488 | AF488; C25H15Li2N3O13S2 | 496 | 519 | LifeTechnologies | 247144-99-6 |
| ISAC9 | Alexa Fluor 500 | AF500; CAS#798557-08-1 | 503 | 525 | LifeTechnologies | 798557-08-1 |
| ISAC10 | Alexa Fluor 514 | AF514; C31H27N3O13S2 | 517 | 542 | LifeTechnologies | 798557-07-0 |
| ISAC11 | Alexa Fluor 532 | AF532; 1H-Pyrano[3,2-f:5,6-f']diindole-10,12-disulfonic acid, 5-[4-[[(2,5-dioxo-1-pyrrolidinyl)oxy]carbonyl]phenyl]-2,3,7,8-tetrahydro-2,3,3,7,7,8-hexamethyl-; 271795-14-3 | 532 | 553 | LifeTechnologies | 222159-92-4 |
| ISAC13 | Alexa Fluor 546 | AF546; C50H62Cl3N5O14S3 | 556 | 573 | LifeTechnologies | 247145-23-9 |
| ISAC14 | Alexa Fluor 555 | AF555 | 555 | 565 | LifeTechnologies | 644990-77-2 |
| ISAC15 | Alexa Fluor 568 | AF568 | 578 | 603 | LifeTechnologies | 247145-38-6 |
| ISAC16 | Alexa Fluor 594 | AF594 | 590 | 617 | LifeTechnologies | 247145-86-4 |
| ISAC17 | Alexa Fluor 610 | AF610; C58H77Cl3N6O14S3 | 612 | 628 | LifeTechnologies | 900528-62-3 |
| ISAC18 | Alexa Fluor 633 | AF633 | 632 | 647 | LifeTechnologies | 477780-06-6 |
| ISAC19 | Alexa Fluor 635 | AF635 | 633 | 647 | LifeTechnologies | 945850-82-8 |
| ISAC20 | Alexa Fluor 647 | AF647 | 650 | 665 | LifeTechnologies | 400051-23-2 |
| ISAC21 | Alexa Fluor 660 | AF660 | 663 | 690 | LifeTechnologies | 422309-89-5 |
| ISAC22 | Alexa Fluor 680 | AF680 | 679 | 702 | LifeTechnologies | 422309-67-9 |
| ISAC23 | Alexa Fluor 700 | AF700 | 702 | 723 | LifeTechnologies | 697795-05-4 |
| ISAC24 | Alexa Fluor 750 | AF750 | 749 | 775 | LifeTechnologies | 697795-06-5 |
| ISAC25 | Alexa Fluor 790 | AF790 | 784 | 814 | LifeTechnologies | 950891-33-5 |
| ISAC26 | AMCA | | 346 | 448 | SantaCruzBiotech | 106562-32-7 |
| ISAC27 | AmCyan | | 457 | 489 | BDBioscences | 1216872-44-4 |
| ISAC28 | APC | Allophycocyanin | 650 | 660 | SigmaAldrich | No names found |
| ISAC29 | APC-Alexa Fluor 680 | APC-AF680 | 655 | 704 | LifeTechnologies | No names found |
| ISAC30 | APC-Alexa Fluor 700 | APC-AF700 | 655 | 718 | LifeTechnologies | No names found |
| ISAC31 | APC-Alexa Fluor 750 | APC-AF750 | 650 | 775 | LifeTechnologies | No names found |
| ISAC32 | APC-Cy5.5 | Allophycocyanin-Cy5.5 | 650 | 695 | LifeTechnologies | No names found |
| ISAC33 | APC-Cy7 | Allophycocyanin-Cy7 | 650 | 767 | LifeTechnologies | No names found |

TABLE 2-continued

| ID | NAME | Alternate Names | Excitation | Emission | Vendor/Source | ACS CAS# |
|---|---|---|---|---|---|---|
| ISAC34 | APC-eFluor 750 | eFluor750APC | 650 | 750 | eBioscience | No names found |
| ISAC35 | APC-eFluor 780 | eFluor780APC | 650 | 780 | eBioscience | 1472056-77-1 |
| ISAC36 | APC-H7 | H7APC | 650 | 765 | BDBiosciences | 1366000-62-5 |
| ISAC37 | APC-Vio770 | Vio770APC | 652 | 775 | Miltenyl Biotech | No names found |
| ISAC38 | Atto488 | | 501 | 523 | ATTO-TEC | 923585-42-6 |
| ISAC39 | BIOTIN | | 0 | 0 | PubChem | 58-85-5 |
| ISAC40 | BODIPY FL | | 502 | 511 | SantaCruzBiotech | 165599-63-3 |
| ISAC41 | BODIPY R6G | 4,4-difluoro-5-phenyl-4-bora-3a,4a-diaza-s-indacene-3-propionic acid, succinimidyl ester; C22H18BF2N3O4 | 527 | 547 | LifeTechnologies | 335193-70-9 |
| ISAC43 | Brilliant Violet 421 | BV421 | 406 | 423 | Biolegend | 1428441-68-2 |
| ISAC44 | Brilliant Violet 510 | BV510 | 405 | 510 | Biolegend | No names found |
| ISAC45 | Brilliant Violet 570 | BV570 | 407 | 571 | Biolegend | 1428441-76-2 |
| ISAC46 | Brilliant Violet 605 | BV605 | 407 | 603 | Biolegend | 1632128-60-9 |
| ISAC47 | Brilliant Violet 612 | BV612 | 0 | 0 | Biolegend | 1428441-91-1 |
| ISAC48 | Brilliant Violet 650 | BV650 | 407 | 647 | Biolegend | No names found |
| ISAC49 | Brilliant Violet 711 | BV711 | 405 | 711 | Biolegend | No names found |
| ISAC50 | Brilliant Violet 785 | BV785 | 405 | 786 | Biolegend | 1613592-44-1 |
| ISAC53 | Calcein | CAS#:1461-15-0 | 493 | 514 | LifeTechnologies | 1461-15-0 |
| ISAC51 | Calcein AM | | 496 | 517 | PubChem | 148504-34-1 |
| ISAC52 | Calcein Blue AM | | 360 | 445 | PubChem | 168482-84-6 |
| ISAC54 | Calcein Violet AM | | 400 | 452 | LifeTechnologies | No names found |
| ISAC55 | Calcium Sensor Dye eFluor 514 | | 490 | 514 | eBioscience | No names found |
| ISAC56 | Cascade Blue | | 401 | 420 | PubChem | 1325-87-7 |
| ISAC57 | Cascade Yellow | | 400 | 550 | Synchem UG & Co. KG | 220930-95-0 |
| ISAC58 | Cell Proliferation Dye eFluor 450 | | 405 | 445 | eBioscience | No names found |
| ISAC59 | Cell Proliferation Dye eFluor 670 | | 652 | 672 | eBioscience | No names found |
| ISAC60 | CellTrace Violet Cell Proliferation | | 392 | 455 | LifeTechnologies | No names found |
| ISAC61 | CellVue Claret | | 655 | 657 | SigmaAldrich | 1042142-46-0 |
| ISAC62 | CFSE | | 492 | 525 | SantaCruzBiotech | 150347-59-4 |
| ISAC63 | CPC | O-cresolphthalein complexone | 488 | 660 | Chemical Book | 2411-89-4 |
| ISAC65 | Cy2 | | 492 | 507 | GElifesciences | 102185-03-5 |
| ISAC66 | Cy3 | | 552 | 566 | GElifesciences | 146368-16-3 |
| ISAC67 | Cy3.5 | | 581 | 598 | GElifesciences | 189767-45-1 |
| ISAC68 | Cy5 | | 633 | 670 | GElifesciences | 144377-05-9 |
| ISAC69 | Cy5.5 | | 677 | 695 | GElifesciences | 210892-23-2 |
| ISAC70 | Cy7 | | 743 | 767 | GElifesciences | 169799-14-8 |
| ISAC71 | Cychrome | | 565 | 667 | BDBiosciences | 245670-67-1 |
| ISAC73 | CyQUANT DNA | | 502 | 522 | LifeTechnologies | No names found |
| ISAC74 | CyTRAK Orange | 1,5-bis{[2-(di-methylamino)ethyl]amino)-4,8-dihydroxyanthracene-9,10-dione | 514 | 609 | Abcam (eBioscience) | 1195771-25-5 |
| ISAC76 | DAPI | | 358 | 462 | PubChem | 47165-04-8 |
| ISAC77 | DCFH | | 505 | 525 | SigmaAldrich | 106070-31-9 |
| ISAC79 | DiA | DiA: 4-Di-16-ASP (4-(4-(Dihexadecylamino)styryl)-N-Methylpyridinium Iodide): C46H79IN2 | 455 | 586 | LifeTechnologies | 371114-38-4 |
| ISAC81 | DiD | DiD' solid; DiIC18(5) solid (1,1'-Dioctadecyl-3,3,3',3'-Tetramethylindodicarbocyanine, 4-Chlorobenzenesulfonate | 647 | 669 | LifeTechnologies | 127274-91-3 |

TABLE 2-continued

| ID | NAME | Alternate Names | Excitation | Emission | Vendor/Source | ACS CAS# |
|---|---|---|---|---|---|---|
| ISAC84 | DiI | Salt); C67H103ClN2O3S Dil Stain (1,1'- Dioctadecyl-3,3,3',3'- Tetramethylindocarbocyanine Perchlorate ('DiI'; DilC18(3))); C59H97ClN2O4; 3H- Indolium, 2-(3-(1,3- dihydro-3,3-dimethyl- 1-octadecyl-2H- indol-2-ylidene)-1- propenyl)-3,3- dimethyl-1- octadecyl-, perchlorate/ | 550 | 568 | LifeTechnologies | 41085-99-8 |
| ISAC88 | DiO | DiO'; DiOC18(3) (3,3'- Diociadecyloxacarbocyanine Perchlorate); C53H85ClN2O6; Benzoxazolium, 3- octadecyl-2-[3-(3- octadecyl-2(3H)- benzoxazolylidene)- 1-propenyl]- perchlorate/ | 489 | 506 | LifeTechnologies | 34215-57-1 |
| ISAC92 | DiR | DiR'; DilC18(7) (1,1'- Dioctadecyl-3,3,3',3'- Tetramethylindotricarbocyanine Iodide); C63H101IN2 | 750 | 781 | LifeTechnologies | 100068-60-8 |
| ISAC95 | DRAQ5 | | 645 | 683 | CellSignalingTech | 254098-36-7 |
| ISAC96 | DRAQ7 | | 599 | 694 | CellSignalingTech | 1533453-55-2 |
| ISAC97 | DsRED | | 532 | 595 | Clontech | 469863-23-8 |
| ISAC98 | dsRed2-RFP | | 555 | 582 | Clontech | No names found |
| ISAC99 | DY547 | 547 Dyomics | 557 | 574 | Dynomics | 947138-67-2 |
| ISAC100 | DY634 | 634 Dyomics | 635 | 658 | Dynomics | 1189010-49-8 |
| ISAC101 | DY647 | 647 Dyomics | 650 | 665 | Dynomics | 890317-39-2 |
| ISAC102 | DyLight 350 | DL350 | 353 | 432 | PierceNet | 1436849-83-0 |
| ISAC103 | DyLight 405 | DL405 | 400 | 420 | PierceNet | 1051927-09-3 |
| ISAC104 | DyLight 488 | DL488 | 493 | 518 | PierceNet | 1051927-12-8 |
| ISAC105 | DyLight 549 | DL549 | 562 | 576 | JacksonImmunoRes | 1051927-13-9 |
| ISAC106 | DyLight 550 | DL550 | 562 | 576 | PierceNet | 1340586-78-8 |
| ISAC107 | DyLight 594 | DL594 | 593 | 618 | PierceNet | 1268612-00-5 |
| ISAC108 | DyLight 633 | DL633 | 638 | 658 | PierceNet | 1051927-14-0 |
| ISAC109 | DyLight 649 | DL649 | 654 | 670 | JacksonImmunoRes | 1051927-15-1 |
| ISAC110 | DyLight 650 | DL650 | 652 | 672 | PierceNet | 1364214-13-0 |
| ISAC111 | DyLight 680 | DL680 | 682 | 712 | PierceNet | 1051927-24-2 |
| ISAC112 | DyLight 800 | DL800 | 777 | 794 | PierceNet | 1051927-23-1 |
| ISAC113 | EB | Ethidium Bromide | 523 | 604 | SigmaAldrich | 1239-45-8 |
| ISAC114 | ECD | | 563 | 613 | LifeTechnologies | 88475-75-6 |
| ISAC116 | ECFP | enhanced cyan fluorescent protein | 435 | 477 | MyBiosource | No names found |
| ISAC118 | EdU | EdU(5-ethynyl- 2\u2032- deoxyuridine); C11H12N2O5 | 0 | 0 | LifeTechnologies | 61135-33-9 |
| ISAC120 | EdU Alexa Fluor 488 | | 496 | 516 | LifeTechnologies | No names found |
| ISAC121 | EdU Alexa Fluor 647 | | 650 | 665 | LifeTechnologies | No names found |
| ISAC122 | EdU Pacific Blue | | 405 | 455 | LifeTechnologies | No names found |
| ISAC123 | eFluor 450 | | 400 | 450 | eBioscience | 1592653-87-6 |
| ISAC124 | eFluor 450 Fixable Viability Dye | | 400 | 450 | eBioscience | No names found |
| ISAC125 | eFluor 490 | | 350 | 490 | eBioscience | No names found |
| ISAC126 | eFluor 506 Fixable Viability Dye | | 420 | 506 | eBioscience | No names found |
| ISAC127 | eFluor 525 | | 350 | 525 | eBioscience | No names found |

TABLE 2-continued

| ID | NAME | Alternate Names | Excitation | Emission | Vendor/Source | ACS CAS# |
|---|---|---|---|---|---|---|
| ISAC128 | eFluor 565 | | 350 | 565 | eBioscience | No names found |
| ISAC129 | eFluor 585 | | 350 | 604 | eBioscience | No names found |
| ISAC130 | eFluor 605 | | 350 | 605 | eBioscience | 1248429-27-7 |
| ISAC131 | eFluor 615 | | 590 | 622 | eBioscience | No names found |
| ISAC132 | eFluor 625 | | 350 | 625 | eBioscience | No names found |
| ISAC133 | eFluor 650 | | 350 | 650 | eBioscience | No names found |
| ISAC134 | eFluor 660 | | 633 | 658 | eBioscience | 1634649-16-3 |
| ISAC135 | eFluor 670 | | 0 | 0 | eBioscience | 1437243-07-6 |
| ISAC136 | eFluor 700 | | 350 | 700 | eBioscience | No names found |
| ISAC137 | eFluor 710 | | 350 | 710 | eBioscience | No names found |
| ISAC138 | eFluor 780 Fixable Viability Dye | | 755 | 780 | eBIoscience | No names found |
| ISAC139 | EGFP | enhanced green fluorescent protein | 480 | 510 | MyBiosource | No names found |
| ISAC141 | Emerald 300 | | 289 | 530 | LifeTechnologies | No names found |
| ISAC142 | Eosin | | 525 | 546 | SigmaAldrich | 17372-87-1 |
| ISAC143 | Ethidium Homodimer-1 | | 528 | 617 | SigmaAldrich | 61926-22-5 |
| ISAC144 | Ethidium Monoazide EMA | | 510 | 590 | SigmaAldrich | 58880-05-0 |
| ISAC145 | EYFP | enhanced yellow fluorescent protein | 515 | 528 | MyBiosource | No names found |
| ISAC147 | FAM | | 492 | 518 | PubChem | 76823-03-5 |
| ISAC149 | FITC | Fluorescein | 500 | 520 | PubChem | 27072-45-3 |
| ISAC153 | Fluo-3 | C51H50Cl2N2O23; Glycine, N-[4-[6-[(acetyloxy)methoxy]-2,7-dichloro-3-oxo-3H-xanthen-9-yl]-2-[2-[2-[bis[2-[(acetyloxy)methoxy]-2-oxyethyl]amino]-5-methylphenoxy]ethoxy]phenyl]-N-[2-[(acetyloxy)methoxy]-2-oxyethyl]-.(acetyloxy)methyl ester/ | 506 | 526 | LifeTechnologies | 123632-39-3 |
| ISAC155 | Fluo-4 | C51H50F2N2O23; Glycine, N-[4-[6-[(acetyloxy)methoxy]-2,7-difluoro-3-oxo-3H-xanthen-9-yl]-2-[2-[2-[bis[2-[(acetyloxy)methoxy]-2-oxoethyl]amino]-5-methylphenoxy]ethoxy]phenyl]-N-[2-[(acetyloxy)methoxy]-2-oxoethyl]-,(acetyloxy)methyl ester/ | 494 | 516 | LifeTechnologies | 273221-59-3 |
| ISAC152 | FLMA | Fluorescein-5-maleimide | 495 | 520 | PierceNet | 75350-46-8 |
| ISAC157 | Fluoro-Emerald | Dextran, Fluorescein, 10,000 MW, Anionic, Lysine Fixable | 495 | 523 | LifeTechnologies | 194369-11-4 |
| ISAC159 | Fura Red | | | | LifeTechnologies | 149732-62-7 |
| ISAC162 | Fura3 | Fura-2 LeakRes (AM) | 325 | 510 | SigmaAldrich | 172890-84-5 |
| ISAC164 | FxCycle Far Red | | 640 | 658 | LifeTechnologies | No names found |
| ISAC165 | FxCycle Violet | C16H17Cl2N5; 1H-Indole-6-carboximidamide, 2- | 358 | 462 | LifeTechnologies | 28718-90-3 |

TABLE 2-continued

| ID | NAME | Alternate Names | Excitation | Emission | Vendor/Source | ACS CAS# |
|----|------|-----------------|------------|----------|---------------|----------|
| | | [4-(aminoiminomethyl)phenyl]-, dihydrochloride/ | | | | |
| ISAC167 | GFP | green fluorescent protein | 488 | 515 | MyBiosource | No names found |
| ISAC169 | GFP Violet Excited | | 398 | 515 | MyBiosource | No names found |
| ISAC170 | GFP-Vex1 | | 398 | 515 | MyBiosource | No names found |
| ISAC171 | HiLyte Fluor 488 | | 501 | 527 | Anaspec | 1051927-29-7 |
| ISAC172 | HiLyte Fluor 555 | | 550 | 566 | Anaspec | 1051927-30-0 |
| ISAC173 | HiLyte Fluor 647 | | 649 | 674 | Anaspec | 925693-87-4 |
| ISAC174 | HiLyte Fluor 680 | | 0 | 0 | Anaspec | 1051927-34-4 |
| ISAC175 | HiLyte Fluor 750 | | 754 | 778 | Anaspec | 1051927-32-2 |
| ISAC176 | Hoechst 33258 | | 345 | 455 | SigmaAldrich | 23491-45-4 |
| ISAC177 | Hoechst 33342 | bisBenzimide H 33342 trihydrochloride | 343 | 455 | SigmaAldrich | 23491-52-3 |
| ISAC179 | Hydroxycoumarin | C10H6O5; 7-hydroxycoumarin-3-carboxylic acid; 2H-1-Benzopyran-3-carboxylic acid, 7-hydroxy-2-oxo-/; 4-chloromethyl-7-hydroxycoumarin | 360 | 450 | LifeTechnologies | 43070-85-5 |
| ISAC183 | Indo-1 | Indo-1 AM Calcium Sensor Dye; C47H51N3O22; 1H-Indole-6-carboxylic acid, 2-[4-[bis[2-[(acetyloxy)methoxy]-2-oxoethyl]amino]-3-[2-[2-[bis[2-[(acetyloxy)methoxy]-2-oxoetyl]amino]-5-methylphenoxy]ethoxy]phenyl]-, (acetyloxy)methyl ester/ | 347 | 480 | LifeTechnologies | 96314-96-4 |
| ISAC187 | JC-1 | 5,5',6,6'-tetrachloro-1,1',3,3'-tetraethylbenzimidazolylcarbocyanine iodide; C25H27Cl4IN4 | 593 | 595 | LifeTechnologies | 3520-43-2 |
| ISAC189 | Krome Orange | | 398 | 530 | Beckman Coulter | 1558035-65-6 |
| ISAC190 | Leadmium | | 490 | 520 | LifeTechnologies | No names found |
| ISAC191 | LIVE/DEAD Fixable Aqua Dead Cell Stain | Aqua LIVE/DEAD | 367 | 526 | LifeTechnologies | No names found |
| ISAC193 | LIVE/DEAD Fixable Blue Dead Cell Stain | Blue LIVE/DEAD | 343 | 442 | LifeTechnologies | No names found |
| ISAC195 | LIVE/DEAD Fixable Far Red Dead Cell Stain | | 650 | 670 | LifeTechnologies | No names found |
| ISAC196 | LIVE/DEAD Fixable Green Dead Cell Stain | Green LIVE/DEAD | 498 | 525 | LifeTechnologies | No names found |
| ISAC198 | LIVE/DEAD Fixable Near-IR Dead Cell Stain | | 752 | 776 | LifeTechnologies | No names found |
| ISAC199 | LIVE/DEAD Fixable Red Dead Cell Stain | | 594 | 612 | LifeTechnologies | No names found |
| ISAC200 | LIVE/DEAD Fixable Violet Dead Cell Stain | Violet LIVE/DEAD | 403 | 455 | LifeTechnologies | No names found |
| ISAC202 | LIVE/DEAD Fixable Yellow Dead Cell Stain | Yellow LIVE/DEAD | 401 | 551 | LifeTechnologies | No names found |

TABLE 2-continued

| ID | NAME | Alternate Names | Excitation | Emission | Vendor/Source | ACS CAS# |
|---|---|---|---|---|---|---|
| ISAC204 | Lucifer Yellow | C13H9Li2N5O9S2; 1H-Benz[de]isoquinoline-5,8-disulfonic acid, 6-amino-2-[(hydrazinocarbonyl)amino]-2,3-dihydro-1,3-dioxo-, dilithium salt/ | 428 | 544 | LifeTechnologies | 82446-52-4 |
| ISAC206 | Magnesium Green | C33H17Cl2K5N2O13; Glycine, N-[2-(carboxymethoxy)-4-[[(2',7'-dichloro-3',6' dihydroxy-3-oxospiro[isobenzofuran-1(3H),9'-[9H]xanthen]-5-yl)carbonyl]amino]phenyl]-N-(carboxymethyl)-, pentapotassium salt/ | 507 | 531 | LifeTechnologies | 170516-41-3 |
| ISAC208 | Marina Blue | C16H11F2NO7; 2,5-Pyrrolidinedione, 1-[[(6,8-difluoro-7-hydroxy-4-methyl-2-oxo-2H-1-benzopyrar-3-yl)acetyl]oxy)-/; | 364 | 461 | LifeTechnologies | 215868-23-8 |
| ISAC210 | mBanana | | 540 | 553 | Clontech | 1114839-40-5 |
| ISAC211 | mCherry | | 587 | 610 | Clontech | 1628764-31-7 |
| ISAC212 | mCitrine | | 516 | 529 | Not Commercialized | 1357606-54-2 |
| ISAC213 | MethylCoumarin | AMCA-X, SE (6-((7-Amino-4-Methylcoumarin-3-Acetyl)amino)Hexanoic Acid, Succinimidyl Ester); C22H25N3O7 | 360 | 448 | LifeTechnologies | 1333-47-7 |
| ISAC216 | MitoTracker Green | C34H28Cl5N3O; Benzoxazolium, 2-[3-[5,6-dichloro-1,3-bis[[4-(chloromethyl)phenyl]methyl]-1,3-dihydro-2H-benzimidazol-2-ylidene]-1-propenyl]-3-methyl-, chloride/ | 490 | 512 | LifeTechnologies | 1304563-13-0 |
| ISAC218 | MitoTracker Orange | C24H24Cl2N2O | 550 | 575 | LifeTechnologies | No names found |
| ISAC219 | MitoTracker Red | C39H36Cl5N3 | 578 | 598 | LifeTechnologies | No names found |
| ISAC220 | mOrange | | 548 | 562 | Clontech | 1114839-60-9 |
| ISAC221 | mPlum | | 590 | 649 | Clontech | 1399820-93-9 |
| ISAC222 | mRaspberry | | 597 | 624 | Clontech | 1452799-41-5 |
| ISAC223 | mRFP1 | | 584 | 607 | Not Commercialized | 1452799-30-2 |
| ISAC224 | mStrawberry | | 574 | 596 | Clontech | 1114834-99-9 |
| ISAC225 | Na-Green | Sodium Green ™, tetra(tetramethylammonium) salt: C84H100Cl4N8O19 | 506 | 532 | LifeTechnologies | 195244-55-4 |
| ISAC228 | Nile Red | C20H18N2O2; 5H-Benzo[\u03B1]phenoxazin-5-one, 9-(diethylamino)-/ | 559 | 637 | LifeTechnologies | 7385-67-3 |
| ISAC230 | Oregon Green | | 491 | 519 | LifeTechnologies | 195136-58-4 |
| ISAC232 | Oregon Green 488-X, succinimidyl ester | | 500 | 525 | LifeTechnologies | 890416-18-9 |
| ISAC233 | Oregon Green 514 | Oregon Green ® 514 carboxylic acid, succinimidyl ester; C26H12F5NO9S | 510 | 532 | LifeTechnologies | 198139-53-6 |
| ISAC235 | Pacific Blue | PacBlue; Pacific Blue ™succinimidyl ester; C14H7F2NO7 | 405 | 455 | LifeTechnologies | 215868-31-8 |

TABLE 2-continued

| ID | NAME | Alternate Names | Excitation | Emission | Vendor/Source | ACS CAS# |
|---|---|---|---|---|---|---|
| ISAC236 | Pacific Blue succinimidyl ester | | 405 | 455 | LifeTechnologies | 215868-33-0 |
| ISAC237 | Pacific Orange | PacOrange | 403 | 551 | LifeTechnologies | 1122414-42-9 |
| ISAC240 | PE-Alexa Fluor 610 | RPE-AF610 | 563 | 628 | LifeTechnologies | No names found |
| ISAC241 | PE-Alexa Fluor 647 | RPE-AF647 | 567 | 669 | LifeTechnologies | No names found |
| ISAC242 | PE-Alexa Fluor 680 | RPE-AF680 | 570 | 702 | LifeTechnologies | No names found |
| ISAC243 | PE-Alexa Fluor 700 | RPE-AF700 | 563 | 720 | LifeTechnologies | No names found |
| ISAC244 | PE-Alexa Fluor 750 | RPE-AF750 | 570 | 776 | AbD Serotec | No names found |
| ISAC245 | PE-CF594 | PE-Dazzle 594 | 564 | 612 | BDBioscences | 1613592-67-8 |
| ISAC72 | PE-Cy5 | | 565 | 667 | BDBioscences | 1448849-77-1 |
| ISAC248 | PE-Cy5.5 | | 563 | 695 | AbD Serotec | No names found |
| ISAC249 | PE-Cy7 | | 563 | 760 | AbD Serotec | 1429496-42-3 |
| ISAC250 | PE-DY590 | | 563 | 599 | LSBio | No names found |
| ISAC251 | PE-DY647 | | 563 | 672 | LSBio | No names found |
| ISAC252 | PerCP | | 490 | 675 | AbD Serotec | 422551-33-5 |
| ISAC253 | PerCP-Cy5.5 | | 488 | 695 | AbD Serotec | 1474026-81-7 |
| ISAC254 | PerCP-eFluor 710 | | 488 | 710 | eBioscience | 1353683-31-4 |
| ISAC115 | PE-Texas Red | | 563 | 613 | LifeTechnologies | No names found |
| ISAC256 | PE-Vio770 | | 565 | 775 | Miltenyl Biotech | No names found |
| ISAC257 | pHrodo | pHrodo ™ Red, succinimidyl ester (pHrodo ™ Red, SE); pHrodo ™ Green STP Ester | 560 | 586 | LifeTechnologies | No names found |
| ISAC260 | pHrodo Green STP Ester | | 560 | 586 | LifeTechnologies | No names found |
| ISAC258 | pHrodo Red, succinimidyl ester | | 560 | 586 | LifeTechnologies | No names found |
| ISAC261 | Phycocyanin | | 617 | 646 | SigmaAldrich | 11016-15-2 |
| ISAC262 | PicoGreen | Quant-iT ™ PicoGreen ® dsDNA Reagent | 502 | 522 | LifeTechnologies | 177571-06-1 |
| ISAC264 | PKH2 | PKH2 Green Fluorescent Cell Linker | 490 | 504 | SigmaAldrich | 145687-07-6 |
| ISAC266 | PKH26 | PKH26 Red Fluorescent Cell Linker | 551 | 567 | SigmaAldrich | 154214-55-8 |
| ISAC268 | PKH67 | PKH67 Green Fluorescent Cell Linker | 490 | 504 | SigmaAldrich | 257277-27-3 |
| ISAC270 | POPO-1 | C41H54I4N6O2: Benzoxazolium, 2,2'-[1,3-propanediylbis[(dimethyliminio)-3,1-propanediyl-1(4H)-pyridinyl-4-ylidenemethylidyne]]bis[3-methyl]-, tetraiodide/ | 433 | 457 | LifeTechnologies | 169454-15-3 |
| ISAC272 | PO-PRO-1 | C20H27I2N3O; Benzoxazolium, 3-methyl-2-[[1-[3-(trimethylammonio)propyl]-4(1H)-pyridinylidene]methyl]-, diiodide/; | 435 | 457 | LifeTechnologies | 157199-56-9 |
| ISAC274 | Propidium Iodide | C27H34I2N4 Phenanthridinium, 3,8-diamino-5-[3-(diethylmethylammonio)propyl]-6-phenyl-, diiodide | 350 | 617 | LifeTechnologies | 25535-16-4 |
| ISAC276 | PURE | | 0 | 0 | Not Commercialized | No names found |
| ISAC277 | Pyronin Y | | 547 | 560 | SigmaAldrich | 92-32-0 |

TABLE 2-continued

| ID | NAME | Alternate Names | Excitation | Emission | Vendor/Source | ACS CAS# |
|---|---|---|---|---|---|---|
| ISAC278 | Qdot 525 | | 350 | 525 | LifeTechnologies | 885332-45-6 |
| ISAC279 | Qdot 545 | | 350 | 545 | LifeTechnologies | 948906-89-6 |
| ISAC280 | Qdot 565 | | 350 | 565 | LifeTechnologies | 859509-02-7 |
| ISAC281 | Qdot 585 | | 350 | 585 | LifeTechnologies | 885332-46-7 |
| ISAC282 | Qdot 605 | | 350 | 605 | LifeTechnologies | 849813-89-4 |
| ISAC283 | Odot 625 | | 350 | 625 | LifeTechnologies | 1144512-19-5 |
| ISAC284 | Qdot 655 | | 350 | 655 | LifeTechnologies | 674287-64-0 |
| ISAC285 | Qdot 705 | | 350 | 705 | LifeTechnologies | 885332-47-8 |
| ISAC286 | Qdot 800 | | 350 | 800 | LifeTechnologies | 885332-50-3 |
| ISAC287 | RD1 | R-Phycoerythrin | 563 | 578 | LifeTechnologies | 1376573-14-6 |
| ISAC295 | Rhodamine | | 550 | 570 | LifeTechnologies | No names found |
| ISAC290 | Rho 110 | Rhodamine 110 | 497 | 520 | LifeTechnologies | 13558-31-1 |
| ISAC293 | Rho 123 | Rhodamine 123 | 507 | 529 | LifeTechnologies | 62669-70-9 |
| ISAC296 | Rhodamine Green | Rhodamine Green ™carboxylic acid, succinimidyl ester, hydrochloride; C25H18ClN3O7 | 505 | 527 | LifeTechnologies | 189200-71-3 |
| ISAC297 | Rhodamine Green carboxylic acid, succinimidyl ester, hydrochloride | | 505 | 527 | LifeTechnologies | 254732-34-8 |
| ISAC298 | Rhodamine Red | | 573 | 591 | LifeTechnologies | 99752-92-8 |
| ISAC299 | Rhodamine Red-X | Rhodamine Red ™-X, succinimidyl ester; C37H44N4O10S2 | 570 | 576 | LifeTechnologies | 178623-12-6 |
| ISAC300 | Rhodamine Red-X, succinimidyl ester | | 570 | 576 | LifeTechnologies | 178623-13-7 |
| ISAC301 | RiboFlavin | | 266 | 531 | SigmaAldrich | 83-88-5 |
| ISAC239 | R-Phycoerythrin | PE | 563 | 578 | LifeTechnologies | 11016-17-4 |
| ISAC303 | SNARF-1 carboxylic acid, acetate, succinimidyl ester | | 549 | 586 | LifeTechnologies | No names found |
| ISAC302 | SNARF-1 pH 6 | SNARF ®-1 carboxylic acid, acetate, succinimidyl ester; C33H24N2O9 | 549 | 586 | LifeTechnologies | No names found |
| ISAC304 | SNARF-1 pH 9 | | 576 | 640 | LifeTechnologies | No names found |
| ISAC305 | Spectral Red | | 506 | 665 | MyBiosource | No names found |
| ISAC306 | SureLight P1 | | 545 | 667 | Abcam (Columbia Biosciences) | No names found |
| ISAC307 | SureLight P3 | | 614 | 662 | Abcam | 1365659-06-8 |
| ISAC308 | SureLight PBXL-3 | | 614 | 662 | Abcam | No names found |
| ISAC309 | SYBR Green | | 498 | 522 | SigmaAldrich | 217087-73-5 |
| ISAC310 | SYTO 11 | | 506 | 526 | LifeTechnologies | 173080-67-6 |
| ISAC311 | SYTO 13 | | 488 | 506 | LifeTechnologies | 173080-69-8 |
| ISAC312 | SYTO 16 | | 488 | 520 | LifeTechnologies | 173080-72-3 |
| ISAC313 | SYTO 17 | | 618 | 637 | LifeTechnologies | 189233-66-7 |
| ISAC314 | SYTO 45 | | 450 | 486 | LifeTechnologies | 335078-86-9 |
| ISAC315 | SYTO 59 | | 622 | 643 | LifeTechnologies | 235422-34-1 |
| ISAC316 | SYTO 60 | | 650 | 681 | LifeTechnologies | 335079-14-6 |
| ISAC317 | SYTO 61 | | 618 | 651 | LifeTechnologies | 335079-15-7 |
| ISAC318 | SYTO 62 | | 650 | 681 | LifeTechnologies | 286951-08-4 |
| ISAC319 | SYTO 82 | | 540 | 560 | LifeTechnologies | 335079-10-2 |
| ISAC320 | SYTO 9 | | 482 | 500 | LifeTechnologies | 208540-89-0 |
| ISAC321 | SYTOX AADvanced | | 546 | 646 | LifeTechnologies | No names found |
| ISAC322 | SYTOX Blue | | 431 | 480 | LifeTechnologies | 396077-00-2 |
| ISAC323 | SYTOX Green | | 504 | 523 | LifeTechnologies | 194100-76-0 |
| ISAC324 | SYTOX Orange | | 547 | 570 | LifeTechnologies | 324767-53-5 |
| ISAC325 | SYTOX Red | | 640 | 658 | LifeTechnologies | 915152-67-9 |
| ISAC326 | tdTomato | | 554 | 581 | Clontech | 1114838-94-6 |
| ISAC334 | Tetramethylrhodamine | TMRho | 553 | 581 | LifeTechnologies | 70281-37-7 |
| ISAC329 | Texas Red | Texas Red ®-X, succinimidyl ester; C41H44N4O10S2 | 589 | 615 | LifeTechnologies | 82354-19-6 |
| ISAC330 | Texas Red-X, succinimidyl ester | | 589 | 615 | LifeTechnologies | 216972-99-5 |
| ISAC331 | Thiazole Orange | | 500 | 530 | SigmaAldrich | 107091-89-4 |
| ISAC332 | ThiolTracker Violet | | 406 | 526 | LifeTechnologies | No names found |

TABLE 2-continued

| ID | NAME | Alternate Names | Excitation | Emission | Vendor/Source | ACS CAS# |
|---|---|---|---|---|---|---|
| ISAC335 | TO-PRO-1 | TO-PRO ®-1 iodide (515/531); C24H29I2N3S; Quinolinium, 4-[(3-methyl-2(3H)-benzothiazolylidene) methyl]-1-[3-(trimethylammonio)propyl]-, diiodide/; | 509 | 533 | LifeTechnologies | 157199-59-2 |
| ISAC338 | TO-PRO-3 | TO-PRO ®-3 iodide (642/661); C26H31I2N3S; Quinolinium, 4-[3-(3-methyl-2(3H)-benzothiazolylidene)-1-propenyl]-1-[3-(trimethylammonio)propyl]-, diiodide/ | 642 | 661 | LifeTechnologies | 157199-63-8 |
| ISAC341 | TOTO-1 | TOTO ®-1 iodide (514/533); C49H58I4N6S2; Quinolinium, 1-1'-[1,3-propanediylbis[(dimethyliminio)-3,1-propanediyl]]bis[4-[(3-methyl-2(3H)-benzothiazolylidene) methyl]]-, tetraiodide/ | 509 | 533 | LifeTechnologies | 143413-84-7 |
| ISAC344 | TOTO-3 | TOTO ®-3 iodide (642/660); C53H62I4N6S2 | 642 | 661 | LifeTechnologies | 166196-17-4 |
| ISAC346 | TriColor | | 563 | 670 | LifeTechnologies | 478184-50-8 |
| ISAC347 | TRITC | Tetramethylrhodamine; tetramethylrhodamine-5-(and-6)-isothiocyanate; C25H21N3O3S; Xanthylium, 9-(2-carboxyisothiocyanatophenyl)-3,6-bis(dimethylamino)-, inner salt/ | 547 | 572 | LifeTechnologies | 745735-42-6 |
| ISAC351 | TruRed | | 490 | 695 | Not Commercialized | 396076-95-2 |
| ISAC352 | V19 | | 397 | 572 | Not Commercialized | No names found |
| ISAC353 | V450 | | 405 | 448 | BDBioscences | 1257844-82-8 |
| ISAC354 | V500 | | 415 | 500 | BDBioscences | 1333160-12-5 |
| ISAC355 | VioBlue | | 400 | 452 | Millenly Biotech | 1431147-59-9 |
| ISAC356 | VioGreen | | 388 | 520 | Miltenyl Biotech | No names found |
| ISAC357 | Vybrant DyeCycle Green | | 505 | 535 | LifeTechnologies | 1431152-50-9 |
| ISAC358 | Vybrant DyeCycle Orange | | 518 | 563 | LifeTechnologies | 1055990-89-0 |
| ISAC359 | Vybrant DyeCycle Ruby | | 637 | 686 | LifeTechnologies | 1345202-72-3 |
| ISAC360 | Vybrant DyeCycle Violet | | 370 | 436 | LifeTechnologies | 1015439-88-9 |
| ISAC361 | YFP | Yellow Fluorescent Protein | 505 | 530 | Clontech | No names found |
| ISAC363 | YO-PRO-1 | YO-PRO ®-1 iodide (491/509); C24H29I2N3 | 491 | 506 | LifeTechnologies | 152068-09-2 |
| ISAC365 | YO-PRO-3 | YO-PRO ®-3 iodide (612/631); C26H31I2N3O; Quinolinium, 4-[3-(3-methyl-2(3H)-benzoxazolylidene)-1-propenyl]-1-[3-(trimethylammonio)propyl]-, diiodide/ | 613 | 629 | LifeTechnologies | 157199-62-7 |

TABLE 2-continued

| ID | NAME | Alternate Names | Excitation | Emission | Vendor/Source | ACS CAS# |
|---|---|---|---|---|---|---|
| ISAC368 | YOYO-1 | YOYO ®-1 iodide (491/509); C49H58I4N6O2: | 491 | 509 | LifeTechnologies | 143413-85-8 |
| ISAC370 | YOYO-3 | YOYO ®-3 iodide (612/631); C53H62I4N6O2; Quinolinium, 1,1' [1,3-propanediylbis[(dimethyliminio)-3,1-propanediyl]]bis[4-[3-(3-methyl-2(3H)-benzoxazolylidene)-1-propenyl]]-, tetraiodide/; | 613 | 629 | LifeTechnologies | 156312-20-8 |
| ISAC373 | ZsGreen | | 494 | 517 | Clontech | 1216871-88-3 |

In one embodiment, a fluorescent bead that can be excited at any wavelength from 365 nm-650 nm is embedded in a hydrogel particle. In one embodiment, the bead is a "rainbow particle" that contains a mixture of fluorophores, for example 4 fluorophores, 5 fluorophores, 6 fluorophores, seven fluorophores or eight fluorophores. In this regard, the user selects which wavelength to excite the particle, depending on the fluorophore being interrogated. Rainbow particles are commercially available, for example, from BD Biosciences (catalog nos. 556298 (mid range FL1 fluorescence), 556286 (6 color, 3.0-3.4 µm), 556288 (6 color, 6.0-6.4 µm), 559123 (8 color)) and Spherotech in various diameters (e.g., catalog nos. RCP20-5 (4 color), RCP-30-5 (6 peaks), RCP-30-5A (8 peaks)

A cell sorting set-up bead can be embedded in one or more of the hydrogel particles provided herein. In one embodiment, a cell sorting set-up beads approximates the size, emission wavelength, and intensity of a biological sample, and can be used to calibrate a flow cytometer's cell sorting system, including laser source, optics, and stream flow. In one embodiment, a cell sorting set-up beads is embedded in one or more hydrogel particles and is amenable for use with a UV, blue, green/yellow or red laser. Where a green laser is used, in one embodiment, the embedded bead is excited at 570 nm with emission of 575 nm, but may also be exited at 488 nm. Commercially available cell sorting set-up beads are available, for example, from Life Technologies (catalog nos. C-16506 (UV laser), C-16508 (blue laser), C-16509 (green-yellow laser), C-16507 (red laser)).

A compensation control bead can also be embedded in one or more of the hydrogel particles provided herein. Accurate compensation is an important parameter for effective multicolor analysis in flow cytometry. However, cellular-based compensation controls are not completely effective as many antigens are not highly expressed, and dimly stained cells can lead to inaccurate compensation settings.

A compensation control bead, in one embodiment, includes a fluorescent antibody conjugate capture capacity (positive compensation bead) or is inert (negative compensation bead). The compensation bead is mixed with a fluorophore-conjugated human, mouse, rat, hamster, or rabbit antibody; the two components provide a distinct high-signal positive control with an appropriate negative population that can then be used to set compensation properly regardless of the intensity of the cells in the actual experiment. Once the antibody is mixed with the bead, it is embedded in one or more of the hydrogel particles provided herein. Commercially available compensation beads are available, for example, from Life Technologies (catalog nos. A-10344, A-10389, A10497, A10513) and Spherotech (catalog nos. CMIg-P-08-2K, CMIg-P-30-2K, CMIg-P-50-3K, CMIg-P-70-3K).

In one embodiment, a hydrogel particle with an embedded/encapsulated bead is used as a reference for a cellular assay, for example, a phagocytosis assay cytoxicity assay, motility assay, viability assay, etc. Phagocytosis is the process by which a cell engulfs a solid particle to form an internal vesicle known as a phagosome. In this regard, a hydrogel particle can be tuned to have one or more optical properties substantially similar to a phagocyte, before and after the phagocyte engulfs a particle. Accordingly, in one embodiment, the hydrogel particles provided herein are used as control particles for a phagocytosis assay. In a further embodiment, (i) one or more of the optical properties of a hydrogel particle is substantially similar to a phagocyte prior to particle uptake and (ii) one or more of the optical properties of a second hydrogel particle is substantially similar to a phagocyte after to particle uptake. In this regard, a control is generated for measuring particle uptake by a phagocyte.

In one embodiment, the phagocyte is a professional phagocyte. In another embodiment, the phagocyte is a non-professional phagocyte (i.e., a cell that consumes dying cells and foreign organisms). In a further embodiment, the non-professional phagocyte is an epithelial cell, endothelial cell, fibroblast or mesenchymal cell. Hydrogel particles in one embodiment, are tuned to have one or more optical properties substantially similar to a professional phagocyte set forth in Table 3 below (prior to and/or after particle uptake).

TABLE 3

| Location | Phagocyte type |
|---|---|
| Blood | Neutrophil, monocyte |
| Bone marrow | Macrophage, monocyte, sinusoidal cell, lining cell |
| Bone tissue | Osteoclast |
| Gut and intestinal Peyer's patches | Macrophage |
| Connective tissue | Histiocyte, macrophage, monocyte, dendritic cell |
| Liver | Kupffer cell, monocyte |
| Lung | Self-replicating macrophage, monocyte, mast cell, dendritic cell |
| Lymphoid tissue | Free and fixed macrophages and monocytes, dendritic cell |

TABLE 3-continued

| Location | Phagocyte type |
|---|---|
| Nervous tissue | Microglial cell (CD4+) |
| Spleen | Free and fixed macrophages, monocytes, sinusoidal cell |
| Thymus | Free and fixed macrophages, monocytes |
| Skin | Resident Langerhans cells, dendritic cells, conventional macrophage, mast cell |

In one embodiment, a plurality of hydrogel particles of the invention, embedded with a substance such as nucleic acid or a bead is used as control reagents for a genomic cytometry assay. In this regard, a specific number of copies of a particular chromosome, RNA sequence and/or DNA sequence can be mimicked by the embedded substance. The hydrogel particle can then be used as a control for a sample being probed for genetic information, such as the number of copies of a chromosome, the number of copies of an RNA sequence and/or the number of copies of an RNA sequence.

The three primary modes of deconvolution for flow cytometry are the two passive optical properties of a particle (forward scattering, FSC, corresponding to the refractive index, or RI; and side scattering, SSC) and biomarkers present on the surface of a given cell type. Therefore, compositions that allow hydrogel particles of the disclosure to mimic specific cell types with respect to these three modes are useful for providing synthetic, robust calibrants for flow cytometry.

In one embodiment, the refractive index (RI) of a disclosed hydrogel particle is greater than about 1.10, greater than about 1.15, greater than about 1.20, greater than about 1.25, greater than about 1.30, greater than about 1.35, greater than about 1.40, greater than about 1.45, greater than about 1.50, greater than about 1.55, greater than about 1.60, greater than about 1.65, greater than about 1.70, greater than about 1.75, greater than about 1.80, greater than about 1.85, greater than about 1.90, greater than about 1.95, greater than about 2.00, greater than about 2.10, greater than about 2.20, greater than about 2.30, greater than about 2.40, greater than about 2.50, greater than about 2.60, greater than about 2.70, greater than about 2.80, or greater than about 2.90.

In another embodiment, the refractive index (RI) of a disclosed hydrogel particle is about 1.10 to about 3.0, or about 1.15 to about 3.0, or about 1.20 to about 3.0, or about 1.25 to about 3.0, or about 1.30 to about 3.0, or about 1.35 to about 3.0, or about 1.4 to about 3.0, or about 1.45 to about 3.0, or about 1.50 to about 3.0, or about 1.6 to about 3.0, or about 1.7 to about 3.0, or about 1.8 to about 3.0, or about 1.9 to about 3.0, or about 2.0 to about 3.0.

In some embodiments, the refractive index (RI) of a disclosed hydrogel particle is less than about 1.10, less than about 1.15, less than about 1.20, less than about 1.25, less than about 1.30, less than about 1.35, less than about 1.40, less than about 1.45, less than about 1.50, less than about 1.55, less than about 1.60, less than about 1.65, less than about 1.70, less than about 1.75, less than about 1.80, less than about 1.85, less than about 1.90, less than about 1.95, less than about 2.00, less than about 2.10, less than about 2.20, less than about 2.30, less than about 2.40, less than about 2.50, less than about 2.60, less than about 2.70, less than about 2.80, or less than about 2.90.

The SSC of a disclosed hydrogel particle is most meaningfully measured in comparison to that of target cell. In some embodiments, a disclosed hydrogel particle has an SSC within 30%, within 25%, within 20%, within 15%, within 10%, within 5%, or within 1% that of a target cell, as measured by a cytometric device.

The SSC of a hydrogel particle in one embodiment, is modulated by incorporating a high-refractive index molecule (or plurality thereof) in the hydrogel. In one embodiment, a high-refractive index molecule is provided in a hydrogel particle, and in a further embodiment, the high-refractive index molecule is colloidal silica, alkyl acrylate, alkyl methacrylate or a combination thereof. Thus in some embodiments, a hydrogel particle of the disclosure comprises alkyl acrylate and/or alkyl methacrylate. Concentration of monomer in one embodiment is adjusted to further adjust the refractive index of the hydrogel particle.

Alkyl acrylates or Alkyl methacrylates can contain 1 to 18, 1 to 8, or 2 to 8, carbon atoms in the alkyl group, such as methyl, ethyl, n-propyl, isopropyl, n-butyl, isobutyl or tertbutyl, 2-ethylhexyl, heptyl or octyl groups. The alkyl group may be branched or linear.

High-refractive index molecules can also include vinylarenes such as styrene and methylstyrene, optionally substituted on the aromatic ring with an alkyl group, such as methyl, ethyl or tert-butyl, or with a halogen, such as chlorostyrene.

In some embodiments, FSC is modulated by adjusting the percentage of monomer present in the composition thereby altering the water content present during hydrogel formation. In one embodiment, where a monomer and co-monomer are employed, the ratio of monomer and co-monomer is adjusted to change the hydrogel particle's forward scatter properties. This is shown in both FIG. 11 and FIG. 12.

For example, the ratio of monomer and co-monomer can be used to adjust the hydrogel particle's elasticity (i.e., Young's Modulus) to be substantially similar to the elasticity of the target cell. The ratio of the monomer and co-monomer can change the Young's Modulus for the hydrogel particle can range from 0.2 kiloPascals (kPa) to 400 kPa, based on the elasticity of the target cell. The elasticity of the hydrogel particle (e.g., softness or firmness) can affect the function of the target cell with which the hydrogel particle interacts.

The FSC of a disclosed hydrogel particle is most meaningfully measured in comparison to that of target cell. In some embodiments, a disclosed hydrogel particle has an FSC within 30%, within 25%, within 20%, within 15%, within 10%, within 5%, or within 1% that of a target cell, as measured by a cytometric device.

FSC is related to particle volume, and thus can be modulated by altering particle diameter, as described herein. Generally, it has been observed that large objects refract more light than smaller objects leading to high forward scatter signals (and vice versa). Accordingly, particle diameter in one embodiment is altered to modulate FSC properties of a hydrogel particle. For example, hydrogel particle diameter is increased in one embodiment is altered by harnessing larger microfluidic channels during particle formation.

SSC can be engineered by encapsulating nanoparticles within hydrogels to mimic organelles in a target cell. In some embodiments, a hydrogel particle of the disclosure comprises one or more types of nanoparticles selected from the group consisting of: polymethyl methacrylate (PMMA) nanoparticles, polystyrene (PS) nanoparticles, and silica nanoparticles. See also FIGS. 11 and 12 which show that addition of various concentrations of nanoparticles allow for the adjustment of side scatter of a particle. Without wishing to be bound by theory, the ability to selectively tune both forward and side scatter of a hydrogel, as described herein, allows for a robust platform to mimic a vast array of cell types.

Although the invention is mainly described with respect to the modification of optical properties, the invention is not limited thereto. For example, hydrogel particles can be fabricated and adjusted to tune the capacitance of the particles, e.g., to calibrate coulter counters. In one embodiment, a hydrogel particle's capacitance is adjusted by altering the amount of hydrogel monomer in the composition. For example, polyanaline, polyacetylene; polyphenylene vinylene; polypyrrole (X═NH) and polythiophene (X═S) co-monomers; and polyaniline (X═NH/N) and polyphenylene sulfide (X═S) co-monomer concentrations can all be adjusted to alter capacitance. In one embodiment, the concentration of one or more of these monomers is increased to increase the capacitance of the hydrogel particle.

In some embodiments, a hydrogel particle of the disclosure has material modulus properties (e.g., elasticity) more closely resembling that of a target cell as compared to a polystyrene bead of the same diameter.

After the hydrogel particle is formed, one or more of the particle's surfaces can be functionalized, for example, to mimic one or more optical properties of a target cell or a labeled target cell, or to imbue the particle with immunostimulatory properties. The functionalized hydrogel particle can also include an embedded bead or substance such as a biomolecule, as described above. In one embodiment, one or more hydrogel particles are functionalized with one or more fluorescent dyes, one or more cell surface markers/immunostimulatory biomolecules (or epitope binding regions thereof), or a combination thereof. In one embodiment, the hydrogel particle is formed by polymerizing at least one bifunctional monomer and after formation, the hydrogel particle includes one or more functional groups that can be used for further attachment of a cell surface marker, an epitope binding region of a cell surface marker, a fluorescent dye, or combination thereof. The free functional group, in one embodiment, is an amine group, a carboxyl group, a hydroxyl group or a combination thereof. Depending on the functionalization desired, it is to be understood that multiple bifunctional monomers can be used, for example, to functionalize the particle using different chemistries and with different molecules.

A hydrogel particle can be functionalized with any fluorescent dye known in the art, including fluorescent dyes listed in The MolecularProbes® Handbook—A Guide to Fluorescent Probes and Labeling Technologies, incorporated herein by reference in its entirety for all purposes. Functionalization can be mediated by a compound comprising a free amine group, e.g. allylamine, which can be incorporated into a bifunctional monomer used to form the hydrogel, as discussed above.

Non-limiting examples of known fluorescent dyes that can be used to functionalize the surface of a hydrogel particle described herein include: 6-carboxy-4', 5'-dichloro-2', 7'-dimethoxyfluorescein succinimidylester; 5-(and-6)-carboxyeosin; 5-carboxyfluorescein; 6 carboxyfluorescein; 5-(and-6)-carboxyfluorescein; S-carboxyfluorescein-bis-(5-carboxymethoxy-2-nitrobenzyl)ether,-alanine-carboxamide, or succinimidyl ester; 5-carboxyfluoresceinsuccinimidyl ester; 6-carboxyfluorescein succinimidyl ester; 5-(and-6)-carboxyfluorescein succinimidyl ester; 5-(4,6-dichlorotriazinyl) amino fluorescein; 2', 7'-difluoro fluorescein; eosin-5-isothiocyanate; erythrosin5-isothiocyanate; 6-(fluorescein-5-carboxamido) hexanoic acid or succinimidyl ester; 6-(fluorescein-5-(and-6)-carboxamido)hexanoic acid or succinimidylester; fluorescein-S-EX succinimidyl ester; fluorescein-5-isothiocyanate; fluorescein-6-isothiocyanate; OregonGreen® 488 carboxylic acid, or succinimidyl ester; Oregon Green® 488 isothiocyanate; Oregon Green® 488-X succinimidyl ester; Oregon Green® 500 carboxylic acid; Oregon Green® 500 carboxylic acid, succinimidylester or triethylammonium salt; Oregon Green® 514 carboxylic acid; Oregon Green® 514 carboxylic acid or succinimidyl ester; RhodamineGreen™ carboxylic acid, succinimidyl ester or hydrochloride; Rhodamine Green™ carboxylic acid, trifluoroacetamide or succinimidylester; Rhodamine Green™-X succinimidyl ester or hydrochloride; RhodolGreen™ carboxylic acid, N,O-bis-(trifluoroacetyl) or succinimidylester; bis-(4-carboxypiperidinyl) sulfonerhodamine or di(succinimidylester); 5-(and-6)carboxynaphtho fluorescein, 5-(and-6)carboxynaphthofluorescein succinimidyl ester; 5-carboxyrhodamine 6G hydrochloride; 6-carboxyrhodamine6Ghydrochloride, 5-carboxyrhodamine 6G succinimidyl ester; 6-carboxyrhodamine 6G succinimidyl ester; 5-(and-6)-carboxyrhodamine6G succinimidyl ester; 5-carboxy-2',4',5',7'-tetrabromosulfonefluorescein succinimidyl esterorbis-(diisopropylethylammonium) salt; 5-carboxytetramethylrhodamine; 6-carboxytetramethyirhodamine; 5-(and-6)-carboxytetramethylrhodamine; 5-carboxytetramethyirhodamine succinimidyl ester; 6-carboxytetramethylrhodaminesuccinimidyl ester; 5-(and-6)-carboxytetramethylrhodamine succinimidyl ester; 6-carboxy-X-rhodamine; 5-carboxy-X-rhodamine succinimidyl ester; 6-carboxy-Xrhodamine succinimidyl ester; 5-(and-6)-carboxy-Xrhodaminesuccinimidyl ester; 5-carboxy-X-rhodamine triethylammonium salt; Lissamine™ rhodamine B sulfonyl chloride; malachite green; isothiocyanate; NANOGOLD® mono(sulfosuccinimidyl ester); QSY® 21carboxylic acid or succinimidyl ester; QSY® 7 carboxylic acid or succinimidyl ester; Rhodamine Red™-X succinimidyl ester; 6-(tetramethylrhodamine-5-(and-6)-carboxamido) hexanoic acid; succinimidyl ester; tetramethylrhodamine-5-isothiocyanate; tetramethylrhodamine-6-isothiocyanate; tetramethylrhodamine-5-(and-6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; and X-rhodamine-5-(and-6) isothiocyanate.

Other examples of fluorescent dyes for use with the hydrogel particles described herein include, but are not limited to, BODIPY® dyes commercially available from Invitrogen, including, but not limited to BODIPY® FL; BODIPY® TMR STP ester; BODIPY® TR-X STP ester; BODIPY® 630/650-X STPester; BODIPY® 650/665-X STP ester; 6-dibromo-4, 4-difluoro-5, 7-dimethyl-4-bora-3 a, 4a-diaza-s-indacene-3-propionic acid succinimidyl ester; 4,4-difluoro-4-bora-3a,4a-diaza-s-indacene-3,5-dipropionic acid; 4,4-difluoro-5,7-dimethyl-4-bora-3a,4a-diaza-s-indacene-3-pentanoicacid; 4,4-difluoro-5,7-dimethyl-4-bora3a,4a-diaza-s-indacene-3-pentanoicacid succinimidyl ester; 4,4-difluoro-5,7-dimethyl-4-bora-3 a, 4a-diaza-s-indacene-3propionicacid; 4, 4-difluoro-5, 7-dimethyl-4-bora-3 a, 4adiaza-s-indacene-3-propionicacid succinimidyl ester; 4, 4difluoro-5, 7-dimethyl-4-bora-3a,4a-diaza-s-indacene-3propionic acid; sulfosuccinimidyl ester or sodium salt; 6-((4,4-difluoro-5, 7-dimethyl-4-bora-3a,4a-diaza-s-indacene-3propionyl)amino) hexanoic acid; 6-((4,4-difluoro-5, 7 dimethyl-4-bora-3a,4a-diaza-s-indacene-3-propionyl) amino) hexanoic acid or succinimidyl ester; N-(4, 4-difluoro 5, 7-dimethyl-4-bora-3 a, 4a-diaza-s-indacene-3-propionyl) cysteic acid, succinimidyl ester or triethylammonium salt; 6-4,4-difluoro-1,3-dimethyl-5-(4-methoxyphenyl)-4- bora3a, 4a4,4-difluoro-5, 7-diphenyl-4-bora-3a,4a-diaza-sindacene-3-propionicacid; 4, 4-difluoro-5, 7-diphenyl-4-bora3 a, 4a-diaza-s-indacene-3-propionic acid succinimidyl ester; 4, 4-difluoro-5-phenyl-4-bora-3 a, 4a-diaza-s-indacene-3-propionic acid; succinimidyl ester; 6-((4, 4-difluoro-5-phenyl-4 bora-3 a, 4a-diaza-s-indacene-3-propionyl)amino) hexanoicacid or succinimidyl ester; 4,4-difluoro-5-(4-phenyl-1,3butadienyl)-4-bora-3 a, 4a-diaza-s-indacene-3-propionicacid succinimidyl ester; 4, 4-difluoro-5-(2-pyrrolyl)-4-bora-3a,4a-diaza-s-indacene-3-propionic acid succinimidyl ester; 6-(((4,4-difluoro-5-(2-pyrrolyl)-4-bora-3a,4a-diaza-s-indacene-3-yl)styryloxy)acetyl)amino-hexanoicacid or succinimidyl ester; 4,4-difluoro-5-styryl-4-bora-3 a, 4a-diaza-s-indacene-3-propionic acid; 4, 4-difluoro-5-styryl-4-bora-3 a, 4a-diaza-sindacene-3-propionic acid; succinimidyl ester; 4,4-difluoro-1,3,5,7-tetramethyl-4-bora-3a,4adiaza-s-indacene-8-propionicacid; 4,4-difluoro-1,3,5,7-tetramethyl-4bora-3a,4a-diaza-sindacene-8-propionicacid succinimidyl ester; 4,4-difluoro-5-(2-thienyl)-4-bora-3a,4a-diaza-sindacene-3-propionicacid succinimidyl ester; 6-(((4-(4, 4-difluoro-5-(2-thienyl)-4-bora-3 a, 4adiazas-indacene-3-yl)phenoxy)acetyl)amino) hexanoic acid or succinimidyl ester; and 6-(((4,4-difluoro-5-(2-thienyl)-4-bora-3a,4a-diaza-s-indacene-3-yl) styryloxy)acetyl) aminohexanoic acid or succinimidyl ester.

Fluorescent dyes for derivatization of the surface of one or more hydrogel particles in one embodiment, include, but are not limited to, Alexa fluor dyes commercially available from Invitrogen, including but not limited to Alexa Fluor® 350 carboxylic acid; Alexa Fluor®430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 64 7 carboxylic acid; Alexa Fluor® 660 carboxylic acid; and Alexa Fluor® 680 carboxylic acid. In another embodiment, fluorescent dyes for use with the hydrogel particles and methods described herein include cyanine dyes commercially available from Amer-sham-Pharmacia Biotech, including, but not limited to Cy3 NHS ester; Cy 5 NHS ester; Cy5.5 NHSester; and Cy7 NHS ester.

It is within the ordinary skill in the art to select a suitable dye or dyes based on the desired spectral excitation and emission properties of the hydrogel particle.

Hydrogel particles, in one embodiment, are functionalized with one or more cell surface markers (see, e.g., Tables 4 and 7-8), or fragments thereof, for example, extracellular portions thereof in the case of transmembrane proteins, for example, by attaching the one or more cell surface markers, extracellular portions or ligand binding regions thereof to the particle via a free amine, free carboxyl and/or free hydroxyl group present on the surface of the hydrogel particle. Functionalization of a hydrogel particle with a dye or cell surface molecule can also occur through a linker, for example a streptavidin/biotin conjugate.

Depending on the target cell, individual hydrogel particles can be derivatized with one or more cell surface markers, or fragments thereof, for example, extracellular portions thereof in the case of transmembrane proteins to further mimic the structural properties of the target cell. Tables 4 and 7-8, provided below, sets forth a non-limiting list of cell surface markers that can be used to derivative hydrogel particles, depending on the target cell. Although the cell surface marker is provided, it is understood that a portion of the cell surface marker, for example, a receptor binding portion, a ligand binding portion, or an extracellular portion of the marker can be used to derivative the hydrogel particle (at the free functional group, as described above). See also FIGS. 11 and 12 which show that hydrogel surface modification with for example, a cell surface receptor, together with the selective tuning of FSC and/or SSC, allows for the fabrication of a hydrogel particle with the desired feature (s)/properties. That is, in some embodiments, the particles of the present disclosure mimic target cells as measured by experimental assays (e.g., cytometry). In other embodiments, the particles mimic the properties of one or more target cells, as exhibited in a biological context. Thus, in some embodiments, the particles of the present disclosure exhibit immunostimulatory or feeder properties.

TABLE 4

| Target Cell | Cell Surface Marker(s) (human) | Cell Surface Marker(s) (mouse) |
| --- | --- | --- |
| B Cell | CD19, CD20 | CD19, CD22 (B cell activation marker), CD45R/B220 |
| T Cell | CD3, CD4, CD8 | CD3, CD4, CD8 |
| Activated T Cells | CD25, CD69 | CD25, CD69 |
| Dendritic Cell | CD1c, CD83, CD123, CD141, CD209, MHC II | CD11c, CD123, MHC II |
| Plasmacytoid Dendritic Cells* | CD123, CD303, CD304 | CD11c$^{int}$, CD317 |
| Platelet (resting) | CD42b | CD41 |
| Platelet (activated) | CD62P | CD62P |
| Natural Killer Cells | CD16, CD56 | CD49b (clone DX5) |
| Hematopoietic Stem Cell | CD34, CD90 | CD48, CD117, CD150, Sca-1 |
| Macrophage | CD11b, CD68, CD163 | F4/80, CD68 |
| Monocyte | CD14, CD16, CD64 | CD11b, CD115, Ly-6C |
| Plasma Cell | CD138 | CD138 |
| Red Blood Cell | CD235a | TER-119 |
| Neutrophil | CD15, CD16 | CD11b, Ly-6B.2, Ly6G, Gr-1 |
| Basophil | 2D7 antigen, CD123, CD203c, FcεRIα | CD200R3, FcεRIα |
| Eosinophil | CD11b, CD193, EMR1, Siglec-8 | CD11b, CD193, F4/80, Siglec-F |
| Granulocyte | CD66b | CD66b, Gr-1/Ly6G, Ly6C |
| Endothelial cell | CD146 | CD146 MECA-32, CD106, CD31, CD62E (activated endothelial cell) |
| Epithelial cell | CD326 | CD326 (EPCAM1) |
| Natural Killer (NK) cell | CD56 | CD335 (NKp46) |

TABLE 4-continued

| Target Cell | Cell Surface Marker(s) (human) | Cell Surface Marker(s) (mouse) |
|---|---|---|
| Myeloid derived suppressor cell (MDSC) | CD11b, CD14, CD33 (Siglec-3) | CD11b, GR1 |
| APC/Immune cell activation | Anti CD3, anti CD28, and optionally CD19 | Anti CD3, anti CD28, and optionally CD19 |

Cell types including but not limited to various cell lines such as CHO, HEK-293, BHK-21, NS0, MDCK, VERO, MRC-S, W1-38 and Sp2/0 Mouse Myeloma (hybridomas). Table 5 and Table 6 each provides other cell types for use with the hydrogel particles described herein.

TABLE 5

| | |
|---|---|
| keratinocyte of epidermis | Pancreatic acinar cell |
| basal cell of epidermis | Paneth cell of small intestine |
| keratinocyte of fingernails and toenails | pneumocyte of lung |
| basal cell of nail bed | Clara cell of lung |
| hair shaft cells | anterior pituitary cells |
| medullary hair shaft cells | Somatotropes |
| cortical hair shaft cells | Lactotropes |
| cuticular hair shaft cells | Thyrotropes |
| hair-root sheath cells | Gonadotropes |
| cuticular hair-root sheath cells | Corticotropes |
| hair-root sheath cells of Huxley's layer | melanocyte-stimulating hormone |
| hair-root sheath cells of Henle's layer | Magnocellular neurosecretory cells secreting: |
| external hair-root sheath cells | Gut and respiratory tract cells secreteing: |
| hair matrix cell (stem cell) | Thyroid gland cells |
| surface epithelial cell of stratified squamous epithelium of tongue | thyroid epithelial cell |
| surface epithelial cell of stratified squamous epithelium of oral cavity | parafollicular cell |
| surface epithelial cell of stratified squamous epithelium of esophagus | Parathyroid gland cells |
| surface epithelial cell of stratified squamous epithelium of anal canal | Parathyroid chief cell |
| surface epithelial cell of stratified squamous epithelium of distal urethra | Oxyphil cell |
| surface epithelial cell of stratified squamous epithelium of vagina | Adrenal gland cells |
| basal cell of these epithelia | chromaffin cells |
| cell of urinary epithelium | secreting steroid hormones (mineralcorticoids and gluco corticoids) |
| cells of salivary gland | Leydig cell of testes secreting testosterone |
| Mucous cells of salivary gland | Theca interna cell of ovarian follicle secreting estrogen |
| Serous cell of salivary gland | Corpus luteum cell of ruptured ovarian follicle secreting progesterone |
| cell of von Ebner's gland in tongue | Granulosa lutein cells |
| cell of mammary gland | Theca lutein cells |
| cell of lacrimal gland | Juxtaglomerular cell (renin secretion) |
| cell of ceruminous gland of ear | Macula densa cell of kidney |
| cell of eccrine sweat gland | Peripolar cell of kidney |
| cell of eccrine sweat gland | Mesangial cell of kidney |
| cell of apocrine sweat gland | epidermal keratinocyte |
| cell of gland of Moll in eyelid | Epidermal basal cell |
| cell of sebaceous gland | Keratinocyte of fingernails and toenails |
| cell of Bowman's gland in nose | Nail bed basal cell (stem cell) |
| cell of Brunner's gland in duodenum | Medullary hair shaft cell |
| cell of seminal vesicle | Cortical hair shaft cell |
| cell of prostate gland | Cuticular hair shaft cell |
| cell of bulbourethral gland | Cuticular hair root sheath cell |
| cell of Bartholin's gland | Hair root sheath cell of Huxley's layer |
| cell of gland of Littre | Hair root sheath cell of Henle's layer |
| cell of endometrium of uterus | External hair root sheath cell |
| isolated goblet cell of respiratory and digestive tracts | Hair matrix cell (stem cell) |
| mucous cell of lining of stomach | epithelial cell of stratified squamous epithelium of cornea, |
| zymogenic cell of gastric gland | epithelial cell of stratified squamous epithelium of tongue |
| oxyntic cell of gastric gland | epithelial cell of stratified squamous epithelium of oral cavity |
| acinar cell of pancreas | epithelial cell of stratified squamous epithelium of esophagus |

TABLE 5-continued

| | |
|---|---|
| Paneth cell of small intestine | epithelial cell of stratified squamous epithelium of anal canal |
| type II pneumocyte of lung | epithelial cell of stratified squamous epithelium of distalurethra |
| Clara cell of lung | epithelial cell of stratified squamous epithelium of vagina |
| cells of anterior pituitary | basal cell (stem cell) of epithelia of cornea |
| cell of intermediate pituitary | basal cell (stem cell) of epithelia of tongue |
| cells of posterior pituitary | basal cell (stem cell) of epithelia of oral cavity |
| cells of gut and respiratory tract | basal cell (stem cell) of epithelia of esophagus |
| cells of thyroid gland | basal cell (stem cell) of epithelia of anal canal |
| cells of parathyroid gland | basal cell (stem cell) of epithelia of distal urethra |
| cells of adrenal gland | basal cell (stem cell) of epithelia of vagina |
| steroid hormones | Urinary epithelium cell |
| cells of gonads | Auditory inner hair cell of organ of Corti |
| cells of juxtaglomerular apparatus of kidney | Auditory outer hair cell of organ of Corti |
| juxtaglomerular cell | basal cell of olfactory epithelium |
| macula | Cold-sensitive primary sensory neurons |
| densa cell | Heat-sensitive primary sensory neurons |
| peripolar cell | Merkel cell of epidermis (touch sensor) |
| mesangial cell | Olfactory receptor neuron |
| brush border cell of intestine | Pain-sensitive primary sensory neurons (various types) |
| striated duct cell of exocrine glands | Photoreceptor cells of retina in eye: |
| gall bladder epithelial cell | Photoreceptor rod cells |
| brush border cell of proximal tubule of kidney | Photoreceptor blue-sensitive cone cell of eye |
| distal tubule cell of kidney | Photoreceptor green-sensitive cone cell of eye |
| nonciliated cell of ductulus efferens | Photoreceptor red-sensitive cone cell of eye |
| epididymal principal cell | Proprioceptive primary sensory neurons |
| epididymal basal cell | Touch-sensitive primary sensory neurons |
| hepatocyte | Type I carotid body cell |
| white fat cell | Type II carotid body cell |
| brown fat cell | Type I hair cell of vestibular system of ear |
| lipocyte of liver | Type II hair cell of vestibular system of ear |
| type I pneumocyte | Type I taste bud cell |
| pancreatic duct cell | Cholinergic neural cell |
| parietal cell of kidney glomerulus | Adrenergic neural cell |
| podocyte of kidney glomerulus | Peptidergic neural cell |
| cell of thin segment of loop of Henle | Inner pillar cell of organ of Corti |
| collecting duct cell (in kidney) | Outer pillar cell of organ of Corti |
| duct cell of seminal vesicle | Inner phalangeal cell of organ of Corti |
| duct cell of prostate gland | Outer phalangeal cell of organ of Corti |
| vascular endothelial cells of blood vessels and lymphatics | Border cell of organ of Corti |
| fenestrated vascular endothelial cells | Hensen cell of organ of Corti |
| continuous vascular endothelial cells | Vestibular apparatus supporting cell |
| splenic vascular endothelial cells | Taste bud supporting cell |
| synovial cell | Olfactory epithelium supporting cell |
| serosal cell | Schwann cell |
| squamous cell lining perilymphatic space of ear | Satellite glial cell |
| cells lining endolymphatic space of ear | Enteric glial cell |
| squamous cell | Astrocyte |
| columnar cells of endolymphatic sac | Neuron cells |
| "dark" cell | Oligodendrocyte |
| vestibular membrane cell | Spindle neuron |
| stria vascularis basal cell | Anterior lens epithelial cell |
| stria vascularis marginal cell | Crystallin-containing lens fiber cell |
| cell of Claudius | Hepatocyte |
| cell of Boettcher | Adipocytes (white fat cell, brown fat cell, liver lipocyte) |
| choroid plexus cell | Kidney parietal cell |
| squamous cell of pia-arachnoid | Kidney glomerulus podocyte |
| cells of ciliary epithelium of eye | Kidney proximal tubule brush border cell |
| corneal "endothelial" cell | Loop of Henle thin segment cell |
| Ciliated Cells of respiratory tract | Kidney distal tubule cell |
| Ciliated Cells of oviduct and of endometrium of uterus | Kidney collecting duct cell |
| Ciliated Cells of rete testis and ductulus efferens | Type I pneumocyte |
| Ciliated Cells of central nervous system | Pancreatic duct cell |
| epithelial | Nonstriated duct cell |
| ameloblast | principal cell |
| nonepithelial | Intercalated cell |
| chondrocytes | Duct cell |
| osteoblast/osteocyte | Intestinal brush border cell |
| osteoprogenitor cell | Exocrine gland striated duct cell |
| hyalocyte of vitreous body of eye | Gall bladder epithelial cell |
| stellate cell of perilymphatic space of ear | Ductulus efferens nonciliated cell |
| skeletal muscle cells | Epididymal principal cell |
| heart muscle cells | Epididymal basal cell |
| smooth muscle cells (various) | Ameloblast epithelial cell |

TABLE 5-continued

| | |
|---|---|
| myoepithelial cells | Planum semilunatum epithelial cell of vestibular system of ear |
| red blood cell | Organ of Corti interdental epithelial cell |
| megakaryocyte | Loose connective tissue fibroblasts |
| macrophages and related cells | Corneal fibroblasts (corneal keratocytes) |
| neutrophil | Tendon fibroblasts |
| eosinophil | Bone marrow reticular tissue fibroblasts |
| basophil | nonepithelial fibroblasts |
| mast cell | Pericyte |
| T lymphocyte | Nucleus pulposus cell of intervertebral disc |
| B lymphocyte | Cementoblast/cementocyte |
| photoreceptors (rods, cones, and can be blue sensitive, green sensitive, red sensitive) | Odontoblast/odontocyte |
| inner hair cell of organ of Corti | Hyaline cartilage chondrocyte |
| outer hair cell of organ of Corti | Fibrocartilage chondrocyte |
| type I hair cell of vestibular apparatus of ear | Elastic cartilage chondrocyte |
| type II hair cell of vestibular apparatus of ear | Osteoblast/osteocyte |
| type II taste bud cell | Osteoprogenitor cell |
| olfactory neuron | Hyalocyte of vitreous body of eye |
| basal cell of olfactory epithelium | Stellate cell of perilymphatic space of ear |
| carotid body cell type I | Hepatic stellate cell (Ito cell) |
| carotid body cell type II | Pancreatic stelle cell |
| Merkel cell of epidermis | skeletal muscle Cell |
| primary sensory neurons specialized for touch (various) | Red skeletal muscle cell (slow) |
| primary sensory neurons specialized for temperature - cold sensitive | White skeletal muscle cell (fast) |
| primary sensory neurons specialized for temperature - heat sensitive | Intermediate skeletal muscle cell |
| primary sensory neurons specialized for pain (various) | nuclear bag cell of muscle spindle |
| proprioceptive primary sensory neurons (various) | nuclear chain cell of muscle spindle |
| Autonomic Neurons | Satellite cell (stem cell) |
| inner pillar cell | Heart muscle cells |
| outer pillar cell | Ordinary heart muscle cell |
| inner phalangeal cell | Nodal heart muscle cell |
| outer phalangeal cell | Purkinje fiber cell |
| border cell | Smooth muscle cell |
| Hensen cell | Myoepithelial cell of iris |
| supporting cell of vestibular apparatus | Myoepithelial cell of exocrine glands |
| supporting cell of taste bud (type I taste bud cell) | Erythrocyte |
| supporting cell of olfactory epithelium | Megakaryocyte |
| Schwann cell | Monocyte |
| satellite cell (encapsulating peripheral nerve cell bodies) | Connective tissue macrophage |
| enteric glial cell | Epidermal Langerhans cell |
| neurons | Osteoclast (in bone) |
| glial cells | Dendritic cell (in lymphoid tissues) |
| anterior lens epithelial cell | Microglial cell (in central nervous system) |
| lens fiber (crystallin-containing cell) | Neutrophil granulocyte |
| melanocyte | Eosinophil granulocyte |
| retinal pigmented epithelial cell | Basophil granulocyte |
| oogonium/oocyte | Hybridoma cell |
| spermatocyte | Mast cell |
| spermatogonium (stem cell for spermatocyte) | Helper T cell |
| ovarian follicle cell | Suppressor T cell |
| Sertoli cell (in testis) | Cytotoxic T cell |
| thymus epithelial cell | Natural Killer T cell |
| Salivary gland mucous cell | B cell |
| Salivary gland number 1 | Natural killer cell |
| Von Ebner's gland cell in tongue | Reticulocyte |
| Mammary gland cell | Stem cells and committed progenitors for the blood and immune system (various types) |
| Lacrimal gland cell | Oogonium/Oocyte |
| Ceruminous gland cell in ear | Spermatid |
| Eccrine sweat gland dark cell | Spermatocyte |
| Eccrine sweat gland clear cell | Spermatogonium cell |
| Apocrine sweat gland cell | Spermatozoon |
| Gland of Moll cell in eyelid | Ovarian follicle cell |
| Sebaceous gland cell | Sertoli cell (in testis) |
| Bowman's gland cell in nose | Thymus epithelial cell |
| Brunner's gland cell in duodenum | Interstitial kidney cells |
| Seminal vesicle cell | |
| Prostate gland cell | |
| Bulbourethral gland cell | |
| Bartholin's gland cell | |
| Gland of Littre cell | |
| Uterus endometrium cell | |
| goblet cell of respiratory and digestive tracts | |
| Stomach lining mucous cell | |

TABLE 5-continued

Gastric gland zymogenic cell
Gastric gland oxyntic cell

TABLE 6

Keratinizing Epithelial Cells keratinocyte of epidermis (=differentiating epidermal cell)
basal cell of epidermis (stem cell)
keratinocyte of fingernails and toenails
basal cell of nail bed (stem cell)
hair shaft cells
medullary
cortical
cuticular
hair-root sheath cells
Cuticular root sheath cells
root sheath cells of Huxley's layer
root sheath cells of Henle's layer
external root sheath cells
hair matrix cell (stem cell)
Cells of Wet Stratified Barrier Epithelial surface epithelial cell of stratified squamous epithelium of cornea, tongue, oral
cavity, esophagus, anal canal, distal urethra, vagina
basal cell of these epithelia (stem cell)
cell of urinary epithelium (lining bladder and urinary ducts)
Epithelial Cells Specialized for Exocrine Secretion cells of salivary gland
mucous cell (secretion rich in polysaccharide)
serous cell (secretion rich in glycoprotein enzymes)
cell of von Ebner's gland in tongue (secretion to wash over taste buds)
cell of mammary gland, secreting milk
cell of lacrimal gland, secreting tears
cell of ceruminous gland of ear, secreting wax
cell of eccrine sweat gland, secreting glycoproteins (dark cell)
cell of eccrine sweat gland, secreting small molecules (clear cell)
cell of apocrine sweat gland (odoriferous secretion, sex-hormone sensitive)
cell of gland of Moll in eyelid (specialized sweat gland)
cell of sebaceous gland, secreting lipid-rich sebum
cell of Bowman's gland in nose (secretion to wash over olfactory epithelium)
cell of Brunner's gland in duodenum, secreting alkaline solution of mucus and enzymes
cell of seminal vesicle, secreting components of seminal fluid, including fructose (as fuel for swimming sperm)
cell of prostate gland, secreting other components of seminal fluid
cell of bulbourethral gland, secreting mucus
cell of Bartholin's gland, secreting vaginal lubricant
cell of gland of Littre, secreting mucus
cell of endometrium of uterus, secreting mainly carbohydrates
isolated goblet cell of respiratory and digestive tracts, secreting mucus
mucous cell of lining of stomach
zymogenic cell of gastric gland, secreting pepsinogen
oxyntic cell of gastric gland, secreting HCl
acinar cell of pancreas, secreting digestive enzymes and bicarbonate
Paneth cell of small intestine, secreting lysozyme
type II pneumocyte of lung, secreting surfactant
Clara cell of lung (function unknown)
Cells Specialized for Secretion of Hormones cells of anterior pituitary, secreting growth hormone, follicle-stimulating hormone, luteinizing hormone, prolactin, adrenocorticotropic hormone, and/or thyroid-stimulating hormone
cell of intermediate pituitary, secreting melanocyte-stimulating hormone
cells of posterior pituitary, secreting oxytocin and/or vasopressin
cells of gut and respiratory tract, secreting serotonin, endorphin, somatostatin, gastrin, secretin, cholecystokinin, insulin, glucagon, and/or bombesin
cells of thyroid gland, secreting TABLE 6-continued thyroid hormone
calcitonin
cells of parathyroid gland, secreting
parathyroid hormone
oxyphil cell (function unknown)
cells of adrenal gland, secreting
epinephrine
norepinephrine
steroid hormones
mineralocorticoids
glucocorticoids
cells of gonads, secreting
testosterone (Leydig cell of testis)
estrogen (theca interna cell of ovarian follicle)
progesterone (corpus luteum cell of ruptured ovarian follicle)
cells of juxtaglomerular apparatus of kidney
juxtaglomerular cell (secreting renin)
macula densa cell { (uncertain but probably related in
peripolar cell     function; possibly involved in secretion
mesangial cell     of erythropoietin)
Epithelial Absorptive Cells in Gut, Exocrine Glands, and Urogenital Tract brush border cell of intestine (with microvilli)
striated duct cell of exocrine glands
gall bladder epithelial cell
brush border cell of proximal tubule of kidney
distal tubule cell of kidney
nonciliated cell of ductulus efferens
epididymal principal cell
epididymal basal cell
Cells Specialized for Metabolism and Storage hepatocyte (liver cell)
fat cells
white fat
brown fat
lipocyte of liver
Epithelial Cells Serving Primarily a Barrier Function, Lining the Lung, Gut, Exocrine Glands, and Urogenital Tract type I pneumocyte (lining air space of lung)
pancreatic duct cell (centroacinar cell)
nonstriated duct cell of sweat gland, salivary gland, mammary gland, etc.
(various)
parietal cell of kidney glomerulus
podocyte of kidney glomerulus
cell of thin segment of loop of Henle (in kidney)
collecting duct cell (in kidney)
duct cell of seminal vesicle, prostate gland, etc. (various)
Epithelial Cells Lining Closed Internal Body Cavities vascular endothelial cells of blood vessels and lymphatics
fenestrated
continuous
splenic
synovial cell (lining joint cavities, secreting largely hyaluronic acid)
serosal cell (lining peritoneal, pleural, and pericardial cavities)
squamous cell lining perilymphatic space of ear
cells lining endolymphatic space of ear
squamous cell
columnar cells of endolymphatic sac
with microvilli
without microvilli
"dark" cell
vestibular membrane cell
stria vascularis basal cell
stria vascularis marginal cell
cell of Claudius
cell of Boettcher
choroid plexus cell (secreting cerebrospinal fluid)

TABLE 6-continued squamous cell of pia-arachnoid
cells of ciliary epithelium of eye
        pigmented
        nonpigmented
corneal "endothelial" cell
Ciliated Cells with Propulsive Function Ciliated Cells of respiratory tract
Ciliated Cells of oviduct and of endometrium of uterus (in female)
Ciliated Cells of rete testis and ductulus efferens (in male)
Ciliated Cells of central nervous system (ependymal cell lining
brain cavities)
Cells Specialized for Secretion of Extracellular Matrix epithelial
        ameloblast (secreting enamel of tooth)
        planum semilunatum cell of vestibular apparatus of ear
                (secreting proteoglycan)
        interdental cell of organ of Corti (secreting tectorial
        "membrane" covering
        hair cells of organ of Corti)
nonepithelial (connective tissue)
        fibroblasts (various-of loose connective tissue, of cornea, of
                tendon, of reticular tissue of bone marrow,
                etc.)
        pericyte of blood capillary
        nucleus pulposus cell of intervertebral disc
        cementoblast/cementocyte (secreting bonelike cementum of
                root of tooth)
        odontoblast/odontocyte (secreting dentin of tooth)
        chondrocytes
                of hyaline cartilage
                of fibrocartilage
                of elastic cartilage
        osteoblast/osteocyte
        osteoprogenitor cell (stem cell of osteoblasts)
        hyalocyte of vitreous body of eye
        stellate cell of perilymphatic space of ear
Contractile Cells skeletal muscle cells
        red (slow)
        white (fast)
        intermediate
        muscle spindle-nuclear bag
        muscle spindle-nuclear chain
        satellite cell (stem cell)
heart muscle cells
        ordinary
        nodal
        Purkinje fiber
smooth muscle cells (various)
myoepithelial cells
        of iris
        of exocrine glands
Cells of Blood and Immune System red blood cell
megakaryocyte
macrophages and related cells
        monocyte
        connective-tissue macrophage (various)
        Langerhans cell (in epidermis)
        osteoclast (in bone)
        dendritic cell (in lymphoid tissues)
        microglial cell (in central nervous system)
neutrophil
eosinophil
basophil
mast cell
T lymphocyte
        helper T cell
        suppressor T cell
        killer T cell
B lymphocyte
        IgM
        IgG
        IgA
        IgE TABLE 6-continued killer cell
stem cells and committed progenitors for the blood and
        immune system (various)
Sensory Transducers photoreceptors
        rod
        cones
                blue sensitive
                green sensitive
                red sensitive
hearing
        inner hair cell of organ of Corti
        outer hair cell of organ of Corti
acceleration and gravity
        type I hair cell of vestibular apparatus of ear
        type II hair cell of vestibular apparatus of ear
taste
        type II taste bud cell
smell
        olfactory neuron
basal cell of olfactory epithelium (stem cell for olfactory neurons)
blood pH
        carotid body cell
                type I
                type II
touch
        Merkel cell of epidermis
        primary sensory neurons specialized for touch (various)
temperature
        primary sensory neurons specialized for temperature
                cold sensitive
                heat sensitive
pain
        primary sensory neurons specialized for pain (various)
configurations and forces in musculoskeletal system
        proprioceptive primary sensory neurons (various)
Autonomic Neurons cholinergic (various)
adrenergic (various)
peptidergic (various)
Supporting Cells of Sense Organs and of Peripheral Neurons supporting cells of organ of Corti
inner pillar cell
        outer pillar cell
        inner phalangeal cell
        outer phalangeal cell
        border cell
        Hensen cell
supporting cell of vestibular apparatus
supporting cell of taste bud (type I taste bud cell)
supporting cell of olfactory epithelium
Schwann cell
satellite cell (encapsulating peripheral nerve cell bodies)
enteric glial cell
Neurons and Glial Cells of Central Nervous System neurons (huge variety of types-still poorly classified)
glial cells
        astrocyte (various)
        oligodendrocyte
Lens Cells anterior lens epithelial cell
lens fiber (crystallin-containing cell)
Pigment Cells melanocyte
retinal pigmented epithelial cell
Germ Cells oogonium/oocyte
spermatocyte
spermatogonium (stem cell for spermatocyte)

TABLE 6-continued

Nurse Cells ovarian follicle cell
Sertoli cell (in testis)
thymus epithelial cell
Exocrine secretory epithelial cells Salivary gland mucous cell (polysaccharide-rich secretion)
Salivary gland number 1 (glycoprotein enzyme-rich secretion)
Von Ebner's gland cell in tongue (washes taste buds)
Mammary gland cell (milk secretion)
Lacrimal gland cell (tear secretion)
Ceruminous gland cell in ear (earwax secretion)
Eccrine sweat gland dark cell (glycoprotein secretion)
Eccrine sweat gland clear cell (small molecule secretion)
Apocrine sweat gland cell (odoriferous secretion, sex-hormone sensitive)
Gland of Moll cell in eyelid (specialized sweat gland)
Sebaceous gland cell (lipid-rich sebum secretion)
Bowman's gland cell in nose (washes olfactory epithelium)
Brunner's gland cell in duodenum (enzymes and alkaline mucus)
Seminal vesicle cell (secretes seminal fluid components, including fructose for swimming sperm)
Prostate gland cell (secretes seminal fluid components)
Bulbourethral gland cell (mucus secretion)
Bartholin's gland cell (vaginal lubricant secretion)
Gland of Littre cell (mucus secretion)
Uterus endometrium cell (carbohydrate secretion)
Isolated goblet cell of respiratory and digestive tracts (mucus secretion)
Stomach lining mucous cell (mucus secretion)
Gastric gland zymogenic cell (pepsinogen secretion)
Gastric gland oxyntic cell (hydrochloric acid secretion)
Pancreatic acinar cell (bicarbonate and digestive enzyme secretion)
Paneth cell of small intestine (lysozyme secretion)
Type II pneumocyte of lung (surfactant secretion)
Clara cell of lung
Hormone secreting cells Anterior pituitary cells
Somatotropes
Lactotropes
Thyrotropes
Gonadotropes
Corticotropes
Intermediate pituitary cell, secreting melanocyte-stimulating hormone
Magnocellular neurosecretory cells
secreting oxytocin
secreting vasopressin
Gut and respiratory tract cells
secreting serotonin
secreting endorphin
secreting somatostatin
secreting gastrin
secreting secretin
secreting cholecystokinin
secreting insulin
secreting glucagon
secreting bombesin
Thyroid gland cells
thyroid epithelial cell
parafollicular cell
Parathyroid gland cells
Parathyroid chief cell
Oxyphil cell
Adrenal gland cells
chromaffin cells
secreting steroid hormones (mineralcorticoids and gluco corticoids)
Leydig cell of testes secreting testosterone
Theca interna cell of ovarian follicle secreting estrogen
Corpus luteum cell of ruptured ovarian follicle secreting progesterone
Granulosa lutein cells
Theca lutein cells
Juxtaglomerular cell (renin secretion)
Macula densa cell of kidney
Peripolar cell of kidney
Mesangial cell of kidney TABLE 6-continued Derived primarily from ectoderm
Integumentary system
Keratinizing epithelial cells Epidermal keratinocyte (differentiating epidermal cell)
Epidermal basal cell (stem cell)
Keratinocyte of fingernails and toenails
Nail bed basal cell (stem cell)
Medullary hair shaft cell
Cortical hair shaft cell
Cuticular hair shaft cell
Cuticular hair root sheath cell
Hair root sheath cell of Huxley's layer
Hair root sheath cell of Henle's layer
External hair root sheath cell
Hair matrix cell (stem cell)
Wet stratified barrier epithelial cells Surface epithelial cell of stratified squamous epithelium of cornea, tongue, oral cavity, esophagus, anal canal, distalurethra and vagina
basal cell (stem cell) of epithelia of cornea, tongue, oral cavity, esophagus, anal canal, distal urethra and vagina
Urinary epithelium cell (lining urinary bladder and urinary ducts)
Nervous system There are nerve cells, also known as neurons, present in our human body. They are branched out. These cells make upnervous tissue. A neuron consists of a cell body with a nucleus and cytoplasm, from which long thin hair-like parts arise.
Sensory transducer cells Auditory inner hair cell of organ of Corti
Auditory outer hair cell of organ of Corti
Basal cell of olfactory epithelium (stem cell for olfactory neurons)
Cold-sensitive primary sensory neurons
Heat-sensitive primary sensory neurons
Merkel cell of epidermis (touch sensor)
Olfactory receptor neuron
Pain-sensitive primary sensory neurons (various types)
Photoreceptor cells of retina in eye:
Photoreceptor rod cells
Photoreceptor blue-sensitive cone cell of eye
Photoreceptor green-sensitive cone cell of eye
Photoreceptor red-sensitive cone cell of eye
Proprioceptive primary sensory neurons (various types)
Touch-sensitive primary sensory neurons (various types)
Type I carotid body cell (blood pH sensor)
Type II carotid body cell (blood pH sensor)
Type I hair cell of vestibular system of ear (acceleration and gravity)
Type II hair cell of vestibular system of ear (acceleration and gravity)
Type I taste bud cell
Autonomic neuron cells Cholinergic neural cell
Adrenergic neural cell
Peptidergic neural cell
Sense organ and peripheral neuron supporting cells Inner pillar cell of organ of Corti
Outer pillar cell of organ of Corti
Inner phalangeal cell of organ of Corti
Outer phalangeal cell of organ of Corti
Border cell of organ of Corti
Hensen cell of organ of Corti
Vestibular apparatus supporting cell
Taste bud supporting cell
Olfactory epithelium supporting cell
Schwann cell
Satellite glial cell (encapsulating peripheral nerve cell bodies)
Enteric glial cell TABLE 6-continued Central nervous system neurons and glial cells Astrocyte (various types)
Neuron cells (large variety of types, still poorly classified)
Oligodendrocyte
Spindle neuron
Lens cells Anterior lens epithelial cell
Crystallin-containing lens fiber cell
Derived primarily from mesoderm
Metabolism and storage cells Hepatocyte (liver cell)
Adipocytes:
White fat cell
Brown fat cell
Liver lipocyte
Barrier function cells (lung, gut, exocrine glands and urogenital tract)
Kidney Kidney parietal cell
Kidney glomerulus podocyte
Kidney proximal tubule brush border cell
Loop of Henle thin segment cell
Kidney distal tubule cell
Kidney collecting duct cell[disambiguation needed]
Type I pneumocyte (lining air space of lung cell)
Pancreatic duct cell (centroacinar cell)
Nonstriated duct cell (of sweat gland, salivary gland, mammary
gland, etc.)
principal cell
Intercalated cell
Duct cell (of seminal vesicle, prostate gland, etc.)
Intestinal brush border cell (with microvilli)
Exocrine gland striated duct cell
Gall bladder epithelial cell
Ductulus efferens nonciliated cell
Epididymal principal cell
Epididymal basal cell
Extracellular matrix cells Ameloblast epithelial cell (tooth enamel secretion)
Planum semilunatum epithelial cell of vestibular system of ear
(proteoglycan secretion)
Organ of Corti interdental epithelial cell (secreting tectorial
membrane covering hair cells)
Loose connective tissue fibroblasts
Corneal fibroblasts (corneal keratocytes)
Tendon fibroblasts
Bone marrow reticular tissue fibroblasts
Other nonepithelial fibroblasts
Pericyte
Nucleus pulposus cell of intervertebral disc
Cementoblast/cementocyte (tooth root bonelike ewan cell
secretion)
Odontoblast/odontocyte (tooth dentin secretion)
Hyaline cartilage chondrocyte
Fibrocartilage chondrocyte
Elastic cartilage chondrocyte
Osteoblast/osteocyte
Osteoprogenitor cell (stem cell of osteoblasts)
Hyalocyte of vitreous body of eye
Stellate cell of perilymphatic space of ear
Hepatic stellate cell (Ito cell)
Pancreatic stelle cell
Contractile cells skeletal muscle Cell
Red skeletal muscle cell (slow)
White skeletal muscle cell (fast)
Intermediate skeletal muscle cell
nuclear bag cell of muscle spindle
nuclear chain cell of muscle spindle
Satellite cell (stem cell)
Heart muscle cells
Ordinary heart muscle cell
Nodal heart muscle cell
Purkinje fiber cell
Smooth muscle cell (various types)

TABLE 6-continued

Myoepithelial cell of iris
Myoepithelial cell of exocrine glands
Blood and immune system cells Erythrocyte (red blood cell)
Megakaryocyte (platelet pecursor)
Monocyte (white blood cell)
Connective tissue macrophage (various types)
Epidermal Langerhans cell
Osteoclast (in bone)
Dendritic cell (in lymphoid tissues)
Microglial cell (in central nervous system)
Neutrophil granulocyte
Eosinophil granulocyte
Basophil granulocyte
Hybridoma cell
Mast cell
Helper T cell
Suppressor T cell
Cytotoxic T cell
Natural Killer T cell
B cell
Natural killer cell
Reticulocyte
Stem cells and committed progenitors for the blood and immune
system (various types)
Germ cells Oogonium/Oocyte
Spermatid
Spermatocyte
Spermatogonium cell (stem cell for spermatocyte)
Spermatozoon
Nurse cells Ovarian follicle cell
Sertoli cell (in testis)
Thymus epithelial cell
Interstitial cells Interstitial kidney cells

TABLE 7

| B Cell maturation markers for use with the hydrogel particles described herein. | |
| --- | --- |
| B-cell type | Cell surface marker(s) |
| Pro-B | CD19, CD20, CD34, CD38, CD45R |
| Pre-B | CD19, CD20, CD38, CD45R |
| Immature B | CD19, CD20, CD40, CD45R, IgM |
| Tr-B | CD10, CD19, CD20, CD24, CD28 |
| Naïve-B | CD19, CD20, CD23, CD40, CD150 (SLAM), IgD, IgM |
| B-1 | CD19, CD20, CD27, IgM |
| Memory B | CD19, CD20, CD28, CD40, IgA, IgG |
| Plasma Cell | CD9, CD28, CD31, CD38, CD40, CD95 (FAS), CD184 (CXCR4) |

TABLE 8

| Cell surface markers for use with the hydrogel particles described herein. | | |
|---|---|---|
| 14-3-3 Î ± Î² | Cdc-123 | HPx2 |
| 14-3-3 Îµ | Cdc-2 (p34) | Hrk |
| 14-3-3 Î¶ | Cdc-25A Phosph (Ser17) | Hsc70 |
| 14-3-3 Îs | Cdc-25C | HSD17B1 |
| 14-3-3 Îf | Cdc-37 | HSD3B1 |
| 15-Lipoxygenase 1 | Cdc-45L | HSF1 |
| 160 kD Neurofilament Medium | Cdc-6 | HSF2 |
| 200 kD Neurofilament Heavy | CDc-7 | HSF4 |
| 2H2 | Cdk1 | HSL |
| 3G11 sialoganglioside antigen | Cdk2 | Hsp105 |
| 4E-BP1 | Cdk4 | Hsp14 |
| 4E-BP1 Phospho (Thr37/46) | Cdk5 | Hsp22 |
| 5-Methylcytidine | Cdk6 | HSP25 |
| 5HT3A receptor | Cdk7 | Hsp27 |
| 5T4 | Cdk9 | Hsp40 |
| 68 kDa Neurofilament Light | CdkA1 | Hsp47 |
| 7.1 | CdkN2A | Hsp60 |
| 70 kD Neurofilament Light | CdkN3 | Hsp70 |
| A20 | CDT1 | Hsp70-2 |
| A2B5 | CDX2 | Hsp90 |
| AAK1 | CEACAM19 | Hsp90Î± |
| ABCA1 | CEACAM20 | Hsp90Î² |
| ABCA7 | CEACAM7 | HspA4 |
| ABCB4 | CEBPÎ± | HspA6 |
| ABCB5 | CEBPÎ² | HSPA9 |
| ABCC10 | CEND1 | HspB2 |
| ABCC11 | CENPA | HspB7 |
| ABCG1 | CENPE | HSV tag |
| ABI2 | CENPF | HTLV I gp46 |
| ABIN3 | CENPH | HTLV I p19 |
| ABIN3Î² | Centrin 2 | HtrA2/Omi |
| ABL2 | CFAH | Human Papillomavirus 16 (E7) |
| Abraxas | cFos | Huntingtin |
| ACAA1 | CFTR | HUS1 |
| ACADM | CGB5 | Hydrogen Potassium ATPase Î² |
| ACAT2 | cGK1 | I-Ak (AÎ± ± k) |
| ACBD3 | CH2 | I-Ak (AÎ²k) |
| ACD | CHCHD5 | Ia (B cells) |
| ACE2 | CHD3 | IBA1 |
| Acetyl Coenzyme A Carboxylase | CHD4 | IBP2 |
| Acetyl Coenzyme A Carboxylase Î± | Chemerin | ICAD |
| Acetyl Coenzyme A Synthetase | CHIPS, C-terminus | IDO |
| Acetylated Lysine | CHIPS, N-terminus | IFABP |
| AChRÎ± | Chk1 | IFN-Î± |
| AChRÎ² | Chk2 | IFN-Î± ± 1 |
| AChRÎ³ | Chondroitin Sulfate | IFN-Î± ± 2Î² |
| Aconitase2 | CHOP | IFN-Î² |
| ACOT12 | Chromogranin C | IFN-Î³ |
| ACSA2 | ChT1 | IFN-Î³RÎ² |
| ACSF2 | chTOG | IFN-Î© © |
| ACSM5 | cIAP1 | IFNA1 |
| Act1 | cIAP2 | IFNAR1 |
| Activation molecule 8 (B cells) | CIAS1 | IFT88 |
| Activin A Receptor Type IB | CIDEA | Ig |
| Activin A Receptor Type IIB | CIP4 | Ig (polyspecific) |
| ACTN3 | CISD1 | Ig light chain Îº |
| ACY1 | CITED1 | Ig light chain Î» |
| ACY3 | CITED2 | Ig light chain Î»1, Î»2, Î»3 |
| ADA | cJun | IgA |
| ADAM12 | cJun Phospho (Tyr91/Tyr93) | IgA (Fab2) |
| ADE2 | CKIIÎ± | IgA (H) |
| Adenosine A1 Receptor | CKMT2 | IgA, Îº |
| Adenosine A2aR | CLASP1 | IgA, Î» |
| Adenovirus | Clathrin | IgA1 |
| Adenovirus Fiber monomer and trimer | Claudin-1 | IgA2 |
| Adenovirus hexon protein | Claudin-10 | IgD |
| Adenylate Kinase 1 | Claudin-15 | IgD (Î´ heavy chain) |
| Adenylosuccinate Lyase | Claudin-16 | IgDa |
| ADFP | Claudin-18 (C-term) | IgDb |
| ADH1B | Claudin-18 (Mid) | IgE |
| ADH6 | Claudin-4 | IgE, Îº |

TABLE 8-continued

Cell surface markers for use with the hydrogel particles described herein.

| | | |
|---|---|---|
| ADH7 | Claudin-5 | IgEa |
| ADI1 | Claudin-8 | IgEb |
| Adiponectin | CLAW-H | IgG |
| Adiponectin Receptor 2 | CLEC12A | IgG (Fab H/L) |
| Adipose Triglyceride Lipase | CLEC1B | IgG (Fab) |
| ADP Ribosylation Factor | CLEC4A | IgG (Fab2 Fc) |
| ADP-ribosyltransferase 2.2 gene | CLEC4M | IgG (Fab2 H/L) |
| Adrenodoxin | CLEC9A | IgG (Fab2) |
| AF10 | CLIP | IgG (Fc) |
| AFAP1 | CLOCK | IgG (H/L) |
| AFP | *Clostridium botulinum* Toxin B | IgG ($\hat{I}^3$ chain specific) |
| AG2 | CLPP | IgG Fd |
| AGAP1 | cMaf | IgG light chain |
| AGPAT5 | cMet | IgG, $\hat{I}^o$ |
| AGR2 | CMKLR1 | IgG/IgM |
| AHSG | CMRF44 | IgG/IgM/IgA |
| AICDA | CMRF56 | IgG/IgM/IgA (Fab2 H/L) |
| AID | cMyb | IgG/IgM/IgA (Fab2) |
| AIF | cMyc | IgG/IgM/IgA (H/L) |
| AIM-2 | CNDP2 | IgG/IgY |
| Aiolos | CNTFR$\hat{I}\pm$ | IgG1 |
| AIPL1 | COASY | IgG1 (heavy chain) |
| AIRE | Coatomer $\hat{I}'$ | IgG1, $\hat{I}^o$ |
| AK3 | Cofilin | IgG1, $\hat{I}»$ |
| AK3L1 | Colec12 | IgG1/2a |
| AK5 | Collagen I | IgG1/3 |
| Akt | Collagen I/III | IgG1a |
| Akt (pS473) | Collagen II | IgG1b |
| Akt (pT308) | Collagen III | IgG2 |
| Akt1 | Collagen IV | IgG2, $\hat{I}^o$ |
| Akt2 | Collagen V | IgG2, $\hat{I}»$ |
| Akt3 | Collagen VI | IgG2/3 |
| Albumin | Collagen VII | IgG2a |
| Alcohol Dehydrogenase | COMMD1 | IgG2a, $\hat{I}^o$ |
| Aldehyde Reductase | Complement Factor B | IgG2a, $\hat{I}»$ |
| ALDH1A1 | Complex I Immunocapture | IgG2a/b |
| ALDH1L1 | Conjugated Choline Glutaric acid | IgG2b |
| ALDH2 | Connexin 26 | IgG2b, $\hat{I}^o$ |
| ALDH3A1 | Connexin 30 | IgG2c |
| ALDH3A2 | Connexin 30.2 | IgG2c, $\hat{I}^o$ |
| ALDH5A1 | Connexin 30.3 | IgG3 |
| ALDH6A1 | Connexin 32 | IgG3, $\hat{I}^o$ |
| ALDH7A1 | Connexin 36 | IgG3, $\hat{I}»$ |
| ALDOB | Connexin 37 | IgG4 |
| Aldolase B | Connexin 37 (C-term) | IgGDa |
| Alexa Fluor 405/ Cascade Blue | Connexin 37 (Mid) | IgK |
| Alexa Fluor 488 | Connexin 39 | IGKC |
| ALG2 | Connexin 39 (Mid) | IgL |
| Alix | Connexin 40 (C-term) | IGLC2 |
| Allergin1 | Connexin 40 (Mid) | IgM |
| alpha 1 Antitrypsin | Connexin 43 | IgM (Fab2) |
| alpha 1 Catenin | Connexin 45 | IgM (Fc) |
| alpha 1 Sodium Potassium ATPase | Connexin 45 (C-term) | IgM (H/L) |
| alpha 2 Catenin | Connexin 46 | IgM, $\hat{I}^o$ |
| alpha 2 Macroglobulin | Connexin 47 | IgM, $\hat{I}»$ |
| alpha Actin 1 | Connexin 57 (C-term) | IgMa |
| alpha Actin 2 | Connexin 57 (Mid) | IgMb |
| alpha Actinin | Contactin 2 | IgY |
| alpha Actinin 2 | COPS3 | Igâ€™s |
| alpha Actinin 3 | Coronavirus | Ihh |
| alpha Actinin 4 | Coronin 1A | Ikaros |
| alpha Adaptin | Coronin 1B | IkB$\hat{I}\pm$ |
| alpha Adducin | Cortactin | IkB$\hat{I}^2$ |
| alpha B Crystallin | Cortical Thymocytes | IkB$\hat{I}¶$ |
| alpha Fodrin | COX I | IKK$\hat{I}\pm$ |
| alpha Internexin | COX I/III | IKK$\hat{I}^2$ |
| alpha Synuclein | COX II | IKK$\hat{I}^3$ p(S376) |
| ALS1 | COX IV | IKK$\hat{I}\mu$ |
| AMACR | COX VA | IL-10 |
| Aminopeptidase P | COX VIA1 | IL-11R$\hat{I}\pm$ |
| AML1 | Coxsackie Adenovirus Receptor | IL-12 |

TABLE 8-continued

Cell surface markers for use with the hydrogel particles described herein.

| | | |
|---|---|---|
| Amphiphysin | CPF | IL-12 (p35) |
| AMPKα | CPI17α | IL-12 (p70) |
| AMPKα 1 | Cpn10 | IL-12 Rβ1 |
| AMPKα 2 | CPO | IL-12 Rβ2 |
| AMPKβ1 | CPS1 | IL-12/IL-23 (p40) |
| AMPKγ1 | CPT2 | IL-13 |
| Amyloidβ 42 | CRABP1 | IL-15 |
| ANAPC2 | CRABP2 | IL-15/IL-15R |
| AND1 | CRALBP | IL-15Rα |
| Androgen Receptor | Creatine Kinase BB | IL-16 |
| Angiotensin I | Creatine Kinase MM | IL-17D |
| Angiotensin II Receptor 2 | CREB | IL-17A |
| Angiotensin III | CREB Phospho (Ser133) | IL-17A/F |
| ANKRD53 | cRel | IL-17B |
| Annexin IV | Cripto1 | IL-17C |
| Annexin V | CRISP3 | IL-17E |
| ANP | Crk p38 | IL-17F |
| Anti-*Kudoa thrysites* | CrkL | IL-18 |
| Anti-*T. brucei* procyclin (GPEET) | CrkL (pY207) | IL-18BP |
| Anti-*T. brucei* procyclin (phosphorylated GPEET) | CROT | IL-19 |
| Antiglobulin (Coombs) | CRRY | IL-1RA |
| Antithrombin III | CRTAM | IL-1RN |
| AP2 α | CRTC3 | IL-1α |
| AP2 α ± β² | CRY2 | IL-1β |
| AP2 β³ | Cryptochrome I | IL-2 |
| AP2M1 | *Cryptosporidium* | IL-20R2 |
| AP2S1 | *Cryptosporidium Parvum* | IL-20Rα |
| APAF1 | CRYZL1 | IL-20Rβ |
| APBB3 | CSK | IL-21 |
| APC | CSK Binding Protein | IL-22 |
| APC-1 | CSPS | IL-22Rα ± 2 |
| APC-10 | cSrc | IL-23 (p19) |
| APC-11 | CST2 | IL-23R |
| APC-2 | CTDSP1 | IL-24 |
| APC-3 | CTNNA3 | IL-25 |
| APC-5 | CTNNBL1 | IL-27 |
| APC-7 | Cullin 1 | IL-27 (p28) |
| APC-8 | Cullin 2 | IL-27Rα |
| APE1 | Cullin 3 | IL-28 |
| APG12 | Cullin 4A | IL-28Rα |
| APG3 | Cullin 4A/B | IL-29 |
| APG5 | Cullin 4B | IL-3 |
| APG7 | Cutaneous Lymphocyte Antigen | IL-31 |
| APMAP | CUTL1 | IL-32α ± β²γ³δ' |
| Apo-2.7 | CX3CL1 | IL-32α ± β²δ' |
| Apo-2.7 (7A6) | CX3CR1 | IL-33 |
| ApoE | CXCL1 | IL-34 |
| ApoE4 | CXCL10 | IL-4 |
| APOER2 | CXCL12α | IL-4Rα |
| Apolipoprotein AI | CXCL12β² | IL-5 |
| Apolipoprotein AII | CXCL13 | IL-6 |
| Apolipoprotein AIV | CXCL9 | IL-7 |
| Apolipoprotein B | CXCR7 | IL-7Rα |
| Apolipoprotein CIII | CXorf26 | IL-8 |
| Apolipoprotein D | Cyanine | IL-9 |
| Apolipoprotein E | CYB5R2 | ILF3 |
| Apolipoprotein F | CYB5R3 | ILK |
| Apolipoprotein H | Cyclin A | ILK1 |
| Apolipoprotein J | Cyclin A2 | Immunofluorescence N-γ³ |
| Apolipoprotein L1 | Cyclin B1 | IMP3 |
| Apolipoprotein M | Cyclin B2 | Importin9 |
| Apoptotic neutrophils | Cyclin D1 | Influenza A Virus M2 Protein |
| APP | Cyclin D2 | Influenza B Virus Nucleoprotein |
| Aquaporin 1 | Cyclin D3 | ING1 |
| Aquaporin 5 | Cyclin E | ING2 |
| ARF1 | Cyclin E2 | ING3 |
| ARF5 | Cyclin H | ING4 |
| ARFGAP1 | Cyclins D1/D2/D3 | Inhibin α |
| ARFRP1 | Cyclophilin 40 | iNOS |
| Argonaute-1 | CYLD | INPP4A |
| ARH | CysLT1 | INPP4B |
| ARHGAP25 | Cystatin C | Insulin |
| ARHGAP4 | Cystatin S | Insulin Degrading Enzyme (IDE) |

US 12,669,427 B2
69 70

TABLE 8-continued

| Cell surface markers for use with the hydrogel particles described herein. | | |
| --- | --- | --- |
| ARL11 | Cytochrome B245 heavy chain | Insulin Receptor R |
| ARL5B | Cytochrome B245 light chain | Integrin Î ± 4/Î²7 |
| ARPC5 | Cytochrome c | Integrin Î ± 9/Î²1 |
| Artemis | Cytochrome P450 17A1 | Integrin Î ± V/Î²5 |
| Aryl hydrocarbon Receptor | Cytochrome P450 19A1 | Integrin Î ± V/Î²6 |
| ASB-1 | Cytochrome P450 1A2 | Integrin Î²1 Phospho (Tyr783) |
| ASCC1 | Cytochrome P450 2A6 | Integrin Î²1 Phospho (Tyr795) |
| ASCC2 | Cytochrome P450 2B6 | Integrin Î²5 |
| ASGPR | Cytochrome P450 2C9 | Integrin Î²6 |
| Asialo-GM1 | Cytochrome P450 2J2 | Integrin Î²7 |
| ASK1 | Cytochrome P450 3A4 | Intercalated DNA |
| Asparagine synthetase | Cytochrome P450 3A5 | Intra Acrosomal Protein |
| Ataxin 1 | Cytochrome P450 Reductase | Intra-Acrosomal Proteins |
| ATF1 | Cytokeratin | Invariant NK T |
| ATF2 | Cytokeratin (acidic) | IP10 |
| ATG4A | Cytokeratin (basic) | IQGA1 |
| ATG9A | Cytokeratin (Pan-reactive) | IRAK1 |
| ATIC | Cytokeratin 1 | IRAK3 |
| Atlantic Salmon Ig | Cytokeratin 10 | IRAK4 |
| ATM | Cytokeratin 10/13 | IRE1 |
| ATP citrate lyase | Cytokeratin 13 | IRF1 |
| ATP1B3 | Cytokeratin 14 | IRF3 |
| ATP5A | Cytokeratin 14/15/16/19 | IRF4 |
| ATP5H | Cytokeratin 15 | IRF5 |
| ATP5J | Cytokeratin 16 | IRF6 |
| ATP5O | Cytokeratin 17 | IRF7 |
| ATP6V0D1 | Cytokeratin 18 | IRF7 (pS477/pS479) |
| ATP6V1B1 | Cytokeratin 19 | IRF8 |
| ATPB | Cytokeratin 2 | IRF9 |
| ATRIP | Cytokeratin 20 | IRS1 |
| Aurora A | Cytokeratin 4 | IRS1 (pY896) |
| Aurora A Phospho (Thr288) | Cytokeratin 4/5/6/8/10/13/18 | IRS2 |
| Aurora B | Cytokeratin 40 | IRS4 |
| Aurora B Phospho (Thr232) | Cytokeratin 5 | ISG15 |
| AVEN | Cytokeratin 5/6/18 | ISG20 |
| Avian Influenza A Neuraminidase | Cytokeratin 5/8 | ISL1 |
| Avidin | Cytokeratin 6 | Isthmin1 |
| Axin 2 | Cytokeratin 6a | ITCH |
| Axl | Cytokeratin 7 | Integrin Î ± 7 |
| B and Activated T Cells | Cytokeratin 7/17 | ITK |
| B Cell | Cytokeratin 8 | ITPR1 |
| B Cell Subset | Cytokeratin 8/18/19 | Jagged2 |
| B cells (pan reactive) | D4-GDI | JAK2 |
| B lymphocytes antibody [UCH-B1] | DAB2 | JAK3 |
| b-Endorphin | DACH1 | JAM2 |
| B-Raf Phospho (Thr598/Ser601) | DAND5 | JAML |
| B18R | DAP1 | Japanese encephalitis virus NS1 glycoprotein |
| B7-H4 | DAP12 | JNK |
| BACE1 | DAPK1 | JNK Phospho (Thr183/Tyr185) |
| BACE2 | DAPK2 | JNK1/JNK2/JNK3 |
| BACH1 | DARPP32 | JNK2 |
| baculovirus envelope gp64 protein | Daxx | Junctional Adhesion Molecule C |
| BAG1 | DAZL | Junctophilin-1 (C-term) |
| BAG2 | DBC1 | Junctophilin-1 (Mid) |
| BAG3 | DCAMKL1 | Junctophilin-2 (C-term) |
| BAG4 | DCC | Junctophilin-3 (C-term) |
| BAIAP2 | DCIR2 | KAP1 |
| BAK | DCLRE1B | KATNA1 |
| BAMBI | DCP1a | KCNH1 |
| BAP31 | DcR3 | KDEL |
| BAP37 | DCTN2 | KDM4D |
| basal cell Cytokeratin | DcTRAIL-R1 | Ki-67 |
| Basophils | DcTRAIL-R2 | KIF22 |
| Bassoon | DCXR | KIF3A |
| BATF | DDB1 | KIF4A |
| Bax | DDDDK tag | KIFA3 |
| BCAR1 | DDX3 | Kindlin2 |
| BCAR2 | DDX4 | Kinetoplastid Membrane Protein 11 (KMP-1)) |
| BCKD complex E2 subunit | DDX50 | KIR-2.1 |
| Bcl-10 | DECR1 | KIR-2D (pan CD158) |
| Bcl-2 | Dectin1 | KLF4 |
| Bcl-2 (pS70) | Dectin2 | KLF6 |

TABLE 8-continued

Cell surface markers for use with the hydrogel particles described herein.

| | | |
|---|---|---|
| Bcl-2 like 12 | DEF8 | KLH |
| Bcl-2 like 2 | Defensin Î ± 1 | KLHL11 |
| Bcl-22 | DELETE | KLRA3 |
| Bcl-2A1 | delta 1 Catenin | KLRC1 |
| Bcl-2Î± | Delta like protein 1 | KLRG1 |
| Bcl-3 | Delta like protein 4 | KMT4 |
| Bcl-6 | Delta Opioid Receptor | KMT5A |
| Bcl-xL | DeltaC | KOR-SA3544 |
| Bcl-XS/L | DeltaD | KS1/4 |
| BCR | Dendritic Cell Marker | Ksp37 |
| BCSC1 | Deoxycytidine kinase | KSR1 |
| BDH2 | Desmin | Ku70 |
| BDKRB2 | Desmoglein 2 | Ku70/80 |
| BDNF | Desmoglein1 | Ku80 |
| Beclin1 | Desmoplakin | *Kudoa Thyrsites* |
| Bestrophin 3 | Destrin | Kunitz Protease Inhibitor |
| beta 2 Adrenoreceptor | Dextran | Kv4.2 |
| Beta 3 Adrenergic Receptor | DGKA | L/S-MAG |
| beta 3 Sodium Potassium | Dicer | Labeling Check Reagent |
| ATPase | | |
| beta Actin | DISC1 (C-term) | Lactate Dehydrogenase |
| beta Arrestin 1 | DISC1 (Mid) | Lactate Dehydrogenase B |
| beta Arrestin 2 | Dishevelled 3 | Lambda |
| beta Catenin | Disialoganglioside GD2 | Lamin A |
| beta Catenin (npaa 27-37) | Disialoganglioside GD3 | Lamin A/C |
| beta Catenin (npaa 35-50) | Dkk1 | Lamin B Receptor |
| beta Catenin (pS45) | Dkk3 | Lamin B1 |
| beta Dystroglycan | DLC8 | Lamin B2 |
| beta galactosidase | DLK1 | Lamin C |
| beta galactosidase | Dlx5 | Laminin |
| fusion proteins | | |
| beta Synuclein | DM-GRASP | Laminin 5 |
| beta2 Microglobulin | DMT1 | Laminin Receptor |
| BHMT | DNA-PKcs | Laminin Î²1 |
| Bid | DNA-PKcs Phospho (Thr2609) | LAMP2a |
| Biglycan | DNAI1 | LAMP2b |
| Bilirubin Oxidase | DNAJA2 | LAT |
| Bim | DNAJB2 | LAT (pY171) |
| BimL | DNAJC3 | LAT (pY226) |
| BIN1 | DNAPK | LBP |
| BIN3 | DNM1L | LC3 |
| Biotin | Dnmt1 | LC3B |
| BiP | Dnmt3b | LCAT |
| BLBP | DNP | Lck |
| Blimp-1 | DOK2 | Lck (pY505) |
| BLK | DOK7 | LDH1 |
| BLNK | Dopamine Receptor D1 | LDH1/B/C |
| BLNK (pY84) | Dopamine Receptor D3 | LDL (MDA oxidized) |
| Blood Group A Antigen | Dopamine Receptor D5 | LDLR |
| Blood Group AB Antigen | Dopamine Î² Hydroxylase | LEF1 |
| Blood Group B Antigen | Doublecortin | *Leishmania* LPG |
| | | (repeat epitope) |
| Blood Group H ab Antigen | DP1 | *Leishmania* Major Surface |
| | | Protease (GP-63) |
| Blood Group H ab | DPH2 | LEKTI |
| Antigen/n Antigen | | |
| Blood Group H inhibitor | DPP10 | Leukemia Inhibitory Factor |
| Blood Group Lewis a | DPP3 | Leukotriene A4 hydrolase |
| Blood Group M Antigen | DPP9 | Leukotriene B4 Receptor |
| Blood Group N Antigen | Dppa4 | LHX3 |
| Blooms Syndrome | DPYD | LI-Cadherin |
| Protein Blm | | |
| BM1 | DR3 | LIF |
| BMAL1 | DRAK1 | DNA Ligase I |
| BMI1 | DRAK2 | DNA Ligase III |
| Bmk | Drebrin | LIM kinase 2 |
| BMP15 | DTYMK | LIME1 |
| BMP4 | DUSP23 | LIMK1 |
| BMP7 | DUSP27 | LIMS1 |
| BMPR1A | DUSP3 | Lin28 |
| BMPR2 | DUSP5 | Lineage Cocktail |
| BMX | DUSP6 | Lipin 1 |
| bMyc | DUX4 | LIS1 |
| BNIP2 | DYKDDDDK Epitope Tag | Liver Carboxylesterase 1 |
| BNIP3 | Dynamin | LKB1 |
| BNIP3L | Dynamin1 | LMO2 |
| BOB1 | Dynamitin | LOX |
| BORA | Dynein light chain 2 | LOX1 |

TABLE 8-continued

Cell surface markers for use with the hydrogel particles described herein.

| | | |
|---|---|---|
| Borealin | Dysbindin | LRP5/6 |
| *Borrelia burgdorferi* | Dysferlin | LRP6 |
| BPI | Dystrobrevin Î± | LRPAP1 |
| BRaf | Dystrobrevin Î² | LSD1 |
| BRCA1 | Dystroglycan Phospho (Tyr893) | LSP1 |
| BRCC36 | *E. Coli* O/E | LSS |
| BRD3 | E2A-Pbx1 | LTÎ± |
| BrdU | E2F1 | Luciferase |
| BRF1 | E47 | LXRÎ± |
| BRG1 | E4BP4 | Ly-108 |
| BRN3A | Ea52-68 peptide bound to I-A | Ly-49A |
| Btk | Ea52-68 peptide bound to the I-A | Ly-49A/D |
| Btk (pY551)/Itk (pY511) | EAAT1 | Ly-49AB6 |
| BTLN-2 | Early B Lineage | Ly-49C/F/I/H |
| BTN1A1 | EBF1 | Ly-49C/I |
| Bu1 | EBI3 | Ly-49D |
| Bu1a | EBP50 | Ly-49E/F |
| Bu1a/Bu1b | ECGF1 | Ly-49F |
| Bu1b | ECH1 | Ly-49G |
| BubR1 | ECRG4 | Ly-49G2 |
| Bulb | EDA | Ly-49G2B6 |
| Butyrylcholinesterase | EDA-A2R | Ly-49H |
| C peptide | EDG1 | Ly-49I |
| C reactive protein | EDG2 | Ly-51 |
| C/EBPÎ² | EDG3 | Ly-6A.2/Ly-6E.1 |
| C1 Inhibitor | EDG6 | Ly-6A/E |
| C15orf40 | EEA1 | Ly-6b |
| C16orf72 | EEF1G | Ly-6B.2 |
| C1orf50 | EEF2 | Ly-6C |
| C1Q | EEF2K | Ly-6D |
| C1QA | EEN | Ly-6G |
| C1QB | EFEMP1 | Ly-6G/C |
| C1QC | EFEMP2 | Ly-6K |
| C1QG | Eg5 | Ly-77 |
| C1r | Eg5 Phospho (Thr927) | Lymphotoxin Î² |
| C1s | EGF | Lymphotoxin Î² Receptor |
| C20orf30 | EGF Receptor | Lyn |
| C20orf43 | EGF Receptor (pY1173) | LYRIC |
| C21orf56 | EGF Receptor (pY845) | Lysophospholipase 1 |
| C21orf59 | EGF Receptor (pY992) | Lysosomal acid lipase |
| C2orf43 | EGR1 | Lysozome |
| C3 | EGR2 | Lysozyme |
| C3aR | EHD1 | Lyve1 |
| C3b | eIF1 | M-CSF |
| C3c | eIF2C2 | M13 Bacteriophage Coat Protein g8p |
| C3d | EIF2S1 | M13 Bacteriophage Protein |
| C4 | eIF2Î³ | MAA |
| C4 binding protein | eIF3 | Mac-2BP |
| C4b | eIF3D | macroH2A.1 |
| C4c | eIF3D (p66) | Macrophage |
| C4d | eIF3F | Macrophage Activator |
| C4orf42 | eIF3G | Macrophage galactose lectin |
| C5 | eIF3H (p40) | Macrophage/Granulocyte |
| C5aR1 | eIF3I (p36) | Macrophages/Monocytes |
| C5L2 | eIF3J | MAD2 |
| C6 | eIF3K | MadCAM1 |
| C6orf64 | eIF4B | MADD |
| C8A/B/G | eiF4E | MADH7 |
| C9 | eIF4E (pS209) | MAFB |
| C9orf41 | eIF4E2 | MAG |
| CA125 | eIF5A | MAGE-A |
| CA19.9 | eIF6 | MAGE1 |
| CAB39 | Elastase | MAIR2 |
| CACNA1S | Elk1 | MAIR4 |
| CACNA2 | Elk1 (pS383) | MALT1 |
| CACNG1 | ELK3 | Mammaglobin A |
| CAD | Elongin B | MAP1LC3A |
| Cadherin 1 | Elongin C | MAP2 |
| Cadherin 10 | EMAP II | MAP2B |
| Cadherin 11 | Embigin | MAP2K1IP1 |
| Cadherin 7 | EMG1 | MAP3K8 |
| Cadherin 8 | Emi1 | MAP4 Phospho (Ser768) |
| Cadherin 9 | EMR3 | MAP4K1 |
| Cadherin E | EMSY | MAP4K4 |

TABLE 8-continued

Cell surface markers for use with the hydrogel particles described herein.

| | | |
|---|---|---|
| Cadherin H | Ena/Vasp-like | MAPK12 |
| Cadherin K | EndoG | MAPK6 |
| Cadherin P | EndoGlyx-1 | MAPKAP Kinase 2 |
| Cadherin R | Endomucin | MAPKAP Kinase 2 Phospho (Thr334) |
| CAK C Terminus | Endothelial Cells | MARCKS |
| CAK N Terminus | Endothelial Lipase | MARCO |
| CAK Phospho (Ser164/Thr170) | Endothelial Venule Marker | Marginal Zone B Cells |
| Calbindin | Endothelium | MARK2 |
| Calcineurin A | Engrailed1 | MARK3 |
| Calcitonin Receptor | ENO1 | MART1 |
| Calcium Sensing Receptor | Enolase1 | Mast Cell |
| Caldesmon | eNOS | Mast Cell Protease 11 |
| Calgranulin A | eNOS (pS1177) | mature macrophage marker |
| Calgranulin B | Entpd2 | MBD1 |
| Calmodulin | Eomes | MBD2 |
| Calnexin-ER membrane marker | Eos | MBL |
| Calpain 1 | Epac1 | MCL1 |
| Calpain 2 | Eph Receptor A1 | MCM2 |
| Calpain 9 | Eph Receptor A2 | MCM3 |
| Calpain S1 (small subunit) | Eph Receptor A4 | MCM4 |
| Calpastatin | Eph Receptor B4 | MCM5 |
| Calponin | Eph Receptor B6 | MCM6 |
| Calreticulin | Ephrin A2 | MCM7 |
| Calretinin | Ephrin A3 | MCP-1 |
| Calsequestrin 2 | EPHX2 | MCP-4 |
| CaMKI | EPM2AIP1 | MCP-8 |
| CaMKII | EPOR | MCSF |
| CaMKII Phospho (Thr286) | EPS15R | MD1 |
| CaMKIÎ | Epsin 1 | MD2 |
| CamKIV | Epsin 2 | MDC |
| CaMKIÎ± | ER-HR3 | MECT1 |
| CAMLG | ER-MP54 | MEF2A |
| cAMP Protein Kinase Catalytic subunit | ER-TR7 | MEIS1 |
| cAMP Protein Kinase Catalytic subunit Î± | ER81 | MEK1 |
| Cannabinoid Receptor I | ERAB | MEK1 (p298) |
| Cannabinoid Receptor II | ERCC1 | MEK1 (pS218)/MEK2 (pS222) |
| CAP-G2 | ERG | MEK1/2 (pS222) |
| CAP18 | ERK1 | MEK2 |
| CAP2 | ERK1/2 (pT185/pY187) | MEK3 |
| CAP3 | ERK1/2 (pT202/pY204) | MEK4 |
| Carbonic Anhydrase I | ERK1/ERK2 | MEK5 |
| Carbonic Anhydrase IX | ERK2 | MEK6 |
| Carboxylesterase 1 | ERK5 | MEK7 |
| Carboxypeptidase A1 | ERMAP | MEKK1 |
| Carboxypeptidase A2 | ERp29 | MEKK2 |
| CARD11 | ERp72 | MEKK3 |
| CARD8 | Erythroid Cells | MEKK4 |
| CARD9 | Erzin/Radixin/Moesin | Melanoma |
| Cardiac Troponin T | ERÎ± Phospho (Ser167) | MELK |
| CARKL | ESAM | MEMO1 |
| CARM1 | Estrogen Inducible Protein pS2 | Mena |
| Casein Kinase 1 Î± | Estrogen Receptor | Menin |
| Casein Kinase 1 Î³2 | Estrogen Receptor Î± | MEOX2 |
| Casein Kinase 2 Î² | Estrogen Receptor Î² | Merlin |
| Caspase 1 | Estrogen Related Receptor alpha | MERTK |
| Caspase 10 | ETAR | Mesothelin |
| Caspase 11 | Ethenoadenosine | Metallothionein |
| Caspase 12 | ETS1 | MetRS |
| Caspase 2 | EVI2A | mGluR5 |
| Caspase 2L | EVI2B | MGMT |
| Caspase 3 | EWSR1 | MHC Class I |
| Caspase 4 | EXD1 | MHC Class I (H-2Db) |
| Caspase 5 | EXOSC3 | MHC Class I (H-2Dd) |
| Caspase 6 | EXOSC7 | MHC Class I (H-2Dk) |
| Caspase 7 | EYA2 | MHC Class I (H-2Dq/Lq) |
| Caspase 8 | EZH1/2 | MHC Class I (H-2Kb) |
| Caspase 9 | Ezrin | MHC Class I (H-2Kb/Db) |
| Catalase | Ezrin (pY353) | MHC Class I (H-2Kb/Dd) |
| Catechol-O-methyltransferase | F-actin | MHC Class I (H-2Kd a3 domain) |
| Cathepsin D | F10A1 | MHC Class I (H-2Kd) |
| Cathepsin K | F4/80 | MHC Class I (H-2Kd/Dd) |

TABLE 8-continued

Cell surface markers for use with the hydrogel particles described herein.

| | | |
|---|---|---|
| Cathepsin L | FAA4 | MHC Class I (H-2Kd/Dd/q/u/v) |
| Caveolin1 | FABP4 | MHC Class I (H-2Kk) |
| Caveolin1 (pY14) | Factor I | MHC Class I (H-2Kq) |
| Caveolin2 | Factor IX | MHC Class I (H-2Ks) |
| Cbl | Factor VIII.vWF (delete) | MHC Class I (H-2Ld) |
| CBP | Factor XIIIa | MHC Class I (H-2Ld/Db) |
| CBWD1 | FADD | MHC Class Ib (H2-M3) |
| CBX1 | FAHD2A | MHC Class II |
| cCbl (pY700) | FAK | MHC Class II (DQ) |
| cCbl (pY774) | FAK (pS910) | MHC Class II (DR) |
| CCDC98 | FAM119A | MHC Class II (I-A) |
| CCK4 | FAM175A | MHC Class II (I-A/E) |
| CCL11 | FAM84B | MHC Class II (I-Ab) |
| CCL17 | FAM91A1 | MHC Class II (I-Ab/Ad) |
| CCL18 | FANCC | MHC Class II (I-Ab/As) |
| CCL19-Fc | FANCD2 | MHC Class II (I-Ad) |
| CCL20 | Fanconi anemia D2 Phospho (Ser222) | MHC Class II (I-Ak) |
| CCL21 | FAP | MHC Class II (I-Ak/Ad/Ab/Aq/Ar) |
| CCL25 | Fascin | MHC Class II (I-Ak/As) |
| CCL3 | FBP1 | MHC Class II (I-Ap) |
| CCL5 | FBXO21 | MHC Class II (I-Aq) |
| CCL6 | FBXO31 | MHC Class II (I-E) |
| CCNB1IP1 | FBXO42 | MHC Class II (I-Eî°) |
| CCR10 | FBXO43 | MHC Class II (RT1B) |
| CCR11 | Fc Receptor Binding Inhibitor | MHC Class II (RT1Bu) |
| CCRD6 | Fc receptor IgA + IgM | MHC Class II(RT1D) |
| CCRL2 | FcR | MHC Class II Î2 |
| CD1 | FcRL6 | MHC Qa1b |
| CD1.1 | FcRLA | MICA |
| CD10 | FcÎ¼RI | MICA/MICB |
| CD100 | FDC | MICB |
| CD101 | FDFT1 | Microfold (M) Cells |
| CD102 | FDPS | Microtubule Associated Protein 2ab |
| CD103 | FE65 | Microtubule Associated Protein RP/EB 2 |
| CD104 | FeLV p27 | Midkine |
| CD105 | FEN1 | Mineralocorticoid Receptor |
| CD106 | FER | MIP-1Î2 |
| CD107a | Ferritin Heavy Chain | MIPEP |
| CD107b | Ferritin Light Chain | Mitochondria |
| CD108 | Ferritin, mitochondrial | Mitofilin |
| CD109 | FES | Mitofusin 1 |
| CD11 | Fetal Hemoglobin | Mitofusin 2 |
| CD110 | FGF acidic | Mitotic Cells |
| CD111 | FGF basic | MKK6 |
| CD112 | FGF21 | MLH1 |
| CD113 | FGFR1 | MLK3 |
| CD114 | FGFR2 | MLL1 |
| CD115 | FGR | MLLT11 |
| CD116 | FH | MMP1 |
| CD117 | FHL1 | MMP10 |
| CD118 | Fibrillarin | MMP11 |
| CD119 | Fibrillin | MMP12 |
| CD11a | Fibrinogen | MMP13 |
| CD11a, strain polymorphism | Fibrinogen Î± chain | MMP14 |
| CD11a/CD18 | Fibrinogen Î³ chain | MMP15 |
| CD11b | Fibrinopeptide A | MMP17 |
| CD11b/c | Fibrinopeptide B | MMP19 |
| CD11c | Fibroblast activation protein Î± | MMP2 |
| CD11d | Fibroblast Surface Protein | MMP20 |
| CD120a | Fibroblasts/Epithelial cells | MMP21 |
| CD120b | Fibronectin | MMP26 |
| CD121a | Fibronectin Receptor | MMP3 |
| CD121b | Fibulin5 | MMP8 |
| CD122 | Ficolin B | MMP9 |
| CD123 | Filaggrin | Mnk1 |
| CD124 | Filamin A | mNOS |
| CD125 | FITC | MnSOD |
| CD126 | FITC/Oregon Green | Moesin |
| CD127 | FIV | Monoamine Oxidase B |
| CD129 | FIV gp120 | Monocyte/Granulocyte |
| CD13 | FIV gp95 | Mononuclear Phagocyte |

TABLE 8-continued

Cell surface markers for use with the hydrogel particles described herein.

| | | |
|---|---|---|
| CD130 | FIV p24 | Mouse Embryonic Fibroblast (mEF) Feeder Cells |
| CD131 | FIV p24 gag | Mouse Lineage |
| CD132 | FKBP12 | MPP1 |
| CD133 | FKBP4 | MRCL3 |
| CD133/2 | FKBP6 | MRE11 |
| CD134 | FKBPL | MRGPR-X2 |
| CD135 | FLiC | MRI1 |
| CD136 | Flightless1 | MRP14 |
| CD137 | FLIP | MRP2 |
| CD137L | Flt3L | MRP3 |
| CD138 | Fluorescent Protein | MRP4 |
| CD139 | FLV gp70 | MRP5 |
| CD14 | FLYWCH2 | MRP6 |
| CD140a | FMC7 | MRP8 |
| CD140b | fMLP Receptor | MRP8/14 |
| CD140b (pY1009) | FMRP | MSC (W8B2) |
| CD140b (pY1021) | FNTA | MSC (W3D5) |
| CD140b (pY771) | FNTB | MSC (W5C5) |
| CD140b (pY857) | Follicular Dendritic Cells | MSC (W7C6) |
| CD141 | Fos | MSC/NPC |
| CD142 | FOXA1 | MSH2 |
| CD143 | FOXA2 | MSH6 |
| CD144 | FOXC2 | MSI2H |
| CD146 | FOXD3 | MSK1 |
| CD147 | FOXI1 | MST1 |
| CD148 | FOXJ1 | MST1/MST2 |
| CD15 | FOXM1 | MST3 |
| CD150 | FOXO1 | MST4 |
| CD151 | FOXO3A | MST4/MST3/STK25 |
| CD152 | FOXP1 | mTOR |
| CD153 | FOXP3 | Muc-16 |
| CD154 | FPRL1 | Muc-2 |
| CD155 | FR4 | Muc-3 |
| CD156c | Fra2 | Muc-4 |
| CD157 | Fragilis | Muc-7 |
| CD158a | FRAT1 | MULT-1 |
| CD158a/h | Frataxin | Munc13-4 |
| CD158b | Frequenin | Munc18 |
| CD158b1/b2/j | Frizzled-1 | MUPP1 |
| CD158d | FSHÎ± | Mus81 |
| CD158e | FSHÎ² | Musashi1 |
| CD158e/k | FUK | Muscarinic Acetylcholine Receptor 2 |
| CD158e1 | FUS | muscle Actin |
| CD158e1/e2 | FXYD3 | Muscleblind-like 1 |
| CD158f | FYB | MVP |
| CD158g | Fyn | MYBBP1A |
| CD158h | Fyn (pY528)/c-Src (pY530) | MYBPC3 |
| CD158i | Fyn-Related Kinase | Myc tag |
| CD158j | FZR1 | MyD88 |
| CD159a | G-CSF | Myelin Basic Protein |
| CD159c | G3BP | Myelin oligodendrocyte glycoprotein |
| CD15s | G6PD | Myelin PLP |
| CD16 | GAB1 | Myeloid Antigen |
| CD16/32 | GAB2 | Myeloid Cell Nuclear Differentiation Antigen |
| CD16/56 | GABA B Receptor 2 | Myeloid Lineage |
| CD160 | GABARAP | Myocilin |
| CD161 | GAD65 | Myogenin |
| CD161a | GAD67 | Myosin heavy chain |
| CD162 | GADD34 | Myosin IIA |
| CD162R | Galacto-cerebroside | Myosin light chain 2 |
| CD163 | Galactocerebroside | Myosin light chain 3 |
| CD164 | Galectin 1 | Myosin light chain kinase |
| CD165 | Galectin 10 | Myosin Phosphatase |
| CD166 | Galectin 3 | Myosin Phosphatase 1/2 |
| CD167a | Galectin 4 | MYST2 |
| CD168 | Galectin 7 | NADH2 |
| CD169 | Galectin 8 | Nafl |
| CD16b | Galectin 9 | NAK |
| CD17 | gamma Synuclein | Nanog |
| CD170 | Ganglioside GD2 | NAPE-PLD |
| CD171 | Ganglioside GD3 | NAT1 |
| CD172 | Ganglioside GM1 | Native Lipoteichoic Acid |
| CD172a | Gankyrin | Natriuretic Peptide Receptor A |

TABLE 8-continued

Cell surface markers for use with the hydrogel particles described herein.

| | | |
|---|---|---|
| CD172a/b | GAP | Natural Killer Cell |
| CD172b | GAP43 | Natural Killer Cell |
| | | Activation Structures |
| CD172g | GAPDH | NBS1 |
| CD173 | GARP | NC1.1 |
| CD177 | GAS2 | NCF4 |
| CD178 | GAS7 | Nck |
| CD178.1 | GAT2 | NCOA1 |
| CD179a | GATA1 | NCOA2 |
| CD179b | GATA2 | NCX1 |
| CD18 | GATA3 | NDUFAF1 |
| CD180 | GATA4 | NDUFB4 |
| CD181 | GATM | NDUFS3 |
| CD182 | GBA3 | NEDD8 |
| CD183 | GBE1 | NEK2 |
| CD184 | GBP1 | NEK6 |
| CD185 | GBP2 | NEK7 |
| CD186 | GBP5 | NEK9 |
| CD19 | GC1qR | NEK9 Phospho (Thr210) |
| CD191 | GCDFP15 | Nestin |
| CD192 | GCDH | NETO2 |
| CD193 | GCK1 | Neurabin1 |
| CD194 | GCLM | Neuregulin1 |
| CD195 | GCN2 | Neuregulin3 |
| CD195 (cytoplasmic) | GCN5 | Neuroblastoma |
| CD195 Phospho (Ser337) | GCTM2 | NeuroD1 |
| CD195 Phospho (Ser349) | GDAP1L1 | NeuroD2 |
| CD196 | GDF15 | Neurofibromin |
| CD197 | Gelsolin | Neurofilament Heavy Protein |
| CD198 | Gemin1 | Neurofilament Medium Protein |
| CD199 | Gephyrin | Neurogenin 2 |
| CD1a | GFAP | Neurokinin 1 Receptor |
| CD1b | GFP | Neuron Specific Enolase |
| CD1b/c | GILZ | Neuronal Growth |
| | | Factor Receptor |
| CD1c | GIMAP4 | Neurotensin Receptor 1 |
| CD1d | GIPR | NFκB p50/p105 |
| CD1d α GalCer Complex | GIT2 | NFκB p65 (pS536) |
| CD2 | GITRL | NFATc1 |
| CD20 | GLAST | NFκB p50 |
| CD200 | Gli1 | NFκB p50/p105 |
| CD200R | Glial Fibrilary Acidic Protein | NFκB p52/p100 |
| CD200R3 | Glicentin | NFκB p65 |
| CD201 | GLIPR1L1 | NFκB p65 (pS529) |
| CD202b | Glucagon | NG2 |
| CD203a | Glucocorticoid Receptor | NGF |
| CD203c | Glucocorticoid Receptor alpha | Nhedc2 |
| CD204 | Glucose 1 Dehydrogenase | NHERF1 |
| CD205 | Glucose 6 Phosphate Isomerase | Nicastrin |
| CD206 | GLUH1 | Ninein |
| CD207 | GLUT1 | Nitrotyrosine |
| CD208 | GLUT2 | NKG2A/C/E |
| CD209 | GLUT4 | NKG2AB6 |
| CD209b | GLUT5 | NKp80 |
| CD21 | Glutamate receptor 2 | NKX3.1 |
| CD21/CD35 | Glutamate receptor 2/3 | NM23A |
| CD210 | Glutamate receptor 3 | NMDA Receptor 2A |
| CD212 | Glutamate receptor 4 | NMDA Receptor 2B |
| CD213a1 | Glutaminase | NMDE2 |
| CD213a2 | Glutamine Synthetase | NMDZ1 |
| CD217 | Glutaredoxin 2 | NMNA2 |
| CD218a | Glutathione NEM | nMyc |
| CD22 | Glutathione NEW | nNOS |
| CD22 (pY822) | Glutathione Peroxidase 1 | NNTM |
| CD22.2 | Glutathione Peroxidase 4 | Nociceptin |
| CD220 | Glutathione Reductase | Nod2 |
| CD220α | Glutathione S Transferase α, 2 | Nodal |
| CD221 | Glutathione S Transferase π1 | Noggin |
| CD221 (pY1131) | Glutathione S Transferase ¼ | NONO |
| CD222 | Glutathione Synthetase | Nonspecific Cytotoxic Cells |
| CD223 | Glycogen synthase 1 | Notch1 |
| CD224 | Glycoprotein IX | Notch2 |
| CD226 | Glycoprotein VI | Notch3 |
| CD227 | GM-CSF | Notch4 |
| CD229 | GM130 | NOX2 |
| CD229.1 | GM3.2 | NOX4 |
| CD23 | GNB2 | NOXA2 |
| CD230 | GNB2L1 | NPC |

TABLE 8-continued

Cell surface markers for use with the hydrogel particles described herein.

| | | |
|---|---|---|
| CD231 | GNLY | NPM-ALK |
| CD233 | GNMT | NPM/B23 Phospho (Thr199) |
| CD234 | GnRHR | NPM/B23 Phospho (Thr234/Thr237) |
| CD235a | Golgi Protein (58K) | NPY5R |
| CD235ab | Golgi Zone | NQO1 |
| CD236 | GOLM1 | NR2E1 |
| CD239 | GOLPH2 | NRC2C |
| CD24 | GOSR1 | Nrf2 |
| CD240CE | gp340 | NRG3 |
| CD240DCE | gp49R | NSPA/B |
| CD243 | GPA33 | NTAL |
| CD244 | GPCR5C | NTF97 |
| CD244.1 | GPR-120 | Nucleolin |
| CD244.2 | GPR-143 | Nucleolin Phospho (Thr76/Thr84) |
| CD245 | GPR-151 | Nucleophosmin |
| CD246 | GPR-18 | NUDC |
| CD247 | GPR-30 | NUMA1 |
| CD247 (pY142) | GPR-40 | Nur77 |
| CD249 | GPR-48 | O acetyl GD3 |
| CD25 | GPR-49 | Oct2 |
| CD252 | GPR-50 | Oct3/4 |
| CD253 | GPR-56 | Oct3/4A |
| CD254 | GPR-73A | Oct4 |
| CD255 | GPR-73B | ODAG |
| CD256 | GPR-77 | OGDH |
| CD257 | GPR-83 | OLIG1 |
| CD258 | GPR-86 | OLIG2 |
| CD26 | GPR-C5C | Oligodendrocyte Marker |
| CD261 | GPR-C5D | Oligodendrocyte Marker O1 |
| CD262 | Granulin | Oligodendrocyte Marker O4 |
| CD263 | Granulysin | Oncostatin M Receptor |
| CD264 | Granzyme A | Orai1 |
| CD265 | Granzyme B | OSCAR |
| CD266 | Granzyme K | OSR1 |
| CD267 | GRAP2 | Osteonectin |
| CD268 | GRASP1 | Osteopontin |
| CD269 | GRASP65 | Osteoprotegerin |
| CD27 | GRB2 | Otx2 |
| CD270 | GRB7 | OVA (SIINFEKL) H-2Kb |
| CD271 | GRHPR | Oval Cell Marker |
| CD272 | GRIM19 | Ovalbumin |
| CD273 | GRK1 | Ovarian Carcinoma-associated Antigen |
| CD274 | GRK2 | OX-62 |
| CD275 | GRK3 | p110Î' |
| CD276 | GRK5 | p120 Catenin |
| CD277 | GRK6 | p120 Catenin (pS268) |
| CD278 | Growth hormone receptor | p120 Catenin (pS288) |
| CD279 | GRP170 | p120 Catenin (pS879) |
| CD28 | GRP94 | p120 Catenin (pT310) |
| CD280 | GSC | p120 Catenin (pT916) |
| CD281 | GSK3Î± | p120 Catenin (pY228) |
| CD282 | GSK3Î±/Î² | p13 |
| CD283 | GSK3Î² | p130 |
| CD284 | GSPT2 | p130 Cas |
| CD284/MD2 Complex | GST | p130 Cas (pY249) |
| CD286 | GST Epitope Tag | p14ARF |
| CD289 | GSTA4 | p150, 95 |
| CD29 | GTF2D1 | p19ARF |
| CD290 | GTPase HRAS | p21 |
| CD294 | GTPBP4 | p22phox |
| CD298 | Guanylate kinase | p23 |
| CD299 | H-2 | p27Kip1 |
| CD2a | H-2.m31 | P2RX4 |
| CD3 | H-2Db | P2RY8 |
| CD3/CD44 | H-2Dd | P2X3 |
| CD30 | H-2Kd | P2X7 |
| CD300 | H2-M | P2Y6 |
| CD300a | H2-M3 | p34Cdc-2 |
| CD300e | H2A.X | p38 |
| CD300f | H2A.X Phospho (Ser139) | p38 MAPK (pT180/pY182) |
| CD301 | H2A1J | p400 |
| CD303 | H60 | p53 |
| CD303a | HA tag | p53 Acetylated (Lys305) |
| CD304 | HADHA | p53 Acetylated (Lys382) |
| CD305 | HADHA/HADHB | p53 Phospho (Ser15) |

TABLE 8-continued

Cell surface markers for use with the hydrogel particles described herein.

| CD307d | HADHB | p53 Phospho (Ser37) |
| CD309 | HADHSC | p53 Phospho (Ser392) |
| CD31 | HAND1 | p53BP1 (Ser1778) |
| CD310 | HAO1 | p57Kip2 |
| CD312 | Haptoglobin | p60 CAF1 |
| CD314 | HARS | p62 |
| CD314 (activating) | HARS2 | p63 |
| CD314 (blocking) | HBF | p63 (TA) |
| CD317 | hCGÎ± | p70 S6 Kinase Î² |
| CD318 | hCGÎ² | p90 Rsk |
| CD319 | hCGÎ²4 | p90 Rsk Phospho (Thr368/Ser372) |
| CD32 | HCN4 | p95 NBS1 |
| CD321 | HDAC1 | p97 |
| CD323 | HDAC10 | PA28Î³ |
| CD324 | HDAC2 | PABP1 |
| CD325 | HDAC3 | PABP2 |
| CD326 | HDAC4 | PABPN1 |
| CD328 | HDAC6 | PAC1 |
| CD329 | HDAC9 | PAD2 |
| CD32B | HDHD1A | PAG1 |
| CD33 | HDHD2 | PAK1 |
| CD334 | HDJ2 | PAK2 |
| CD335 | HDLBP | PAK3 |
| CD336 | HE4 | pan Actin |
| CD337 | HEC1 | pan Macrophage |
| CD338 | HEF1 | Panendothelial Cell Antigen |
| CD339 | Helios | PAR1 |
| CD34 | Hematopoiesis related Macrophage | Parainfluenza Virus type 1 |
| CD340 | Hematopoietic Lineage Cocktail | Parainfluenza Virus type 2 |
| CD344 | Hematopoietic Progenitor Cell | Parainfluenza Virus type 3 |
| CD349 | Hemoglobin | PARC |
| CD35 | Hemoglobin F | PARD3 |
| CD351 | Hemoglobin subunit Î± | PARK7/DJ1 |
| CD354 | Hepatitis B Virus | PARP, Cleaved Form |
| CD357 | Hepatitis B Virus Core Antigen | PARP16 |
| CD358 | Hepatitis B Virus E Antigen | PARP4 |
| CD36 | Hepatitis B Virus Surface Antigen (Ad/Ay) | PARVA |
| CD360 | Hepatitis C Virus | Pax2 |
| CD361 | Hepatitis C Virus Core Antigen | Pax5 |
| CD36L1 | Hepatitis C Virus NS4 | Pax6 |
| CD37 | Hepsin | Pax7 |
| CD38 | HER2 | Pax8 |
| CD39 | HER3 | Pax9 |
| CD39L4 | HER4 | Paxillin |
| CD3D | Hes1 | Paxillin Phospho (Tyr118) |
| CD3G | Hexokinase | Paxillin Phospho (Tyr31) |
| CD3Î³ | Hexokinase1 | PBEF |
| CD3Î´ | Hexokinase2 | PBK |
| CD3Îµ | HFE1 | PBP |
| CD3Îµ (CD3 Molecular Complex) | HGF | PBR |
| CD4 | HGFA Inhibitor 1 | PBX3 |
| CD4 (domain 1) | HHEX | PCB |
| CD4 (domain 2) | HHV8 GPCR | PCNA |
| CD4 v4 | HIBCH | PCYT1A |
| CD40 | HID1 | PD-1H |
| CD40bp | HIF-1Î± | PD-ECGF |
| CD41 | HIF-2Î± | PDC-TREM |
| CD41/CD61 | HIF1AN | PDCD4 |
| CD41a | HINT1 | PDCD6 |
| CD41b | HIP2 | PDE3B |
| CD42a | HIPK2 | PDECGF |
| CD42b | Hippocalcin | PDGF-AA |
| CD42d | Histamine H3 Receptor | PDI |
| CD43 | Histocytes | PDK1 |
| CD44 | Histone H1 | PDK2 |
| CD44 (v3) | Histone H1.0 | PDPK1 |
| CD44 (v4) | Histone H2A | PDPK1 (pS241) |
| CD44 (v5) | Histone H2B | PDX1 |
| CD44 (v6) | Histone H2B type 1B | PDZK1 |
| CD44 (v7) | Histone H3 | PE |
| CD44.2 | Histone H3 Phospho (Ser10) | PECR |

TABLE 8-continued

Cell surface markers for use with the hydrogel particles described herein.

| | | |
|---|---|---|
| CD44std | Histone H3 Phospho (Ser28) | PEI-Transferrinfection |
| CD44v6 | Histone H3.3 | Pellino 1 |
| CD44var (v10) | Histone H4 | Pentraxin 3 |
| CD44var (v3) | HIV1 Core Antigen | PEPD |
| CD44var (v3-v10) | HIV1 p17 | Perforin |
| CD44var (v4) | HIV1 p24 | Peroxiredoxin 1 |
| CD44var (v5) | HIV1 p55/p17 | Peroxiredoxin 2 |
| CD44var (v6) | HIV1 tat | Peroxiredoxin 6 |
| CD44var (v7) | HL60 | PEX5 |
| CD44var (v7-v8) | HLA Class I | PF4 |
| CD45 | HLA-2Kb/2Db | PGC1α̂± |
| CD45.1 | HLA-2kb/2Dd | PGIS |
| CD45.2 | HLA-A | PGP9.5 |
| CD45R | HLA-A/B/C | PGRP-Ia |
| CD45RA | HLA-A1/A11/A26 | PGRP-S |
| CD45RB | HLA-A1/A36 | PHD1 |
| CD45RC | HLA-A10/A11 | PHD2 |
| CD45RO | HLA-A10/A28/B75 | Phosphatidylserine |
| CD46 | HLA-A10/B62/B71 | Phospho SHIP |
| CD47 | HLA-A11 | Phospholipase A2 activator protein (PLAP) |
| CD48 | HLA-A2 | Phospholipase C $\hat{I}^2$3 |
| CD49a | HLA-A2/A25/A32 | Phospholipase C $\hat{I}^3$1 |
| CD49a/CD29 | HLA-A2/A28 | Phospholipase D1 |
| CD49b | HLA-A2/A3/A29 | Phosphoserine/ threonine/tyrosine |
| CD49b/CD29 | HLA-A2/A69 | Phosphotyrosine |
| CD49b/CD61 | HLA-A2/B17 | PI 3 Kinase catalytic subunit α̂± |
| CD49c | HLA-A2/B5 | PI 3 Kinase catalytic subunit α̂3 |
| CD49d | HLA-A2/B57 | PI 3 Kinase p110 $\hat{I}^2$ |
| CD49d/CD29 | HLA-A23/A24 | PI 3 Kinase p110 α̂' |
| CD49e | HLA-A24/A11/A2403 | PI 3 Kinase p150 |
| CD49e/CD29 | HLA-A25 | PI 3 Kinase p85 α̂± |
| CD49f | HLA-A25/A26 | PI 4 kinase $I^2$ |
| CD49f/CD29 | HLA-A25/A26/A34 | PIAS1 |
| CD4α̂± | HLA-A25/A32 | PIAS3 |
| CD5 | HLA-A26/A34/B71/B62 | PICK1 |
| CD5.1 | HLA-A29 | PIM1 |
| CD5.2 | HLA-A3 | PIM2 |
| CD5.6 | HLA-A30/A31 | Pin1 |
| CD50 | HLA-A33/B8 | PINK1 |
| CD51 | HLA-A34/B71/A26 | PIP5K2α̂± |
| CD51/61 | HLA-A9 | PIP5Kα̂3 |
| CD52 | HLA-A9/A25/A32 | PIR-A/B |
| CD53 | HLA-A9/A32/B13 | Pirh2 |
| CD54 | HLA-B | PIST |
| CD55 | HLA-B12 | PiTX3 |
| CD56 | HLA-B13/B62/B15 | PIWIL2 |
| CD57 | HLA-B14 | PKA RIIα̂± (pS99) |
| CD58 | HLA-B17 | PKA RIα̂2 (pS114) |
| CD59 | HLA-B17/B35/B44 | PKA2α̂2 |
| CD59a | HLA-B21/B70/B55 | PKAR2 |
| CD6 | HLA-B27/B44/B47 | PKAα̂3 |
| CD60b | HLA-B35/B57/B75/B77 | PKC |
| CD61 | HLA-B44/B75/B17 | PKCq |
| CD62E | HLA-B48/B60 | PKCα̂± |
| CD62L | HLA-B5/B49/B56 | PKCα̂± (pT497) |
| CD62P | HLA-B7 | PKCα̂± (pT638) |
| CD63 | HLA-B8 | PKCα̂2 |
| CD64 | HLA-B8/B14 | PKCα̂22 |
| CD64 a, b alloantigens | HLA-BC | PKCα̂3 |
| CD64.1 | HLA-Bw4/A9/A32 | PKCα̂' |
| CD65 | HLA-Bw6 | PKCα̂μ |
| CD65s (CD65 sialylated) | HLA-Bw6/B77 | PKCα̂¶ |
| CD66 | HLA-class I free chain | PKCα̂, |
| CD66a | HLA-D | PKCα̂ . . . |
| CD66a/b/c/e | HLA-DM | PKN |
| CD66a/c/d | HLA-DO | PKN2 |
| CD66a/c/d/e | HLA-DP | PKR |
| CD66a/c/e | HLA-DQ | PKX1 |
| CD66a/e | HLA-DQ/DR | PLA2G1B |
| CD66b | HLA-DQ1/DQ3 | Placental alkaline phosphatase |
| CD66c | HLA-DQ1/DR7 | Placental Protein 14 |
| CD66c/e | HLA-DQ3 | Plakophilin 3 |
| CD66e | HLA-DQ6 | Plastin L |

TABLE 8-continued

Cell surface markers for use with the hydrogel particles described herein.

| | | |
|---|---|---|
| CD66f | HLA-DQ7 | Platelet |
| CD68 | HLA-DQA1 | PLAU |
| CD69 | HLA-DQB1 | PLCÎ³1 |
| CD7 | HLA-DQw1 | PLCÎ³1 (pY783) |
| CD70 | HLA-DR | PLCÎ³2 |
| CD70b | HLA-DR/DP | PLCÎ³2 (pY759) |
| CD71 | HLA-DR/DP/DQ | Plectin |
| CD72 | HLA-DR1 | Pleiotrophin |
| CD72 a, b, c alloantigens | HLA-DR11 | PlexinA1 |
| CD72 b, c alloantigens | HLA-DR3/DR6 | PlexinB2 |
| CD72.1 | HLA-DR4 | PLGF |
| CD73 | HLA-DR7 | PLK1 |
| CD74 | HLA-DR7/DRÎ²2 | PLK1 Phospho (Thr210) |
| CD75 | HLA-DR8/DR12 | PLK4 |
| CD77 | HLA-DR9 | PLSCR1 |
| CD78 | HLA-DRA | PLVAP |
| CD79a | HLA-DRÎ²2 | PLZF |
| CD79b | HLA-DRÎ²23 | PMCA(1-4) |
| CD8 | HLA-E | PMCA4 |
| CD80 | HLA-G | PMEL17/SILV |
| CD81 | HLCS | PMN |
| CD82 | HLF | PMP70 |
| CD83 | HLXB9 | PMS2 |
| CD84 | HMG14 | PNAd |
| CD85 | HMG17 | PNPH |
| CD85a | HMG4 | Podocalyxin |
| CD85d | HMGB1 | Podoplanin |
| CD85g | HMGB2 | POKEMON |
| CD85h | HMOX1 | Polyhistidine Tag |
| CD85j | HMOX2 | PON1 |
| CD85k | HNF4Î± | PON3 |
| CD86 | hnRNPA1 | PP2AÎ± |
| CD87 | hnRNPC1/C2 | PP2AÎ± ± Î²2 |
| CD88 | hnRNPD | PPM1A |
| CD89 | hnRNPK | PPP1A |
| CD8Î± | hnRNPL | PPP5C |
| CD8Î± ± .1 | hnRNPU | PPP6C |
| CD8Î± ± .2 | hnRNPUL1 | PR3 |
| CD8Î²2 | Homing Receptor | PRA1 |
| CD9 | HOXB4 | PRC1 |
| CD90.1 | HOXB5 | Pre-BCR |
| CD90.2 | HP1Î± | Pre-T Cell Receptor Î± Chain |
| CD90.9 | HPa1 | Prealbumin |
| CD91 | HPa2 | Presenilin1 |
| CD91Î± | HPD | Presenilin2 |
| CD91Î²2 | HPd1 | Prion protein PrP |
| CD93 | HPd2 | PRKRA |
| CD94 | HPi1 | PRLR |
| CD95 | HPi2 | PRMT1 |
| CD96 | HPi3 | PRMT5 |
| CD97 | HPi4 | pro Relaxin 1/2 |
| CD98 | HPR1 | pro Relaxin 2 |
| CD98hc | HPRT1 | Profilin1 |
| CD99 | HPV16 E1/E4 | Progesterone Receptor |
| CD99R | HPx1 | Prohibitin |
| Coagulation Factor VII | DSCAM-L1 | Eph Receptor A5 |
| CXCL1/2/3 | FLRT1 | Ephrin B2 |
| DDR2 | Frizzled-6 | CD316 |
| DPCR1 | Glypican1 | Kremen1 |
| Dipeptidyl peptidase 6 | IGSF4B | Eph Receptor B1 |
| Epithelial membrane protein 3 | IL-1R9 | PlexinB3 |
| Endoglycan | BAZ2B | DMBT1 |
| Calgranulin C | BRD4 | FcRn |
| FATP2 | Kell | LIMPII |
| FATP5 | Kremen2 | MUCDHL |
| FcRLB | LAX1 | Patched1 |
| GLP-2R | CD85c | SLC39A4 |
| GLUT3 | MIF | IGSF4A |
| Glypican6 | Neprilysin2 | PRAT4B |
| GPR-22 | OBCAM | HHV8-ORF74 |
| GPR-37 | PlexinC1 | 4E-BP1 Phospho (Thr36/45) |
| GPR-37L1 | RGM-B | 4E-BP1 Phospho (Thr69) |
| INSRR | Wilmsâ€™ Tumor protein 1 | DCAR1 |
| LINGO1 | Xg | Von Hippel-Lindau |
| LINGO2 | DCBLD2 | Isotype Control |
| mGluR2 | ASAM | Granzyme M |
| mGluR7 | Desmocollin1 | REA Isotype Control |

TABLE 8-continued

Cell surface markers for use with the hydrogel particles described herein.

| | | |
|---|---|---|
| MMP25 | Frizzled-3 | CD300LG |
| Neuromedin B Receptor | MMP24 | MR1 |
| NRAGE | TOR | CD327 |
| Osteoactivin | WNT3a | B7-H6 |
| Porimin | Glypican5 | CLEC4G |
| Prokineticin Receptor 1 | Jagged1/Jagged2 | BATF3 |
| Prominin2 | Pax3 | IL-38 |
| Semaphorin 3A | CELSR2 | Monocarboxylic Acid Transporter 1 |
| SLAP-130 | Cyclin D1/D2 | MC5R |
| Somatostatin Receptor 5 | PlexinA2 | TCF7 |
| SCARF1 | TAFA5 | TM4SF1 |
| STAMP2 | FR4 | GPR-49 (CRL Region) |
| TAFA3 | CD315 | CD156a |
| TAFA4 | NKG2I | ADAM33 |
| TM4SF18 | RAMP2 | ADAMTS13 |
| Tuberous Sclerosis 1 | TNFRH3 | CCL16 |
| TCF8 | Biotin | CXCL17 |
| CMG2 | GPVI | Deltex1 |
| IL-17D Receptor | MS4A4B | FBXO15 |
| Macrophage Stimulating Protein Receptor | PIR-B | GPR34 |
| Siglec-11 | Semaphorin 4F | GPRC5A |
| Syndecan3 | IL-1F6 | Proinsulin |
| TGF-β2R3 | CD39L3 | JAK1 |
| CD85e | Contactin 3 | MEP1A |
| SOX7 | CLEC4B | Hypocretin receptor 2 |
| Activin A Receptor Type IA | MC3R | p70S6K |
| Carbohydrate Sulfotransferase 15 | PGRP-L | RAE-1Îμ |
| CD300b | PLET1 | STRA6 |
| CELSR3 | ADAM9 | Fcβ3RIIA |
| Coagulation Factor II | AMIGO3 | Insulin R/IGF-I R Heterotetramer |
| DC-SCRIPT | CD99-L2 | SPARCL1 |
| CD79Î ± cy | CD92 | XBP1 |
| Prokineticin 1 | SULT1A1 | XBP1 (COOH terminus) |
| Prokineticin 2 | SULT1A3/SULT1A4 | XBPs |
| Prolactin | SULT1C2 | XCL1 |
| ProMBP1 | SULT2A1 | XIAP |
| Prostaglandin D2 Receptor | SUMO1 | XPC |
| Prostaglandin dehydrogenase 1 | SUMO2 | XPNPEP3 |
| Prostaglandin E Receptor EP3 | SUMO3 | XRCC2 |
| Prostate Cell Surface Antigen | SUN1 | XTP4 |
| Prostate Specific Antigen | Suppressor of Fused | YAP1 |
| Prostatic Acid Phosphatase | SUPT16H | YB1 |
| Proteasome 20S C2 | Survivin | YES1 |
| Proteasome 20S Î ± 2 | Survivin Phospho (Thr34) | YY1 |
| Proteasome 20S Î ± 3 | SV40 Large T and Small t Antigens | ZAP-70 |
| Proteasome 20S Î ± 5 | SWC1a | ZAP-70 (pY292) |
| Proteasome 20S Î ± 6 | SWC6 | ZAP-70 (pY319) |
| Proteasome 20S Î ± 7 | SYBL1 | ZAP-70 (pY319)/ Syk (pY352) |
| Proteasome 20SÎ ± 1/2/3/5/6/7 | Syk | ZBP-1 |
| Protein A | Syk (pY348) | ZIPK |
| Protein G | Synapsin I | ZO-1 (Mid) |
| Protein Kinase D2 | Synapsin II | ZONAB (Mid) |
| Protein Phosphatase 1β2 | Synaptojanin2 | Zyxin |
| Protein phosphotase inhibitor 1 | Synaptophysin | IL-33R |
| Protein S | Syndecan4 | Globo H |
| Proteinase Activated Receptor 4 | SynGAP | CCL8 |
| Prothrombin | Synip | Siglec-G |
| PSA-NCAM | Syntaxin | CD307e |
| PSD95 | Syntaxin6 | CLEC6 |
| Pseudomonas Aeruginosa | Syntrophin | Snail1 |
| PSMA | SYWC | SMAD1 (pS463/pS465)/ SMAD8 (pS465/pS467) |
| PSMD14 | T cells (pan reactive) | SMAD2 (pS465/pS467)/ SMAD3 (pS423/pS425) |
| Psoriasin | T Lymphocytes | GSK-3β2 (pY216) |
| PTAFR | T- and B-Cell Activation Antigen | NKX6.1 |
| PTBP1 | T7 tag | FAK (pY397) |

TABLE 8-continued

Cell surface markers for use with the hydrogel particles described herein.

| | | |
|---|---|---|
| PTEN | TAB1 | Btk (pY223)/Itk (pY180) |
| PTGER2 | TACE | ERK3 |
| PTGER4 | TACI | CD276β |
| PTHLH | TAF172 | MCP-3 |
| PTK7 | TAF250 | FcμR |
| PTP1B | TAG72 | CD238 |
| PTP4A2 | Talin1 | beta2 Microglobulin [b, c] |
| PTPS | Talin2 | Nucleostemin |
| PTPγ/4 | Tamm Horsfall (Uromucoid) | GPR-49 (Central LRR) |
| PTRH2 | TANK1 | GPR-49 (N-Terminal) |
| PU.1 | TAP1 | Phospholipase C β4 |
| PU60 | TAP2 | coilin |
| PUMA | TARDBP | HNF1β |
| PUMAγ | TARP | Trinitrophenal |
| Pumilio1 | Tartrate-resistant acid phosphatase | Annexin VII |
| Pumilio2 | TAS1R1 | CD301a |
| PXR | Tau | CD301b |
| PYCARD | TBA1B | mTOR (pS2448) |
| Pygopus2 | Tbet | PI16 |
| Pyk2 | TBK1 (pS172) | MSC (W5C5) |
| Pyk2 (pY402) | TBX1 | LAMP5 |
| Pyruvate Dehydrogenase E1α | TC10 | GPR-19 |
| Pyruvate Dehydrogenase E2 | TCF3 | FPRL2 |
| Pyruvate Dehydrogenase E2/E3bp | TCF7L1 | CXCL5 |
| q2 | TCF7L2 | PAR2 |
| Qa1(b) | TCL1 | PDGF-Rα |
| Qa2 | TCP1α | ULBP6 |
| RAB11A | TCP1β | ULBP2/5/6 |
| RAB25 | TCR | IL-17B Receptor |
| RAB27A | TCR DO11.10 | ULBP3 |
| RAB4 | TCR HY | Arginase 1 |
| RAB5a | TCR Vα11 | Alkaline Phosphatase |
| RAB9 | TCR Vα11.1/11.2b, d | ULBP3 |
| Rac1 | TCR Vα2 | TrkB |
| Rac1/Cdc42 | TCR Vα24 | Osteocalcin |
| RAD17 | TCR Vα24-Jα18 | IL-22Rα1 |
| RAD17 Phospho (Ser645) | TCR Vα3.2 | APJ |
| RAD23A | TCR Vα3.2b, c | IFN-α/β Receptor Subunit 2 |
| RAD51 | TCR Vα7.2 | FGFR3 |
| RAD54 | TCR Vα8 | SR-A1 |
| RAD9A | TCR Vα8.3 | Rae-1 (pan) |
| Radixin | TCR Vβ1 | CXCL12 |
| RAE-1γ | TCR Vβ10a | TREM2 |
| RAE-1δ | TCR Vβ10b | Brachyury |
| RAF1 | TCR Vβ11 | CLEC5A |
| RAGE | TCR Vβ12 | Integrin α7 |
| RAIDD | TCR Vβ12b | Mer |
| Rainbow Trout Ig | TCR Vβ13 | XCR1 |
| RalBP1 | TCR Vβ13.1 | AML2 |
| RanBP9 | TCR Vβ13.2 | von Willebrands factor A2 |
| RanGAP1 | TCR Vβ13.6 | MMP7 |
| RAP1A/RAP1B | TCR Vβ14 | GLP-1R |
| RAP1GAP | TCR Vβ16 | FR1 |
| Raptor | TCR Vβ17 | IL-1RAcP |
| RARα | TCR Vβ17α | Claudin-6 |
| RAS | TCR Vβ18 | Leptin Receptor |
| RASGAP | TCR Vβ2 | Caherin 6 |
| RASGRF1 | TCR Vβ20 | IL-1R type II |
| RASSF1A | TCR Vβ21.3 | Nectin4 |
| Rb | TCR Vβ22 | Delta like protein 3 |
| Rb (a.a. 332-344) | TCR Vβ23 | ChemR23 |
| Rb (pS780) | TCR Vβ3 | GPR-39 |
| Rb (pS807/pS811) | TCR Vβ4 | CD158b2 |
| RbAp46 | TCR Vβ5 | IL-10Rα |
| RbAp48 | TCR Vβ5.1 | LRIG1 |
| RBC | TCR Vβ5.1/5.2 | Neuropilin2 |
| RBC (Polyclonal Rabbit) | TCR Vβ5.2 | IL-10Rβ |
| RBM35A | TCR Vβ5.3 | IL-18Rβ |
| RBP4 | TCR Vβ6 | GPR-44 |
| RBX1 | TCR Vβ7 | Eph Receptor B2 |
| RCC1 | TCR Vβ7.1 | Glypican3 |
| RcRL6 | TCR Vβ7.2 | IFN-γR2 |
| Red Blood Cell | TCR Vβ8 | IL-17C Receptor |
| Relaxin 1 | TCR Vβ8.1/8.2 | BMPR1B |
| Relaxin 1/2 | TCR Vβ8.2 | IL-31RA |

TABLE 8-continued

Cell surface markers for use with the hydrogel particles described herein.

| | | |
|---|---|---|
| Relaxin 2 | TCR VÎ²8.2/8.3 | OCIL |
| RelB | TCR VÎ²8.2/8.4 | Frizzled-7 |
| RELMÎ² | TCR VÎ²8.3 | IL-26 |
| RELT | TCR VÎ²8.5 | GPR-15 |
| Renin | TCR VÎ²9 | PlexinD1 |
| RENT1 | TCR VÎ³1.1 | CD158 |
| Reptin | TCR VÎ³1.1/Î³1.2 | FPR1 |
| Repulsive Guidance Molecule C | TCR VÎ³2 | HBEGF |
| Resistin | TCR VÎ³3 | Vitamin D3 |
| REST | TCR VÎ³9 | PlexinB1 |
| Ret | TCR VÎ´1 | Somatostatin Receptor 2 |
| Reticular Fibroblasts and Reticular Fibres | TCR VÎ´2 | OV-6 |
| Reticulon1A | TCR VÎ´4 | CXCL16 |
| Reticulum Cells | TCR VÎ´6.3/2 | Siglec-E |
| Retinoblastoma 1 | TCR Î± | EDG5 |
| RFLAT1 | TCR Î± ± Î² | Ninjurin-1 |
| RFP | TCR Î² | Integrin Î± ± 9 |
| RGS6 | TCR Î³Î´ | MHC Class II (I-Ed/j/k/p/r/u/v) |
| RGS7 | TCR Î¶ | ThB |
| RGS9 | TCTP | MAP-2 (2a & 2b) |
| RHEB | TdT | IgM Î¼-chain |
| Rho | Tec | MHC Class I (H-2b/p) |
| RhoA | TEF1 | MHC Class I (H-2s/p/q/d/u/r) |
| RHOC | TEM8 | MHC Class I (H-2s/f) |
| RhoGAP | Tenascin C | CDw60 |
| RhoGDI | TER119 | Bad Phospho (Ser112) |
| RIAM | TERF2 | Caspase 3 Cleaved (Asp175) |
| RICTOR | Terminal-Deoxynucleotidyl Transferase | Chk1 Phospho (Ser345) |
| RIG1 | TERT | Chk2 Phospho (Thr68) |
| RIP1 | Tetranectin | Cyclin D1 Phospho (Thr286) |
| RIP2 | TFF3 | cFos Phospho (Ser32) |
| Rituximab | TFIIB | FosB |
| RLA DQ | TGF-Î² | GSK-3Î² (pSer9) |
| RLA DR | TGF-Î²1 | Histone H3 Acetylated (Lys9) |
| RNA polymerase II | TGF-Î²3 | HS1 Phospho (Tyr397) |
| RNA polymerase II CTD repeat YSPTSPS | TGF-Î²R1 | Hsp27 Phospho (Ser82) |
| RNASE-L | TGF-Î²R2 | ID3 |
| RNASE1 | TGN38 | CD221Î² |
| RNF144B | TGN46 | Phospho-IRAK4 (Thr345/Ser346) |
| RNF168 | THAP11 | Phospho-cJun (Ser73) |
| RNF36 | THEMIS | S6 (pS240/pS244) |
| RNPEP | Thioredoxin | Syk (pY525/pY526) |
| ROCK1 | Thioredoxin Reductase 1 | C23 |
| ROR1 | ThPOK | Hemoglobin Î² |
| ROR2 | Thrombin Receptor | CD221Î± |
| RORÎ± | Thrombocyte | p27 |
| RORÎ³ | Thrombospondin | cJun Phospho (Ser63) |
| ROS | Thymidine Kinase 1 | PPARÎ³ |
| RPA32/RPA2 | Thyroglobulin | ENPP1 |
| RPA70 | TIA-1 | PILRÎ± |
| RPS6 | TIAM2 | PILRÎ² |
| RSF1 | Tie1 | Twist1 |
| RSK1 p90 | Tie2 (pY1102) | Cadherin M |
| RSK2 | Tie2 (pY992) | CD302 |
| RSK3 | TIF1Î² Phospho (Ser473) | CD66d |
| RSK4 | TIGIT | CLEC14A |
| RT1A | Tim1 | CD242 |
| RT1Aa | Tim2 | Syndecan2 |
| RT1Aa, b | Tim3 | IL-32Î± |
| RT1Aa, b, l | Tim3 Fc Fusion Protein | CDO |
| RT1Ac | Tim4 | Cryptic |
| RT1Au | Tim50 | Endothelin B Receptor |
| RT1B | Timeless | FR3 |
| RT6.1 | TIMP1 | IGSF3 |
| RT6.2 | TIMP2 | CD85f |
| Ryanodine Receptor | TIP49A | Matriptase |
| RYK | TIRAP | MCEMP1 |
| RyR | TIS11b | mGluR4 |
| S-Tag | TL1A | Stabilin1 |
| S100A1 | TLK1 | Stabilin2 |
| S100A10 | TLR11 | Cadherin 13 |
| S100A13 | TLR12 | GPR-109A |

TABLE 8-continued

Cell surface markers for use with the hydrogel particles described herein.

| | | |
|---|---|---|
| S100A4 | CD285 | TSPAN8 |
| S100A6 | TLR7 | Reg1A |
| S100A9 | TLR8 | Cadherin 12 |
| S100Î± | TMEFF2 | ECE1 |
| S100Î ± 2 | TMPS2 | FABP5 |
| s100Î² | TMSA | IGSF4C |
| S6 (pS235/pS236) | TMTSP | Trem-like 1 |
| S6 (pS240) | TNAP | Activin A Receptor Type IIA |
| S6 (pS244) | TNAP3 | ALK7 |
| S6K | TNF-Î± | BCAM |
| SAA4 | TNF-Î² | BLAME |
| Sall4 | TNFR Related Protein | CEACAM4 |
| *Salmonella Paratyphi* A | TNPO3 | Claudin-3 |
| *Salmonella Typhimurium* | Tollip | CLP24 |
| Salmonid Ig (H and L chain) | TOMM20 | CRHR1 |
| Salmonid Ig (H chain) | TOMM22 | DC-STAMP |
| SAM68 | TOP1 | Eph Receptor B3 |
| SAMD2 | TOP2A | FATP4 |
| SAP | TOP2B | FcRL1 |
| SARA | TORC2 | FcRL2 |
| SATB1 | Torsin A | FcRL3 |
| SATB2 | TOX | FSH-R |
| SC5A5 | TPH1 | Gi24 |
| SC6A4 | TPPP | Histamine H1 Receptor |
| SCAI | TPTE | Neu5Gc |
| SCD1 | TR11B | Lin28A |
| Scramblase1 | TRA-1-60 | IL-33RÎ± |
| SCY1-like 3 | TRA-1-60R | ATM (pSer1981) |
| SDF1 | TRA-1-81 | Integrin Î ± 8 |
| SDF1Î± | TRA-2-49 | Integrin Î²7 |
| SDHA | TRA-2-54 | Integrin Î²8 |
| SDHB | TRADD | CD158k |
| Secretory component | TRAF2 | KOR |
| Securin | TRAF4 | CD85i |
| SELP | TRAF5 | LRIG3 |
| Sema4A | TRAF6 | LRP4 |
| Sema7A | TRAM2 | MMP16 |
| SENP1 | Transferrin | MS4A4A |
| SEPP1 | Transglutaminase | NAALADase-like 2 |
| SERCA2 | Transglutaminase2 | Neuropeptide Y receptor t ype 1 |
| SerpinB1 | Transketolase | Oncostatin M Receptor Î² |
| SerpinB2 | TRAP1 | MS4A3 |
| SerpinB6 | TRAPPC2 | PEAR1 |
| Sestrin1 | TRAPÎ± | PEDF Receptor |
| SFRP2 | Trem-like 2 | PlexinA4 |
| SGK1 | Trem-like 4 | Protocadherin1 |
| SHC1 | TRIB2 | ROBO2 |
| *Shigella Boydii* | TRIB3 | ROBO4 |
| SHIP1 | TRIM | EDG8 |
| SHP1 | TRIM25 | Scavenger receptor A5 |
| SHP2 | TRIM29 | Semaphorin 4A |
| SHP2 (pY542) | TRK | Semaphorin 4B |
| SIAH2 | TrkA | Semaphorin 6A |
| SIGIRR | TrkC | Siglec-16 |
| Siglec-10 | Trop2 | Somatostatin Receptor 3 |
| Siglec-8 | Tropomyosin 1 | STING |
| Siglec-9 | TROY | GPBAR1 |
| Siglec-F | TRPC6 | TM4SF4 |
| Siglec-H | TRPM2 | TMEM87A |
| SIK2 | TRPM8 | TSPAN2 |
| SIRT1 | TRX1 | VEGF-R1, 2, 3 |
| SIRT2 | *Trypanosoma brucei* Major Lysosomal Protein | ADAM15 |
| SIRT3 | *Trypanosoma brucei* procyclin (EP) | Calreticulin2 |
| SIRT5 | *Trypanosoma congolense* procyclin | Complement Factor H-related 4 |
| SIT1 | *Trypanosoma cruzi* LPG | CXCL6 |
| SIX2 | TSC2 Phospho (Ser664) | CD158a/h/b2/f/g |
| SKP1A | TSC2 Phospho (Thr1462) | Ea52-68 peptide bound to I-Ab |
| SLA-DR | TSG101 | HLA-Bw4 |
| Slan | TSHR | ATF1 Phospho (Ser63) |
| SLC1A3 | TSLP | Epiregulin |
| SLC1A7 | TSLP Receptor | FATP1 |
| SLC22A1 | TSPO | Fibromodulin |

TABLE 8-continued

Cell surface markers for use with the hydrogel particles described herein.

| | | |
|---|---|---|
| SLC22A5 | TTF1 | Furin |
| SLC26A6 | Tubb3 | Galanin |
| SLC26A7 | Tuberin | IL-11 |
| SLC30A4 | Tubulin α | CD306 |
| SLC39A11 | Tubulin α 1B | MFG-E8 |
| SLC4A3 | Tubulin α 4a | MINA |
| SLC6A19 | Tubulin α 3E | Oct4A |
| SLC6A6 | Tubulin α 8 | OLIG1, 2, 3 |
| SLC7A10 | Tubulin β | Oncostatin M |
| SLC7A14 | Tubulin β class III | Semaphorin 3E |
| SLC7A3 | Tubulin β4 | Slug |
| SLC7A8 | Tubulin γ | SOX3 |
| SLC8A2 | tumor antigens of epithelial origin | STYK1 |
| SLC9A6 | Twist2 | LTBP1 |
| SLP76 | TXNIP | TIMP3 |
| SLP76 (pY128) | TYK2 | VAP-B |
| SM22α | TYMS | WNT9a |
| SMAC | Tyro3 | 5HT2C |
| SMAC3 | Tyrosinase | AATK |
| SMAD1 | Tyrosine Hydroxylase | ACLP |
| SMAD1 (pS463/465) | UACA | ADAMTS15 |
| SMAD1/5 | UBA52 | alpha 1B Adrenoreceptor |
| SMAD1/9 | UBC9 | APLP1 |
| SMAD2 | UBE2 | Fluorescein/Oregon Green |
| SMAD2/3 (pS465/467) DELETE | UBE2L3 | RXR-β |
| SMAD3 | UBE2L6 | L3MBTL3 |
| SMAD4 | UBE2M | CCL1 |
| SMAD5 | UBE2N | PRDM4 |
| SMAD6 | UBF | ACTH |
| SMC1 | UBF1 | PDZ binding kinase |
| SMC1L1 | Ubiquitin | HuC/HuD neuronal protein |
| SMN | UBK63 | TDRD3 |
| Smoothelin | UCH37 | EP300 |
| SMURF2 | UCK | Carbonic Anhydrase VI |
| SNAP25 | UCP2 | Cholecystokinin A Receptor |
| SNX1 | UCP3 | CCL23 |
| SOAT1 | UFM1 | CD1e |
| SOCS1 | ULBP1 | Chondrolectin |
| SOCS2 | ULBP2 | Chordin-Like 2 |
| SOCS3 | ULBP4 | Claudin-10b |
| SOCS6 | ULK3 | Claudin-11 |
| SOD2 | UNC5A | Claudin-12 |
| Sodium Potassium ATPase | UNC5B | Claudin-17 |
| Sonic Hedgehog | UNG | CLEC2A |
| Sortilin | uPA | Spi-B |
| SOSC3 | UQCRC1 | TRAM |
| SOX1 | UQCRC2 | Carboxypeptidase E |
| SOX10 | Urm1 | Islet Cell Autoantigen 1 |
| SOX17 | URP2 | Patched2 |
| SOX18 | USF1 | ST8SIA2 |
| SOX2 | USP11 | AML1 (pS249) |
| SOX2 (COOH terminus) | USP13 | AMPKβ1 (pS182) |
| SOX2 (NH2 terminus) | USP22 | BRF1/2 |
| SOX9 | USP28 | Histone H3 Phospho (Thr11) |
| SP-D | USP7 | MEK1 (pT286) |
| Sp1 | UTF1 | MMP16 |
| Sp3 | V5 tag | MNK Phospho (T197/T202) |
| Spectrin α 1 | VAMP5/8 | NUMB |
| SPHK1 | VAP1 | Hsp27 Phospho (Ser78) |
| Spt16 | VASA | PKCδ (pT538) |
| Src (pY418) | VASP | SIRT1 (pS47) |
| SREBP1 | VAV1 | ZAP-70 (pY493) |
| ssDNA | VAV2 | ZAP-70 (pY315/pY319) |
| SSEA3 | VAV3 | sRAGE |
| SSEA4 | VDAC1 | mCherry |
| SSEA5 | VEGF | PI 3 Kinase regulatroy subunit α |
| SSH3BP1 | VEGF-120 | TIMP4 |
| SSR2 | VEGF-A | SRC |
| SSR5 | VEGF-R1 | ZAP-70 (pT493) |
| SSRP1 | VELIS-3 | TSC2 Phospho (S939) |
| SSX2IP | VGLU1 | RagC |
| Stat1 | Villin | SHIP2 |
| Stat1 (N-Terminus) | Vimentin | MKK4 (pS257) |
| Stat1 (pS727) | Vinculin | CD79a (pY182) |
| Stat1 (pY701) | Viperin | TRAF1 |

TABLE 8-continued

| Cell surface markers for use with the hydrogel particles described herein. | | |
|---|---|---|
| Stat1Î± | VIPR1 | EVI1 |
| Stat2 | Vitamin D Binding protein | SRC3 |
| Stat3 | Vitamin D Receptor | SOX11 |
| Stat3 (pS727) | Vitronectin | IL-17F homodimer |
| Stat3 (pY705) | VMAT2 | CCRL1 |
| Stat4 | vMyb/cMyb | FOXP2 |
| Stat4 (pY693) | von Willebrands factor | IFNAR2 |
| Stat5 | VRK1 | REA Control |
| Stat5 (pY694) | VSV-G tag | CD228 |
| Stat5a | WAPL | Muc-13 |
| Stat5b | WASP | P2X7R |
| Stat6 | WC14 | Btk (pY223/Itk (pY180) |
| Stat6 (pY641) | WC15 | CD248 |
| Stathmin/Op18 | WCD44 | GILT |
| Phospho (Ser16) | | |
| Stathmin1 | WIP (pS488) | Recoverin |
| Stefin B | WNT1 | Cardiac Troponin I |
| Stem Cell Factor | WNT16 | PTF1Î± |
| STIM1 | WNT2 | NKX2.2 |
| STK3 | WNT5B | HLA-B7/B27 |
| STK33 | WNT6 | Myosin light chain 2a |
| STK39 | WSTF | Myosin light chain 2v |
| STOM | WWOX | Epithelial Antigen |
| STRO1 | Xanthine Oxidase | |

In one embodiment, a plurality of hydrogel particles is used to determine the dynamic range and/or sensitivity of detection of a particular cell surface marker or combination thereof on a population of target cells. For example, the population of hydrogel particles can be tuned to have the SSC and/or FSC profile of the target cell, and subpopulations of the hydrogel particle are derivatized with a specific number of copies of a cell surface marker, e.g., a cell surface receptor, or a domain thereof, for example, an epitope binding region thereof. For example, individual subpopulations of hydrogel particles can each be derivatized to have a unique number of copies, e.g., one subpopulation will contain 100 copies of a cell surface marker, a second subpopulation will contain 1,000 copies of the same cell surface marker, a third subpopulation will contain 10,000 copies of the same cell surface marker, etc. The populations of hydrogel particles are fluorescently stained for the respective cell surface marker and fluorescence is detected for hydrogel particles in each subpopulation. In this regard, the subpopulations of hydrogel particles can be used to generate a standard curve of fluorescence emission for target cells with the respective cell marker. The cell surface marker can be any of the cell surface markers provided thereof, or binding regions thereof, or a cell surface marker known to one of ordinary skill in the art.

Hydrogel particles of the disclosure behave similarly to target cells in procedures such as staining and analysis by flow cytometry or FACS. For example, in one embodiment, a hydrogel particle has one or more optical properties substantially similar to one of the cell types set forth in Table 4, Table 5, Table 6, or Table 7.

In some embodiments, a target cell is an immune cell. Non-limiting examples of immune cells include B lymphocytes, also called B cells, T lymphocytes, also called T cells, natural killer (NK) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor infiltrating (TIL) cells, gene modified immune cells including hybridomas, drug modified immune cells, and derivatives, precursors or progenitors of any of the cell types listed herein.

In some embodiments, a target cell encompasses all cells of a particular class of cell with shared properties. For example, a target cell can be a lymphocyte, including NK cells, T cells, and B cells. A target cell can be an activated lymphocyte.

In some embodiments, a target cell is a primary cell, cultured cell, established cell, normal cell, transformed cell, infected cell, stably transfected cell, transiently transfected cell, proliferating cell, or terminally differentiated cells.

In one embodiment, a target cell is a primary neuronal cell. A variety of neurons can be target cells. As non-limiting examples, a target cell can be a primary neuron; established neuron; transformed neuron; stably transfected neuron; or motor or sensory neuron.

In other embodiments, a target cell is selected from the group consisting of: primary lymphocytes, monocytes, and granulocytes.

A target cell can be virtually any type of cell, including prokaryotic and eukaryotic cells.

Suitable prokaryotic target cells include, but are not limited to, bacteria such as *E. coli*, various *Bacillus* species, and the extremophile bacteria such as thermophiles.

Suitable eukaryotic target cells include, but are not limited to, fungi such as yeast and filamentous fungi, including species of *Saccharomyces, Aspergillus, Trichoderma*, and *Neurospora*; plant cells including those of corn, sorghum, tobacco, canola, soybean, cotton, tomato, potato, alfalfa, sunflower, etc.; and animal cells, including fish, birds and mammals. Suitable fish cells include, but are not limited to, those from species of salmon, trout, tilapia, tuna, carp, flounder, halibut, swordfish, cod and zebrafish. Suitable bird cells include, but are not limited to, those of chickens, ducks, quail, pheasants and turkeys, and other jungle foul or game birds. Suitable mammalian cells include, but are not limited to, cells from horses, cows, buffalo, deer, sheep, rabbits, rodents such as mice, rats, hamsters and guinea pigs, goats, pigs, primates, marine mammals including dolphins and whales, as well as cell lines, such as human cell lines of any tissue or stem cell type, and stem cells, including pluripotent and non-pluripotent, and non-human zygotes.

Suitable cells also include those cell types implicated in a wide variety of disease conditions, even while in a nondiseased state. Accordingly, suitable eukaryotic cell types include, but are not limited to, tumor cells of all types (e.g., melanoma, myeloid leukemia, carcinomas of the lung, breast, ovaries, colon, kidney, prostate, pancreas and testes), cardiomyocytes, dendritic cells, endothelial cells, epithelial cells, lymphocytes (T-cell and B cell), mast cells, eosinophils, vascular intimal cells, macrophages, natural killer cells, erythrocytes, hepatocytes, leukocytes including mononuclear leukocytes, stem cells such as hematopoietic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. In certain embodiments, the cells are primary disease state cells, such as primary tumor cells. Suitable cells also include known research cells, including, but not limited to, Jurkat T cells, NIH3T3 cells, CHO, COS, etc. See the ATCC cell line catalog, hereby expressly incorporated by reference.

In some embodiments, a target cell is a tumor microvesicle or tumor macrovesicle. Tumor microvesicles, also known as tumor-secreted microvesicles or tumor-secreted exosomes, can be found in circulating blood and may have immune-suppressive activities. Tumor microvesicles typically range in size from 30-200 nm in diameter. Larger tumor micro vesicles may be referred to as tumor macro vesicles, and can range in size from 3-10 μm in diameter.

The hydrogel particles described herein can be employed in any flow cytometer known to those of ordinary skill in the art. For example, one or more of the flow cytometers provided in Table 9 below are amenable for use with the hydrogels and assays described herein.

TABLE 9

Instruments for use with embodiments described herein

| Instrument | Manufacturer |
| --- | --- |
| MACSQuant ® Analyzer 10 | Miltenyi |
| MACSQuant ® VYB | Miltenyi |
| BD FACSCalibur ™ | BD Biosciences |
| BD FACSCanto ™ High Throughput Sampler | BD Biosciences |
| BD FACSCanto II | BD Biosciences |
| BD FACSCanto ™ | BD Biosciences |
| BD FACSCount ™ | BD Biosciences |
| BD Accuri ™ C6 | BD Biosciences |
| BD LSRFortessa ™ X-20 | BD Biosciences |
| BD FACSCanto ™ II | BD Biosciences |
| BD LSR II | BD Biosciences |
| BD LSRFortessa ™ | BD Biosciences |
| BD FACSVerse ™ | BD Biosciences |
| BD FACSAria ™ Fusion | BD Biosciences |
| BD FACSAria ™ | BD Biosciences |
| BD FACSAria ™ III | BD Biosciences |
| BD FACSJazz ™ | BD Biosciences |
| BD Influx ™ | BD Biosciences |
| Fortessa X50. | BD Biosciences |
| FlowSight Flow Cytometer | Millipore |
| Guava easyCyte 6-2L Benchtop Flow Cytometer | Millipore |
| guava easyCyte 5HT Benchtop Flow Cytometer | Millipore |
| guava easyCyte 8 Benchtop Flow Cytometer | Millipore |
| guava easyCyte 5 Benchtop Flow Cytometer | Millipore |
| guava easyCyte 8HT Benchtop Flow Cytometer | Millipore |
| guava easyCyte 6HT-2L Benchtop Flow Cytometer | Millipore |
| ImageStreamX Mark II Imaging Flow Cytometer | Millipore |
| Muse Cell Analyzer | Millipore |

TABLE 9-continued

Instruments for use with embodiments described herein

| Instrument | Manufacturer |
| --- | --- |
| guava easyCyte 12HT Benchtop Flow Cytometer | Millipore |
| guava easyCyte 12 Benchtop Flow Cytometer | Millipore |
| S3e ™ Cell Sorter | Bio-Rad |
| S3 ™ Cell Sorter | Bio-Rad |
| Avalon Cell Sorter | Bio-Rad / Propel Labs |
| CytoFLEX | Beckman Coulter |
| FP 1000 Cell Preparation System | Beckman Coulter |
| Vi-CELL ® XR Cell Viability Analyzer | Beckman Coulter |
| FC 500 Series | Beckman Coulter |
| MoFlo ® Astrios ™ | Beckman Coulter |
| Coulter Epics XL ™ and XL-MCL ™ | Beckman Coulter |
| Gallios ™ | Beckman Coulter |
| CyAn ™ ADP Analyzer | Beckman Coulter |
| Attune ™ Acoustic Focusing Cytometer | Life Technologies |
| Attune ® NxT Acoustic Focusing Cytometer | Life Technologies |
| EVOS | Life Technologies |
| Countess II FL | Life Technologies |
| EC800 Cell Analyzer | Sony |
| SH800 Cell Sorter | Sony |
| SP6800 Spectral Analyzer | Sony |
| SY3200 Cell Sorter | Sony |
| A50-Micro' | Apogee Flow Systems |
| A50-Universal | Apogee Flow Systems |
| Auto40 | Apogee Flow Systems |
| FlowSight | Amnis |
| ImageStream$^X$ Mark II | Amnis |
| JSAN | Bay Bioscience |
| CytoSense | CytoBuoy |
| CytoSub | CytoBuoy |
| CytoSense | CytoBuoy |
| CytoBuoy | CytoBuoy |
| Cytonome Viva ™ G1 | CYTONOME |
| GigaSort ™ | CYTONOME |
| Hydris | CYTONOME |
| Agilent 2100 Bioanalyzer | Agilent Technologies |
| NovoCyte | ACEA Biosciences |
| CyFlow ® Space | Partec technology |
| CyFlow ® Cube 8 | Partec technology |
| CyFlow ® Cube 6 | Partec technology |
| CyFlow ® Ploidy Analyser | Partec technology |
| CyFlow ® Counter | Partec technology |
| CyFlow ® miniPOC | Partec technology |
| CyFlow ® SL | Partec technology |
| CyFlow ® Sorter | Partec technology |
| CyFlow ® CCA | Partec technology |
| CyFlow ® Oenolyser | Partec technology |
| NucleoCounter ® NC-3000 ™ | Chemometec |
| NucleoCounter ® NC-250 ™ | Chemometec |
| NucleoCounter ® NC-200 ™—High Precision Cell Counter | Chemometec |
| HPC-100 Portable Flow Cytometer | Cronus Technologies Ltd |
| Cytell Cell Imaging System | GE Healthcare |
| MAGPIX | Luminex |
| Luminex ® 100/200 ™ System | Luminex |
| FLEXMAP 3D ® | Luminex |
| ImageXpress ® Velos Laser Scanning Cytometer | molecular devices |
| ClonePix ™ 2 | molecular devices |
| SpectraMax ® i3 | molecular devices |
| AQ1 Discrete Analyzer | SEAL Analytical Ltd. |
| AQ2 Discrete Analyzer | SEAL Analytical Ltd. |
| AQ400 Discrete Analyzer | SEAL Analytical Ltd. |
| AQUA 900 | SEAL Analytical Ltd. |

TABLE 9-continued

Instruments for use with embodiments described herein

| Instrument | Manufacturer |
|---|---|
| AA3 HR AutoAnalyzer | SEAL Analytical Ltd. |
| AA1 AutoAnalyzer | SEAL Analytical Ltd. |
| QuAAtro39 | SEAL Analytical Ltd. |
| Infralyzer 2000 | SEAL Analytical Ltd. |
| Technicon AutoAnalyzer II (AAII) | SEAL Analytical Ltd. |
| Technicon/Bran + Luebbe TrAAcs 800-2000 | SEAL Analytical Ltd. |
| Bran + Luebbe FIA Analyzer | SEAL Analytical Ltd. |
| BioSorter ® Large Particle Flow Cytometer | Union Biometrica, Inc. |
| COPAS ™ Large Particle Flow Cytometers | Union Biometrica, Inc. |
| Cellometer Mini Cell Counter | Nexcelom |
| Cellometer Auto T4 Cell Viability Counter | Nexcelom |
| Cellometer Auto X4 Cell Viability Counter | Nexcelom |
| Cellometer Auto 1000 Cell Viability Counter | Nexcelom |
| Cellometer Auto 2000 Cell Viability Counter | Nexcelom |
| Cellometer Vision CBA | Nexcelom |
| Celigo S | Nexcelom |
| NovoCyte ™ 1000 | ACEA |
| NovoCyte ™ 2000 | ACEA |
| NovoCyte ™ 2060 | ACEA |
| NovoCyte ™ 3000 | ACEA |
| HPC-100 | Handyem |
| S1000EXi | Stratedigm |
| SE520Xi | Stratedigm |
| Sysmex ® DI-60 | Sysmex |
| Cella Vision ® DM96 | Sysmex |
| Cella Vision ® DM1200 | Sysmex |
| Cytation | BioTek |
| EasyCell Assistant | Medica |
| IN Cell Analyzer | GE Healthcare |
| Fluorish List | |
| Big Blue | BD Biosciences |
| Kermit | Miltenyi |
| ac6 | BD Biosciences |
| srDAs | BD Biosciences |
| a | BD Biosciences |
| FACSCanto II Immunology | BD Biosciences |
| Test Cyt | Millipore |
| milt | Miltenyi |
| ac | BD Biosciences |
| ietest | BD Biosciences |
| Curiel's Aria | BD Biosciences |
| AttuneÂ ® Acoustic Focusing Cytometer Blue/Violet | Life Technologies |
| Medawar LSRII | BD Biosciences |
| Medawar Calibur | BD Biosciences |
| FACSAria INER | BD Biosciences |
| Attune R/A | Life Technologies |
| Fortessa | BD Biosciences |
| Aria | BD Biosciences |
| SORTER | BD Biosciences |
| Cyan | Beckman Coulter |
| LSR II | BD Biosciences |
| ARIA | BD Biosciences |
| Canto II | BD Biosciences |
| F09 - LSR Fortessa 1 | BD Biosciences |
| "The Hoff" | BD Biosciences |
| 6th Floor Hess Fortessa A | BD Biosciences |
| Cerebro BDFACSAriaII | BD Biosciences |
| Mystique BDFACSAriaII | BD Biosciences |
| Godzilla BDFACSAriaII | BD Biosciences |
| Wolverine BDFACSAriaII | BD Biosciences |
| Megatron BDFACSAriaII | BD Biosciences |
| Megatron BDFACSAriaII | BD Biosciences |
| Fortessa B | BD Biosciences |
| 6 colour Canto II | BD Biosciences |
| 10 colour LSR II | BD Biosciences |

TABLE 9-continued

Instruments for use with embodiments described herein

| Instrument | Manufacturer |
|---|---|
| 4 laser 13 colour Influx sorter | BD Biosciences |
| 14 colour X20 | BD Biosciences |
| SORP | BD Biosciences |
| FACSAria INER | BD Biosciences |
| LSR561 | BD Biosciences |
| Fortessa FCF UZH | BD Biosciences |
| LSR 2 B | BD Biosciences |
| LSRII-C | BD Biosciences |
| Cal 3 | BD Biosciences |
| Aria II A | BD Biosciences |
| LSR 16 | BD Biosciences |
| LSB Fortessa | BD Biosciences |
| IMMUN LSRII | BD Biosciences |
| IRC | BD Biosciences |
| UV LSR | BD Biosciences |
| 5 Laser Aria | BD Biosciences |
| Curiel's LSR II | BD Biosciences |
| LSR Fortessa | BD Biosciences |
| Mauzeroll Aria | BD Biosciences |
| Frenette | BD Biosciences |
| Fallon | Beckman Coulter |
| Galios | Beckman Coulter |
| LSRIIFortessa | BD Biosciences |
| FACSCanto II CLSB | BD Biosciences |
| LSR II SC | BD Biosciences |
| UNCA Fortessa | BD Biosciences |
| VERSE | BD Biosciences |
| ARIAII | BD Biosciences |
| ARIAIII | BD Biosciences |
| F09 - BD LSRFortessa | BD Biosciences |
| HMRI FACSCanto II A | BD Biosciences |
| HMRI FACSCantoII B (HTS) | BD Biosciences |
| HMRI Aria III | BD Biosciences |
| L2 | BD Biosciences |
| UoN Canto | BD Biosciences |
| LSRII M902 | BD Biosciences |
| Fortessa 1 | BD Biosciences |
| F05—FACSAria | BD Biosciences |
| F02—FACSAria III | BD Biosciences |
| F10—BD FACSAria III | BD Biosciences |
| F03—Guava | Millipore |
| Aria Blue 11 Color | BD Biosciences |
| Aria Red | BD Biosciences |
| Aria Orange | BD Biosciences |
| Aria Cyan | BD Biosciences |
| Aria Emerald | BD Biosciences |
| Aria Silver BSL3 | BD Biosciences |
| LSR Fortessa | BD Biosciences |
| LSR II Bldg 4 | BD Biosciences |
| LSR Fortessa bldg 4 | BD Biosciences |
| CANTO II Bldg 50 | BD Biosciences |
| 4 Laser LSR II | BD Biosciences |
| 5 Laser LSR II | BD Biosciences |
| FACSArray BL-2 | BD Biosciences |
| FACSCalibur | BD Biosciences |
| DUAL for long term studies | BD Biosciences |
| MoFlo 1095 Production only | Beckman Coulter |
| BL-2 FACSAria III sorter | BD Biosciences |
| Astrios BL-2 sorter | Beckman Coulter |
| Tessy | BD Biosciences |
| LSR II-1 | BD Biosciences |
| Fortessa | BD Biosciences |
| 4 laser AriaIII | BD Biosciences |
| LSRFortessa | BD Biosciences |
| UoN FACSAria II cell sorter | BD Biosciences |
| Door | Beckman Coulter |
| Fortessa | BD Biosciences |
| WCI—FACSAria I | BD Biosciences |
| LSRII Karp8 | BD Biosciences |
| Karp 8 | BD Biosciences |
| Canto | BD Biosciences |
| Aria sorter | BD Biosciences |
| DI lab | BD Biosciences |
| DI FACSAria | BD Biosciences |
| Constance | BD Biosciences |
| DI FACSAria III | BD Biosciences |

TABLE 9-continued

Instruments for use with embodiments described herein

| Instrument | Manufacturer |
|---|---|
| WCI_FACS Canto | BD Biosciences |
| MACSQuant 10 | Miltenyi |
| VAMC Memphis LSR | BD Biosciences |
| VAMC Memphis S3 | Bio-Rad |
| ARIA INER | BD Biosciences |
| Uhura | BD Biosciences |
| Kirk | BD Biosciences |
| Data | Millipore |
| Spock | BD Biosciences |
| McCoy | BD Biosciences |

Further to the above, current methods used to activate and subsequently expand immune cells (e.g., T-cells) in vitro lead to cell exhaustion or require multi-step processes to remove activation agents from culture due to incompatibility with long-term cell survival. Accordingly, the present disclosure provides methods for improving the in vitro activation and expansion of immune cells.

In an embodiment, the present disclosure further relates to the use of the above-described hydrogel particles, or modifications thereof, as synthetic biomolecule presenting particles. Generally, the synthetic biomolecule presenting particles herein may be referred to as synthetic particles, or more generally as hydrogel particles.

In embodiments, in order to be used as a biomolecule presenting particle, the particles may be functionalized. After the particles are formed, a biomolecule (or other stimulating factor or marker) can be attached to a surface of the particles using binding chemistries based on the particle composition (i.e., polymer). These biomolecules may be selected based on particular cell surface markers of interest. These markers of interest may be one or more cell surface markers, or fragments thereof, for example, extracellular portions thereof in the case of transmembrane proteins, for example. For instance, the biomolecules may be antibodies or antigen-binding fragments thereof related to the particular cell surface marker of interest. In another instance, the biomolecules may be one or more cell surface markers, extracellular portions or ligand binding regions thereof and may be attached to the particle via a free amine, free carboxyl and/or free hydroxyl group present on the surface of the particle. Functionalization of a particle with a cell surface molecule can also occur through a linker, such as by a streptavidin/biotin conjugate, a biotin/streptavidin conjugate, a streptavidin/biotin/streptavidin conjugate, and/or a biotin/streptavidin/biotin conjugate. For instance, when the particle comprises acrylamide, a streptavidin-biotin linkage can be exploited to attach particular biomolecules to the surface of the particles. Of course, other known binding/linkage methods can be used without departing from the spirit of the present disclosure.

In embodiments, the particles of the present disclosure may be particles with enhanced porosity. Compared to non-porous particles, the alteration of pore size distribution allows more surface area per unit hydrogel particle or more surface area per unit volume for advanced cell therapy. The porosity of the porous particle may be controlled by adjusting manufacturing parameters. For instance, the porosity may be controlled through the use of a porogen.

The generation of pores offers a number of advantages over nonporous structures. This includes enhanced nutrient transport and higher surface to area to volume ratio. This 3-dimensional scaffold mimics a bioreactor. This bioreactor is achieved by allowing the porous hydrogels to absorb water, maintain an optimal ion nutrient gradient, and maintain an optimal osmotic pressure which favors cellular growth and cell activation.

Generally speaking, any material that a) can phase separate (is not miscible) with the hydrogel matrix and b) does not get incorporated into/tethered to the hydrogel matrix and can be removed after formation of the hydrogel matrix can be used as a porogen for the synthesis of porous hydrogel particles. In this way, the porous hydrogel particle comprises a plurality of micropores, which are formed inherently by monomer polymerization, and a plurality of macropores, which are formed when the porogen is removed from the hydrogel particle. In embodiments, the plurality of micropores, which may be formed during polymerization of the monomer within the dispersed phase, may have an average diameter of between about 1 nm and about 20 nm and/or between about 2 nm and about 4 nm. In embodiments, the plurality of macropores may have an average diameter of between about 200 nm and about 2 μm. In embodiments, the macropore-laden hydrogel particle may have a diameter substantially similar to the hydrogel particles described elsewhere herein. For instance, the macropore-laden hydrogel particle may have a diameter of between about 1 μm and about 25 μm and/or between about 2 μm and about 5 μm. Moreover, similar to the hydrogel particles described earlier, the macropore-laden hydrogel particles may exhibit a Young's modulus of between about 0.2 kPa and about 400 kPa.

In some embodiments, the present disclosure refers to methods of producing particles comprising a dispersed monomer phase and a continuous suspension phase, such as oil. Embodiments of these methods recite the presence of a porogen mixed with the monomer phase. As noted in earlier portion of this disclosure, porogens may be immiscible within the monomer, and thus may be said to form a further dispersed phase within the monomer phase (i.e., where porogen may be considered the dispersed phase and the monomer phase would be considered a continuous phase). These embodiments could be described as an emulsion within an emulsion. For the purposes of this disclosure however, the monomer phase is referred to as the dispersed phase, regardless of whether it also includes porogens. The continuous phase refers to the suspension (e.g., oil) phase.

In embodiments, the monomer to be polymerized may be within a first phase and the porogen may be within a second phase. In embodiments, the porogen may be one or more of a porogen polymer, a water-soluble polymer, a salt, carbon black, a biodegradable polymer, a degradable polymer, seaweed polysaccharides, and a paraffin wax. In an embodiment, the salt comprises one or more of sodium chloride, ammonium bicarbonate, lithium chloride, zinc chloride, silicon dioxide, calcium carbonate, and combinations thereof. For example, calcium carbonate particles can phase separate in hydrogel and get washed away with a low pH buffer. In an embodiment, the porogen polymer comprises one or more of polyethylene glycol, poly(vinylpyrrolidone), polyvinyl alcohol, and combinations thereof. For instance, the porogen polymer may include polymers that are water soluble but also gel matrix polymer immiscible may also be used. For example, polyethylene glycol (PEG), which is water soluble, may be used because it is also immiscible with polyacrylamide, described above with reference to the hydrogel particles herein. As a porogen, inert, linear PEG polymer, for example, can be introduced in the water phase of our microfluidic synthesis of hydrogel particles. During the curing process, the linear PEG polymers, immiscible with the gel matrix polymer (poly acrylamide in this case), become phase separated with the gel matrix and form its own domains, spatially excluding polyacrylamide hydrogels. After synthesis, the beads are washed with water where the PEG polymers are removed from the hydrogel matrix. This leaves hollow pores within the hydrogels. These pores create more water/hydrogel interface and thus increase the side scattering of the entire particle. The porous hydrogel also have unique sponge-like morphology that can be observed with microscopy and also useful as cell control for imaging cytometry or any imaging based cell characterization techniques.

In embodiments, the porogen polymer can have a linear, branched, hyperbranched, or a bottlebrush structure. In an embodiment, the porogen polymer may comprise polymeric particles that become water soluble after a stimulus is applied. For example, hydrogel particles with a degradable crosslinker (e.g. N,N'-Bis(acryloyl)cystamine) can be embedded into hydrogel particles and then degraded with a cleaving agent. (e.g. reducing agent for N,N'-Bis(acryloyl) cystamine).

Porous structures can be created on the hydrogel particles where biomarkers may be conjugated and remain accessible to interactions with antibodies or in inverse, where conjugated antibodies can interact with their antigens on cells. In some embodiments, the porous structures allow for conjugation of a large number of biomolecules (i.e., greater than 100,000, greater than 1,000,000). All previously demonstrated attachment chemistries can be used with or incorporated into this technique.

Moreover, the side scatter properties of porous hydrogel particles may more closely match the optical properties of living cells. Addition of polyethylene glycol (PEG) to the hydrogel matrix during synthesis creates pores in the hydrogel beads that can scatter incident light due to phase transitions between the hydrogel matrix and the pores containing. Addition of PEG as a porogen can also increase the biomarker binding capacity of the hydrogel beads by creating a porous surface with increased surface area for the binding of biomarkers. In embodiments, creating a porous bead structure increases the surface area of the hydrogel particle.

Modification of the percentage of the material forming the hydrogel particle, the molecular weight of the porogen and the % concentration of the porogen added can be adjusted to achieve a desired porosity and resultant side scatter profile when measured on a flow cytometer. Table 10 shows previously characterized hydrodynamic radius of various PEG polymer molecular weights, and thus the minimum implied pore size introduced by their inclusion in hydrogels, as an example of a porogen polymer used within the hydrogel particles of the present disclosure.

TABLE 10

| Molecular Weight (kDA) | Hydrodynamic Radius (nm) |
| --- | --- |
| PEG 200 | 0.49 |
| PEG 400 | 0.65 |
| PEG 1000 | 0.93 |
| PEG 4000 | 1.60 |
| PEG 10,000 | 2.29 |
| PEG 20,000 | 3.01 |
| PEG 40,000 | 3.95 |

Porogens can also be used to increase the diffusion coefficient of large macromolecules (such as DNA, proteins, etc.) within hydrogels, or to increase cell affinity of hydrogels for tissue engineering purposes.

In the present disclosure, polyethylene glycol (PEG) provides an inert, pore-forming agent that can be used in the aqueous dispersion phase during microfluidic droplet generation. Adding PEG solution during the preparation of raw droplets, followed by removal after polymerization, allows cavities and tunnels to be irreversibly introduced into the matrix of the particle. Adjusting the initial PEG concentration added during the preparation of the raw droplets (e.g., within the dispersed phase) impacts pore size and distribution. In an embodiment, varying the PEG concentration introduced to the particle formulation determines a number of pores per unit volume of the resulting particle matrix. For instance, the PEG concentration within the dispersed phase may be between about 1% w/v and about 99% w/v. For instance, the PEG concentration may be at least about 1%, at least about 2%, at least about 4%, at least about 6% at least about 8%, at least about 10%, at least about 12%, at least about 14%, at least about 16%, at least about 18%, at least about 20%, at least about 25%, at least about 30%, at least about 35% and/or at least about 40% w/v. In an embodiment, the PEG concentration introduced during preparation of the particles may be about 9% w/v. In an embodiment, the PEG concentration introduced during preparation of the particles may be about 2.25%, about 3.4%, or about 4.5% w/v. In another embodiment, the PEG concentration within the dispersed phase may be between about 1% v/v and about 99% v/v. In embodiments, the PEG solution comprises a variable concentration of PEG 8000. In an embodiment, the particles of the present disclosure can be further modified by varying the size of the microsphere (i.e., particle) produced. Size can be controlled by flow rates and/or pressure of the aqueous and oil phase during the microfluidic droplet generation process.

Figure 14:
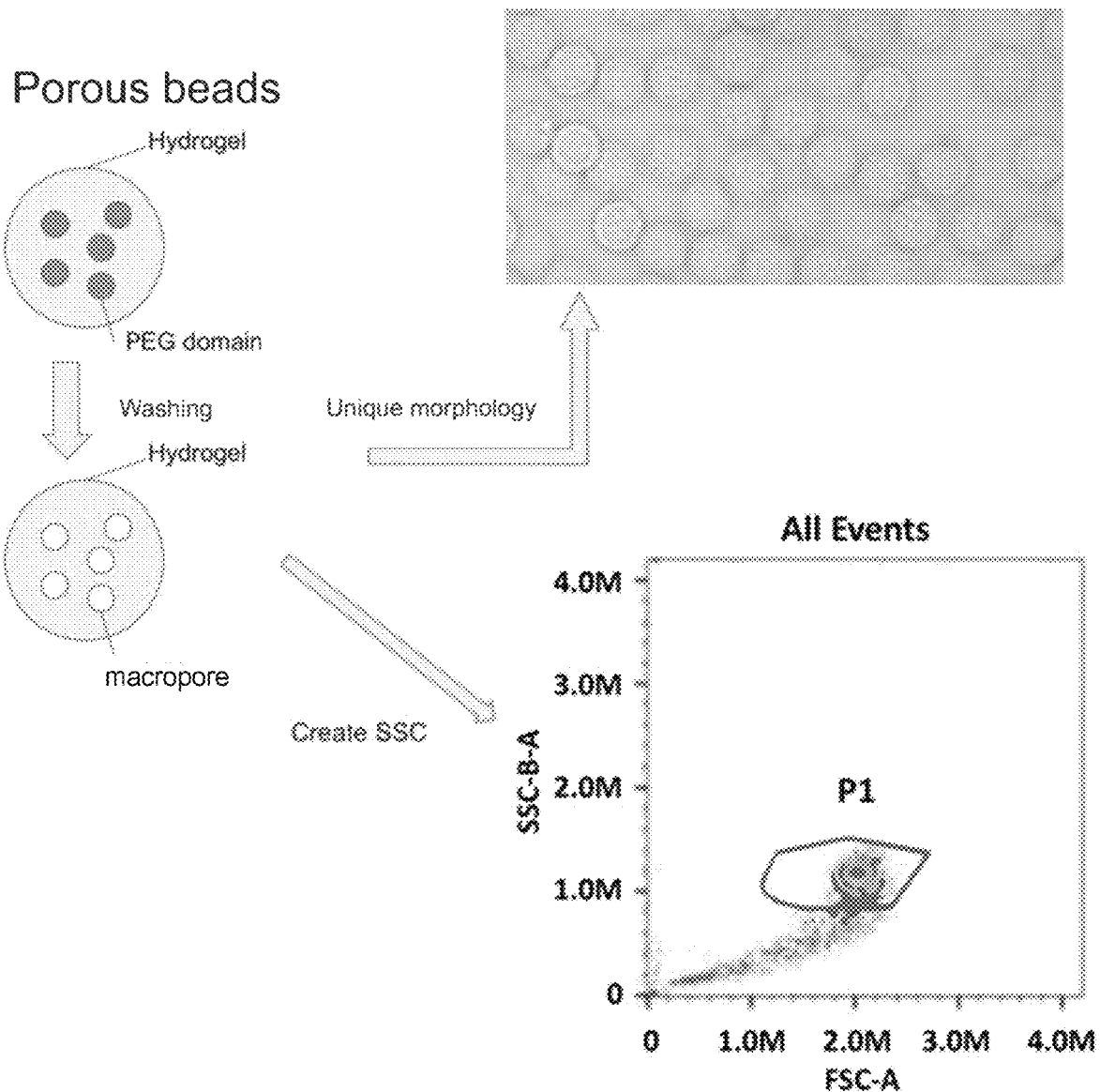
FIG. 14 shows a scatter plot of a porous particle and a general step for manufacturing of porous particles.

FIG. 14 provides a high-level flow diagram of formation of porous hydrogel particles, including polymerization of a dispersed phase into a hydrogel particle, encapsulation of PEG domains therein, and washing of the hydrogel particle to remove the PEG domains to form macropores. In embodiments, the PEG domains may alternatively, or additionally, be removed by leaching. Unlike washing, which may refer to a solute that is readily dissolvable, leaching may be appropriate when the solute requires more time to dissolve and thus to be removed from the material.

Figure 15:
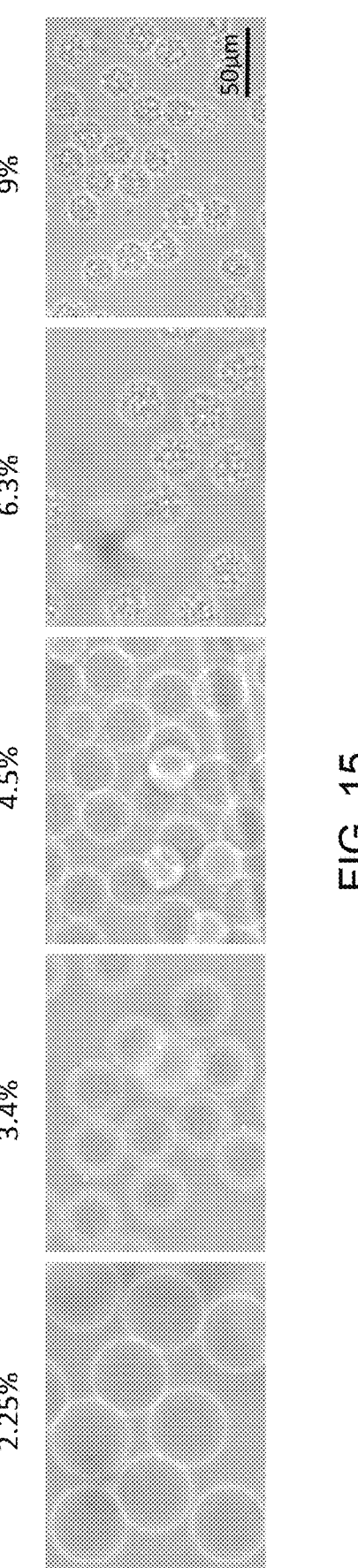
FIG. 15 provides illustrations of porous particles formed from porogens at a range of concentrations (weight by volume) within the dispersed phase.
Figure 16:
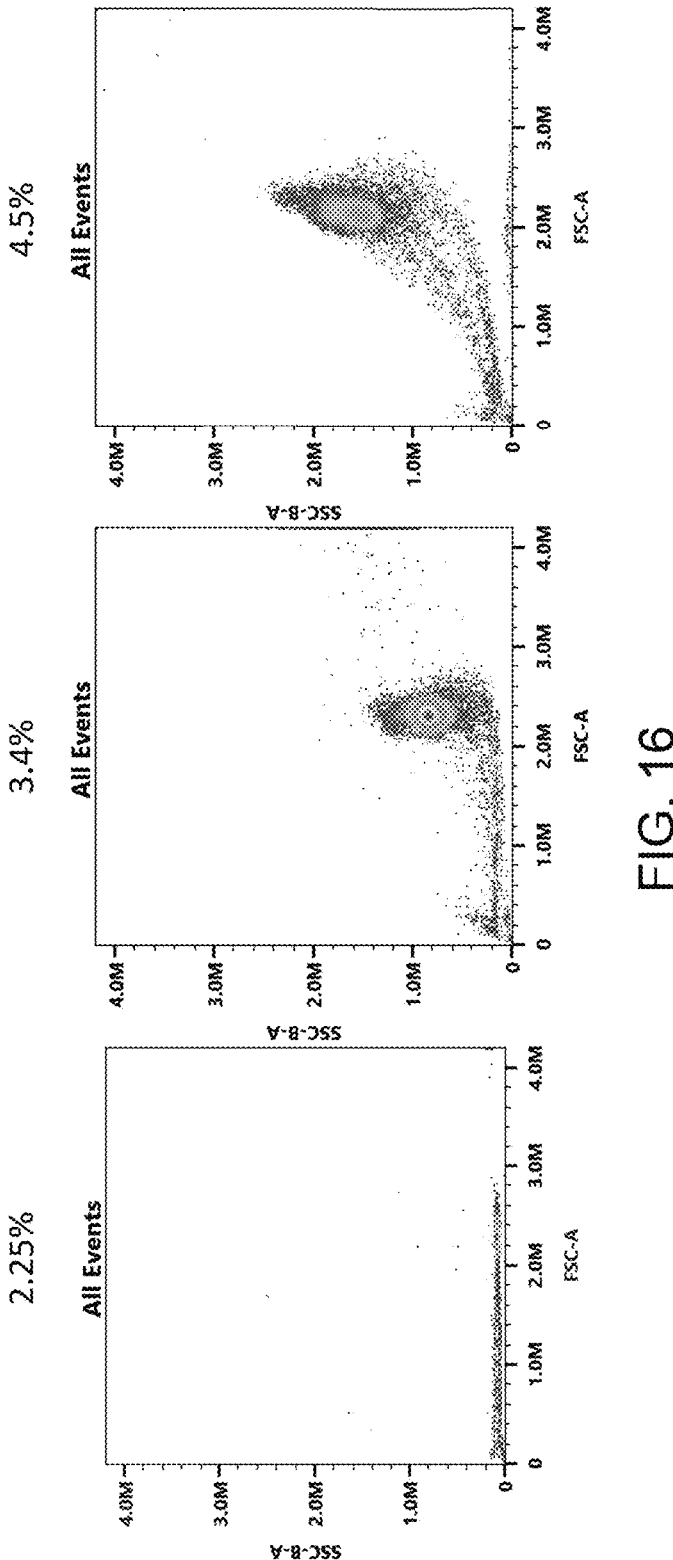
FIG. 16 provides scatter plots of side scatter data and forward scatter data for porous particles formed by varying porogen concentrations (weight by volume) within the dispersed phase. From left to right, the porous particles comprise polyethylene glycol 8000 at concentrations of 2.25%, 3.4%, and 4.5% w/v. The side scatter of the porous particles measured by flow cytometry increases with increasing content of polyethylene glycol 8000 in the water phase formulations, while the forward scatter is largely unchanged.
Figure 17:
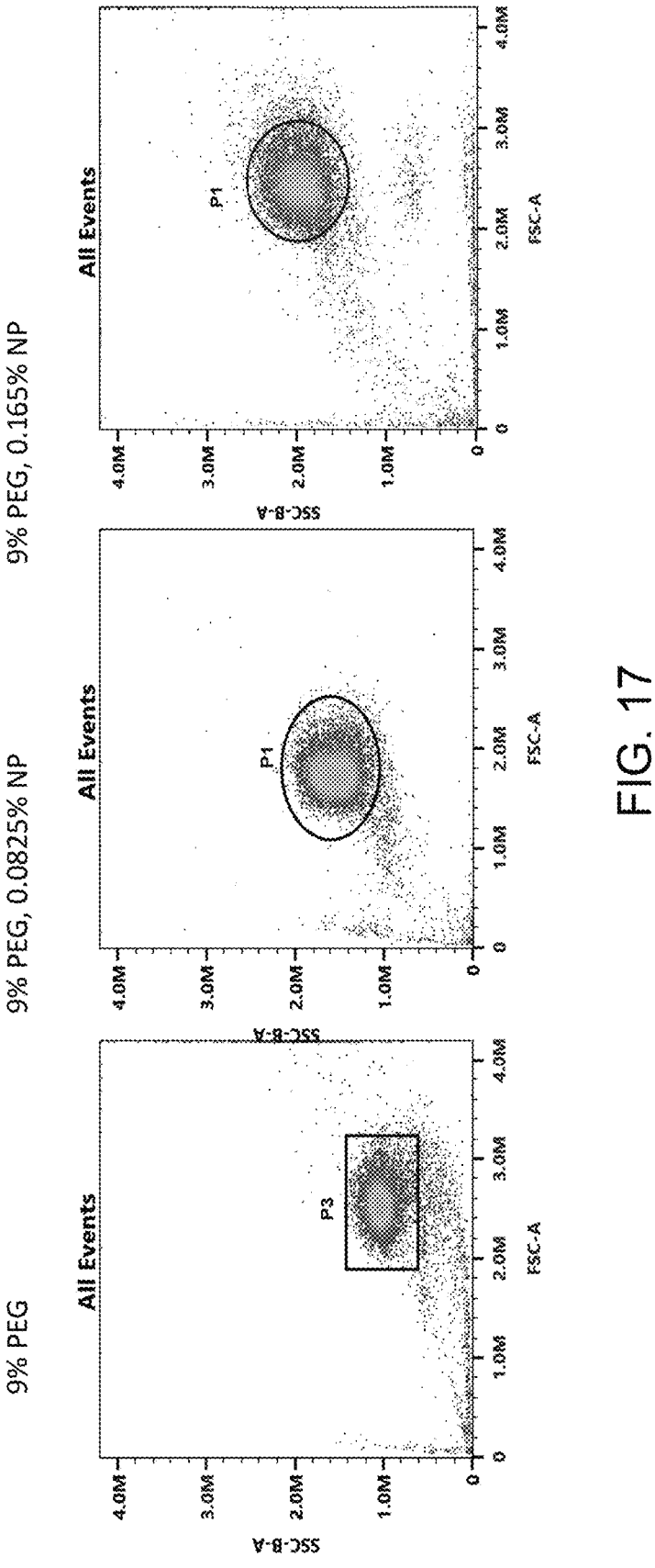
FIG. 17 provides scatter plots of side scatter data and forward scatter data for porous particles comprising a constant concentration of porogen and nanoparticles. From left to right, the porous particles are formed from 9% polyethylene glycol with nanoparticles at concentrations (weight by volume) of 0%, 0.0825%, and at 0.165% w/v. The plots illustrate that the side scatter of a particle can be controlled independently of its porosity.
Figure 18:
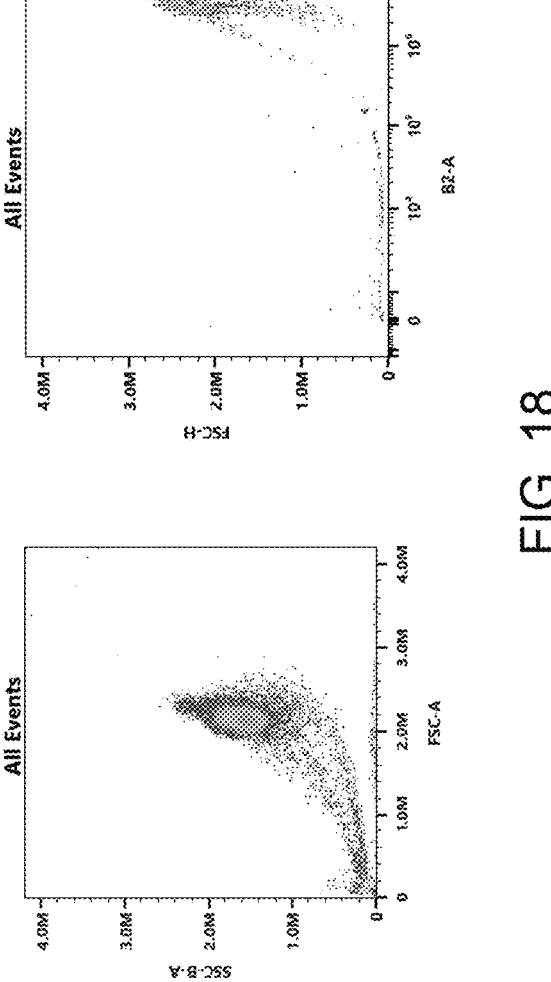
FIG. 18 provides scatter plots of optical scatter of porous particles conjugated with fluorescent dyes. Fluorophores or dyes can be conjugated to the porous particles, which can then be used to mimic a stained cell in the applications of image cytometry or histology.

A microscopic image of the porous hydrogel particles is shown at top right and a side scatter plot is shown at bottom left. FIG. 15 provides a series of microscopic images of porous hydrogel particles formed with varying levels of PEG, increasing in concentration from left to right. FIG. 16 demonstrates the ability to modify PEG concentrations used during formation to modify side scatter profiles of the resulting porous hydrogel particle. As discussed above, nanoparticles can be used in conjunction with porous hydrogel particles. FIG. 17 demonstrates the ability to modify nanoparticle concentrations within the porous hydrogel particles to mimic organelles in a target cell. Without wishing to be bound by theory, the ability to selectively tune both forward and side scatter of a hydrogel, as described herein, allows for a robust platform to mimic a vast array of cell types. FIG. 18 demonstrates the ability to conjugate fluorophores to the porous hydrogel particles. Suitable fluorophores will be described further below.

In view of the above, cell therapy activation can be performed. In embodiments, where the base polymer was formed using a porogen, each particle can be functionalized with biotinylated-proteins for advanced cell activation.

Exploiting the pore structure of this porous network permits improvements in cell response and cell proliferation. The introduction of pores into these particles, via e.g., PEG, could be used to improve biological response and lead to improved outcomes in biomedical, diagnostic, and therapeutics applications, especially cell activation therapy. It may be that the increased surface area to volume ratio introduced by these pores can enhance biological cell seeding by enabling more efficient mass transport such as cell signaling and cell cargo transport with enhanced liquid diffusion such as cell media to maximize cell proliferation. In any event, the generation of pores offers a number of advantages over non-porous structures. This includes enhanced nutrient transport and higher surface to area to volume ratio.

In embodiments, the particles may be hydrogels as described herein. In this instance, the particles may be bioreactors, achieved by allowing the porous particles to absorb water, maintain an optimal ion nutrient gradient, and maintain an optimal osmotic pressure which favors cellular growth and cell activation. In addition, when the particles are hydrogels, and appreciating it is well established in tissue engineering that cell migration is influenced by hydrogel stiffness and rough surface area, it is likely the particles of the present disclosure lead to the formation of much stronger cell-ligand bonds, thereby leading to enhanced growth and proliferation.

In embodiments, the present disclosure relates to a PEG-based porous particle having a porosity that allows for higher protein/biomolecule loading capacity, further allowing for improved cell stimulation. The fabricated particle allows for stronger bead-to-cell contact, and possible changes in Young's modulus, thereby affecting the quality of the stimulatory signal that the T cell receives and adhesion when compared to a monolayer slab (i.e., plate-bound activation method).

Further, through utilizing streptavidin-biotin binding, biotinylated αCD3 and αCD28 antibodies are attached to streptavidin coated, porous particles, thereby allowing for engagement of T-cell receptors (TCR) and co-stimulatory receptors on T-cells. For instance, when incubated with primary T-cells at 37° C. for 300 hours, cells were activated and showed early signs of IL-2 secretion and TCR engagement with early-stage and late-stage cell activation markers, CD25 and CD69, respectively, within 24 hours of culture. Long-term activation is also reported from readouts at 300 hours through fluorescence activated cell sorting, indicating a sustained response.

In embodiments, the present disclosure relates to the use of a biodegradable polymer as a base polymer for the particles. The fabricated particle allows for stronger bead-to-cell contact, thereby affecting the quality of the stimulatory signal that the T cell receives and adhesion when compared to a monolayer slab (i.e., plate-bound activation method). In an example, utilizing streptavidin-biotin binding, biotinylated αCD3 and αCD28 antibodies are attached to streptavidin coated, particles, thereby allowing for engagement of T-cell receptors (TCR) and co-stimulatory receptors on T-cells.

According to an embodiment, each particle of a plurality of particles can be fabricated according to the methods described previously herein. This includes polymerizing one or more monomers, i.e., to form a homopolymer or copolymer. As discussed above, the use of bifunctional monomers allows for the further derivatization of particles, e.g., with cell surface markers or epitope binding fragments thereof, or a combination thereof. Methods for tuning the properties of each particle were described above. The ability to adjust a range of parameters including particle components and concentration of the same allows for the ability to tune a particle to mimic a wide range of cells, for example one of the cell types described above.

After the particle is formed, one or more of the particle's surfaces can be functionalized, for example, to mimic one or more optical properties of a target cell or a labeled target cell. The functionalized particle can also include an embedded bead or substance such as a biomolecule, as described above. In one embodiment, one or more particles are functionalized with one or more fluorescent dyes, one or more cell surface markers (or epitope binding regions thereof), or a combination thereof. In one embodiment, the particle is formed by polymerizing at least one bifunctional monomer and after formation, the particle includes one or more functional groups that can be used for further attachment of a cell surface marker, an epitope binding region of a cell surface marker, a fluorescent dye, or combination thereof. The free functional group, in one embodiment, is an amine group, a carboxyl group, a hydroxyl group or a combination thereof. Depending on the functionalization desired, it is to be understood that multiple bifunctional monomers can be used, for example, to functionalize the particle using different chemistries and with different molecules.

A particle can be functionalized with any fluorescent dye known in the art, including fluorescent dyes listed in The MolecularProbes® Handbook—A Guide to Fluorescent Probes and Labeling Technologies, incorporated herein by reference in its entirety for all purposes. Functionalization can be mediated by a compound comprising a free amine group, e.g. allylamine, which can be incorporated into a bifunctional monomer used to form the particle, as discussed above.

Non-limiting examples of known fluorescent dyes that can be used to functionalize the surface of a particle described herein are described above and shown in Table 2.

Fluorescent dyes for derivatization of the surface of one or more particles in one embodiment, include, but are not limited to: Alexa fluor dyes commercially available from Invitrogen, including but not limited to Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 64 7 carboxylic acid; Alexa Fluor® 660 carboxylic acid; and Alexa Fluor® 680 carboxylic acid. In another embodiment, fluorescent dyes for use with the particles and methods described herein include cyanine dyes commercially available from Amersham-Pharmacia Biotech, including, but not limited to Cy3 NHS ester; Cy 5 NHS ester; Cy5.5 NHSester; and Cy7 NHS ester.

It is within the ordinary skill in the art to select a suitable dye or dyes based on the desired spectral excitation and emission properties of the particle.

Particles, in one embodiment, are functionalized with one or more cell surface markers (see, e.g., Tables 4 and 7), or fragments thereof, for example, extracellular portions thereof in the case of transmembrane proteins, for example, by attaching the one or more cell surface markers, extracellular portions or ligand binding regions thereof to the particle via a free amine, free carboxyl and/or free hydroxyl group present on the surface of the particle. Functionalization of a particle with a dye or cell surface molecule can also occur through a linker, for example a streptavidin/biotin conjugate.

Particles Support Target Cell Growth

Figures 19, 20, 21:
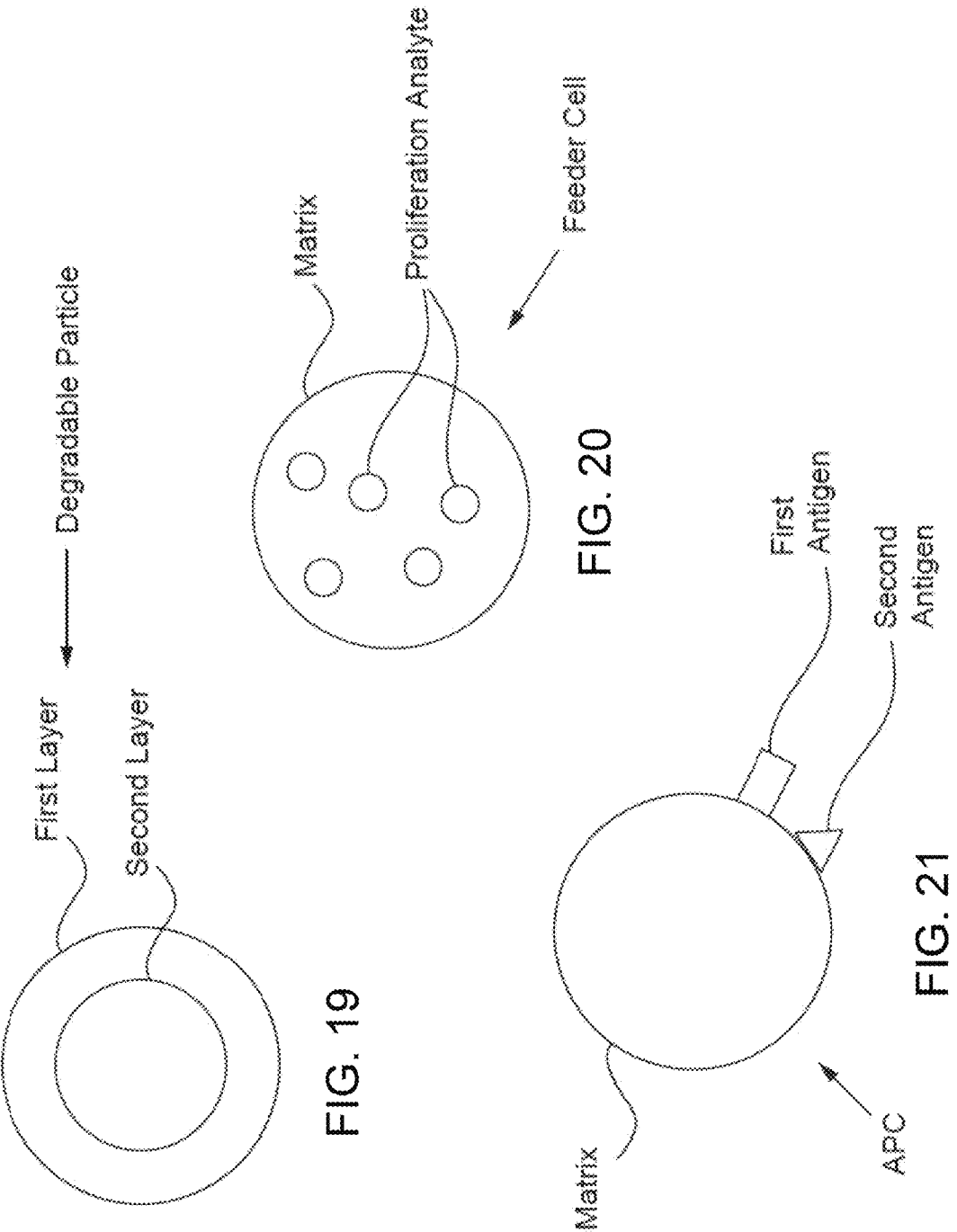
FIG. 19 is a schematic of a degradable particle, according to embodiments of the present disclosure.
FIG. 20 is a schematic of a particle as a synthetic feeder cell, according to embodiments of the present disclosure.
FIG. 21 is a schematic of a particle as a synthetic biomolecule presenting particle, according to embodiments of the present disclosure.

Feeder cells support the growth of target cells by releasing biomolecules such as growth factors, adhesion molecules, and/or extracellular matrix to the culture media, but can introduce issues such as viruses and unwanted antigens into the cell culture. Here, as shown in FIG. 20, the present disclosure provides particles that act as feeder cells and comprise one or more growth factors, adhesion molecules, and/or extracellular matrix to the culture media/target cells. In some aspects of the present disclosure the feeder particles comprise a polymer matrix and one or more polypeptides or fragments thereof that support the growth of target cells. In some aspects of the present disclosure the feeder particles comprise one or more polypeptides or fragments (e.g., proliferation analyte) thereof that stimulate the proliferation and/or activation of the target cell.

In some embodiments, the biomolecules are attached to the surface of the particle. In some embodiments, the biomolecules are in the matrix of the particle itself. In some embodiments, the particle is engineered to degrade to provide such biomolecule to the target cell. The rate of degradation can be modulated to provide slow degradation of the particle and thus slow release of the biomolecule to the target cell. In some embodiments, the biomolecules are attached to both the surface of the particle and in the matrix of the particle. In some embodiments, the biomolecules on the surface and in the matrix of the particle are the same. In some embodiments, the biomolecules on the surface and in the matrix of the particle are different.

Particles as Biomolecule Presenting Particles

Though the present disclosure is described with reference to immune cells, and in particular, to a T cell, the disclosure is not intended to be so limited in its scope of application. The present disclosure may be used for plasma cells, lymphocytes, immune cells, biomolecule presenting cells (e.g., dendritic cells, macrophages, B cells), naïve B cells, memory B cells, naïve T cells, memory T cells, chimeric antigen receptor T cell (CAR T cell), regulatory T cells, cytotoxic T cells, NK cells, or any other appropriate cell. Additionally, the method may be used for any number of cells or analytes, such as one, at least one, a plurality, etc.

Generally, T cell activation is triggered by a peptide antigen bound to a major histocompatibility complex (MHC) molecule on the surface of an antigen presenting cell (APC), a T cell receptor/CD3 complex (TCR/CD3). While this is the primary signal in T cell activation, other receptor-ligand interactions between APC and T cells are also required for full activation. For example, TCR stimulation in the absence of other molecular interactions can induce an anergic state such that these cells cannot respond to a complete activation signal upon restimulation. Thus, optimal functionality may be conferred through the use of a second signaling molecule, such as a membrane bound protein or APC secretion product. For these membrane-bound proteins, such second interactions are usually adhesive in nature and enhance the contact between the two cells. Other signaling molecules (e.g., further activation signaling from APC to T cells) may also be relevant. For example, CD28 is a surface glycoprotein that is present in 80% of peripheral T cells in humans and is present in both quiescent and activated T cells. CD28 binds to B7-1 (CD80) or B7-2 (CD86) and is one of the most potent of the known costimulatory molecules. Combined with TCR engagement, CD28 ligation on T cells induces the production of interleukin-2 (IL-2). Secreted IL-2 is an important factor for ex vivo T cell expansion.

Here, as shown in FIG. 21, the present disclosure provides particles (comprising a polymer matrix) that act as APCs and comprise one or more immunostimulatory biomolecules that stimulate the expansion and/or activation of a T cell. In some embodiments, these synthetic biomolecule presenting particles comprise one or more of an activation biomolecule, a stimulatory biomolecule, a costimulatory biomolecule and/or a T cell homeostasis factor.

Furthermore, the present disclosure can detect, induce, or detect and induce activation events including, but not limited to, cell expansion, cell proliferation, cell differentiation, activation maintenance, cell maturation, cell receptor clustering, synapse formation (e.g., between a lymphocyte and a tumor cell), cytokine production, gene expression, protein expression, or any other appropriate occurrence by which the target cell is activated upon recognition of or stimulation by the proper antigen, antibody, immunoglobulin (e.g., CD3, CD19, CD20, CD28, CD80, CD86, CD69, CD154, CD137, IgM, IgG, IgE, IgA, IgD, or antibodies targeting said biomolecules), toll-like receptors (TLR, such as, for example, TLR1-13), or the like.

In some embodiments, these activation events can be induced based on proximity of a particle to a cell of interest. In one example, the particle can be conjugated to the cell of interest, whether via direct or indirect conjugation. In another example, the particle can be proximal to but not in contact with the cell of interest. The particle and the cell of interest can be separated by less than 1 nm, less than 1 micron, less than 1 millimeter, or any appropriate separation distance by which the activation event can still occur.

Action may be distant from an area of introduction of the particle. in which a signal event or cascade event occurs remotely. The distance can be at least 1 millimeter, at least 1 centimeter, at least 1 meter, etc. For example, the particle may be introduced intramuscularly or intravenously and the action is in a lymph node or distant immune organ or other target organ. Alternatively, the particle may be introduced on one side of a membrane and the action maybe on another side of a membrane (for e.g., via a semi-permeable membrane).

In some embodiments, the molecule that can stimulate T cell expansion and/or activation is a polypeptide or fragment thereof. In some embodiments, the polypeptide or fragment thereof that can stimulate T cell expansion and/or activation is a peptide antigen. In some embodiments, the molecule that can stimulate T cell expansion and/or activation is a component of a MHC molecule. In some embodiments, the molecule that can stimulate T cell expansion and/or activation is a component of a T cell receptor/CD3 complex. In some embodiments, the molecule that can stimulate T cell expansion and/or activation is an antibody that specifically binds a component of a T cell receptor/CD3 complex. In some embodiments, the particle of the present disclosure comprises an antibody or antigen-binding fragment therefore that specifically binds to CD3.

In some embodiments, the particle of the present disclosure comprises one or more T cell activation molecules and one or more T cell costimulatory molecules. In some embodiments, the particle of the present disclosure comprises one or more antibodies or antigen-binding fragments thereof that specifically bind T cell activation molecules and one or more T cell costimulatory molecules. In some embodiments, the particle of the present disclosure comprises a T cell activation molecule of CD3 and a T cell costimulatory molecule selected from CD28, ICOS, CD27, CD40, CD40L, CD137L, and CD137 (or antibodies targeting said activation/costimulatory molecules. In some embodiments, the particle of the present disclosure comprises one or more antibodies or antigen-binding fragments thereof that specifically bind to CD3 and one or more antibodies or antigen-binding fragments thereof that specifically bind to CD28, ICOS, CD27, CD40, CD40L, CD137L, CD137, the like, or combinations thereof.

In some embodiments, the receptor molecule on the particle would be a MHC-tetramer (MHC class I or class II) and the CD3 CD28 molecules would be encapsulated within and/or attached to the surface of the particle such that the primary recognition would be dictated by antigen-specificity by the MHC tetramer with the CD3, CD28 stimulation of such targeted cells occurring later with the consequence that only Ag-specific cells are co-stimulated allowing for lower magnitude of Cytokine Release Syndrome.

An embodiment of the present disclosure is to use synthetic particles to eliminate a pathogenic subset of T-cells, B-cells, NK cells or other immune cells. For example, to eliminate pathogenic T-cells in auto-immune disease. Take a synthetic cell, make it specific to a B-Cell which makes Abs against autoantigens as in Systemic Lupus Erythematosus (SLE). This results in elimination of B-Cells that produce Abs against various auto antigens.

In some embodiments, the T cell activation molecule may be an anti-CD3 antibody or an antigen-binding fragment thereof, an anti-macrophage scavenger receptor (MSR1) antibody or an antigen-binding fragment thereof, an anti-T cell receptor (TCR) antibody or an antigen-binding fragment thereof, an anti-CD2 antibody or an antibody thereof, anti-gen-binding fragments, anti-CD47 antibodies or antigen-binding fragments thereof, major histocompatibility complex (MHC) molecules loaded with MHC peptides or multimers thereof, and MHC-immunoglobulin (Ig) conjugates or multimers thereof, or combinations thereof.

In some embodiments, the particle comprises one or more T cell costimulatory molecules including, but not limited to, CD28, 4.1BB (CD137), OX40 (CD134), CD27 (TNFRSF7), GITR (CD357), CD30 (TNFRSF8), HVEM (CD270), LTOR (TNFRSF3), DR3 (TNFRSF25)), ICOS (CD278), CD226 (DNAM1), CRTAM (CD355), TIM1 (HAVCR1, KIM1), CD2 (LFA2, OX34), SLAM (CD150, SLAMF1), 2B4 (CD244, SLAMF4), Ly108 (NTBA, CD352), SLAMF6), CD84 (SLAMF5), Ly9 (CD229, SLAMF3) and/or CRACC (CD319, BLAME). In some embodiments, the particles comprises one or more antibodies or antigen-binding fragments thereof that specifically bind to CD28, 4.1BB (CD137), OX40 (CD134), CD27 (TNFRSF7), GITR (CD357), CD30 (TNFRSF8), HVEM (CD270), LTOR (TN-FRSF3), DR3 (TNFRSF25)), ICOS (CD278), PD1 (CD279) CD226 (DNAM1), CRTAM (CD355), TIM1 (HAVCR1, KIM1), CD2 (LFA2, OX34), SLAM (CD150, SLAMF1), 2B4 (CD244, SLAMF4), Ly108 (NTBA, CD352), SLAMF6), CD84 (SLAMF5), Ly9 (CD229, SLAMF3) and/or CRACC (CD319, BLAME). In some embodiments, the particle of the present disclosure comprises an anti-CD28 antibody or antigen-binding fragment thereof.

In some embodiments, the particle of the present disclosure comprises one or more polypeptides that promote expansion of a particular T cell subtype while simultaneously inhibiting the development of the other subset. In some embodiments, the polypeptide that promotes expansion of a particular T cell subtype is a cytokine. In some embodiments, the cytokine is an interleukin, interferon, lymphotoxin, a member of the TNF superfamily, or an antibody or antigen-binding fragment thereof that binds to one of the foregoing. In some embodiments, the cytokine is selected from a list including, but not limited to, IL-1, IL-2, IL-4, IL-5, IL-7, IL-10, IL-12, IL-15, IL-17, IL-21, interferon γ, IFN alpha, IFN beta, lymphotoxin α, TNFα, TNFβ or a combination thereof.

In some embodiments, the particle of the present disclosure comprises one or more T cell homeostasis factors. In some embodiments, the T cell homeostasis factor is selected from a list including, but not limited to, transforming growth factor β (TGF-β), or agonists thereof, mimetics thereof, variants thereof, functional fragments thereof, or a combination thereof. In some embodiments, the T cell homeostasis factor is IL-2, an agonist, mimetic, variant, or functional fragment or a combination thereof.

In some embodiments, the particle comprises a CD3 and a CD28 biomolecule or fragment thereof. In some embodiments, the particle comprises an anti-CD3 and an anti-CD28 antibody or antigen-binding fragment thereof.

In some embodiments, the biomolecules are attached to the surface of the particle (e.g., a synthetic particle or a feeder particle). In some embodiments, the biomolecules are in the matrix of the particle itself (e.g., encapsulated or embedded within the particle). In some embodiments, the biomolecules are attached to both the surface of the particle and within the matrix of the particle. In some embodiments, the biomolecules on the surface and in the matrix of the particle are the same. In some embodiments, the biomolecules on the surface and in the matrix of the particle are different.

In some embodiments, the T cell stimulated and/or expanded and or depleted/removed by the particle of the present disclosure is selected from the nonlimiting group consisting of natural killer (NK) cells, CD3+ T cells, CD4+ T cells, CD8+ T cells, and regulatory T cells (Treg), or a combination thereof. In some embodiments, the T cell is a helper T cell. In some embodiments, the T cell is a cytotoxic T cell. In some embodiments, the T cell is a Th1 or a Th2 cell. In some embodiments, the T cell is a recombinant T cell. In some embodiments, the recombinant T cell is a CAR T cell. In embodiments, T cells depleted/removed by the particles of the present disclosure are CD25+ regulatory T cells and/or CD4+ T cells.

In some embodiments, the T cell is freshly collected from a subject. In some embodiments, the T cell is a cultured cell line. In some embodiments, the T cell is an established cell line. In some embodiments, the T cell is cultured from a preserved or frozen sample.

In some embodiments, the particles of the present disclosure induce the expansion, proliferation, and/or activation of any appropriate T cell. In some embodiments, the T cell does not expand, proliferate, and/or activate in culture without the synthetic particles. In some embodiments, the T cell does not expand, proliferate, and/or activate well in culture without the synthetic particles.

In some embodiments, the T cells, or subsets thereof are eliminated as a consequence of incubating with the synthetic particles.

In some embodiments, the T cells are derived from any appropriate source within an animal. The animals from which the T cells are harvested may be vertebrate or invertebrate, mammalian or non-mammalian, human or non-human. Examples of animal sources include, but are not limited to, primates, rodents, canines, felines, equines, bovines and porcines. In embodiments, the target cell is as described above and in Tables 3, 4, 5, and 6.

In some embodiments, the particles of the present disclosure support the growth of any appropriate target cell. In some embodiments, the target cell does not proliferate in culture without the feeder particles. In some embodiments, the target cell does not proliferate well in culture without the feeder particles.

In some embodiments, the target cell is a stem cell. In some embodiments, the stem cell is, without limitation, an embryonic stem cell, a ICM/epiblast cell, a primitive ecto-derm cell, a primordial germ cell, a cancer cell, or a teratocarcinoma cell.

In some embodiments, the stem cell is a pluripotent stem cell, a totipotent stem cell, a multipotent stem cell, an oligopotent, or a unipotent stem cell. In some embodiments, the pluripotent stem cell is an embryonic stem cell. In some embodiments, the stem cell is an undifferentiated pluripotent stem cell. In some embodiments, the totipotent stem cell is, without limitation, an embryonic stem cell, a neural stem cell, a bone marrow stem cell, a hematopoietic stem cell, a cardiomyocytes, a neuron, an astrocyte, a muscle cell, or a connective tissue cell. In some embodiments, the multipo-tent stem cell is, without limitation, a myeloid progenitor cell, or a lymphoid progenitor cell. In some embodiments, the stem cell is an induced pluripotent stem cell (iSPC). In some embodiments, the stem cell is an adult stem cell. In some embodiments, the stem cell is an undifferentiated pluripotent stem cell. In some embodiments, the stem cell is a mammalian stem cell. In some embodiments, the stem cell is a primate stem cell. In some embodiments, the stem cell is a human stem cell.

In some embodiments, the stem cells are derived from any source within an animal. For example, stem cells may be harvested from embryos, or any primordial germ layer therein, from placental or chorion tissue, or from more mature tissue such as adult stem cells including, but not limited to adipose, bone marrow, nervous tissue, mammary tissue, liver tissue, pancreas, epithelial, respiratory, gonadal and muscle tissue. In some embodiments, the stem cells are placental- or chorionic-derived stem cells.

In some embodiments, the present disclosure contem-plates using differentiable cells from any animal capable of generating differentiable cells, e.g., pancreatic type cells such as beta cells. The animals from which the differentiable cells are harvested may be vertebrate or invertebrate, mam-malian or non-mammalian, human or non-human. Examples of animal sources include, but are not limited to, primates, rodents, canines, felines, equines, bovines and porcines.

In some embodiments, the target cell is a blood cell. In some embodiments, the target cell is a peripheral blood mononuclear cell (PMBC). In some embodiments, the peripheral blood mononuclear cell is a lymphocyte, a mono-cyte, or a dendritic cell. In some embodiments, the lympho-cyte is a T-cell, B-cell, or NK cell. In some embodiments, the target cell is a natural killer (NK) cell.

In certain embodiments of the present disclosure, the cell culture is enriched. The term "enriched" refers to a cell culture that contains at least 10%, 15%, 20%, 25%, 30%, 35%, 40%, 45%, 50%, 55%, 60%, 65%, 70%, 75%, 80%, 85%, 90%, 95%, or 100% of the desired cell lineage.

As used herein, the term "substantially undifferentiated" cell culture refers to a population of stem cells comprising at least about 50%, preferably at least about 60%, 70%, or 80%, and even more preferably, at least about 90%, undif-ferentiated, stem cells. Fluorescence-activated cell sorting using labeled antibodies or reporter genes/proteins (e.g., enhanced green fluorescence protein [EGFP]) to one or more markers indicative of a desired undifferentiated state can be used to determine how many cells of a given stem cell population are undifferentiated. For purposes of making this assessment, one or more cell surface markers correlated with an undifferentiated state (e.g., SSEA-4, Tra-1-60, and Tra-1-81), as well as the typical pluripotent stem cell transcrip-tion factor marker, Oct-4, can be detected. Telomerase reverse transcriptase (TERT) activity and alkaline phos-phatase can also be assayed. In the context of primate stem cells, positive and/or negative selection can be used to detect, for example, by immuno-staining or employing a reporter gene (e.g., EGFP), the expression (or lack thereof) of certain markers (e.g., Oct-4, SSEA-4, Tra-1-60, Tra-1-81, SSEA-1, SSEA-3, nestin, telomerase, Myc, p300, and Tip60 histone acetyltransferases, and alkaline phosphatase activ-ity) or the presence of certain post-translational modifica-tions (e.g., acetylated histones), thereby facilitating assess-ment of the state of self-renewal or differentiation of the cells. Also, undifferentiated cells described herein have typical stem cell morphology which is well described in the art.

In some aspects of the present disclosure, the feeder particle comprises one or more molecules that support cell growth and/or stimulate target cell proliferation or activa-tion. These molecules include, but are not limited to, cyto-kines, growth factors, cytokine receptors, extracellular matrix, transcription factors, secreted polypeptides and other molecules, and growth factor receptors, or fragments thereof. In some embodiments, the feeder particle comprises a fibroblast growth factor (bFGF), an acidic fibroblast growth factor (aFGF), an epidermal growth factor (EGF), insulin-like growth factor-I (IGF-I), insulin-like growth fac-tor-II (IGF-II), a platelet-derived growth factor-AB (PDGF), a vascular endothelial cell growth factor (VEGF), activin-A, a bone morphogenic protein (BMP), a chemokine, a mor-phogen, a neutralizing antibody, a heregulin, an interferon, a macrophage-derived cytokine, an interleukin, an inter-leukin receptor, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, 11-23, IL-24, IL-25, IL-26, IL-28, IL-29, IL-30, IL-31, IL-32, IL-33, IL-34, IL-35, IL-36, IL-37, IL-38, tumor necrosis factor, TNFα, TNFβ, TNFR1, TNFR2, IFAR1, IFAR2, TGFR1, TGFR2, FGF, granulocyte macrophage colony-stimulating factor, chemokines (e.g. CCL1, CCL2, CCL3, CCL, CCL5, and CXCL8), CD27 ligand (CD27L), CD40L, CD137L, TNF-related apoptosis-inducing ligand (TRAIL), TNF-related activation-induced cytokine (TRANCE), TNF-related weak inducer of apoptosis (TWEAK), B cell activating factor (BAFF), LIGHT (homologous to lymphotoxin, exhibits inducible expression and competes with herpes simplex virus glycoprotein D for binding to herpesvirus entry media-tor, a receptor expressed on T lymphocytes), TNF-like cytokine 1A (TL1A), glucocorticoid-induced TNF receptor-related protein ligand (GITRL), transforming growth factor α (TGF-α), TGF-β, vascular endothelial growth factor (VEGF), nerve growth factor (NGF), macrophage colony-stimulating factor (M-CSF), granulocyte-macrophage colony-stimulating factor (GM-CSF), IFN-α, IFN-β, and IFN-γ.

In some embodiments, the biomolecules on the surface and in the matrix of the particle are different and the components of the matrix dissolve at different rates.

In some embodiments, the particles are engineered to degrade to provide such biomolecules to a cell in culture. Degradation can include, without limitation, dissolution (i.e., dissolving) or lysis. The particle can be engineered to have multiple layers, as shown in FIG. 19, with different rates of degradation for at least two of the layers. The particle, whether in its entirety or various layers thereof, can be degraded chemically (e.g., reagents, detergents, bursting, or the like), mechanically (e.g., vibration, acoustic, freeze-thaw, bursting, or the like), or both chemically and mechanically.

The rate of degradation of the entire particles, individual layers of the particles, or groups or subpopulations of a particle population can be fast (i.e., less than 24 hours) or slow (i.e., 24 hours or more). For example, a first layer of a particle can degrade in less than 24 hours and a second layer of the same particle can degrade in 48 hours. As yet another example, a first subpopulation of particles can degrade in less than 1 hour, a second subpopulation of particles can degrade in 24 hours, and a third subpopulation of particles can degrade in one week. The first, second, and third subpopulations form a population of particles.

In some embodiments, a population of particles can include groups or subpopulations of particles having different rates of degradation.

In some embodiments, the particle can be engineered to have pore sizes which correlate to various rates of degradation. The pore sizes can range from 0.1 nm to 1 μm. For example, a first particle can have a first pore size, such that the first particle has a first rate of degradation; and, a second can have a second pore size, such that the particle has a second rate of degradation with the first and second rates of degradation not being equal (e.g., first rate is faster than the second rate; or the first rate is slower than the second rate).

In some embodiments, the particle can be engineered to have a rate of degradation based on a plurality of factors, including, without limitation, pore size, chemical composition (i.e., chemical bonds, monomers, co-monomer), layer composition, the like, and combinations thereof.

In some embodiments, the particle contains growth factor, cytokines or hormone precursors that must be processed by a protease to release the active growth factor. In some embodiments the corresponding proteases capable of producing the active growth factor may be added to the growth media, naturally secreted by the target cells or included in the composition of the particles.

In some embodiments, the particle contains disulfide cross links enabling the particle to dissolve upon the addition of a reducing agent. In some embodiments the particle can be dissolved by the addition of a protease. In some embodiments the growth factors are crosslinked to each other or to the matrix via disulfide crosslinks that may be broken by the addition of a reducing agent, releasing active growth factors. Appropriate reducing agents may include but are not limited to dithiothreitol, Tris(2-carboxyethyl)phosphine hydrochloride and 2-mercaptoethanol. In some embodiments, the feeder particle comprises only one type of molecule that supports cell growth and/or stimulates target cell proliferation or activation. In some embodiments, the feeder particle comprises only one class of molecule that supports target cell growth and/or stimulates target cell proliferation or activation. In some embodiments, the feeder particle comprises multiple types and/or classes of molecules that support cell growth and/or stimulate target cell proliferation or activation.

In some embodiments, the feeder particle comprises an interleukin and a cell surface molecule. In some embodiments, the feeder particle comprises at least two interleukins and a cell surface molecule. In some embodiments, the feeder particle comprises IL-2, IL-15, IL-21, CD137L, and CD137 (TNFRSF9; 4-1BB). In some embodiments, the feeder particle comprises IL-15, IL-21, CD137L, and CD137 and activates NK cells.

In some embodiments, the feeder particle comprises one or more components of the extracellular matrix. In some embodiments, the feeder particle provides physical support for the target cells.

In some embodiments, the feeder particle comprises between about 1 and about 100,000,000 copies of one or more molecules that support cell growth and/or stimulate target cell proliferation or activation. In some embodiments, the feeder particle is approximately the same size as the target cell and comprises between about 500 and 100,000,000 copies of one or more molecules that support cell growth and/or stimulate target cell proliferation or activation. In some embodiments, the feeder particle is approximately about 5 μm to about 200 μm and comprises between about 500 and 100,000,000 copies of one or more molecules that support cell growth and/or stimulate target cell proliferation or activation. In some embodiments, the particle has a diameter of at least 5 nm. In some embodiments, the feeder particle comprises at least the same number of the one or more molecules that support cell growth and/or stimulate target cell proliferation or activation as binding sites of the target cell. In some embodiments, the feeder particle comprises more of the one or more molecules that support cell growth and/or stimulate target cell proliferation or activation as binding sites of the target cell. In some embodiments, the feeder particle comprises at least 1, at least 10, at least 100, at least 1,000, at least 10,000, at least 100,000, at least 1,000,000, at least 10,000,000, or at least 100,000,000 copies of one or more molecules that support cell growth and/or stimulate target cell proliferation or activation.

In one embodiment, a plurality of particles is used to determine the dynamic range and/or sensitivity of detection of a particular cell surface marker or combination thereof on a population of target cells. For example, the population of particles can be tuned to have the SSC and/or FSC profile of the target cell, and subpopulations of the particle are derivatized with a specific number of copies of a cell surface marker, e.g., a cell surface receptor, or a domain thereof, for example, an epitope binding region thereof. For example, individual subpopulations of particles can each be derivatized to have a unique number of copies, e.g., one subpopulation will contain 100 copies of a cell surface marker, a second subpopulation will contain 1,000 copies of the same cell surface marker, a third subpopulation will contain 10,000 copies of the same cell surface marker, etc. The populations of particles are fluorescently stained for the respective cell surface marker and fluorescence is detected for particles in each subpopulation. In this regard, the subpopulations of particles can be used to generate a standard curve of fluorescence emission for target cells with the respective cell marker. The cell surface marker can be any of the cell surface markers provided thereof, or binding regions thereof, or a cell surface marker known to one of ordinary skill in the art.

In some aspects, the present disclosure provides methods of culturing a target cell with one or more feeder particles as described herein. In some aspects, the culturing media is useful in culturing the target cells. In some embodiments, the media is substantially isotonic as compared to the cells being cultured. In some embodiments where undifferentiated stem cells are cultured, the particular medium comprises a base medium and an amount of various factors necessary to support substantially undifferentiated growth of embryonic stem cells. In some embodiments, the base medium comprises salts, essential amino acids, a carbon source that can be metabolized by the target cells, and human serum. In some embodiments, for instance when the target cell is a T cell, the base medium comprises cytokines such as IL-2, IL-7, and IL-15. All these ingredients are supplied in an amount that will support respective target cells.

In some embodiments, the disclosure, provides a cell culture composition comprising a target cell, a defined culture media comprising human serum (hS), and a feeder particle as described herein, and wherein the composition is essentially free of feeder cells. In some embodiments, the disclosure provides a cell culture composition comprising a natural killer cell, a defined culture media comprising human serum (hS), and a feeder particle as described herein, and wherein the composition is essentially free of feeder cells. In some embodiments, the disclosure provides a cell culture composition comprising a natural killer cell, a defined culture media comprising human serum (hS), and a feeder particle as described herein comprising one or more of an interleukin and/or a member of the tumor necrosis factor superfamily, and wherein the composition is essentially free of feeder cells. In some embodiments, the disclosure provides a cell culture composition comprising a natural killer cell, a defined culture media comprising human serum (hS), and a feeder particle as described herein comprising one or more of IL-15, IL-21, CD137L, and/or CD137 and wherein the composition is essentially free of feeder cells. In some embodiments, the disclosure provides a cell culture composition comprising a natural killer cell, a defined culture media comprising human serum (hS), and different feeder particles as described herein comprising one or more of IL-15, IL-21, CD137L, and/or CD137 and wherein the composition is essentially free of feeder cells. In some embodiments, the disclosure provides, as partially shown in FIG. 5A and as partially described in FIG. 5B, a feeder particle comprising IL-15, IL-21, CD137L, and CD137.

In some embodiments, the disclosure provides a cell culture composition comprising a T cell, a defined culture media comprising human serum (hS), and a synthetic particle as described herein, and wherein the composition is essentially free of feeder cells. In some embodiments, the disclosure provides a cell culture composition comprising a B cell, a defined culture media comprising human serum (hS), and a CD19-expressing synthetic particle as described herein, and wherein the composition is essentially free of feeder cells. In some embodiments, the disclosure provides a cell culture composition comprising a T cell, a defined culture media comprising human serum (hS), and a synthetic particle as described herein comprising one or more antibodies or antigen-binding fragments thereof that specifically bind CD3 and one or more antibodies or antigen-binding fragments thereof that specifically bind CD28, and wherein the composition is essentially free of feeder cells.

In some embodiments, the disclosure provides a cell culture composition comprising a T cell, a defined culture media comprising human serum (hS), and a synthetic particle, as shown in FIG. 22A and FIG. 22B, comprising one or more antibodies or antigen-binding fragments thereof that specifically bind CD3 and one or more antibodies or antigen-binding fragments thereof that specifically bind CD28, and wherein the composition is essentially free of feeder cells.

In some embodiments, the disclosure provides a cell culture composition comprising a lymphocyte, a defined culture media comprising hS, and a synthetic particle, as shown in FIG. 23A, comprising one or more antibodies or antigen-binding fragments thereof that specifically bind CD4. As shown in FIG. 23A, staining anti-CD4-conjugated magnetic nanoparticle containing particles with a fluorescently labeled secondary antibody shows a mean fluorescence intensity (MFI) of 190k indicating that the particles contain a significant amount of bound anti-CD4. FIG. 23B shows that capture beads can bind specifically with particle lymphocyte mimics. Top panels of FIG. 23B show positive control interactions between streptavidin and biotin particles. Bottom panels of FIG. 23B show Anti-CD4 beads with CD4+ particles.

In some embodiments, the disclosure provides a cell culture composition comprising a hydrogel particle, as described herein, and at least one immune cell. In embodiments, the cell culture composition may comprise a hydrogel particle comprising a matrix comprising a polymerized monomer, said matrix comprising a plurality of micropores and a plurality of macropores and one or more immunostimulatory biomolecules, and at least one immune cell. The one or more immunostimulatory biomolecules may be selected from the group consisting of an anti-CD3 antibody or antigen-binding fragment thereof, an anti-CD28 antibody or antigen-binding fragment thereof, an anti-CD19 antibody or antigen-binding fragment, an anti-41BBL antibody or antigen-binding fragment, an anti-OX40L antibody or antigen-binding fragment, an anti-CD2 antibody or antigen-binding fragment, an anti-CD335 antibody or antigen-binding fragment, an anti-CD16 antibody or antigen-binding fragment, an anti-CD56 antibody or antigen-binding fragment, an anti-CD20 antibody or antigen-binding fragment, an anti-CD80 antibody or antigen-binding fragment, an anti-CD86 antibody or antigen-binding fragment, an anti-CD69 antibody or antigen-binding fragment, an anti-CD154 antibody or antigen-binding fragment, an anti-CD137 antibody or antigen-binding fragment, an IgM antibody or antigen-binding fragment, an IgG antibody or antigen-binding fragment, an IgE antibody or antigen-binding fragment, an IgA antibody or antigen-binding fragment, an IgD antibody or antigen-binding fragment, and/or toll-like receptors. The at least one immune cell may be a target cell selected from one of Tables 3-7.

In some embodiments, the cells and the particles are cultured in media comprising synthetic media supplements and are serum-free.

In some embodiments, the feeder particles form a single monolayer in the cell culture. In some embodiments, the feeder particles form a multi-layer support in the cell culture.

In some embodiments, the cell culture comprises a single type of feeder particle. In some embodiments, the cell culture comprises a combination of different types of feeder particles.

In some embodiments, the cell culture comprises between about $1 \times 10^5$ and about $1 \times 10^8$ feeder particles per mL of cell culture. In some embodiments, the cell culture comprises about $1 \times 10^5$, about $1 \times 10^6$, about $1 \times 10^7$, or about $1 \times 10^8$ feeder particles per mL of cell culture. In some embodiments, the cell culture comprises a similar concentration of feeder particles as feeder cells used in traditional cell culturing methods.

In some embodiments, the feeder particles of the present disclosure are applied to the cell culture at a dilution of about 1:1 to about 1:1000. In some embodiments, the feeder particles are applied to the cell culture at a dilution of about 1:1, about 1:2, about 1:3, about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, about 1:100, about 1:200, about 1:300, about 1:400, about 1:500, about 1:600, about 1:700, about 1:800, about 1:900, or about 1:1000.

In some embodiments, culturing the target cell with a feeder particle of the present disclosure increases target cell proliferation by about 1% to about 10000% compared to culturing of the target cell without the feeder particle. In some embodiments, target cell proliferation is increased by about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 200%, about 300%, about 400%, about 500%, about 600%, about 700%, about 800%, about 900%, about 1000%, about 2000%, about 3000%, about 4000%, about 5000%, about 6000%, about 7000%, about 8000%, about 9000%, or about 10000% compared to culturing of the target cell without the feeder particle. In some embodiments, cell proliferation can be at least 100,000× the initial cell population.

In some embodiments, culturing the target cell with a feeder particle of the present disclosure increases target cell activation by about 1% to about 10000% compared to culturing of the target cell without the feeder particle. In some embodiments, target cell proliferation is increased by about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 200%, about 300%, about 400%, about 500%, about 600%, about 700%, about 800%, about 900%, about 1000%, about 2000%, about 3000%, about 4000%, about 5000%, about 6000%, about 7000%, about 8000%, about 9000%, or about 10000% compared to culturing of the target cell without the feeder particle. In some embodiments, cell activation can be at least 100,000× the initial cell population.

In some embodiments, the feeder cells can support culturing or proliferation based on proximity of a particle to a cell of interest. In one example, the particle can be conjugated to the cell of interest, whether via direct or indirect conjugation. In another example, the particle can be proximal to but not in contact with the cell of interest. The particle and the cell of interest can be separated by less than 1 nm, less than 1 micron, less than 1 millimeter, or any appropriate separation distance by which the activation event can still occur.

Culturing or proliferation may be distant from an area in which the cell of interest is located (i.e., culturing or proliferation can occur remotely). The distance can be at least 1 millimeter, at least 1 centimeter, at least 1 meter, etc. For example, the particle may be introduced intramuscularly or intravenously and the action is in a lymph node or distant immune organ or other target organ. Alternatively, the particle may be introduced on one side of a membrane and the action maybe on another side of a membrane (for e.g., via a semi-permeable membrane).

In some embodiments, the synthetic particles form a single monolayer in the cell culture. In some embodiments, the synthetic particles form a multi-layer support in the cell culture.

In some embodiments, the cell culture comprises a single type of a synthetic particle. In some embodiments, the cell culture comprises a combination of different types of synthetic particles.

In some embodiments, the cell culture comprises at least about $1×10^1$ synthetic particles per mL of cell culture, e.g., at least about $1×10^1$, at least about $1×10^2$, at least about $1×10^3$, at least about $1×10^4$, at least about $1×10^5$, at least about $1×10^6$, at least about $1×10^7$, at least about $1×10^8$, at least about $1×10^9$, at least about $1×10^{10}$, at least about $1×10^{11}$, at least about $1×10^{12}$, at least about $1×10^{13}$, at least about $1×10^{14}$, at least about $1×10^{15}$, at least about $1×10^{16}$, at least about $1×10^{17}$, at least about $1×10^{18}$, at least about $1×10^{19}$, at least about $1×10^{20}$, or more. In some embodiments, the cell culture comprises from about $1×10^5$ to about $1×10^8$ synthetic particles per mL of cell culture (e.g., $1×10^5$, $2×10^5$, $3×10^5$, $4×10^5$, $5×10^5$, $6×10^5$, $7×10^5$, $8×10^5$, $9×10^5$, $1×10^6$, $2×10^6$, $3×10^6$, $4×10^6$, $5×10^6$, $6×10^6$, $7×10^6$, $8×10^6$, $9×10^6$, $1×10^7$, $2×10^7$, $3×10^7$, $4×10^7$, $5×10^7$, $6×10^7$, $7×10^7$, $8×10^7$, $9×10^7$, including all values and subranges therein). In some embodiments, the cell culture comprises about $1×10^5$, about $1×10^6$, about $1×10^7$, or about $1×10^8$ synthetic particles per mL of cell culture. In some embodiments, the cell culture comprises a similar concentration of synthetic particles as APC cells used in traditional cell culturing methods.

In some embodiments, the synthetic particles of the present disclosure and T cells are cultured for at least about 30 minutes, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, 2, days, 36 hours, 3 days, 4 days, 5 days, 6 days, 7 days, 8 days, 9 days, 10 days, 11 days, 13 days, 14 days, or more, including all values and ranges therein.

Adoptive Cell Therapy

Provided are synthetic particles, and cells produced therefrom, for adoptive cell therapy, e.g., adoptive immunotherapy. The cells include immune cells such as those described above, including T cells and NK cells, and generally express genetically engineered antigen receptors such as engineered TCRs and/or chimeric antigen receptors (CARs).

The particles are engineered by introducing one or more biomolecules that stimulate T cell expansion and/or activation. The biomolecules may interact with antigen receptors, including engineered T cell receptors (TCRs) and functional non-TCR antigen receptors, such as chimeric antigen receptors (CARs), including activating, stimulatory, and costimulatory CARs, and combinations thereof. In some embodiments, the cells cultured with the synthetic particles disclosed herein express an engineered receptor targeting (e.g., specifically binding to or recognizing) a biomolecule, such as a disease-specific target antigen corresponding to the disease or condition to be treated.

In some embodiments, the adoptive cell therapy is tumor-infiltrating lymphocyte therapy. In tumor infiltrating lymphocyte therapy, naturally occurring T cells that have already infiltrated patients' tumors are harvested and cultured with the synthetic particles described herein to activate and expand them. Activated T cells are then re-infused into patients, where they can then seek out and destroy tumors.

In some embodiments, the adoptive cell therapy is engineered TCR therapy. In TCR therapy, T cells from patients are harvested. The T cells are equipped (engineered) with an appropriate T cell receptor (e.g., as described herein) that enables them to target specific cancer biomolecules. The engineered T cells are then cultured with the synthetic particles described herein to activate and expand them.

Activated T cells are then re-infused into patients, where they can then seek out and destroy tumors.

In some embodiments, the adoptive cell therapy is CAR T cell therapy. In CAR T cell therapy, T cells from patients are harvested. T cells are collected via apheresis, a procedure during which blood is withdrawn from the body and one or more blood components (such as plasma, platelets or white blood cells) are removed. The remaining blood is then returned to the body. T cells are then reengineered in a laboratory. To this end, the T cells are sent to a laboratory or a drug manufacturing facility where they are genetically engineered, by introducing nucleic acids, RNA, and/or DNA into them, to produce CARs on the surface of the cells. After this reengineering, the T cells are known as CAR T cells. CARs are proteins that allow the T cells to recognize an antigen on targeted tumor cells. The reengineered CAR T cells are then cultured with the synthetic particles described herein to activate and expand them. The number of the patient's genetically modified T cells is "expanded" by growing cells in the laboratory. When there are enough of them, these CAR T cells are frozen and sent to the hospital or center where the patient is being treated. At the hospital or treatment center, the CAR T cells are thawed and then infused into the patient, where they can then seek out and destroy tumors. CARs can bind to cancer cells even if their antigens are not presented on the surface via major histocompatibility complex, which can render more cancer cells vulnerable to their attacks. Many patients are given a brief course of one or more chemotherapy agents, called "lymphodepletion," before they receive the infusion of CAR T cells. CAR T cells that have been returned to the patient's bloodstream multiply in number. These are the "attacker" cells that will recognize, and attack, cells that have the targeted antigen on their surface.

In some embodiments, the adoptive cell therapy is natural killer (NK) cell therapy.

Depending on the target cell, individual particles can be derivatized with one or more cell surface markers, or fragments thereof, for example, extracellular portions thereof in the case of transmembrane proteins to further mimic the structural properties of the target cell. Tables 4, 7, and 8, provided previously, sets forth a non-limiting list of cell surface markers that can be used to derivative particles, depending on the target cell. Although the cell surface marker is provided, it is understood that a portion of the cell surface marker, for example, a receptor binding portion, a ligand binding portion, or an extracellular portion of the marker can be used to derivative the particle (at the free functional group, as described above). See also FIGS. 29 and 30 which show that particle surface modification with for example, a cell surface receptor, together with the selective tuning of FSC and/or SSC, allows for the fabrication of a particle with the desired feature(s).

Cell types including but not limited to various cell lines such as CHO, HEK-293, BHK-21, NS0, MDCK, VERO, MRC-S, W1-38 and Sp2/0 Mouse Myeloma (hybridomas). Other cell types for use with the particles described herein include keratinocyte of epidermis, basal cell of epidermis, keratinocyte of fingernails and toenails, basal cell of nail bed, hair shaft cells, medullary hair shaft cells, cortical hair shaft cells, cuticular hair shaft cells, hair-root sheath cells, cuticular hair-root sheath cells, hair-root sheath cells of Huxley's layer, hair-root sheath cells of Henle's layer, external hair-root sheath cells, hair matrix cell (stem cell), surface epithelial cell of stratified squamous epithelium of tongue, surface epithelial cell of stratified squamous epithelium of oral cavity, surface epithelial cell of stratified squamous epithelium of esophagus, surface epithelial cell of stratified squamous epithelium of anal canal, surface epithelial cell of stratified squamous epithelium of distal urethra, surface epithelial cell of stratified squamous epithelium of vagina, basal cell of these epithelia, cell of urinary epithelium, cells of salivary gland, mucous cells of salivary gland, serous cell of salivary gland, cell of von Ebner's gland in tongue, cell of mammary gland, cell of lacrimal gland, cell of ceruminous gland of ear, cell of eccrine sweat gland, cell of eccrine sweat gland, cell of apocrine sweat gland, cell of gland of Moll in eyelid, cell of sebaceous gland, cell of Bowman's gland in nose, cell of Brunner's gland in duodenum, cell of seminal vesicle, cell of prostate gland, cell of bulbourethral gland, cell of Bartholin's gland, cell of gland of Littre, cell of endometrium of uterus, isolated goblet cell of respiratory and digestive tracts, mucous cell of lining of stomach, zymogenic cell of gastric gland, oxyntic cell of gastric gland, acinar cell of pancreas, Paneth cell of small intestine, type II pneumocyte of lung, Clara cell of lung, cells of anterior pituitary, cell of intermediate pituitary, cells of posterior pituitary, cells of gut and respiratory tract, cells of thyroid gland, cells of parathyroid gland, cells of adrenal gland, steroid hormones, cells of gonads, cells of juxtaglomerular apparatus of kidney, juxtaglomerular cell, macula, densa cell, peripolar cell, mesangial cell, brush border cell of intestine, striated duct cell of exocrine glands, gall bladder epithelial cell, brush border cell of proximal tubule of kidney, distal tubule cell of kidney, nonciliated cell of ductulus efferens, epididymal principal cell, epididymal basal cell, hepatocyte, white fat cell, brown fat cell, lipocyte of liver, type I pneumocyte, pancreatic duct cell, parietal cell of kidney glomerulus, podocyte of kidney glomerulus, cell of thin segment of loop of Henle, collecting duct cell (in kidney), duct cell of seminal vesicle, duct cell of prostate gland, vascular endothelial cells of blood vessels and lymphatics, fenestrated vascular endothelial cells, continuous vascular endothelial cells, splenic vascular endothelial cells, synovial cell, serosal cell, squamous cell lining perilymphatic space of ear, cells lining endolymphatic space of ear, squamous cell, columnar cells of endolymphatic sac, "dark" cell, vestibular membrane cell, stria vascularis basal cell, stria vascularis marginal cell, cell of Claudius, cell of Boettcher, choroid plexus cell, squamous cell of pia-arachnoid, cells of ciliary epithelium of eye, corneal "endothelial" cell, ciliated cells of respiratory tract, ciliated cells of oviduct and of endometrium of uterus, ciliated cells of rete testis and ductulus efferens, ciliated cells of central nervous system, epithelial, ameloblast, nonepithelial, chondrocytes, osteoblast/osteocyte, osteoprogenitor cell, hyalocyte of vitreous body of eye, stellate cell of perilymphatic space of ear, skeletal muscle cells, heart muscle cells, smooth muscle cells (various), myoepithelial cells, red blood cell, megakaryocyte, macrophages and related cells, neutrophil, eosinophil, basophil, mast cell, T lymphocyte, B lymphocyte, photoreceptors (rods, cones, and can be blue sensitive, green sensitive, red sensitive), inner hair cell of organ of Corti, outer hair cell of organ of Corti, type I hair cell of vestibular apparatus of ear, type II hair cell of vestibular apparatus of ear, type II taste bud cell, olfactory neuron, basal cell of olfactory epithelium, carotid body cell type I, carotid body cell type II, Merkel cell of epidermis, primary sensory neurons specialized for touch (various), primary sensory neurons specialized for temperature—cold sensitive, primary sensory neurons specialized for temperature— heat sensitive, primary sensory neurons specialized for pain (various), proprioceptive primary sensory neurons (various), autonomic neurons, inner pillar cell, outer pillar cell, inner phalangeal cell, outer phalangeal cell, border cell, Hensen cell, supporting cell of vestibular apparatus, supporting cell of taste bud (type I taste bud cell), supporting cell of olfactory epithelium, Schwann cell, satellite cell (encapsulating peripheral nerve cell bodies), enteric glial cell, neurons, glial cells, anterior lens epithelial cell, lens fiber (crystallin-containing cell), melanocyte, retinal pigmented epithelial cell, oogonium/oocyte, spermatocyte, spermatogonium (stem cell for spermatocyte), ovarian follicle cell, Sertoli cell (in testis), thymus epithelial cell, salivary gland mucous cell, salivary gland number 1, Von Ebner's gland cell in tongue, mammary gland cell, lacrimal gland cell, Ceruminous gland cell in ear, Eccrine sweat gland dark cell, eccrine sweat gland clear cell, apocrine sweat gland cell, Gland of Moll cell in eyelid, sebaceous gland cell, Bowman's gland cell in nose, Brunner's gland cell in duodenum, seminal vesicle cell, prostate gland cell, Bulbourethral gland cell, Bartholin's gland cell, Gland of Littre cell, uterus endometrium cell, goblet cell of respiratory and digestive tracts, stomach lining mucous cell, gastric gland zymogenic cell, gastric gland oxyntic cell, pancreatic acinar cell, Paneth cell of small intestine, pneumocyte of lung, Clara cell of lung, anterior pituitary cells, somatotropes, lactotropes, thyrotropes, gonadotropes, corticotropes, melanocyte-stimulating hormone, magnocellular neurosecretory cells, gut and respiratory tract cells, thyroid gland cells, thyroid epithelial cell, parafollicular cell, parathyroid gland cells, parathyroid chief cell, oxyphil cell, adrenal gland cells, chromaffin cells, secreting steroid hormones (mineralcorticoids and gluco corticoids), Leydig cell of testes secreting testosterone, Theca interna cell of ovarian follicle secreting estrogen, corpus luteum cell of ruptured ovarian follicle secreting progesterone, granulosa lutein cells, theca lutein cells, juxtaglomerular cell (renin secretion), macula densa cell of kidney, peripolar cell of kidney, mesangial cell of kidney, epidermal keratinocyte, epidermal basal cell, keratinocyte of fingernails and toenails, nail bed basal cell (stem cell), medullary hair shaft cell, cortical hair shaft cell, cuticular hair shaft cell, cuticular hair root sheath cell, hair root sheath cell of Huxley's layer, hair root sheath cell of Henle's layer, external hair root sheath cell, hair matrix cell (stem cell), epithelial cell of stratified squamous epithelium of cornea, epithelial cell of stratified squamous epithelium of tongue, epithelial cell of stratified squamous epithelium of oral cavity, epithelial cell of stratified squamous epithelium of esophagus, epithelial cell of stratified squamous epithelium of anal canal, epithelial cell of stratified squamous epithelium of distalurethra, epithelial cell of stratified squamous epithelium of vagina, basal cell (stem cell) of epithelia of cornea, basal cell (stem cell) of epithelia of tongue, basal cell (stem cell) of epithelia of oral cavity, basal cell (stem cell) of epithelia of esophagus, basal cell (stem cell) of epithelia of anal canal, basal cell (stem cell) of epithelia of distal urethra, basal cell (stem cell) of epithelia of vagina, urinary epithelium cell, auditory inner hair cell of organ of Corti, auditory outer hair cell of organ of Corti, basal cell of olfactory epithelium, cold-sensitive primary sensory neurons, heat-sensitive primary sensory neurons, Merkel cell of epidermis (touch sensor), olfactory receptor neuron, pain-sensitive primary sensory neurons (various types), photoreceptor cells of retina in eye: photoreceptor rod cells, photoreceptor blue-sensitive cone cell of eye, photoreceptor green-sensitive cone cell of eye, photoreceptor red-sensitive cone cell of eye, proprioceptive primary sensory neurons, touch-sensitive primary sensory neurons, Type I carotid body cell, Type II carotid body cell, Type I hair cell of vestibular system of ear, Type II hair cell of vestibular system of ear, Type I taste bud cell, cholinergic neural cell, adrenergic neural cell, peptidergic neural cell, inner pillar cell of organ of Corti, outer pillar cell of organ of Corti, inner phalangeal cell of organ of Corti, outer phalangeal cell of organ of Corti, border cell of organ of Corti, Hensen cell of organ of Corti, vestibular apparatus supporting cell, taste bud supporting cell, olfactory epithelium supporting cell, Schwann cell, satellite glial cell, enteric glial cell, astrocyte, neuron cells, oligodendrocyte, spindle neuron, anterior lens epithelial cell, crystallin-containing lens fiber cell, hepatocyte, adipocytes (white fat cell, brown fat cell, liver lipocyte), kidney parietal cell, kidney glomerulus podocyte, kidney proximal tubule brush border cell, loop of Henle thin segment cell, kidney distal tubule cell, kidney collecting duct cell, Type I pneumocyte, pancreatic duct cell, nonstriated duct cell, principal cell, intercalated cell, duct cell, intestinal brush border cell, exocrine gland striated duct cell, gall bladder epithelial cell, ductulus efferens nonciliated cell, epididymal principal cell, epididymal basal cell, ameloblast epithelial cell, planum semilunatum epithelial cell of vestibular system of ear, organ of Corti interdental epithelial cell, loose connective tissue fibroblasts, corneal fibroblasts (corneal keratocytes), tendon fibroblasts, bone marrow reticular tissue fibroblasts, nonepithelial fibroblasts, pericyte, nucleus pulposus cell of intervertebral disc, cementoblast/cementocyte, odontoblast/odontocyte, hyaline cartilage chondrocyte, fibrocartilage chondrocyte, elastic cartilage chondrocyte, osteoblast/osteocyte, osteoprogenitor cell, hyalocyte of vitreous body of eye, stellate cell of perilymphatic space of ear, hepatic stellate cell (Ito cell), pancreatic stelle cell, skeletal muscle cell, red skeletal muscle cell (slow), white skeletal muscle cell (fast), intermediate skeletal muscle cell, nuclear bag cell of muscle spindle, nuclear chain cell of muscle spindle satellite cell (stem cell), heart muscle cells, ordinary heart muscle cell, nodal heart muscle cell, Purkinje fiber cell, smooth muscle cell, myoepithelial cell of iris, myoepithelial cell of exocrine glands, erythrocyte, megakaryocyte, monocyte, connective tissue macrophage, epidermal Langerhans cell, osteoclast (in bone), dendritic cell (in lymphoid tissues), microglial cell (in central nervous system), neutrophil granulocyte, eosinophil granulocyte, basophil granulocyte, hybridoma cell, mast cell, helper T cell, suppressor T cell, cytotoxic T cell, natural killer T cell, B cell, natural killer cell, reticulocyte, stem cells and committed progenitors for the blood and immune system (various types), oogonium/oocyte, spermatid, spermatocyte, spermatogonium cell, spermatozoon, ovarian follicle cell, sertoli cell (in testis), thymus epithelial cell, and/or interstitial kidney cells.

In some embodiments, a target cell is a tumor microvesicle or tumor macrovesicle. Tumor microvesicles, also known as tumor-secreted microvesicles or tumor-secreted exosomes, can be found in circulating blood and may have immune-suppressive activities. Tumor microvesicles typically range in size from 30-200 nm in diameter. Larger tumor micro vesicles may be referred to as tumor macro vesicles, and can range in size from 3-10 μm in diameter.

i. Cells, Cell Preparation, and Culture

In some embodiments, the cells are eukaryotic cells, such as mammalian cells, e.g., human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some embodiments, the cells are human cells. The cells typically are primary cells, such as those isolated directly from a subject and/or isolated from a subject and frozen. In some embodiments, the cells include one or more subsets of T cells or other cell types, such as whole T cell populations, CD4+ cells, CDS+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some embodiments, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CDS+ T cells are naïve T (TN) cells, effector T cells (T EFF), memory T cells and sub-types thereof, such as stem cell memory T (T scM), central memory T (TcM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as THI cells, TH2 cells, TH3 cells, THI 7 cells, TH9 cells, TH22 cells, follicular helper T cells, alpha/beta T cells, and delta/gamma T cells.

In some embodiments, one or more of the T cell populations is enriched for or depleted of cells that are positive for (marker+) or express high levels (marker$^{high}$) of one or more particular markers, such as surface markers, or that are negative for (marker−) or express relatively low levels (marker$^{low}$) of one or more markers. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CDS+ cells or the T cells, e.g., CD3+ cells) are enriched for (i.e., positively selected for) cells that are positive or expressing high surface levels of CD45RO, CCR7, CD2S, CD27, CD44, CD127, and/or CD62L and/or depleted of (e.g., negatively selected for) cells that are positive for or express high surface levels of CD45RA. In some embodiments, cells are enriched for or depleted of cells positive or expressing high surface levels of CD122, CD95, CD25, CD27, and/or IL 7-Ra (CD127). In some examples, CDS+ T cells are enriched for cells positive for CD45RO (or negative for CD45RA) and for CD62L.

In some embodiments, a CD4+ T cell population and a CDS+ T cell sub-population, e.g., a sub-population enriched for central memory (T cM) cells. In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

ii. Cell Preparation

The cells typically are isolated from a sample, such as a biological sample, e.g., one obtained from or derived from a subject. In some embodiments, the subject from which the cell is isolated as one having a particular disease or condition or in need of a cell therapy or to which cell therapy will be administered. The subject in some embodiments is a mammal, such as a human, such as a subject in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g., transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some embodiments, the sample from which the cells are derived or isolated is blood or a blood-derived sample or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

iii. Incubation and Culture

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a genetically engineered antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded), and incubating the culture (e.g., for a time sufficient to expand the numbers of T cells). In some embodiments, the non-dividing feeder cells can comprise gamma irradiated PBMC feeder cells. In some embodiments, the PBMC are irradiated with gamma rays in the range of about 3000 to 3600 rads to prevent cell division. In some embodiments, the feeder cells are added to culture medium prior to the addition complex (MHC) molecule. Exemplary antigen receptors, including CARs and recombinant TCRs, as well as methods for engineering and introducing the receptors into cells.

In some embodiments, the T cells are expanded by cell culture with synthetic particles, as described above. For instance, in some embodiments, the cell culture comprises at least about $1\times10^1$ synthetic particles per mL of cell culture, e.g., at least about $1\times10^1$, at least about $1\times10^2$, at least about $1\times10^3$, at least about $1\times10^4$, at least about $1\times10^5$, at least about $1\times10^6$, at least about $1\times10^7$, at least about $1\times10^8$, at least about $1\times10^9$, at least about $1\times10^{10}$, at least about $1\times10^{11}$, at least about $1\times10^{12}$, at least about $1\times10^{13}$, at least about $1\times10^{14}$, at least about $1\times10^{15}$, at least about $1\times10^{16}$, at least about $1\times10^{17}$, at least about $1\times10^{18}$, at least about $1\times10^{19}$, at least about $1\times10^{20}$, or more. In some embodiments, the cell culture comprises from about $1\times10^5$ to about $1\times10^8$ synthetic particles per mL of cell culture (e.g., $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, including all values and subranges therein). In some embodiments, the cell culture comprises about $1\times10^5$, about $1\times10^6$, about $1\times10^7$, or about $1\times10^8$ synthetic particles per mL of cell culture.

In some embodiments, the synthetic particles of the present disclosure and T cells are cultured for at least about 30 minutes, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, 2 days, 3, days, 4 days, 5 days, 6 days, 7 days, 8 days, 9 days, 10 days, 11 days, 13 days, 14 days, or more, including all values and ranges therein.

In some embodiments, the synthetic particles of the present disclosure are applied to the cell culture at a dilution of about 1:1 to about 1:1000. In some embodiments, the synthetic particles are applied to the cell culture at a dilution of about 1:1, about 1:2, about 1:3, about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, about 1:100, about 1:200, about 1:300, about 1:400, about 1:500, about 1:600, about 1:700, about 1:800, about 1:900, or about 1:1000.

In some embodiments, culturing the T cell with a synthetic particle of the present disclosure increases T cell proliferation by about 1% to about 1000s % compared to culturing of the T cell without the synthetic particle. In some embodiments, T cell proliferation is increased by about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 200%, about 300%, about 400%, about 500%, about 600%, about 700%, about 800%, about 900%, or about 1000% compared to culturing of the T cell without the synthetic particle.

In some embodiments, culturing the T cell with a synthetic particle of the present disclosure increases T cell activation by about 1% to about 1000% compared to culturing of the T cell without the synthetic particle. In some embodiments, T cell activation is increased by about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 200%, about 300%, about 400%, about 500%, about 600%, about 700%, about 800%, about 900%, or about 1000% compared to culturing of the T cell without the synthetic particle.

In some embodiments, culturing the T cell with a synthetic particle of the present disclosure increases T cell expansion by about 1% to about 1000% compared to culturing of the T cell without the synthetic particle. In some embodiments, T cell expansion is increased by about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 200%, about 300%, about 400%, about 500%, about 600%, about 700%, about 800%, about 900%, or about 1000% compared to culturing of the T cell without the synthetic particle.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some embodiments is provided in any suitable amount, such as a ratio of LCL feeder cells to initial T lymphocytes of at least about 10:1.

In embodiments, antigen-specific T cells, such as antigenspecific CD4+ and/or CDS+ T cells, are obtained by stimulating naïve or antigen specific T lymphocytes with antigen. For example, antigen-specific T cell lines or clones can be generated to cytomegalovirus antigens by isolating T cells from infected subjects and stimulating the cells in vitro with the same antigen.

In some embodiments, the methods include assessing expression of one or more markers on the surface of the engineered cells or cells being engineered. In one embodiment, the methods include assessing surface expression of one or more target antigen (e.g., antigen recognized by the genetically engineered antigen receptor) sought to be targeted by the adoptive cell therapy, for example, by affinity-based detection methods such as by flow cytometry. In some embodiments, where the method reveals surface expression of the antigen or other marker, the gene encoding the antigen or other marker is disrupted or expression otherwise repressed for example, using the methods described herein.

EXAMPLES

The present invention is further illustrated by reference to the following Examples. However, it should be noted that these Examples, like the embodiments described above, are illustrative and are not to be construed as restricting the scope of the invention in any way.

Example 1: Generation of Hydrogel Particles

Photomasks for UV lithography were sourced from CADart Services Inc, and were designed using AutoCad (AutoDesk, Inc.). SU-8 photo resist (Microchem, Inc.) was photo crosslinked on 4" silicon wafers using a collimated UV light source (OAI, Inc.) to create masters for microfluidic device fabrication. PDMS (polydimethylsiloxane, Sigma Aldrich, Inc.) was prepared and formed using standard published methods for soft lithography and microfluidic device fabrication (See, McDonald J C, et al., 2000, Electrophoresis 21:27-40).

Droplets were formed using flow-focusing geometry where two oil channels focus a central stream of aqueous monomer solution to break off droplets in a water-in-oil emulsion. A fluorocarbon-oil (Novec 7500 3M, Inc.) was used as the outer, continuous phase liquid for droplet formation. To stabilize droplets before polymerization, a surfactant was added at 0.5% w/w to the oil phase (ammonium carboxylate salt of Krytox 157 FSH, Dupont). To make the basic polyacrylamide gel particle, a central phase of an aqueous monomer solution containing N-acrylamide (1-20% w/v), a cross-linker (N,N'-bisacrylamide, 0.05-1% w/v), an accelerator, and ammonium persulfate (1% w/v) was used. An accelerator, (N,N,N',N'tetramethylethylenediamine (2% vol %) was added to the oil-phase in order to trigger hydrogel particle polymerization after droplet formation.

Several co-monomers were added to the basic gel formulation to add functionality. Allyl-amine provided primary amine groups for secondary labeling after gel formation. We modulated forward scatter by adjusting the refractive index of the gel by adding co-monomers allyl acrylate and allyl methacrylate. Side scattering of the droplets was tuned by adding a colloidal suspension of silica nanoparticles and/or PMMA (poly(methyl methacrylate)) particles (~100 nm) to the central aqueous phase prior to polymerization.

Stoichiometric multiplexing of the hydrogel particles was achieved by utilizing co-monomers containing chemically orthogonal side groups (amine, carboxyl, maleimide, epoxide, alkyne, etc.) for secondary labeling.

Droplets were formed at an average rate of 5 kHz and were collected in the fluorocarbon oil phase. Polymerization was completed at 50° C. for 30 minutes, and the resulting hydrogel particles were washed from the oil into an aqueous solution.

Example 2: Generation and Visualization of Hydrogel Particles

Figure 3A:
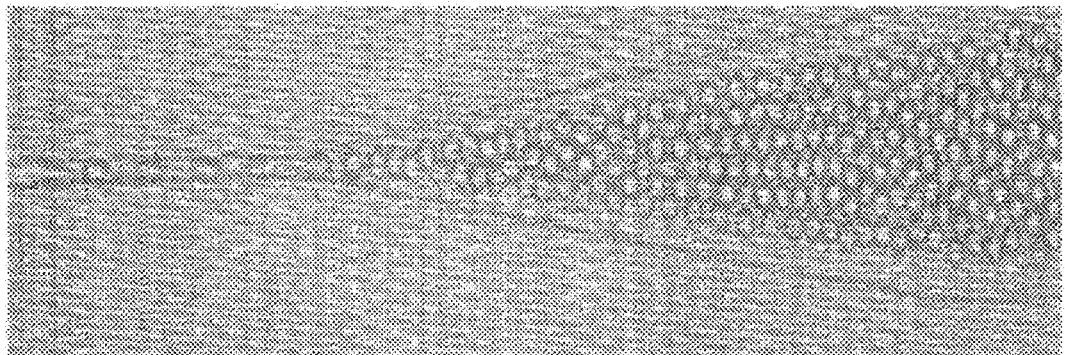
FIG. 3A-3C provides brightfield and fluorescent images of labeled hydrogel particles of the disclosure.
Figure 3B:
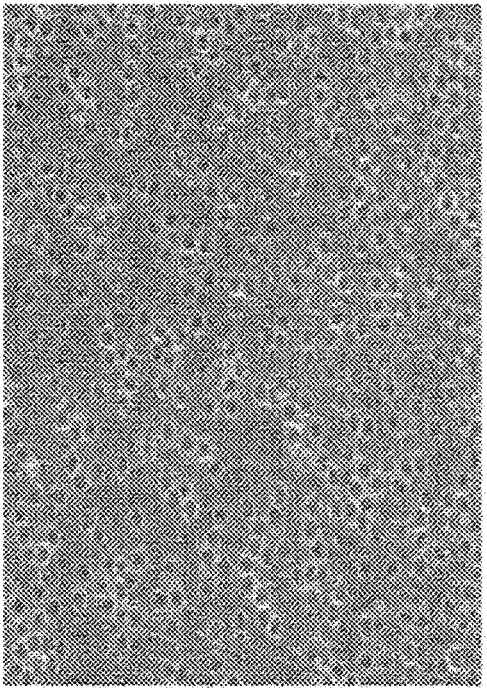
Figure 3C:
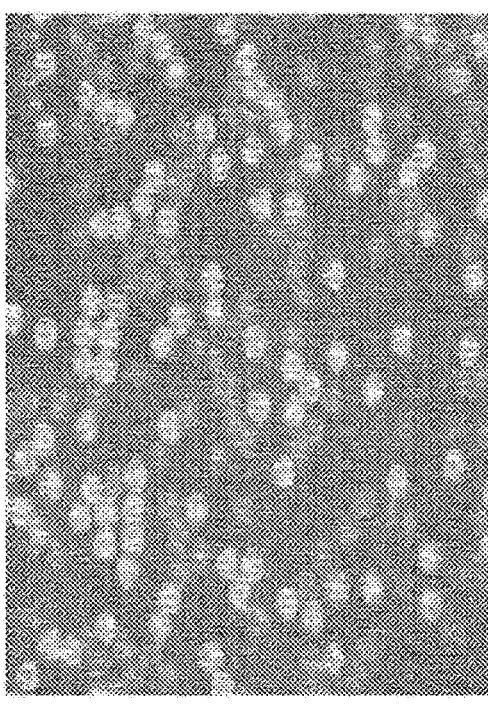

Water containing 5% acrylamide, 0.25% bisacrylamide, 0.05% allyl amine, and 0.1% ammonium persulfate was flowed through a center channel and focused by oil containing 0.1% TEMED through a 10 µm nozzle to produce 10 µm hydrogel particles, shown in FIG. 3A. Following polymerization, the particles were washed in water, shown in FIG. 3B, and conjugated to dyes of interest. The fluorescent hydrogel particles were visualized with fluorescence microscopy, shown in FIG. 3C.

Example 3: Multidimensional Tuning of Hydrogel Particle Optical Properties

Figures 4A, 4B, 4C:
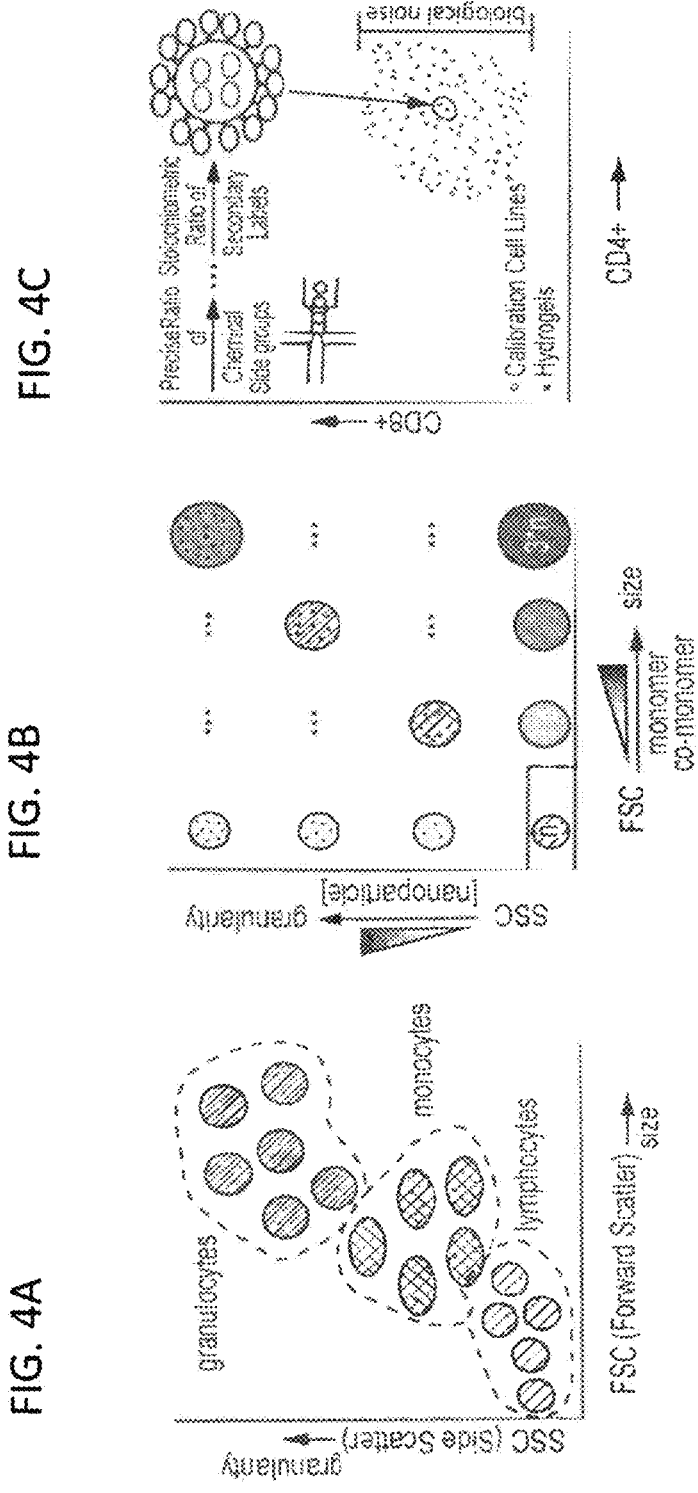
FIG. 4A-4C illustrates the use of hydrogel particles of the disclosure as calibrants for cell types displaying a variety of optical scattering properties.

As depicted in FIG. 4, hydrogel particles are tuned in multiple dimensions to match specific cell types unlike polystyrene beads. Cells are deconvolved using combinations of optical parameters such as FSC and SSC (FIG. 4A) or secondary markers. Hydrogel particles are tuned to match the SSC and FSC of specific cell types unlike polystyrene beads (brown) which are limited in size (FSC) and side scattering (FIG. 4B). Hydrogel particles are further functionalized with stoichiometrically tuned ratios of specific chemical side-groups and secondary labels allowing the cell type to be precisely matched without suffering from biological noise as fixed cell lines do (FIG. 4C).

Figure 5:
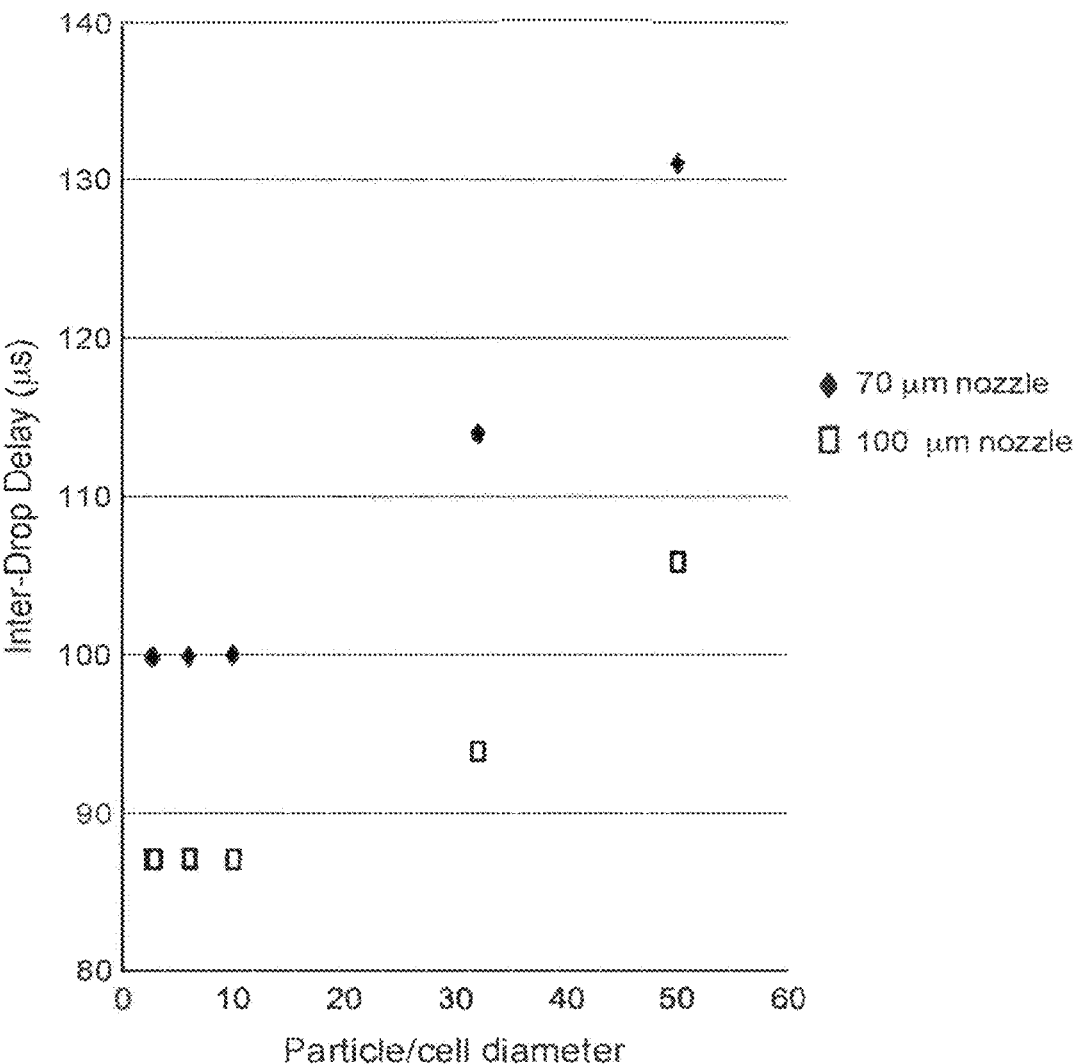
FIG. 5 provides dating showing correlation of inter-drop delay for a flow cytometer with hydrogel particle diameter.

Example 4: Flow Cytometer Delay Time as a Function of Hydrogel Particle Diameter As shown in FIG. 5, the inter-drop delay for a flow cytometer can be precisely correlated to hydrogel particle diameter. Data are shown for hydrogel particles of 3, 6, 10, 32, and 50 µm diameters using flow cytometer nozzle sizes of 70 µm and 100 µm.

Example 5: Comparison of Hydrogel Particles with Encapsulated DNA to Cells

Figures 6A, 6B, 6C, 6D:
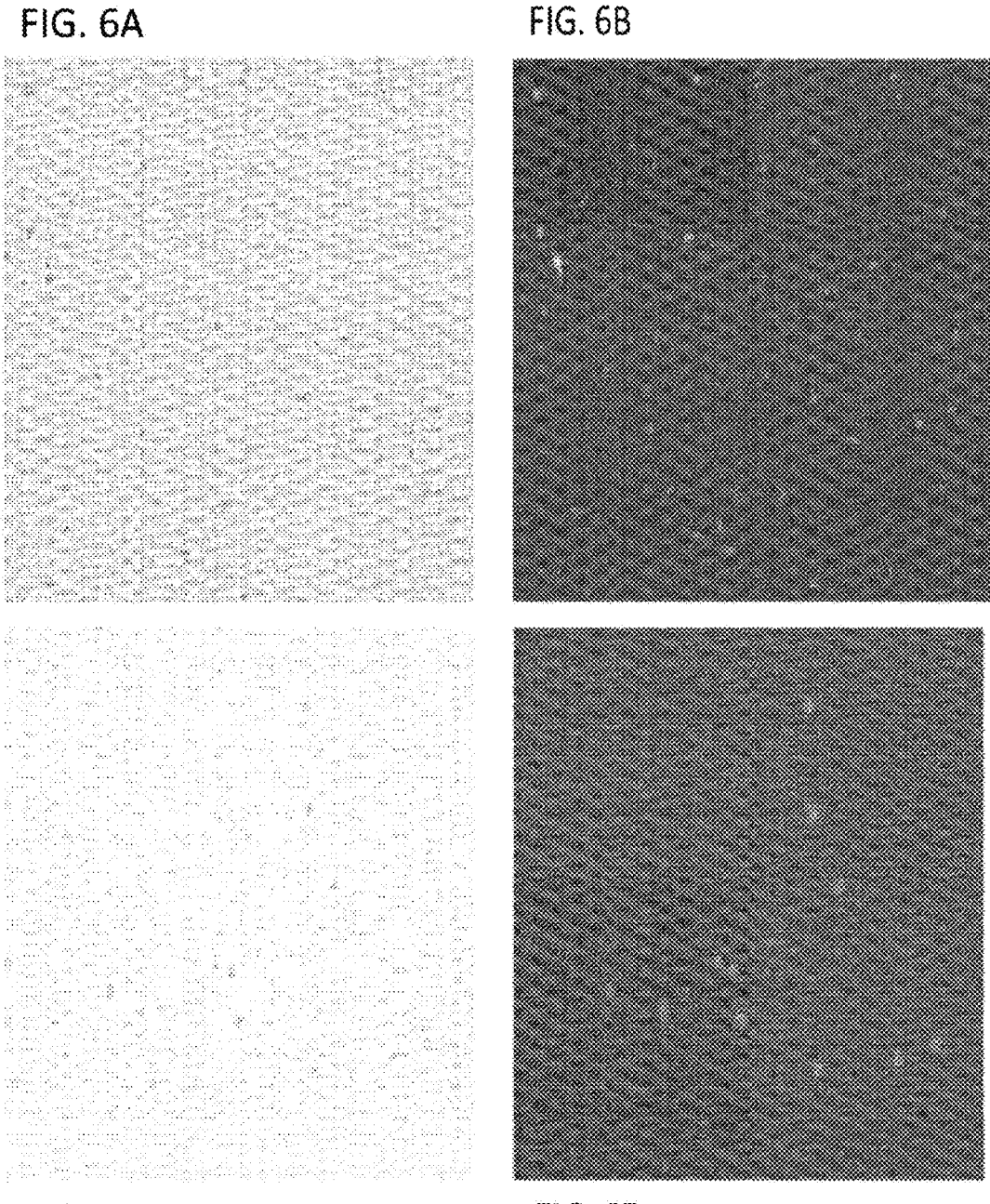
FIG. 6A and FIG. 6C provides brightfield and FIG. 6B and FIG. 6D fluorescent images of Chinese Hamster Ovary cells (FIG. 6A and FIG. 6B) and hydrogel particles of the disclosure (FIG. 6C and FIG. 6D).

To form hydrogel particles with encapsulated DNA, 40 µg/mL-1000) µg/mL of reconstituted calf thymus DNA was added to a polymer mix containing 20% 19:1(acrylamide: bis-acrylamide) and 0.1% allyl amine in water. 0.4% ammoniumpersulfate was added to the mix prior to droplet formation. Hydrogel particles were formed as described in Example 1. Hydrogel particles with 200 µg/mL of encapsulated calf thymus DNA displayed cell-like staining using propidium iodide as visualized using a commercial imaging cytometer and compared to Chinese Hamster Ovary cells stained using the same procedure. Images were obtained using a Nexcelom Cellometer™ (FIG. 6).

Figure 7:
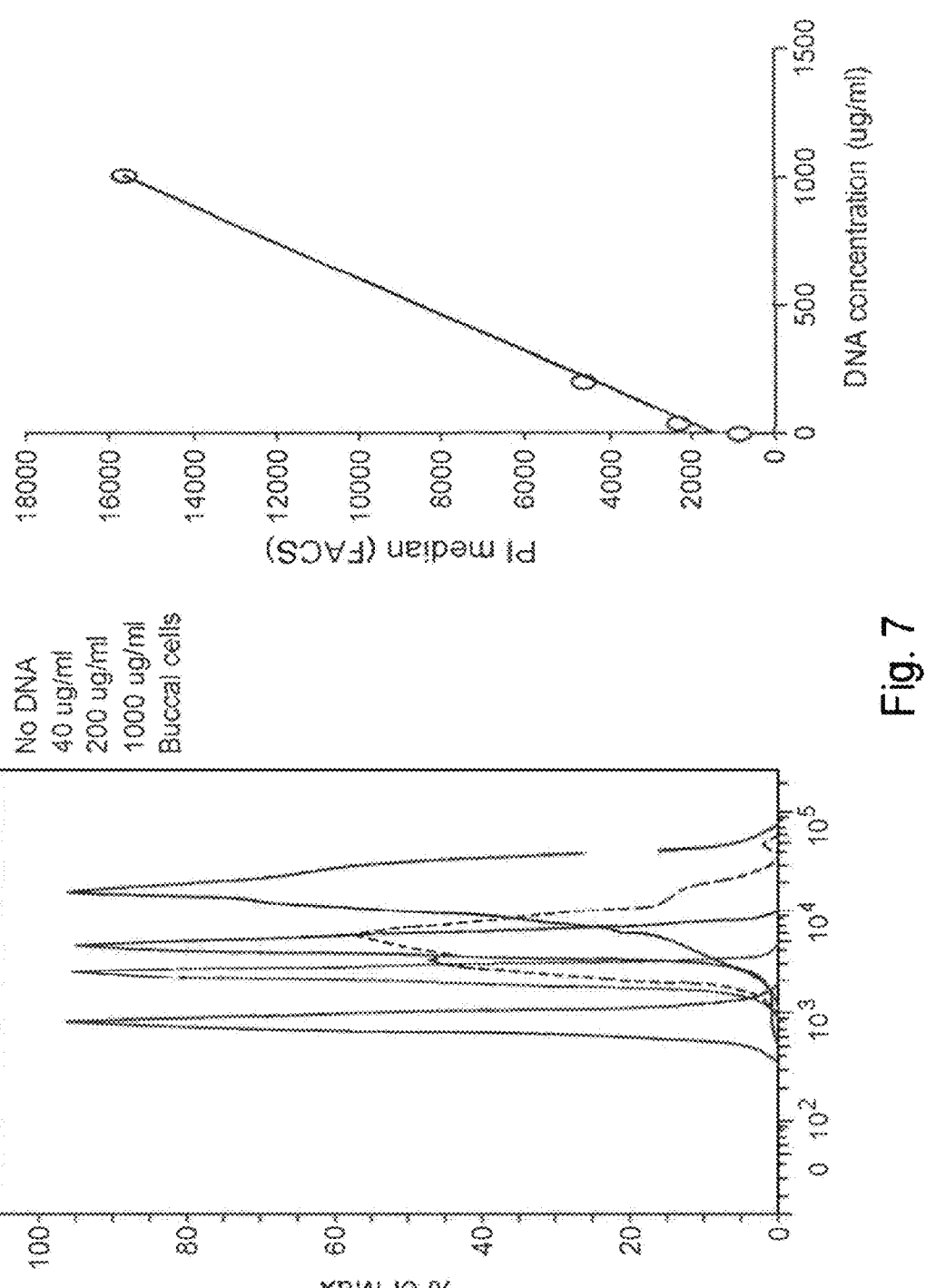
FIG. 7 provides data showing comparison of human buccal cells to hydrogel particles encapsulating different amounts of DNA, as measured by fluorescence-activated cell sorting (FACS).

Cells obtained from a buccal swab were washed in PBS and stained with propidium iodide. In parallel, populations of hydrogel particles containing a range of DNA concentrations were also stained in the same manner. Both the cell and particle suspensions were analyzed on a flow cytometer (488/590 nm excitation/emission). Flow cytometry analysis of cheek cells and the same range of encapsulated DNA particles showed that the particles display a range of cell-like fluorescent properties (FIG. 7, left panel). The intensity of staining shows a linear correlation with the median intensity as measured by flow cytometry (FIG. 7, right panel).

Example 6: Tuning of Hydrogel Particle Side Scattering

Figure 8:
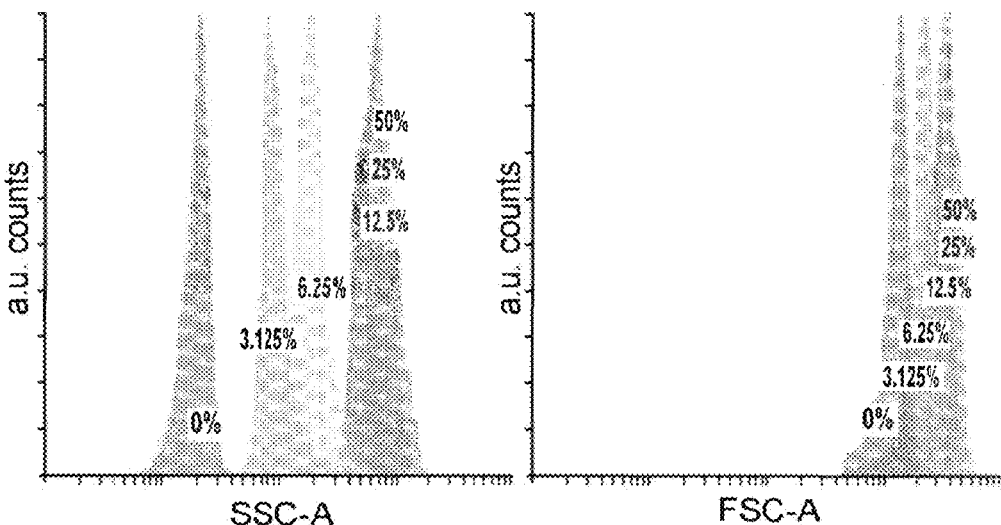
FIG. 8 provides data for hydrogel particles encapsulating nanoparticles at different concentrations, demonstrating tuning of side scattering independent of forward scattering.

Colloidal silica was added at 12.5%, 6.25%, 3.125% and 0% to the aqueous fraction of the polymer mix and hydrogel particles were formed as described in Example 1. Forward and side scattering data were obtained using a flow cytometer. The results showed that side scatter signal (FIG. 8, left panel) increased with higher percentages of encapsulated nanoparticles while forward scatter (FIG. 8, right panel) remained generally unchanged, demonstrating the independent tuning of side scatter and forward scatter.

Example 7: Tuning of Hydrogel Particle Forward Scattering

Figure 9:
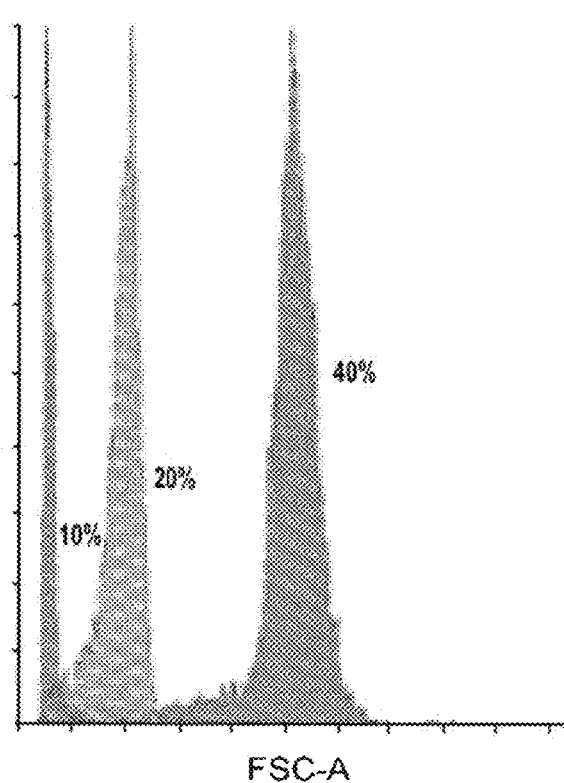
FIG. 9 provides data for hydrogel particles produced with different percentages of polymer, demonstrating tuning of refractive index measured by forward scattering.

In this experiment, the percentage of acrylamide:bisacrylamide in the hydrogel composition was varied from between 10 and 40% to tune the refractive index of the hydrogel particles as measured by forward scattering in a flow cytometer. As shown in FIG. 9, the forward scattering increased with increasing percentages of acrylamide:bisacrylamide as a fraction of water.

Example 8: Tuning of Hydrogel Particle Optical Properties

An example of tuning hydrogel particles to match optical properties of a desired cell subtype. Co/monomers can be combined with nanoparticles to tune both forward and side scatter properties of the hydrogels using passive optical measurements in a flow cytometer. By combining these properties with chemically labile co-monomers (e.g. allyl amine, acrylic acid), additional fluorophores/proteins/biological side groups can be added and labeled (if desired) in order to match cell subpopulation staining in addition to scattering properties. These are the three primary metric by which cells are identified using flow cytometry. Additional side groups, such as those containing heavy metals, can be used for Cy-TOF (cytometry, time of flight mass spectrometry) calibration for example. Finally, biocompatible material can be encapsulated to mimic subcellular organelle staining.

Example 9: Tuning of Hydrogel Particle Optical Properties

Figures 13A, 13B, 13C:
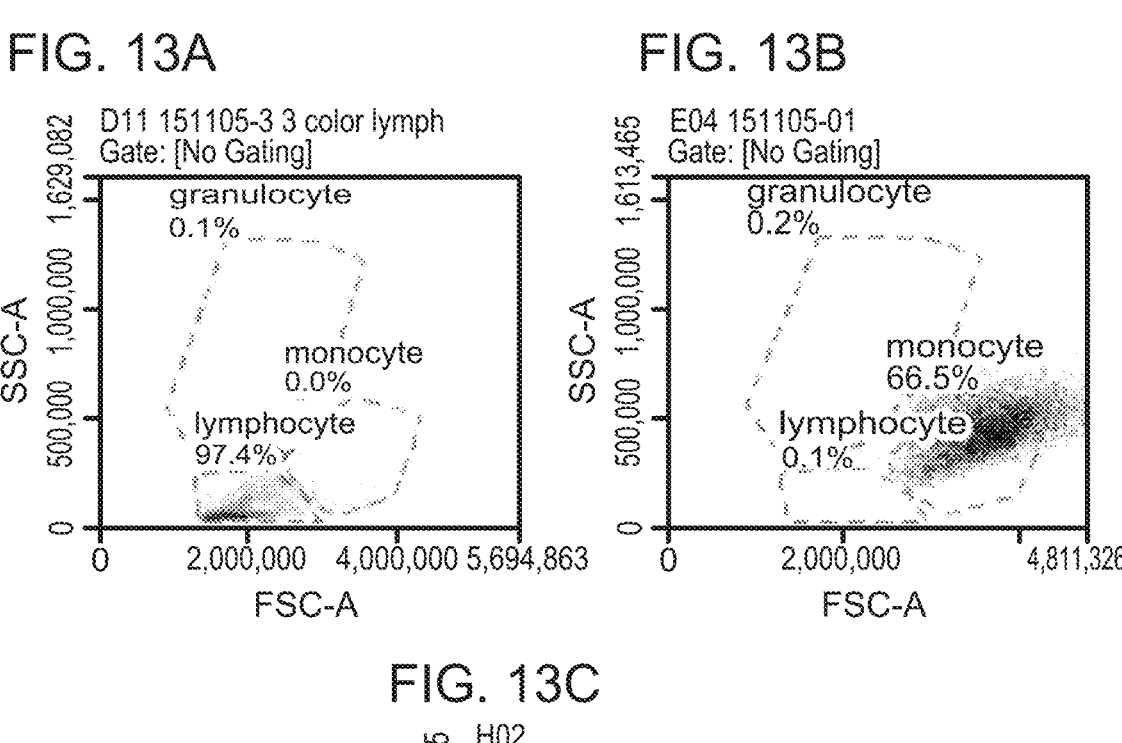
FIG. 13 are scatter plots for various hydrogel particles (FIG. 13A) and (FIG. 13B) and a commercial blood sample (FIG. 13C).

A 50 nm nanoparticle colloidal suspension was incorporated into the hydrogel matrix to mimic the optical properties of lymphocytes and monocytes (FIGS. 13A and 13B). The percent composition of the suspension was altered to match the blood cell subpopulations from the blood sample control (Streck) (FIG. 13C).

Specifically, the concentration of the acrylamide monomer (0.7-0.8M) of the hydrogel particle was adjusted to increase the forward scatter of the particles to match blood cell subpopulations. The percentage of bisacrylamide cross linker can also be changed to affect forward scatter (1-5%). Silica nanoparticles were used at 5% or 10% in the compositions to adjust side scatter. The results of this experiment are shown in FIG. 13A and FIG. 13B.

Example 10: Tuning of Hydrogel Particle Optical Properties

A 50 nm nanoparticle colloidal suspension was incorporated into the hydrogel matrix to mimic the optical properties of lymphocytes and monocytes (FIGS. 13A and 13B). The percent composition of the suspension was altered to match the blood cell subpopulations from the blood sample control (Streck) (FIG. 13C).

Specifically, the concentration of the acrylamide monomer (0.7-0.8M) of the hydrogel particle was adjusted to increase the forward scatter of the particles to match blood cell subpopulations. The percentage of bisacrylamide cross linker can also be changed to affect forward scatter (1-5%).

Silica nanoparticles were used at 5% or 10% in the compositions to adjust side scatter. The results of this experiment are shown in FIG. 13A and FIG. 13B.

Example 11: Formation and Functionalization of Porous Hydrogel Particles

Figure 24:
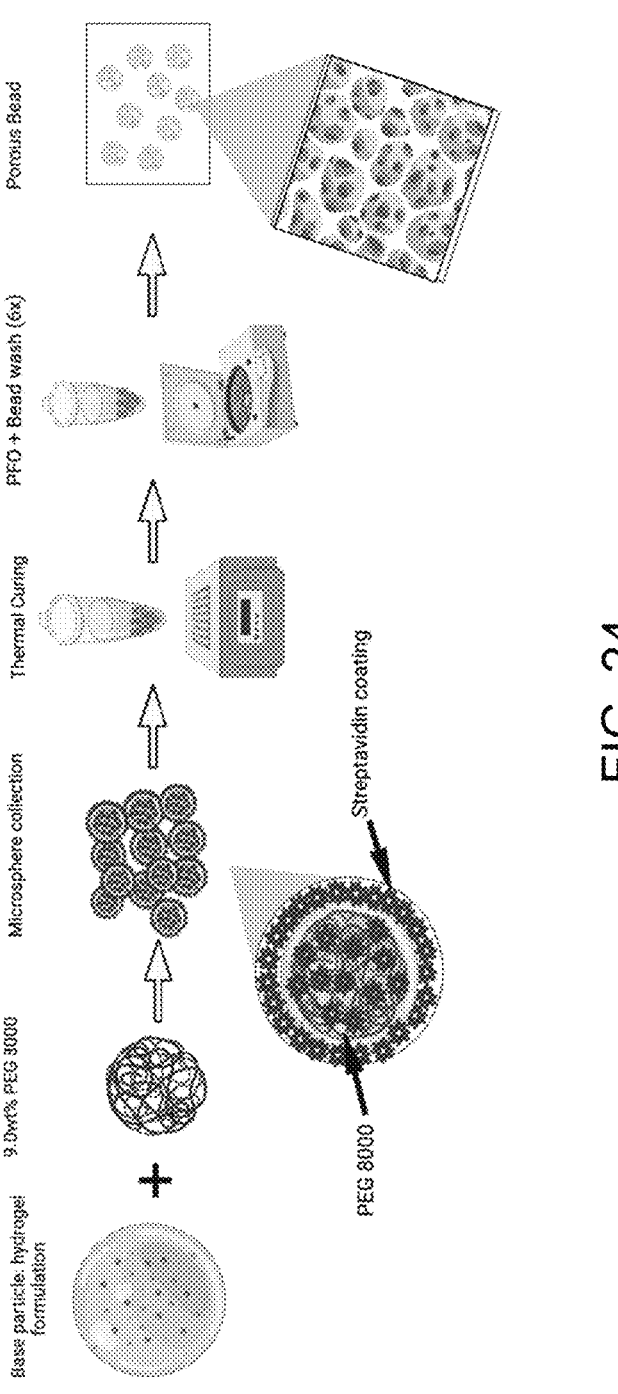
FIG. 24 depicts a method of generating porous particles by a microfluidic droplet process, the process including curing and purification before cell therapy application.
Figure 25:
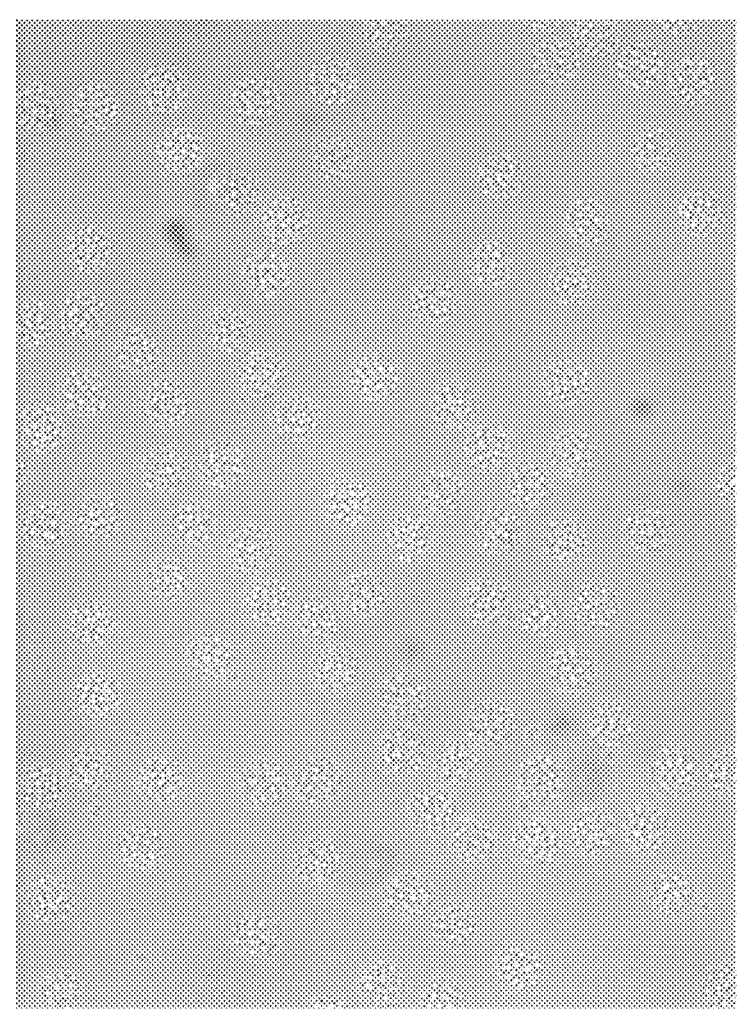
FIG. 25 is a microscopy image of porous particles formed using polyethylene glycol (PEG).

With reference to FIG. 24, to fabricate porous particles, first, an aqueous solution, or continuous phase, of monomers was formed (e.g., acrylamide and bis-acrylamide at 0.62M with the addition of 0.0036M of streptavidin-acrylamide dissolved in a 100 mM pH 7.5 Tris-HCl buffer). An additive (e.g., linear PEG 8000) was added (e.g., at 9 wt %) to the aqueous solution to form a dispersed phase. From the aqueous phase, droplets were formed using a microfluidic polydimethylsiloxane (PDMS) device configured (e.g., using the channels, flow rates, and/or pressures) to control the droplets' form (e.g., having an average droplet diameter of about 20 μm). The droplets were collected, de-gassed, and then cured in the presence of a polymerization agent (e.g., ammonium persulfate at 0.1 wt %). Oil (e.g., 1H, 1H, 2H, 2H-Perfluorooctan-1-ol (PFO)) was added to the cured droplets (e.g., at a 1:1 ratio) to obtain crude particles. The crude particles were washed and purified several times with water to obtain the particles by phase separation. FIG. 25 is a microscopy image of porous particles formed using polyethylene glycol (PEG).

Example 12: Porous Hydrogel Particles as Immune Response Activators

Porous particles generated according to Example 11 were used in immune cell activation assays. With reference to FIG. 26-31, a porous hydrogel particle was fabricated according to the above and the below specifications.

| | |
|---|---|
| PEG mw8000 | 0-9% |
| TrisHCl | 100 mM |
| Acrylamide | 0.62-0.96 M |
| Bis-acrylamide (5% Bis/acrylamide) | 0.62-0.96 M |
| PS100 | 0-1.13% |
| Streptavidin-acrylamide | 0-0.6 mg/mL |
| APS | 0.1-0.2% |

Immunostimulatory biomolecules were added to the hydrogel matrix of the porous particles. A set of particles comprising anti-CD3 and anti-CD28 antibodies were produced, and tested for T-Cell expansion assay. Other combinations were also tested (e.g., comprising CD19).

Using these porous particles for cell activation showed stronger and more retained TCR engagement and stimulation while reducing the magnetic depletion step used in current activation methods.

Figure 26:
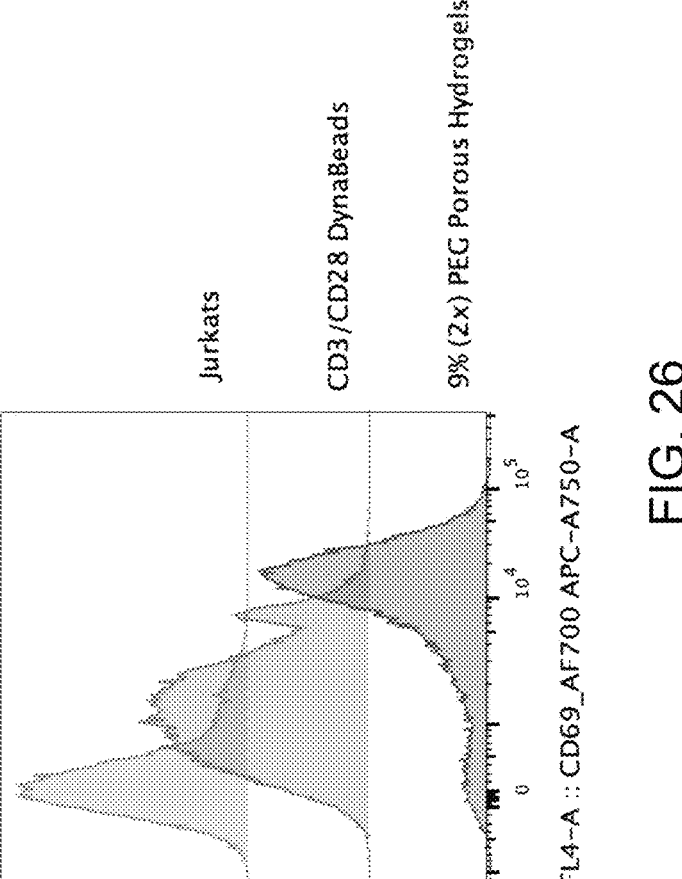
FIG. 26 depicts early-stage (24 hour incubation) activation of Jurkat samples incubated with either Dynabeads™ or porous particles, according to embodiments of the present disclosure. The porous particles of FIG. 26 are particles having pores formed during manufacturing using 9% w/v PEG as a porogen.
Figure 27:
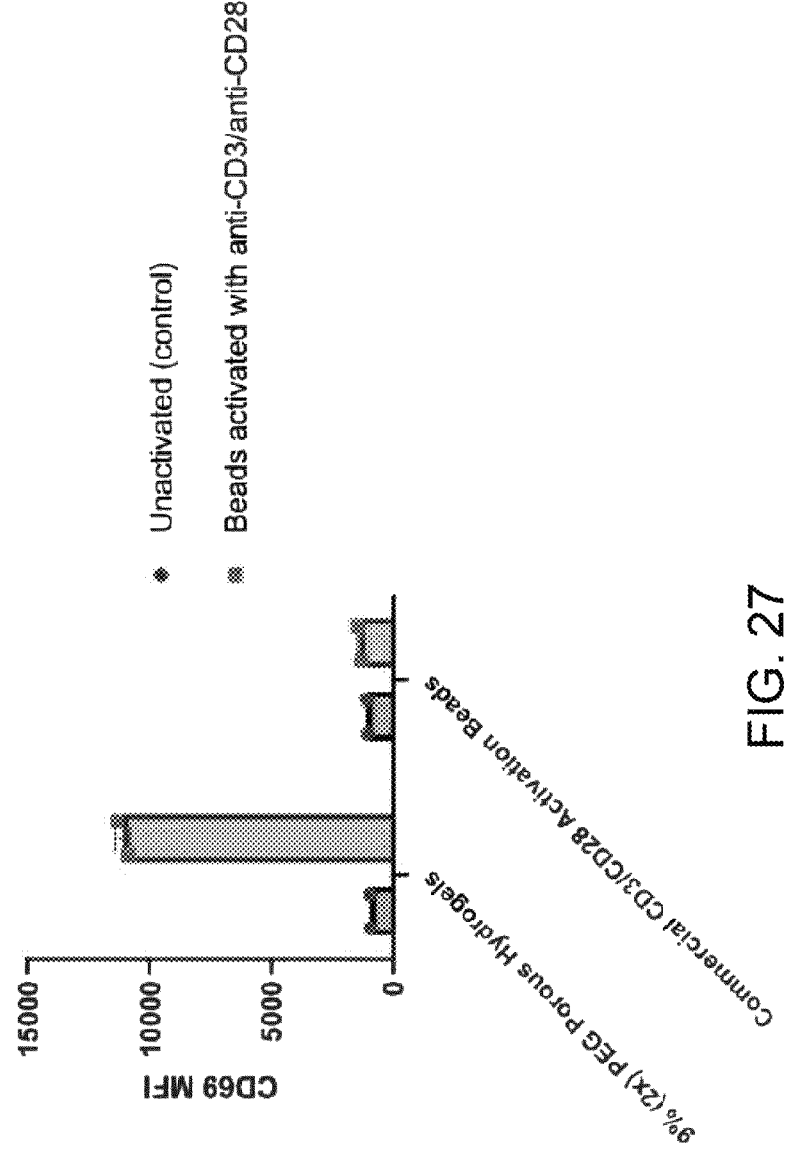
FIG. 27 is a bar chart depicting early-stage T-cell activation (i.e., increase in Jurkat activation) when incubated with porous particles (pores formed by 9% PEG) and Dynabeads™ for 24 hours. As shown, T-cell activation is increased in porous particles samples, as shown by an increase in CD69.
Figure 28:
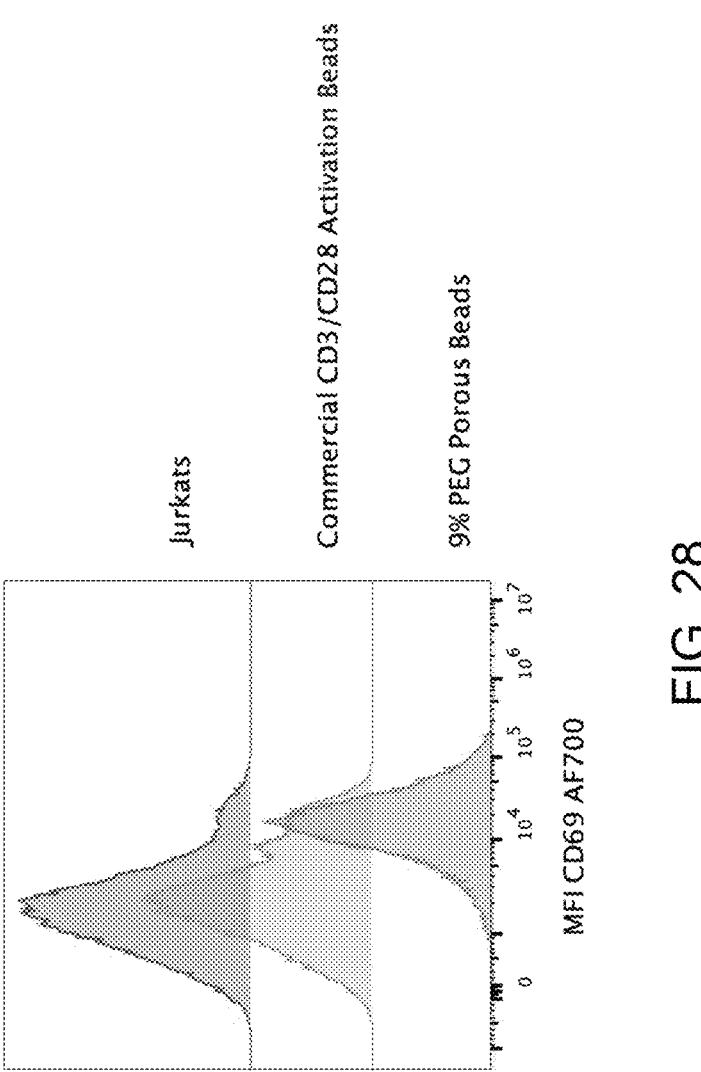
FIG. 28 depicts a relative upregulation of early-stage T-cell activation marker CD69 in Jurkat samples incubated for 48 hours with porous particles (pores formed by 9% PEG) as compared to Dynabeads™. Activation during this prolonged incubation period represents a sustained activation.
Figure 29:
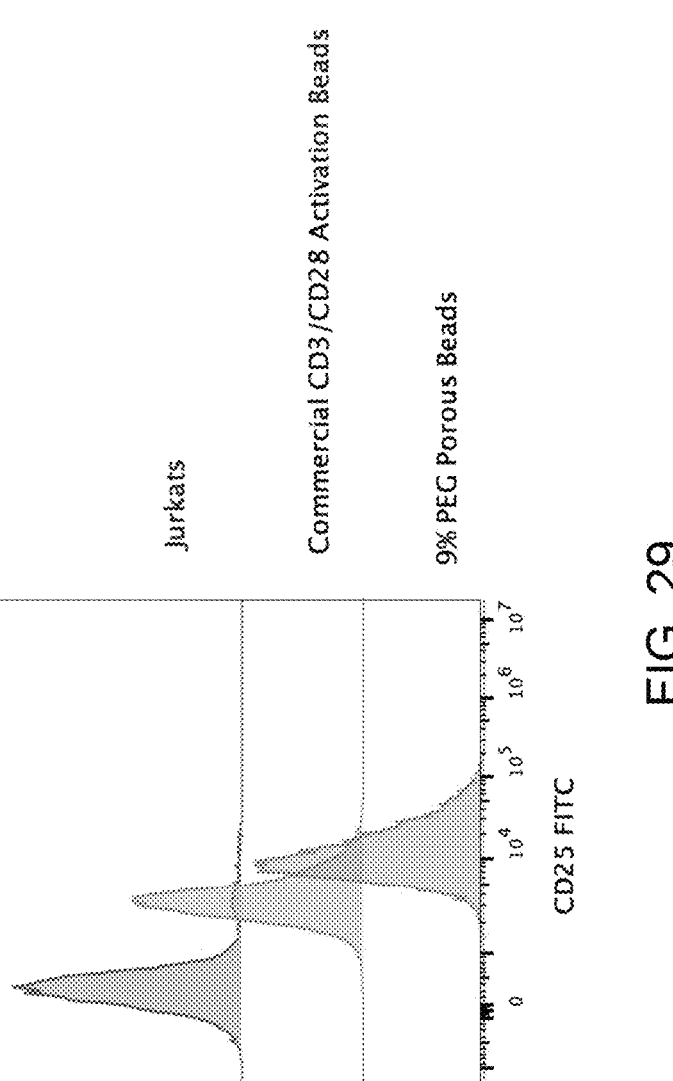
FIG. 29 depicts a relative upregulation of late-stage T-cell activation marker CD25 in Jurkat samples incubated for 48 hours with porous particles (pores formed by 9% PEG) as compared to Dynabeads™. Activation during this prolonged incubation period represents a sustained activation.
Figure 30:
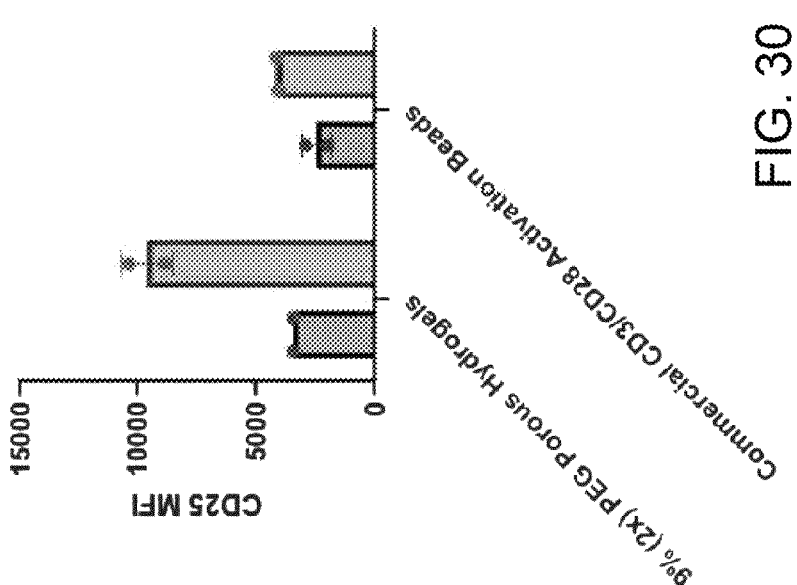
FIG. 30 is a bar chart depicting a relative upregulation of late-stage T-cell activation marker CD25 in Jurkat samples incubated for 48 hours with porous particles (pores formed by 9% PEG) as compared to Dynabeads™.

Activation efficiency was measured using early and late-stage T cell activation markers, CD69, as shown in FIGS. 26-28, and CD25, as shown in FIG. 29 and FIG. 30, at various time points post incubation with T cells. For example, FIG. 26 shows early-stage activation was increased in Jurkat samples incubated with 9% PEG porous hydrogel particles compared to Dynabeads™ at 24 hours, as evidenced by upregulation in CD69, an early-stage activation marker. FIG. 27 shows late-stage activation was increased in Jurkat samples incubated with 9% PEG porous hydrogel particles compared to Dynabeads™ at 48 hours, as evidence by sustained activation of CD25, a late-stage T cell activation marker.

Figure 31:
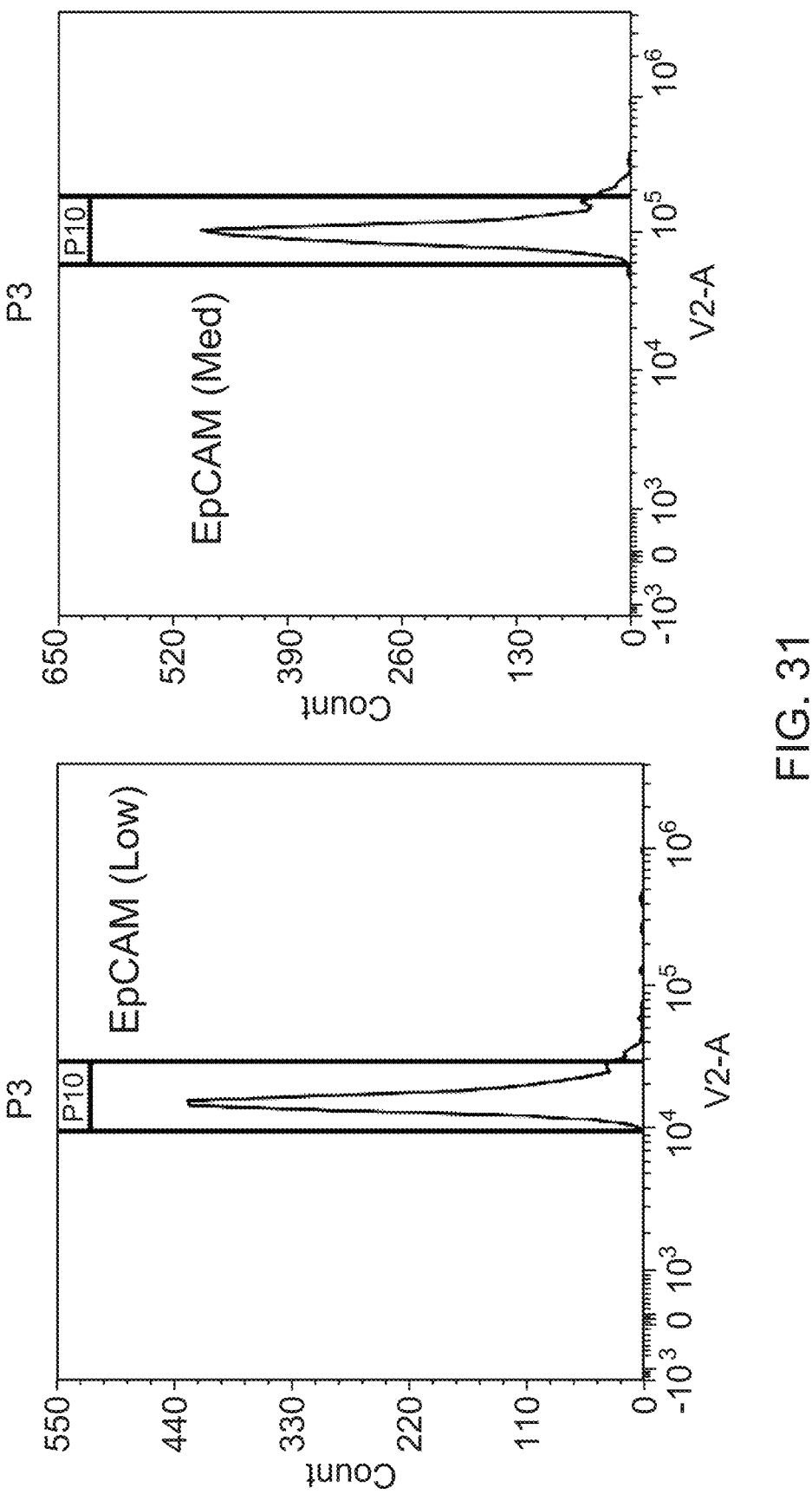
FIG. 31 provides scatter plots of conjugation. 15 µm porous particles with 4.5% polyethylene glycol (MW 3550) and 0.4 mg/mL streptavidin acrylamide conjugated with EpCAM protein were stained with anti-EpCAM (Alexa Fluor 405). Three different levels of EpCAM protein were evaluated (low, medium, high).
Figure 31:
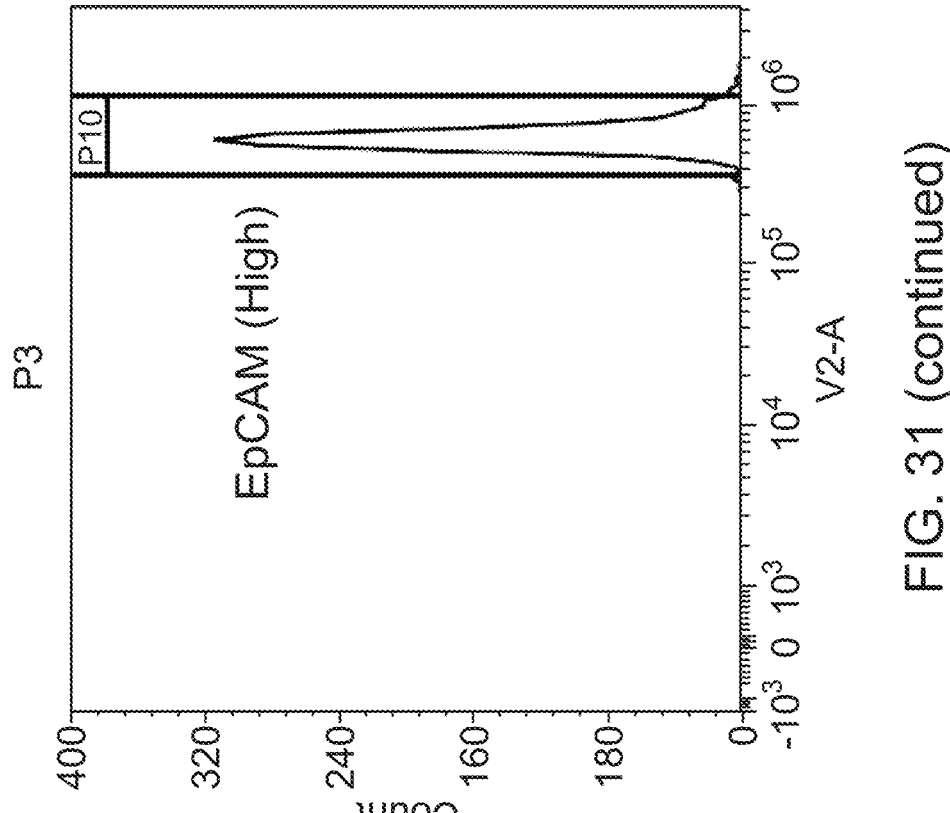

As shown in FIG. 31, 15 μm diameter sized pores with 4.5% PEG at MW 3550 and 0.4 mg/ml streptavidin-acrylamide was conjugated with EpCAM protein at three levels and stained with anti-EpCAM (Alexa Fluor 405). The results are shown from left to right at low levels of EpCAM, medium levels of EpCAM, and high levels of EpCAM.

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

NUMBERED EMBODIMENTS OF THE INVENTION

Notwithstanding the appended claims, the disclosure sets forth the following numbered embodiments:

Embodiment A1. A hydrogel particle, comprising a polymerized monomer comprising a plurality of micropores, and a plurality of macropores within the polymerized monomer, wherein the particle has a porosity of about 5% to about 95% of a volume of the particle.

Embodiment A1.1. The particle of Embodiment A1, wherein an average diameter of the plurality of macropores is larger than an average diameter of the plurality of micropores.

Embodiment A1.2. The particle of Embodiment A1, wherein an average diameter of the plurality of macropores is between about 200 nm and about 2 μm.

Embodiment A1.3. The particle of Embodiment A1, wherein an average diameter of the plurality of micropores is between about 1 nm and about 20 nm.

Embodiment A1.4. The particle of Embodiment A1.3, wherein the average diameter of the plurality of micropores is between about 2 nm and about 4 nm.

Embodiment A2. The particle of Embodiment A1, wherein the plurality of micropores are formed during monomer polymerization.

Embodiment A3. The particle of Embodiment A1 or Embodiment A2, wherein the plurality of macropores comprise between about 2% and about 30% of a total number of pores of the particle, the total number of pores of the particle being a combination of the plurality of micropores and the plurality of macropores.

Embodiment A3.1. The particle of any one of Embodiment A1 to Embodiment A3, wherein the particle comprises the plurality of macropores at a concentration of at least 2.25% v/v, at least 3.4% v/v, and/or at least 4.5% v/v.

Embodiment A4. The particle of any one of Embodiment A1 to Embodiment A3, wherein the particle has a porosity of between about 80% and about 95% of the volume of the particle.

Embodiment A5. The particle of any one of Embodiment A1 to Embodiment A4, wherein the particle comprises a refractive index greater than about 1.10, greater than about 1.15, greater than about 1.20, greater than about 1.25, greater than about 1.30, greater than about 1.35, greater than about 1.40, greater than about 1.45, greater than about 1.50, greater than about 1.55, greater than about 1.60, greater than about 1.65, greater than about 1.70, greater than about 1.75, greater than about 1.80, greater than about 1.85, greater than about 1.90, greater than about 1.95, greater than about 2.00, greater than about 2.10, greater than about 2.20, greater than about 2.30, greater than about 2.40, greater than about 2.50, greater than about 2.60, greater than about 2.70, greater than about 2.80, or greater than about 2.90.

Embodiment A6. The particle of any one of Embodiment A1 to Embodiment A5, wherein the particle exhibits increased side scatter compared to an otherwise identical particle lacking macropores.

Embodiment A7. The particle of Embodiment A6, wherein the particle exhibits increased forward scatter compared to an otherwise identical particle lacking macropores.

Embodiment A8. The particle of any one of Embodiment A1 to Embodiment A7, wherein the particle exhibits a Young's modulus of between about 0.2 kPa and about 400 kPa.

Embodiment A8.1 The particle of any one of Embodiment A1 to Embodiment A8, further comprising one or more biomolecules.

Embodiment A9. The particle of any one of Embodiment A1 to Embodiment A8, further comprising one or more biomolecules conjugated to a surface of the particle.

Embodiment A10. The particle of Embodiment A9, wherein the surface of the particle is an internal surface or an external surface.

Embodiment A11. The particle of Embodiment A10, wherein the internal surface is within the plurality of macropores.

Embodiment A12. The particle of Embodiment A8.1 or Embodiment A9, wherein the one or more biomolecules are one or more selected from the group consisting of: a biologic; an antibody or an antigen-binding fragment thereof; an antibody drug conjugate; a protein; an enzyme; a peptide; a non-ribosomal peptide; CD3; CD4; CD8; CD19; CD14; ccr7; CD45; CD45RA; CD27; CD16; CD56; CD127; CD25; CD38; HLA-DR; PD-1; CD28; CD183; CD185; CD57; IFN-gamma; CD20; TCR gamma/delta; TNF alpha; CD69; IL-2; Ki-67; CCR6; CD34; CD45RO; CD161; IgD; CD95; CD117; CD123; CD11c; IgM; CD39; FoxP3; CD10; CD40L; CD62L; CD194; CD314; IgG; TCR V alpha 7.2; CD11b; CD21; CD24; IL-4; Biotin; CCR10; CD31; CD44; CD138; CD294; NKp46; TCR V delta 2; TIGIT; CD1c; CD2; CD7; CD8a; CD15; CD32; CD103; CD107a; CD141; CD158; CD159c; IL-13; IL-21; KLRG1; TIM-3; CCR5; CD5; CD33; CD45.2; CD80; CD159a (NKG2a); CD244; CD272; CD278; CD337; Granzyme B; Ig Lambda Light Chain; IgA; IL-17A; Streptavidin; TCR V delta 1; CD1d; CD26; CD45R (B220); CD64; CD73; CD86; CD94; CD137; CD163; CD193; CTLA-4; CX3CR1; Fc epsilon R1 alpha; IL-22; Lag-3; MIP-1 beta; Perforin; TCR V gamma 9; CD1a; CD22; CD36; CD40; CD45R; CD66b; CD85j; CD160; CD172a; CD186; CD226; CD303; CLEC12A; CXCR4; Helios; Ig Kappa Light Chain; IgE; IgG1; IgG3; IL-5; IL-8; IL-21 R; KIR3d105; KLRC1/2; Ly-6C; Ly-6G; MHC Class II (I-A/I-E); MHC II; TCR alpha/beta; TCR beta; TCR V alpha 24; Akt (pS473); ALDH1A1; Annexin V; Bcl-2; c-Met; CCR7; cd16/32; cd41a; CD3 epsilon; CD8b;

CD11b/c; CD16/CD32; CD23; CD29; CD43; CD45.1; CD48; CD49b; CD49d; CD66; CD68; CD71; CD85k; CD93; CD99; CD106; CD122; CD133; CD134; CD146; CD150; CD158b; CD158b1/b2; CD158e; CD166; CD169; CD184; CD200; CD200 R; CD235a; CD267; CD268; CD273; CD274; CD317; CD324; CD326; CD328; CD336; CD357; CD366; DDR2; eFluor 780 Fix Viability; EGF Receptor; EGFR (pY845); EOMES; EphA2; ERK1/2 (pT202/pY204); F4/80; FCRL5; Flt-3; FVS575V; FVS700; Granzyme A; HER2/ErbB2; Hesl; Hoechst (33342); ICAM-1; IFN-alpha; IgA1; IgA1/IgA2; IgA2; IgG2; IgG4; IL-1 RAcP; IL-6; IL-10; IL-12; IL-17; Integrin alpha 4 beta 7; Isotype Ctrl; KLRC1; KLRC2; Live/Dead Fix Aqua; Ly-6A/Ly-6E; Ly-6G/Ly-6C; Mannose Receptor; MDR1; Met (pY1234/pY1235); MMP-9; NGF Receptor p75; ORAI1; ORAI2; ORAI3; p53; P2RY12; PARP; cleaved; RT1B; S6 (pS235/pS236); STIM1; STIM2; TCR delta; TCR delta/gamma; TCR V alpha 24 J alpha 18; TCR V beta 11; TCR V gamma 1.1; TCR V gamma 2; TER-119; TIMP-3; TRAF3; TSLP Receptor; VDAC1; Vimentin; XCR1; and YAP1.

Embodiment A12.1 The particle of Embodiment A12, wherein the one or more biomolecules is an antibody or an antigen-binding fragment thereof and the antibody or antigen-binding fragment thereof comprises anti CD3 and/or anti CD28.

Embodiment A12.2 The particle of any one of Embodiment A8.1 to Embodiment A12.1, wherein the antibody or antigen-binding fragment comprises comprising anti-CD19, anti-41BBL, anti-OX40L, anti-CD2, anti-CD335, anti-CD16, anti-CD56, anti-CD20, anti-CD80, anti-CD86, anti-CD69, anti-CD154, and/or anti-CD137.

Embodiment A12.3. The particle of any one of Embodiment A8.1 to Embodiment A12.1, wherein the one or more biomolecules comprise an IgM antibody or antigen-binding fragment, an IgG antibody or antigen-binding fragment, an IgE antibody or antigen-binding fragment, an IgA antibody or antigen-binding fragment, an IgD antibody or antigen-binding fragment, and/or toll-like receptors.

Embodiment A13. The particle of any one of Embodiment A1 to Embodiment A12.1, wherein the polymerized monomer comprises one or more monomers selected from the group consisting of: hydroxyethyl methacrylate; ethyl methacrylate; 2-hydroxyethyl methacrylate (HEMA); propylene glycol methacrylate; acrylamide; N-vinylpyrrolidone (NVP); methyl methacrylate; glycidyl methacrylate; glycerol methacrylate (GMA); glycol methacrylate; ethylene glycol; fumaric acid; 2-hydroxyethyl methacrylate; hydroxyethoxyethyl methacrylate; hydroxydiethoxyethyl methacrylate; methoxyethyl methacrylate; methoxyethoxyethyl methacrylate; methoxydiethoxyethyl methacrylate; poly(ethylene glycol) methacrylate; methoxy-poly(ethylene glycol) methacrylate; methacrylic acid, sodium methacrylate; glycerol methacrylate; hydroxypropyl methacrylate; hydroxybutyl methacrylate; phenyl acrylate; phenyl methacrylate; benzyl acrylate; benzyl methacrylate; 2-phenylethyl acrylate; 2-phenylethyl methacrylate; 2-phenoxyethyl acrylate; 2-phenoxyethyl methacrylate; phenylthioethyl acrylate; phenylthioethyl methacrylate; 2,4,6-tribromophenyl acrylate, 2,4,6-tribromophenyl methacrylate; pentabromophenyl acrylate; pentabromophenyl methacrylate; pentachlorophenyl acrylate; pentachlorophenyl methacrylate, 2,3-dibromopropyl acrylate; 2,3-dibromopropyl methacrylate; 2-naphthyl acrylate; 2-naphthyl methacrylate, 4-methoxybenzyl acrylate; 4-methoxybenzyl methacrylate; 2-benzyloxyethyl acrylate; 2-benzyloxyethyl methacrylate; 4-chlorophenoxyethyl acrylate; 4-chlorophenoxyethyl methacrylate; 2-phenoxyethoxyethyl acrylate; 2-phenoxyethoxyethyl methacrylate; N-phenyl acrylamide; N-phenyl methacrylamide; N-benzyl acrylamide; N-benzyl methacrylamide; N,N-dibenzyl acrylamide; N,N-dibenzyl methacrylamide; N-diphenylmethyl acrylamide N-(4-methylphenyl)methyl acrylamide; N-1-naphthyl acrylamide; N-4-nitrophenyl acrylamide; N-(2-phenylethyl)acrylamide; N-triphenylmethyl acrylamide; N-(4-hydroxyphenyl)acrylamide; N,N-methylphenyl acrylamide; N,N-phenyl phenylethyl acrylamide; N-diphenylmethyl methacrylamide; N-(4-methyl phenyl)methyl methacrylamide; N-1-naphthyl methacrylamide; N-4-nitrophenyl methacrylamide; N-(2-phenylethyl)methacrylamide; N-triphenylmethyl methacrylamide; N-(4-hydroxyphenyl)methacrylamide; N,N-methylphenyl methacrylamide; N,N'-phenyl phenylethyl methacrylamide; N-vinyl carbazole; 4-vinylpyridine; and 2-vinylpyridine.

Embodiment A13.1 The particle of any one of Embodiment A1 to Embodiment A13, further comprising at least one fluorophore.

Embodiment A14. The particle of any one of Embodiment A1 to Embodiment A13, further comprising at least one fluorophore conjugated to a surface of the particle.

Embodiment A15. The particle of Embodiment A14, wherein the surface of the particle is an internal surface or an external surface.

Embodiment A16. The particle of Embodiment A15, wherein the internal surface is within the plurality of macropores.

Embodiment A17. The particle of Embodiment A13.1 or Embodiment A14, wherein the at least one fluorophore is one or more selected from the group consisting of: peridinin chlorophyll protein-cyanine 5.5 dye (PerCP-Cy5.5); phycoerythrin-cyanine7 (PE Cy7); allophyco-cyanin-cyanine 7 (APC-Cy7); fluorescein isothiocyanate (FITC); phycoerythrin (PE); allophyscocyanin (APC); 6-carboxy-4', 5'-dichloro-2', 7'-dimethoxyfluorescein succinimidylester; 5-(and-6)-carboxyeosin; 5-carboxyfluorescein; 6 carboxyfluorescein; 5-(and-6)-carboxyfluorescein; S-carboxyfluorescein-bis-(5-carboxymethoxy-2-nitrobenzyl)ether,-alanine-carboxamide, or succinimidyl ester; 5-carboxy fluorescein succinimidyl ester; 6-carboxyfluorescein succinimidyl ester; 5-(and-6)-carboxyfluorescein succinimidyl ester; 5-(4,6-dichlorotriazinyl) amino fluorescein; 2', 7'-difluoro fluorescein; eosin-5-isothiocyanate; erythrosin5-isothiocyanate; 6-(fluorescein-5-carboxamido) hexanoic acid or succinimidyl ester; 6-(fluorescein-5-(and-6)-carboxamido) hexanoic acid or succinimidylester; fluorescein-S-EX succinimidyl ester; fluorescein-5-isothiocyanate; fluorescein-6-isothiocyanate; OregonGreen® 488 carboxylic acid, or succinimidyl ester; Oregon Green® 488 isothiocyanate; Oregon Green® 488-X succinimidyl ester; Oregon Green® 500 carboxylic acid; Oregon Green® 500 carboxylic acid, succinimidylester or triethylammonium salt; Oregon Green® 514 carboxylic acid; Oregon Green® 514 carboxylic acid or succinimidyl ester; Rhodamine-Green™ carboxylic acid, succinimidyl ester or hydrochloride; Rhodamine Green™ carboxylic acid, trifluoroacetamide or succinimidylester; Rhodamine Green™-X succinimidyl ester or hydrochloride; RhodolGreen™ carboxylic acid, N,O-bis-(trifluoroacetyl) or succinimidylester; bis-(4-carboxypiperidinyl)sulfonerhodamine or di(succinimidylester); 5-(and-6) carboxynaphtho fluorescein, 5-(and-6)carboxynaphthofluorescein succinimidyl ester; 5-carboxyrhodamine 6G hydrochloride; 6-carboxyrhodamine6Ghydrochloride, 5-carboxyrhodamine 6G succinimidyl ester; 6-carboxyrhodamine 6G succinimidyl ester; 5-(and-6)-carboxyrhodamine6G succinimidyl ester; 5-carboxy-2',4',5',7'-tetrabromosulfonefluorescein succinimidyl esteror bis-(diisopropylethylammonium) salt; 5-carboxytetramethylrhodamine; 6-carboxytetramethylrhodamine; 5-(and-6)-carboxytetramethylrhodamine; 5-carboxytetramethylrhodamine succinimidyl ester; 6-carboxytetramethylrhodaminesuccinimidyl ester; 5-(and-6)-carboxytetramethylrhodamine succinimidyl ester; 6-carboxy-X-rhodamine; 5-carboxy-X-rhodamine succinimidyl ester; 6-carboxy-X-rhodamine succinimidyl ester; 5-(and-6)-carboxy-X-rhodamine succinimidyl ester; 5-carboxy-X-rhodamine triethylammonium salt; Lissamine™ rhodamine B sulfonyl chloride; malachite green; isothiocyanate; NANOGOLD® mono(sulfosuccinimidyl ester); QSY® 21carboxylic acid or succinimidyl ester; QSY® 7 carboxylic acid or succinimidyl ester; Rhodamine Red™-X succinimidyl ester; 6-(tetramethylrhodamine-5-(and-6)-carboxamido) hexanoic acid; succinimidyl ester; tetramethylrhodamine-5-isothiocyanate; tetramethylrhodamine-6-isothiocyanate; tetramethylrhodamine-5-(and-6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; X-rhodamine-5-(and-6) isothiocyanate, BODIPY® FL; BODIPY® TMR STP ester; BODIPY® TR-X STP ester; BODIPY® 630/650-X STPester; BODIPY® 650/665-X STP ester; 6-dibromo-4, 4-difluoro-5, 7-dimethyl-4-bora-3 a, 4a-diaza-s-indacene-3-propionic acid succinimidyl ester; 4,4-difluoro-4-bora-3a,4a-diaza-s-indacene-3,5-dipropionic acid; 4,4-difluoro-5,7-dimethyl-4-bora-3a,4a-diaza-s-indacene-3-pentanoicacid; 4,4-difluoro-5,7-dimethyl-4-bora3a,4a-diaza-s-indacene-3-pentanoicacid succinimidyl ester; 4,4-difluoro-5,7-dimethyl-4-bora-3 a, 4a-diaza-s-indacene-3propionicacid; 4, 4-difluoro-5, 7-dimethyl-4-bora-3 a, 4adiaza-s-indacene-3-propionicacid succinimidyl ester; 4, 4-difluoro-5, 7-dimethyl-4-bora-3a,4a-diaza-s-indacene-3propionic acid; sulfosuccinimidyl ester or sodium salt; 6-((4,4-difluoro-5, 7-dimethyl-4-bora-3a, 4a-diaza-s-indacene-3propionyl)amino)hexanoicacid; 6-((4,4-difluoro-5, 7 dimethyl-4-bora-3a,4a-diaza-s-indacene-3-propionyl)amino)hexanoic acid or succinimidyl ester; N-(4, 4-difluoro 5, 7-dimethyl-4-bora-3 a, 4a-diaza-s-indacene-3-propionyl) cysteic acid, succinimidyl ester or triethylammonium salt; 6-4,4-difluoro-1,3-dimethyl-5-(4-methoxyphenyl)-4-bora3a, 4a4, 4-difluoro-5, 7-diphenyl-4-bora-3a,4a-diaza-sindacene-3-propionicacid; 4, 4-difluoro-5, 7-diphenyl-4-bora3 a, 4a-diaza-s-indacene-3-propionicacid succinimidyl ester; 4, 4-difluoro-5-phenyl-4-bora-3 a, 4a-diaza-s-indacene-3-propionic acid; succinimidyl ester; 6-((4, 4-difluoro-5-phenyl-4 bora-3 a, 4a-diaza-s-indacene-3-propionyl)amino) hexanoicacid or succinimidyl ester; 4,4-difluoro-5-(4-phenyl-1,3butadienyl)-4-bora-3 a, 4a-diaza-s-indacene-3-propionicacid succinimidyl ester; 4, 4-difluoro-5-(2-pyrrolyl)-4-bora-3a,4a-diaza-s-indacene-3-propionic acid succinimidyl ester; 6-(((4,4-difluoro-5-(2-pyrrolyl)-4-bora-3a,4a-diaza-s-indacene-3-yl)styryloxy)acetyl)amino-hexanoicacid or succinimidyl ester; 4,4-difluoro-5-styryl-4-bora-3a, 4a-diaza-s-indacene-3-propionic acid; 4, 4-difluoro-5-styryl-4-bora-3 a, 4a-diaza-sindacene-3-propionic acid; succinimidyl ester; 4,4-difluoro-1,3,5,7-tetramethyl-4-bora-3a,4adiaza-s-indacene-8-propionicacid; 4,4-difluoro-1,3,5,7-tetramethyl-4bora-3a,4a-diaza-sindacene-8-propionic acid succinimidyl ester; 4,4-difluoro-5-(2-thienyl)-4-bora-3a,4a-diaza-sindacene-3-propionic acid succinimidyl ester; 6-(((4-(4, 4-difluoro-5-(2-thienyl)-4-bora-3 a, 4adiazas-indacene-3-yl)phenoxy)acetyl)amino) hexanoic acid or succinimidyl ester; and 6-(((4,4-difluoro-5-(2-thienyl)-4-bora-3a,4a-diaza-s-indacene-3-yl)styryloxy)acetyl) aminohexanoic acid or succinimidyl ester, Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 64 7 carboxylic acid; Alexa Fluor® 660 carboxylic acid; Alexa Fluor® 680 carboxylic acid, Cy3 NHS ester; Cy 5 NHS ester; Cy5.5 NHSester; and Cy7 NHS ester.

Embodiment A18. The particle of any one of Embodiment A1 to Embodiment A17, wherein the particle has a diameter of between about 1 μm and about 25 μm.

Embodiment A19. The particle of any one of Embodiment A1 to Embodiment A18, wherein the particle has a diameter of between about 2 μm and about 5 μm.

Embodiment A20. The particle of any one of Embodiment A1 to Embodiment A18, wherein the particle has an optical-scatter property that is substantially similar to a corresponding optical-scatter property of a target cell.

Embodiment A20.1. The particle of Embodiment A20, wherein the optical-scatter property that is substantially similar to the corresponding optical-scatter property of the target cell is side scatter (SSC).

Embodiment A20.2. The particle of Embodiment A20, wherein the optical-scatter property that is substantially similar to the corresponding optical-scatter property of the target cell is forward scatter (FSC).

Embodiment A21. A method of forming a particle, comprising mixing a dispersed phase comprising a monomer and porogens, with a continuous phase, wherein the dispersed phase and the continuous phase are immiscible, polymerizing the monomer in the dispersed phase, thereby encapsulating or embedding porogens within the polymerized monomer, and removing the porogens from the polymerized monomer to form the particle.

Embodiment A21.1. A method of forming a particle, comprising mixing a first phase comprising a monomer and porogens, with a second phase, wherein the first phase and the second phase are immiscible, polymerizing the monomer in the first phase, thereby encapsulating or embedding porogens within the polymerized monomer, and removing the porogens from the polymerized monomer to form the particle.

Embodiment A21.2. A method of forming a particle, comprising mixing an aqueous phase comprising a monomer and porogens, with a non-aqueous phase, wherein the non-aqueous phase and the aqueous phase are immiscible, polymerizing the monomer in the aqueous phase, thereby encapsulating or embedding porogens within the polymerized monomer, and removing the porogens from the polymerized monomer to form the particle.

Embodiment A22. The method of Embodiment A21, wherein the dispersed phase comprises one or more porogens selected from the group consisting of: a porogen polymer; a water-soluble polymer; a salt; carbon black; a biodegradable polymer; seaweed polysaccharides; and a paraffin wax.

Embodiment A23. The method of Embodiment A22, wherein the porogens comprise a salt selected from the group consisting of sodium chloride, ammonium bicarbonate, lithium chloride, zinc chloride, silicon dioxide, calcium carbonate, and combinations thereof.

Embodiment A24. The method of Embodiment A22 or Embodiment A23, wherein the porogens comprise a porogen polymer selected from the group consisting of polyethylene glycol, poly(vinylpyrrolidone), polyvinyl alcohol, and combinations thereof.

Embodiment A25. The method of Embodiment A24, wherein porogen polymer comprises a polyethylene glycol having a molecular weight of between about 200 kDa and about 40,000 kDa.

Embodiment A26. The method of Embodiment A24 or Embodiment A25, wherein the porogen polymer comprises a polyethylene glycol having a linear, branched, hyperbranched, and/or bottlebrush structure.

Embodiment A27. The method of any one of Embodiment A24 to Embodiment A26, wherein the porogen polymer comprises a polyethylene glycol having a hydrodynamic radius of between about 0.5 nm and between about 4 nm.

Embodiment A28. The method of any one of Embodiment A21 to Embodiment A27, wherein the dispersed phase comprises polyethylene glycol at a concentration of between about 1% v/v and about 90% v/v.

Embodiment A28.1. The method of any one of Embodiment A21 to Embodiment A27, wherein the dispersed phase comprises polyethylene glycol at a concentration of between about 1% w/v and about 99% w/v.

Embodiment A29. The method of any one of Embodiment A21 to Embodiment A28, wherein the dispersed phase comprises polyethylene glycol at a concentration of between about 2% v/v and about 20% v/v.

Embodiment A29.1. The method of any one of Embodiment A21 to Embodiment A28, wherein the dispersed phase comprises porogens at a concentration of between about 2% w/v and about 20% w/v.

Embodiment A30. The method of any one of Embodiment A21 to Embodiment A29, wherein removing the porogens from the polymerized monomer comprises washing the polymerized monomer in a solvent.

Embodiment A31. The method of Embodiment A30, wherein the washing is performed iteratively.

Embodiment A32. The method of Embodiment A30 or Embodiment A31, wherein the solvent is selected from the group consisting of water, polydioctylfluorene, and an alcohol.

Embodiment A33. The method of any one of Embodiment A21 to Embodiment A32, wherein removing the porogens comprises leaching the porogen from the polymerized monomer over a period of time.

Embodiment A34. The method of any one of Embodiment A21 to Embodiment A33, wherein removing the porogens forms a plurality of macropores within polymerized monomer.

Embodiment A34.1. The method of Embodiment A34, wherein an average diameter of the plurality of macropores is between about 200 nm and about 2 μm.

Embodiment A35. The method of Embodiment A34, wherein the polymerized monomer comprises a plurality of micropores formed during the polymerizing step.

Embodiment A36. The method of Embodiment A35, wherein an average diameter of the plurality of micropores is between about 1 nm and about 20 nm.

Embodiment A37. The method of Embodiment A36, wherein the average diameter of the plurality of micropores is between about 2 nm and about 4 nm.

Embodiment A38. The method of Embodiment A35 or Embodiment A36, wherein the plurality of macropores comprise between about 2% and about 30% of a total number of pores of the particle, the total number of pores of the particle being a combination of the plurality of micropores and the plurality of macropores.

Embodiment A39. The method of any one of claim 21 to Embodiment A38, wherein the particle has a porosity between about 80% and about 95% of a volume of the particle.

Embodiment A40. The method of any one of Embodiment A21 to Embodiment A39, wherein the particle comprises a refractive index greater than about 1.10, greater than about 1.15, greater than about 1.20, greater than about 1.25, greater than about 1.30, greater than about 1.35, greater than about 1.40, greater than about 1.45, greater than about 1.50, greater than about 1.55, greater than about 1.60, greater than about 1.65, greater than about 1.70, greater than about 1.75, greater than about 1.80, greater than about 1.85, greater than about 1.90, greater than about 1.95, greater than about 2.00, greater than about 2.10, greater than about 2.20, greater than about 2.30, greater than about 2.40, greater than about 2.50, greater than about 2.60, greater than about 2.70, greater than about 2.80, or greater than about 2.90.

Embodiment A41. The method of Embodiment A35 or Embodiment A36, wherein the particle comprises the plurality of macropores at a concentration of at least 2.25% v/v, at least 3.4% v/v, and/or at least 4.5% v/v.

Embodiment A42. The method of any one of Embodiment A35 to Embodiment A41, wherein the particle exhibits increased side scatter compared to an otherwise identical particle lacking macropores.

Embodiment A43. The method of any one of Embodiment A35 to Embodiment A42, wherein the particle exhibits increased forward scatter compared to an otherwise identical property lacking macropores.

Embodiment A44. The method of any one of Embodiment A21 to Embodiment A43, wherein the particle exhibits a Young's modulus of between about 0.2 kPa and about 400 kPa.

Embodiment A45. The method of any one of Embodiment A21 to Embodiment A44, further comprising curing the particle.

Embodiment A46. The method of Embodiment A45, wherein curing comprises thermal curing.

Embodiment A47. A method for calibrating a cytometric device for analysis of a target cell, comprising inserting into the device the particle of any one of Embodiment A1 to Embodiment A20, wherein the particle has at least one optical property substantially similar to a target cell, measuring the at least one optical property of the particle using the cytometric device, and calibrating the cytometric device based on the optical property measurement of the particle.

Embodiment A48. A method for detecting a target cell in a sample, comprising, inserting into the device the particle of any one of Embodiment A1 to Embodiment A20, wherein the particle has at least one optical property substantially similar to a target cell, measuring the at least one optical property of the particle using the cytometric device, inserting a sample in the cytometric device comprising a plurality of cells, measuring the at least one optical property of individual cells of the plurality, determining, based on the optical property measurement, whether the target cell or plurality thereof is present in the sample.

Embodiment A49. A method for calibrating a cytometric device for analysis of a target cell, comprising inserting into the device the particle of any one of Embodiment A1 to Embodiment A20, wherein the particle has at least one morphological property that is substantially similar to a target cell, measuring the at least one morphological property of the particle using the cytometric device, and calibrating the cytometric device based on the morphological property measurement of the particle.

Embodiment A50. A method for detecting a target cell in a sample, comprising inserting into the device the particle of any one of Embodiment A1 to Embodiment A20, wherein the particle has at least one morphological property substantially similar to a target cell, measuring the at least one morphological property of the particle using the cytometric device, inserting a sample in the cytometric device comprising a plurality of cells, measuring the at least one morphological property of individual cells of the plurality, determining, based on the morphological property measurement, whether the target cell or plurality thereof is present in the sample.

Embodiment B1. A hydrogel particle, comprising a matrix comprising a polymerized monomer having a plurality of micropores, a plurality of macropores, and one or more biomolecules.

Embodiment B1.1. The particle of Embodiment B1, wherein the particle has a porosity of about 5% to about 95% of a volume of the particle.

Embodiment B1.2. The particle of Embodiment B1, wherein an average diameter of the plurality of macropores is larger than an average diameter of the plurality of micropores.

Embodiment B1.3. The particle of Embodiment B1, wherein an average diameter of the plurality of macropores is between about 200 nm and about 2 μm.

Embodiment B1.4. The particle of Embodiment B1, wherein an average diameter of the plurality of micropores is between about 1 nm and about 20 nm.

Embodiment B1.5. The particle of Embodiment B1.4, wherein the average diameter of the plurality of micropores is between about 2 nm and about 4 nm.

Embodiment B2. The particle of any one of Embodiment B1 to Embodiment B1.5, wherein the one or more biomolecules are attached to the matrix.

Embodiment B3. The particle of any one of Embodiment B1 to Embodiment B2, wherein the one or more biomolecules are attached to surfaces of the matrix, the surfaces comprising internal surfaces and/or external surfaces.

Embodiment B4. The particle of Embodiment B3, wherein the internal surfaces are within the plurality of micropores and the plurality of macropores.

Embodiment B5. The particle of any one of Embodiment B1 to Embodiment B4, wherein the one or more biomolecules are attached to the matrix via a linker.

Embodiment B6. The particle of Embodiment B5, wherein the linker comprises streptavidin.

Embodiment B7. The particle of any one of Embodiment B1 to Embodiment B6, wherein the one or more biomolecules are biotinylated.

Embodiment B8. The particle of any one of Embodiment B1 to Embodiment B7, wherein the polymerized monomer comprises a bifunctional monomer, and wherein the one or more biomolecules are attached to the bifunctional monomer.

Embodiment B9. The particle of Embodiment B8, wherein the biomolecule is further attached via a linker comprising streptavidin.

Embodiment B10. The particle of any one of Embodiment B1 to Embodiment B9, wherein the polymerized monomer comprises one or more monomers selected from the group consisting of: hydroxyethyl methacrylate; ethyl methacrylate; 2-hydroxyethyl methacrylate (HEMA); propylene glycol methacrylate; acrylamide; N-vinylpyrrolidone (NVP); methyl methacrylate; glycidyl methacrylate; glycerol methacrylate (GMA); glycol methacrylate; ethylene glycol; fumaric acid; 2-hydroxyethyl methacrylate; hydroxyethoxyethyl methacrylate; hydroxydiethoxyethyl methacrylate; methoxyethyl methacrylate; methoxyethoxyethyl methacrylate; methoxydiethoxyethyl methacrylate; poly(ethylene glycol) methacrylate; methoxy-poly(ethylene glycol) methacrylate; methacrylic acid, sodium methacrylate; glycerol methacrylate; hydroxypropyl methacrylate; hydroxybutyl methacrylate; phenyl acrylate; phenyl methacrylate; benzyl acrylate; benzyl methacrylate; 2-phenylethyl acrylate; 2-phenylethyl methacrylate; 2-phenoxyethyl acrylate; 2-phenoxyethyl methacrylate; phenylthioethyl acrylate; phenylthioethyl methacrylate; 2,4,6-tribromophenyl acrylate, 2,4,6-tribromophenyl methacrylate; pentabromophenyl acrylate; pentabromophenyl methacrylate; pentachlorophenyl acrylate; pentachlorophenyl methacrylate; 2,3-dibromopropyl acrylate; 2,3-dibromopropyl methacrylate; 2-naphthyl acrylate; 2-naphthyl methacrylate, 4-methoxybenzyl acrylate; 4-methoxybenzyl methacrylate; 2-benzyloxyethyl acrylate; 2-benzyloxyethyl methacrylate; 4-chlorophenoxyethyl acrylate; 4-chlorophenoxyethyl methacrylate; 2-phenoxyethoxyethyl acrylate; 2-phenoxyethoxyethyl methacrylate; N-phenyl acrylamide; N-phenyl methacrylamide; N-benzyl acrylamide; N-benzyl methacrylamide; N,N-dibenzyl acrylamide; N,N-dibenzyl methacrylamide; N-diphenylmethyl acrylamide N-(4-methylphenyl)methyl acrylamide; N-1-naphthyl acrylamide; N-4-nitrophenyl acrylamide; N-(2-phenylethyl)acrylamide; N-triphenylmethyl acrylamide; N-(4-hydroxyphenyl)acrylamide; N,N-methylphenyl acrylamide; N,N-phenyl phenylethyl acrylamide; N-diphenylmethyl methacrylamide; N-(4-methyl phenyl)methyl methacrylamide; N-1-naphthyl methacrylamide; N-4-nitrophenyl methacrylamide; N-(2-phenylethyl)methacrylamide; N-triphenylmethyl methacrylamide; N-(4-hydroxyphenyl)methacrylamide; N,N-methylphenyl methacrylamide; N,N'-phenyl phenylethyl methacrylamide; N-vinyl carbazole; 4-vinylpyridine; and 2-vinylpyridine.

Embodiment B11. The particle of any one of Embodiment B1 to Embodiment B10, wherein the one or more biomolecules are one or more selected from the group consisting of: a biologic; an antibody or an antigen-binding fragment thereof; an antibody drug conjugate; a protein; an enzyme; a peptide; a non-ribosomal peptide; CD3; CD4; CD8; CD19; CD14; ccr7; CD45; CD45RA; CD27; CD16; CD56; CD127; CD25; CD38; HLA-DR; PD-1; CD28; CD183; CD185; CD57; IFN-gamma; CD20; TCR gamma/delta; TNF alpha; CD69; IL-2; Ki-67; CCR6; CD34; CD45RO; CD161; IgD; CD95; CD117; CD123; CD11c; IgM; CD39; FoxP3; CD10; CD40L; CD62L; CD194; CD314; IgG; TCR V alpha 7.2; CD11b; CD21; CD24; IL-4; Biotin; CCR10; CD31; CD44; CD138; CD294; NKp46; TCR V delta 2; TIGIT; CD1c; CD2; CD7; CD8a; CD15; CD32; CD103; CD107a; CD141; CD158; CD159c; IL-13; IL-21; KLRG1; TIM-3; CCR5; CD5; CD33; CD45.2; CD80; CD159a (NKG2a); CD244; CD272; CD278; CD337; Granzyme B; Ig Lambda Light Chain; IgA; IL-17A; Streptavidin; TCR V delta 1; CD1d; CD26; CD45R (B220); CD64; CD73; CD86; CD94; CD137; CD163; CD193; CTLA-4; CX3CR1; Fc epsilon R1 alpha; IL-22; Lag-3; MIP-1 beta; Perforin; TCR V gamma 9; CD1a; CD22; CD36; CD40; CD45R; CD66b; CD85j; CD160; CD172a; CD186; CD226; CD303; CLEC12A; CXCR4; Helios; Ig Kappa Light Chain; IgE; IgG1; IgG3; IL-5; IL-8; IL-21 R; KIR3d105; KLRC1/2; Ly-6C; Ly-6G; MHC Class II (I-A/I-E); MHC II; TCR alpha/beta; TCR beta; TCR V alpha 24; Akt (pS473); ALDH1A1; Annexin V; Bcl-2; c-Met; CCR7; cd16/32; cd41a; CD3 epsilon; CD8b; CD11b/c; CD16/CD32; CD23; CD29; CD43; CD45.1; CD48; CD49b; CD49d; CD66; CD68; CD71; CD85k; CD93; CD99; CD106; CD122; CD133; CD134; CD146; CD150; CD158b; CD158b1/b2; CD158e; CD166; CD169; CD184; CD200; CD200 R; CD235a; CD267; CD268; CD273; CD274; CD317; CD324; CD326; CD328; CD336; CD357; CD366; DDR2; eFluor 780 Fix Viability; EGF Receptor; EGFR (pY845); EOMES; EphA2; ERK1/2 (pT202/pY204); F4/80; FCRL5; Flt-3; FVS575V; FVS700; Granzyme A; HER2/ErbB2; Hes1; Hoechst (33342); ICAM-1; IFN-alpha; IgA1; IgA1/IgA2; IgA2; IgG2; IgG4; IL-1 RAcP; IL-6; IL-10; IL-12; IL-17; Integrin alpha 4 beta 7; Isotype Ctrl; KLRC1; KLRC2; Live/Dead Fix Aqua; Ly-6A/Ly-6E; Ly-6G/Ly-6C; Mannose Receptor; MDR1; Met (pY1234/pY1235); MMP-9; NGF Receptor p75; ORAI1; ORAI2; ORAI3; p53; P2RY12; PARP; cleaved; RT1B; S6 (pS235/pS236); STIM1; STIM2; TCR delta; TCR delta/gamma; TCR V alpha 24 J alpha 18; TCR V beta 11; TCR V gamma 1.1; TCR V gamma 2; TER-119; TIMP-3; TRAF3; TSLP Receptor; VDAC1; Vimentin; XCR1; and YAP1.

Embodiment B11.1. The particle of any one of Embodiment B1 to Embodiment B11, wherein the one or more biomolecules is an antibody or an antigen-binding fragment thereof and said antibody or antigen-binding fragment thereof comprises anti CD3 and/or anti CD28.

Embodiment B11.2. The particle of any one of Embodiment B1 to Embodiment B11.1, wherein the antibody or antigen-binding fragment comprises comprising anti-CD19, anti-41BBL, anti-OX40L, anti-CD2, anti-CD335, anti-CD16, and/or anti-CD56.

Embodiment B11.3. The particle of any one of Embodiment B1 to Embodiment B11.2, further comprising at least one fluorophore.

Embodiment B12. The particle of any one of Embodiment B1 to Embodiment B11.3, further comprising at least one fluorophore attached to a surface of the particle.

Embodiment B13. The particle of Embodiment B11.3 or Embodiment B12, wherein the at least one fluorophore is one or more selected from the group consisting of: peridinin chlorophyll protein-cyanine 5.5 dye (PerCP-Cy5.5); phycoerythrin-cyanine7 (PE Cy7); allophycocyanin-cyanine 7 (APC-Cy7); fluorescein isothiocyanate (FITC); phycoerythrin (PE); allophyscocyanin (APC); 6-carboxy-4', 5'-dichloro-2', 7'-dimethoxyfluorescein succinimidylester; 5-(and-6)-carboxyeosin; 5-carboxyfluorescein; 6 carboxyfluorescein; 5-(and-6)-carboxyfluorescein; S-carboxyfluorescein-bis-(5-carboxymethoxy-2-nitrobenzyl)ether,-alanine-carboxamide, or succinimidyl ester; 5-carboxy fluorescein succinimidyl ester; 6-carboxyfluorescein succinimidyl ester; 5-(and-6)-carboxyfluorescein succinimidyl ester; 5-(4,6-dichlorotriazinyl) amino fluorescein; 2', 7-difluoro fluorescein; eosin-5-isothiocyanate; erythrosin5-isothiocyanate; 6-(fluorescein-5-carboxamido) hexanoic acid or succinimidyl ester; 6-(fluorescein-5-(and-6)-carboxamido) hexanoic acid or succinimidylester; fluorescein-S-EX succinimidyl ester; fluorescein-5-isothiocyanate; fluorescein-6-isothiocyanate; OregonGreen® 488 carboxylic acid, or succinimidyl ester; Oregon Green® 488 isothiocyanate; Oregon Green® 488-X succinimidyl ester; Oregon Green® 500 carboxylic acid; Oregon Green® 500 carboxylic acid, succinimidylester or triethylammonium salt; Oregon Green® 514 carboxylic acid; Oregon Green® 514 carboxylic acid or succinimidyl ester; Rhodamine-Green™ carboxylic acid, succinimidyl ester or hydrochloride; Rhodamine Green™ carboxylic acid, trifluoroacetamide or succinimidylester; Rhodamine Green™-X succinimidyl ester or hydrochloride; RhodolGreen™ carboxylic acid, N,O-bis-(trifluoroacetyl) or succinimidylester; bis-(4-carboxypiperidinyl) sulfonerhodamine or di(succinimidylester); 5-(and-6) carboxynaphtho fluorescein, 5-(and-6)carboxynaphthofluorescein succinimidyl ester; 5-carboxyrhodamine 6G hydrochloride; 6-carboxyrhodamine6Ghydrochloride, 5-carboxyrhodamine 6G succinimidyl ester; 6-carboxyrhodamine 6G succinimidyl ester; 5-(and-6)-carboxyrhodamine6G succinimidyl ester; 5-carboxy-2',4',5',7'-tetrabromo-sulfonefluorescein succinimidyl esteror bis-(diisopropylethylammonium) salt; 5-carboxytetramethylrhodamine; 6-carboxytetramethylrhodamine; 5-(and-6)-carboxytetramethylrhodamine; 5-carboxytetramethylrhodamine succinimidyl ester; 6-carboxytetramethylrhodaminesuccinimidyl ester; 5-(and-6)-carboxytetramethylrhodamine succinimidyl ester; 6-carboxy-X-rhodamine; 5-carboxy-X-rhodamine succinimidyl ester; 6-carboxy-X-rhodamine succinimidyl ester; 5-(and-6)-carboxy-X-rhodamine succinimidyl ester; 5-carboxy-X-rhodamine triethylammonium salt; Lissamine™ rhodamine B sulfonyl chloride; malachite green; isothiocyanate; NANOGOLD® mono(sulfosuccinimidyl ester); QSY® 21carboxylic acid or succinimidyl ester; QSY® 7 carboxylic acid or succinimidyl ester; Rhodamine Red™-X succinimidyl ester; 6-(tetramethylrhodamine-5-(and-6)-carboxamido) hexanoic acid; succinimidyl ester; tetramethylrhodamine-5-isothiocyanate; tetramethylrhodamine-6-isothiocyanate; tetramethylrhodamine-5-(and-6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; X-rhodamine-5-(and-6) isothiocyanate, BODIPY® FL; BODIPY® TMR STP ester; BODIPY® TR-X STP ester; BODIPY® 630/650-X STPester; BODIPY® 650/665-X STP ester; 6-dibromo-4, 4-difluoro-5, 7-dimethyl-4-bora-3 a, 4a-diaza-s-indacene-3-propionic acid succinimidyl ester; 4,4-difluoro-4-bora-3a,4a-diaza-s-indacene-3,5-dipropionic acid; 4,4-difluoro-5,7-dimethyl-4-bora-3a,4a-diaza-s-indacene-3-pentanoicacid; 4,4-difluoro-5,7-dimethyl-4-bora3a,4a-diaza-s-indacene-3-pentanoicacid succinimidyl ester; 4,4-difluoro-5,7-dimethyl-4-bora-3 a, 4a-diaza-s-indacene-3propionicacid; 4, 4-difluoro-5, 7-dimethyl-4-bora-3 a, 4adiaza-s-indacene-3-propionicacid succinimidyl ester; 4, 4-difluoro-5, 7-dimethyl-4-bora-3a,4a-diaza-s-indacene-3propionic acid; sulfosuccinimidyl ester or sodium salt; 6-((4,4-difluoro-5, 7-dimethyl-4-bora-3a, 4a-diaza-s-indacene-3propionyl)amino)hexanoicacid; 6-((4,4-difluoro-5, 7 dimethyl-4-bora-3a,4a-diaza-s-indacene-3-propionyl)amino)hexanoic acid or succinimidyl ester; N-(4, 4-difluoro 5, 7-dimethyl-4-bora-3 a, 4a-diaza-s-indacene-3-propionyl) cysteic acid, succinimidyl ester or triethylammonium salt; 6-4,4-difluoro-1,3-dimethyl-5-(4-methoxyphenyl)-4-bora3a, 4a4, 4-difluoro-5, 7-diphenyl-4-bora-3a,4a-diaza-sindacene-3-propionicacid; 4, 4-difluoro-5, 7-diphenyl-4-bora3 a, 4a-diaza-s-indacene-3-propionicacid succinimidyl ester; 4, 4-difluoro-5-phenyl-4-bora-3 a, 4a-diaza-s-indacene-3-propionic acid; succinimidyl ester; 6-((4, 4-difluoro-5-phenyl-4 bora-3 a, 4a-diaza-s-indacene-3-propionyl)amino) hexanoicacid or succinimidyl ester; 4,4-difluoro-5-(4-phenyl-1,3butadienyl)-4-bora-3 a, 4a-diaza-s-indacene-3-propionicacid succinimidyl ester; 4, 4-difluoro-5-(2-pyrrolyl)-4-bora-3a,4a-diaza-s-indacene-3-propionic acid succinimidyl ester; 6-(((4,4-difluoro-5-(2-pyrrolyl)-4-bora-3a,4a-diaza-s-indacene-3-yl)styryloxy)acetyl)amino-hexanoicacid or succinimidyl ester; 4,4-difluoro-5-styryl-4-bora-3a, 4a-diaza-s-indacene-3-propionic acid; 4, 4-difluoro-5-styryl-4-bora-3 a, 4a-diaza-sindacene-3-propionic acid; succinimidyl ester; 4,4-difluoro-1,3,5,7-tetramethyl-4-bora-3a,4adiaza-s-indacene-8-propionicacid; 4,4-difluoro-1,3,5,7-tetramethyl-4bora-3a,4a-diaza-sindacene-8-propionic acid succinimidyl ester; 4,4-difluoro-5-(2-thienyl)-4-bora-3a,4a-diaza-sindacene-3-propionic acid succinimidyl ester; 6-(((4-(4, 4-difluoro-5-(2-thienyl)-4-bora-3 a, 4adiazas-indacene-3-yl)phenoxy)acetyl)amino) hexanoic acid or succinimidyl ester; and 6-(((4,4-difluoro-5-(2-thienyl)-4-bora-3a,4a-diaza-s-indacene-3-yl)styryloxy)acetyl) aminohexanoic acid or succinimidyl ester, Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 64 7 carboxylic acid; Alexa Fluor® 660 carboxylic acid; Alexa Fluor® 680 carboxylic acid, Cy3 NHS ester; Cy 5 NHS ester; Cy5.5 NHSester; and Cy7 NHS ester.

B14. A method of inducing an immune cell response, comprising contacting an immune cell with the particle of any one of Embodiment B1-Embodiment B13, wherein the immune cell response comprises activation and/or expansion of the immune cell.

Embodiment B14.1. A method of inducing an immune cell response, comprising contacting an immune cell with a particle comprising, a matrix comprising a polymerized monomer having a plurality of micropores and a plurality of macropores, and one or more biomolecules, wherein the immune cell response comprises activation and/or expansion of the immune cell.

Embodiment B14.2. The method of Embodiment B14.1, wherein the particle has a porosity of about 5% to about 95% of a volume of the particle.

Embodiment B14.3. A method of inducing an immune cell response, comprising culturing immune cells with a particle comprising a matrix comprising a polymerized monomer comprising a plurality of micropores and a plurality of macropores, and one or more biomolecules, wherein the immune cell response comprises activation and/or expansion of the immune cell.

Embodiment B14.4. The method of any one of Embodiment B14 to Embodiment B14.3 wherein the particle has a porosity of about 5% to about 95% of a volume of the particle.

Embodiment B15. The method of any one of Embodiment B14 to Embodiment B14.4, wherein the one or more biomolecules comprise one or more T cell stimulatory molecules and one or more T cell co-stimulatory molecules.

Embodiment B15.1. The method of Embodiment B15, wherein the one or more T cell stimulatory molecules and one or more T cell co-stimulatory molecules comprise CD28, 4.1BB (CD137), OX40 (CD134), CD27 (TNFRSF7), GITR (CD357), CD30 (TNFRSF8), HVEM (CD270), LTOR (TNFRSF3), DR3 (TNFRSF25)), ICOS (CD278), CD226 (DNAM1), CRTAM (CD355), TIM1 (HAVCR1, KIM1), CD2 (LFA2, OX34), SLAM (CD150, SLAMF1), 2B4 (CD244, SLAMF4), Ly108 (NTBA, CD352), SLAMF6), CD84 (SLAMF5), Ly9 (CD229, SLAMF3) and/or CRACC (CD319, BLAME).

Embodiment B16. The method of any one of Embodiment B14 to Embodiment B15, wherein the one or more biomolecules comprise antibodies or antigen-binding fragments thereof that specifically bind one or more T cell stimulatory molecules and/or one or more T cell co-stimulatory molecules.

Embodiment B16.1 The method of any one of Embodiment B14 to Embodiment B15, wherein the one or more biomolecules comprise one or more antibodies or antigen-binding fragments thereof that specifically bind to CD28, 4.1BB (CD137), OX40 (CD134), CD27 (TNFRSF7), GITR (CD357), CD30 (TNFRSF8), HVEM (CD270), LTOR (TNFRSF3), DR3 (TNFRSF25)), ICOS (CD278), PD1 (CD279) CD226 (DNAM1), CRTAM (CD355), TIM1 (HAVCR1, KIM1), CD2 (LFA2, OX34), SLAM (CD150, SLAMF1), 2B4 (CD244, SLAMF4), Ly108 (NTBA, CD352), SLAMF6), CD84 (SLAMF5), Ly9 (CD229, SLAMF3) and/or CRACC (CD319, BLAME).

Embodiment B17. The method of Embodiment B16, wherein the antibodies or antigen-binding fragments thereof comprise an anti-CD3 antibody or antigen-binding fragments thereof, and/or an anti-CD28 antibody or antigen-binding fragments thereof.

Embodiment B17.1. The method of any one of Embodiment B14 to Embodiment B17, wherein the immune cell response from contacting the immune cell with the particle is higher than the immune cell response from a control immune cell contacted with an otherwise identical particle lacking macropores.

Embodiment B17.2. The method of Embodiment B17.1, wherein the immune cell response is determined by IL-2 secretion from the immune cell.

Embodiment B17.3. The method of Embodiment B17.1, wherein the immune cell response is determined by CD25 expression from the immune cell.

Embodiment B17.4. The method of Embodiment B17.1, wherein the immune cell response is determined by CD69 expression from the immune cell.

Embodiment B18. The method of any one of Embodiment B14 to Embodiment B17.4, wherein contacting comprises exposing the immune cell to the particle at a ratio of immune cell:particle of between about 1:0.5 and about 1:20.

Embodiment B19. A method of inducing expansion and/or activation of immune cells in culture, comprising culturing the immune cells with a plurality of the particle of any one of Embodiment B1-Embodiment B13.

Embodiment B20. The method of Embodiment B19, wherein the immune cells are T cells.

Embodiment B21. The method of Embodiment B19, wherein the immune cells are cytotoxic T cells.

Embodiment B22. The method of Embodiment B19, wherein the immune cells are chimeric antigen receptor (CAR) T cells.

Embodiment B23. The method of Embodiment B19, wherein the one or more biomolecules comprise one or more T cell stimulatory molecules and one or more T cell co-stimulatory molecules.

Embodiment B23.1. The method of Embodiment B23, wherein the one or more T cell stimulatory molecules and one or more T cell co-stimulatory molecules comprise CD28, 4.1BB (CD137), OX40 (CD134), CD27 (TNFRSF7), GITR (CD357), CD30 (TNFRSF8), HVEM (CD270), LTOR (TNFRSF3), DR3 (TNFRSF25)), ICOS (CD278), CD226 (DNAM1), CRTAM (CD355), TIM1 (HAVCR1, KIM1), CD2 (LFA2, OX34), SLAM (CD150, SLAMF1), 2B4 (CD244, SLAMF4), Ly108 (NTBA, CD352), SLAMF6), CD84 (SLAMF5), Ly9 (CD229, SLAMF3) and/or CRACC (CD319, BLAME).

Embodiment B23.2. The method of Embodiment B19, wherein the one or more biomolecules comprise polypeptides that promote expansion of a particular T cell subtype.

Embodiment B23.3. The method of Embodiment B23.2, wherein the polypeptides comprise a cytokine selected from one or more cytokines including IL-1, IL-2, IL-4, IL-5, IL-7, IL-10, IL-12, IL-15, IL-17, IL-21, interferon γ, IFN alpha, IFN beta, lymphotoxin α, TNFα, and/or TNFβ.

Embodiment B24. The method of Embodiment B19, wherein the one or more biomolecules comprise antibodies or antigen-binding fragments thereof that specifically bind one or more T cell stimulatory molecules and/or one or more T cell co-stimulatory molecules.

Embodiment B25. The method of Embodiment B24, wherein the antibodies or antigen-binding fragments thereof comprise an anti-CD3 antibody or antigen-binding fragments thereof, and/or an anti-CD28 antibody or antigen-binding fragments thereof.

Embodiment B26. The method of any one of Embodiment B19 to Embodiment B25, wherein the induced proliferation, expansion, and/or activation of the immune cells in culture with the plurality of the particle is higher than the induced expansion and/or activation of control immune cells in culture with an otherwise identical particle lacking macropores.

Embodiment B26.1. The method of Embodiment B26, wherein the immune cell response is determined by IL-2 secretion from the immune cell.

Embodiment B26.2. The method of Embodiment B26, wherein the immune cell response is determined by CD25 expression from the immune cell.

Embodiment B26.3. The method of Embodiment B26, wherein the immune cell response is determined by CD69 expression from the immune cell.

Embodiment B27.3. The method of any one of Embodiment B19 to Embodiment B26.3, wherein contacting comprises exposing the immune cell to the particle at a ratio of immune cell:particle of between about 1:0.5 and about 1:20.

Embodiment C1. A hydrogel particle, comprising a matrix comprising a polymerized monomer, said matrix comprising i) a plurality of micropores and a plurality of macropores, and ii) one or more immunostimulatory biomolecules selected from the group consisting of an anti-CD3 antibody or antigen-binding fragment thereof, an anti-CD28 antibody or antigen-binding fragment thereof, and combinations thereof.

Embodiment C1.1. The particle of Embodiment C1, wherein an average diameter of the plurality of macropores is larger than an average diameter of the plurality of micropores.

Embodiment C1.2. The particle of Embodiment C1, wherein an average diameter of the plurality of macropores is between about 200 nm and about 2 μm.

Embodiment C1.3. The particle of Embodiment C1, wherein an average diameter of the plurality of micropores is between about 1 nm and about 20 nm.

Embodiment C1.4. The particle of Embodiment C1.3, wherein the average diameter of the plurality of micropores is between about 2 nm and about 4 nm.

Embodiment C1.5. The particle of any one of Embodiment C1 to Embodiment C1.4, wherein the particle comprises the plurality of macropores at a concentration of at least 2.25% v/v, at least 3.4% v/v, and/or at least 4.5% v/v.

Embodiment C1.6. The particle of any one of Embodiment C1 to Embodiment C1.5, wherein the particle has a diameter of between about 1 μm and about 25 μm.

Embodiment C1.7. The particle of any one of Embodiment C1 to Embodiment C1.6, wherein the particle has a diameter of between about 2 μm and about 5 μm.

Embodiment C2. The particle of Embodiment C1, wherein the one or more immunostimulatory biomolecules are attached to the matrix.

Embodiment C3. The particle of Embodiment C1 or Embodiment C2, wherein the one or more immunostimulatory biomolecules are attached to surfaces of the matrix, the surfaces comprising internal surfaces and/or external surfaces.

Embodiment C4. The particle of Embodiment C3, wherein the internal surfaces are within the plurality of micropores and the plurality of macropores.

Embodiment C5 The particle of any one of Embodiment C1 to Embodiment C3, wherein the one or more immunostimulatory biomolecules are attached to a surface of the matrix via a linker.

Embodiment C6. The particle of Embodiment C5, wherein the linker comprises streptavidin.

Embodiment C7. The particle of any one of Embodiment C1 to Embodiment C6, wherein the one or more immunostimulatory biomolecules are biotinylated.

Embodiment C8. The particle of Embodiment C5, wherein the polymerized monomer comprises a bifunctional monomer and wherein the one or more immunostimulatory biomolecules are attached to the bifunctional monomer.

Embodiment C9. The particle of Embodiment C8, wherein the one or more immunostimulatory biomolecules is further attached via a linker comprising streptavidin.

Embodiment C10. The particle of any one of Embodiment C1 to Embodiment C9, wherein the polymerized monomer comprises one or more monomers selected from the group consisting of: hydroxyethyl methacrylate; ethyl methacrylate; 2-hydroxyethyl methacrylate (HEMA); propylene glycol methacrylate; acrylamide; N-vinylpyrrolidone (NVP); methyl methacrylate; glycidyl methacrylate; glycerol methacrylate (GMA); glycol methacrylate; ethylene glycol; fumaric acid; 2-hydroxyethyl methacrylate; hydroxyethoxyethyl methacrylate; hydroxydiethoxyethyl methacrylate; methoxyethyl methacrylate; methoxyethoxyethyl methacrylate; methoxydiethoxyethyl methacrylate; poly(ethylene glycol) methacrylate; methoxy-poly(ethylene glycol) methacrylate; methacrylic acid, sodium methacrylate; glycerol methacrylate; hydroxypropyl methacrylate; hydroxybutyl methacrylate; phenyl acrylate; phenyl methacrylate; benzyl acrylate; benzyl methacrylate; 2-phenylethyl acrylate; 2-phenylethyl methacrylate; 2-phenoxyethyl acrylate; 2-phenoxyethyl methacrylate; phenylthioethyl acrylate; phenylthioethyl methacrylate; 2,4,6-tribromophenyl acrylate, 2,4,6-tribromophenyl methacrylate; pentabromophenyl acrylate; pentabromophenyl methacrylate; pentachlorophenyl acrylate; pentachlorophenyl methacrylate, 2,3-dibromopropyl acrylate; 2,3-dibromopropyl methacrylate; 2-naphthyl acrylate; 2-naphthyl methacrylate; 4-methoxybenzyl acrylate; 4-methoxybenzyl methacrylate; 2-benzyloxyethyl acrylate; 2-benzyloxyethyl methacrylate; 4-chlorophenoxyethyl acrylate; 4-chlorophenoxyethyl methacrylate; 2-phenoxyethoxyethyl acrylate; 2-phenoxyethoxyethyl methacrylate; N-phenyl acrylamide; N-phenyl methacrylamide; N-benzyl acrylamide; N-benzyl methacrylamide; N,N-dibenzyl acrylamide; N,N-dibenzyl methacrylamide; N-diphenylmethyl acrylamide N-(4-methylphenyl)methyl acrylamide; N-1-naphthyl acrylamide; N-4-nitrophenyl acrylamide; N-(2-phenylethyl)acrylamide; N-triphenylmethyl acrylamide; N-(4-hydroxyphenyl)acrylamide; N,N-methylphenyl acrylamide; N,N-phenyl phenylethyl acrylamide; N-diphenylmethyl methacrylamide; N-(4-methyl phenyl)methyl methacrylamide; N-1-naphthyl methacrylamide; N-4-nitrophenyl methacrylamide; N-(2-phenylethyl)methacrylamide; N-triphenylmethyl methacrylamide; N-(4-hydroxyphenyl)methacrylamide; N,N-methylphenyl methacrylamide; N,N'-phenyl phenylethyl methacrylamide; N-vinyl carbazole; 4-vinylpyridine; and 2-vinylpyridine.

Embodiment C11. The particle of Embodiment C1, wherein the one or more immunostimulatory biomolecules further comprises an anti-CD19 antibody or antigen-binding fragment, an anti-41BBL antibody or antigen-binding fragment, an anti-OX40L antibody or antigen-binding fragment, an anti-CD2 antibody or antigen-binding fragment, an anti-CD335 antibody or antigen-binding fragment, an anti-CD16 antibody or antigen-binding fragment, an anti-CD56 antibody or antigen-binding fragment, an anti-CD20 antibody or antigen-binding fragment, an anti-CD80 antibody or antigen-binding fragment, an anti-CD86 antibody or antigen-binding fragment, an anti-CD69 antibody or antigen-binding fragment, an anti-CD154 antibody or antigen-binding fragment, an anti-CD137 antibody or antigen-binding fragment, an IgM antibody or antigen-binding fragment, an IgG antibody or antigen-binding fragment, an IgE antibody or antigen-binding fragment, an IgA antibody or antigen-binding fragment, an IgD antibody or antigen-binding fragment, and/or toll-like receptors.

Embodiment C12. The particle of any one of Embodiment C1 to Embodiment C11, further comprising at least one fluorophore.

Embodiment C12.1. The particle of Embodiment C12, wherein the at least one fluorophore is attached to a surface of the matrix.

Embodiment C13. The particle of Embodiment C12 or Embodiment C12.1, wherein the at least one fluorophore is one or more selected from the group consisting of: peridinin chlorophyll protein-cyanine 5.5 dye (PerCP-Cy5.5); phycoerythrin-cyanine7 (PE Cy7); allophycocyanin-cyanine 7 (APC-Cy7); fluorescein isothiocyanate (FITC); phycoerythrin (PE); allophyscocyanin (APC); 6-carboxy-4', 5'-dichloro-2', 7'-dimethoxyfluorescein succinimidylester; 5-(and-6)-carboxyeosin; 5-carboxyfluorescein; 6 carboxyfluorescein; 5-(and-6)-carboxyfluorescein; S-carboxyfluorescein-bis-(5-carboxymethoxy-2-nitrobenzyl)ether,-alanine-carboxamide, or succinimidyl ester; 5-carboxy fluorescein succinimidyl ester; 6-carboxyfluorescein succinimidyl ester; 5-(and-6)-carboxyfluorescein succinimidyl ester; 5-(4,6-dichlorotriazinyl) amino fluorescein; 2', 7-difluoro fluorescein; eosin-5-isothiocyanate; erythrosin5-isothiocyanate; 6-(fluorescein-5-carboxamido) hexanoic acid or succinimidyl ester; 6-(fluorescein-5-(and-6)-carboxamido) hexanoic acid or succinimidylester; fluorescein-S-EX succinimidyl ester; fluorescein-5-isothiocyanate; fluorescein-6-isothiocyanate; OregonGreen® 488 carboxylic acid, or succinimidyl ester; Oregon Green® 488 isothiocyanate; Oregon Green® 488-X succinimidyl ester; Oregon Green® 500 carboxylic acid; Oregon Green® 500 carboxylic acid, succinimidylester or triethylammonium salt; Oregon Green® 514 carboxylic acid; Oregon Green® 514 carboxylic acid or succinimidyl ester; RhodamineGreen™ carboxylic acid, succinimidyl ester or hydrochloride; Rhodamine Green™ carboxylic acid, trifluoroacetamide or succinimidylester; Rhodamine Green™-X succinimidyl ester or hydrochloride; RhodolGreen™ carboxylic acid, N,O-bis-(trifluoroacetyl) or succinimidylester; bis-(4-carboxypiperidinyl) sulfonerhodamine or di(succinimidylester); 5-(and-6)carboxynaphtho fluorescein, 5-(and-6)carboxynaphthofluorescein succinimidyl ester; 5-carboxyrhodamine 6G hydrochloride; 6-carboxyrhodamine6Ghydrochloride, 5-carboxyrhodamine 6G succinimidyl ester; 6-carboxyrhodamine 6G succinimidyl ester; 5-(and-6)-carboxyrhodamine6G succinimidyl ester; 5-carboxy-2',4',5',7'-tetrabromo-sulfonefluorescein succinimidyl esteror bis-(diisopropylethylammonium) salt; 5-carboxytetramethylrhodamine; 6-carboxytetramethylrhodamine; 5-(and-6)-carboxytetramethylrhodamine; 5-carboxytetramethylrhodamine succinimidyl ester; 6-carboxytetramethylrhodaminesuccinimidyl ester; 5-(and-6)-carboxytetramethylrhodamine succinimidyl ester; 6-carboxy-X-rhodamine; 5-carboxy-X-rhodamine succinimidyl ester; 6-carboxy-X-rhodamine succinimidyl ester; 5-(and-6)-carboxy-X-rhodamine succinimidyl ester; 5-carboxy-X-rhodamine triethylammonium salt; Lissamine™ rhodamine B sulfonyl chloride; malachite green; isothiocyanate; NANOGOLD® mono(sulfosuccinimidyl ester); QSY® 21carboxylic acid or succinimidyl ester; QSY® 7 carboxylic acid or succinimidyl ester; Rhodamine Red™-X succinimidyl ester; 6-(tetramethylrhodamine-5-(and-6)-carboxamido) hexanoic acid; succinimidyl ester; tetramethylrhodamine-5-isothiocyanate; tetramethylrhodamine-6-isothiocyanate; tetramethylrhodamine-5-(and-6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; X-rhodamine-5-(and-6) isothiocyanate, BODIPY® FL; BODIPY® TMR STP ester; BODIPY® TR-X STP ester; BODIPY® 630/650-X STPester; BODIPY® 650/665-X STP ester; 6-dibromo-4, 4-difluoro-5, 7-dimethyl-4-bora-3 a, 4a-diaza-s-indacene-3-propionic acid succinimidyl ester; 4,4-difluoro-4-bora-3a,4a-diaza-s-indacene-3,5-dipropionic acid; 4,4-difluoro-5,7-dimethyl-4-bora-3a,4a-diaza-s-indacene-3-pentanoicacid; 4,4-difluoro-5,7-dimethyl-4-bora3a,4a-diaza-s-indacene-3-pentanoicacid succinimidyl ester; 4,4-difluoro-5,7-dimethyl-4-bora-3 a, 4a-diaza-s-indacene-3propionicacid; 4, 4-difluoro-5, 7-dimethyl-4-bora-3 a, 4adiaza-s-indacene-3-propionicacid succinimidyl ester; 4, 4-difluoro-5, 7-dimethyl-4-bora-3a,4a-diaza-s-indacene-3propionic acid; sulfosuccinimidyl ester or sodium salt; 6-((4,4-difluoro-5, 7-dimethyl-4-bora-3a, 4a-diaza-s-indacene-3propionyl)amino)hexanoicacid; 6-((4,4-difluoro-5, 7 dimethyl-4-bora-3a,4a-diaza-s-indacene-3-propionyl)amino)hexanoic acid or succinimidyl ester; N-(4, 4-difluoro 5, 7-dimethyl-4-bora-3 a, 4a-diaza-s-indacene-3-propionyl) cysteic acid, succinimidyl ester or triethylammonium salt; 6-4,4-difluoro-1,3-dimethyl-5-(4-methoxyphenyl)-4-bora3a, 4a4, 4-difluoro-5, 7-diphenyl-4-bora-3a,4a-diaza-sindacene-3-propionicacid; 4, 4-difluoro-5, 7-diphenyl-4-bora3 a, 4a-diaza-s-indacene-3-propionicacid succinimidyl ester; 4, 4-difluoro-5-phenyl-4-bora-3 a, 4a-diaza-s-indacene-3-propionic acid; succinimidyl ester; 6-((4, 4-difluoro-5-phenyl-4 bora-3 a, 4a-diaza-s-indacene-3-propionyl)amino) hexanoicacid or succinimidyl ester; 4,4-difluoro-5-(4-phenyl-1,3butadienyl)-4-bora-3 a, 4a-diaza-s-indacene-3-propionicacid succinimidyl ester; 4, 4-difluoro-5-(2-pyrrolyl)-4-bora-3a,4a-diaza-s-indacene-3-propionic acid succinimidyl ester; 6-(((4,4-difluoro-5-(2-pyrrolyl)-4-bora-3a,4a-diaza-s-indacene-3-yl)styryloxy)acetyl)amino-hexanoicacid or succinimidyl ester; 4,4-difluoro-5-styryl-4-bora-3a, 4a-diaza-s-indacene-3-propionic acid; 4, 4-difluoro-5-styryl-4-bora-3 a, 4a-diaza-sindacene-3-propionic acid; succinimidyl ester; 4,4-difluoro-1,3,5,7-tetramethyl-4-bora-3a,4adiaza-s-indacene-8-propionicacid; 4,4-difluoro-1,3,5,7-tetramethyl-4bora-3a,4a-diaza-sindacene-8-propionic acid succinimidyl ester; 4,4-difluoro-5-(2-thienyl)-4-bora-3a,4a-diaza-sindacene-3-propionic acid succinimidyl ester; 6-(((4-(4, 4-difluoro-5-(2-thienyl)-4-bora-3 a, 4adiazas-indacene-3-yl)phenoxy)acetyl)amino) hexanoic acid or succinimidyl ester; and 6-(((4,4-difluoro-5-(2-thienyl)-4-bora-3a,4a-diaza-s-indacene-3-yl)styryloxy)acetyl) aminohexanoic acid or succinimidyl ester, Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 64 7 carboxylic acid; Alexa Fluor® 660 carboxylic acid; Alexa Fluor® 680 carboxylic acid, Cy3 NHS ester; Cy 5 NHS ester; Cy5.5 NHSester; and Cy7 NHS ester.

Embodiment C14. A method of forming a synthetic human cell mimic particle, comprising mixing a dispersed phase comprising a monomer and porogens, with a continuous phase, wherein the dispersed phase and the continuous phase are immiscible, polymerizing the dispersed phase, thereby encapsulating or embedding porogens of the within the polymerized monomer, removing the porogens from the polymerized monomer to form the particle, and attaching one or more antibodies or antibody fragments to the particle, the one or more antibodies or antibody fragments comprising at least one antibody or antigen-binding fragment thereof selected from the group consisting of: an anti-CD3 antibody or antigen-binding fragment thereof, an anti-CD28 antibody or antigen-binding fragment thereof, and combinations thereof.

Embodiment C14.1. A method of forming a synthetic human cell mimic particle, comprising mixing a first phase comprising a monomer and porogens, with a second phase, wherein the first phase and the second phase are immiscible, polymerizing the first phase, thereby encapsulating or embedding porogens of the within the polymerized monomer, removing the porogens from the polymerized monomer to form the particle, and attaching one or more antibodies or antibody fragments to the particle, the one or more antibodies or antibody fragments comprising at least one antibody or antigen-binding fragment thereof selected from the group consisting of: an anti-CD3 antibody or antigen-binding fragment thereof, an anti-CD28 antibody or antigen-binding fragment thereof, and combinations thereof.

Embodiment C14.2. A method of forming a synthetic human cell mimic particle, comprising mixing an aqueous phase comprising a monomer and porogens, with a non-aqueous phase, wherein the non-aqueous phase and the aqueous phase are immiscible, polymerizing the aqueous phase, thereby encapsulating or embedding porogens of the within the polymerized monomer, removing the porogens from the polymerized monomer to form the particle, and attaching one or more antibodies or antibody fragments to the particle, the one or more antibodies or antibody fragments comprising at least one antibody or antigen-binding fragment thereof selected from the group consisting of: an anti-CD3 antibody or antigen-binding fragment thereof, an anti-CD28 antibody or antigen-binding fragment thereof, and combinations thereof.

Embodiment C15. The method of Embodiment C14, wherein the dispersed phase comprises one or more porogens selected from the group consisting of: a porogen polymer; a water-soluble polymer, a salt; carbon black; a biodegradable polymer; seaweed polysaccharides; and a paraffin wax.

Embodiment C16. The method of Embodiment C15, wherein the porogens comprise a salt selected from the group consisting of: sodium chloride, ammonium bicarbonate, lithium chloride, zinc chloride, silicon dioxide, calcium carbonate, and combinations thereof.

Embodiment C17. The method of Embodiment C15 or Embodiment C16, wherein the porogens comprise a porogen polymer selected from the group consisting of: polyethylene glycol, poly(vinylpyrrolidone), polyvinyl alcohol, and combinations thereof.

Embodiment C18. The method of Embodiment C17, wherein the porogen polymer comprises a polyethylene glycol having a molecular weight of between about 200 kDa and about 40,000 kDa.

Embodiment C19. The method of Embodiment C17, wherein the porogen polymer comprises a polyethylene glycol having a linear, branched, hyperbranched, and/or bottlebrush structure.

Embodiment C20. The method of Embodiment C17, wherein the porogen polymer comprises a polyethylene glycol having a hydrodynamic radius of between about 0.5 nm and between about 4 nm.

Embodiment C21. The method of Embodiment C17, wherein the dispersed phase comprises polyethylene glycol at a concentration of between about 1% v/v and about 99% v/v.

Embodiment C21.1. The method of Embodiment C17, wherein the dispersed phase comprises polyethylene glycol at a concentration of between about 1% w/v and about 99% w/v.

Embodiment C22. The method of any one of Embodiment C14 to Embodiment C21, wherein the dispersed phase comprises porogens at a concentration of between about 2% v/v and about 20% v/v.

Embodiment C22.1. The method of any one of Embodiment C14 to Embodiment C21, wherein the dispersed phase comprises porogens at a concentration of between about 2% w/v and about 20% w/v.

Embodiment C23. The method of Embodiment C22, wherein the particle comprises a plurality of macropores at a concentration of at least 2.25% v/v, at least 3.4% v/v, and/or at least 4.5% v/v, wherein the plurality of macropores are formed by removing the porogens.

Embodiment C24. The method of any one of Embodiment C14 to Embodiment C23, wherein removing the porogens from the polymerized monomer comprises washing the polymerized monomer in a solvent.

Embodiment C25. The method of Embodiment C24, wherein the washing is performed iteratively.

Embodiment C26. The method of Embodiment C25, wherein the solvent is selected from the group consisting of water, polydioctylfluorene, and an alcohol.

Embodiment C27. The method of any one of Embodiment C14 to Embodiment C26, wherein removing the porogens comprises leaching the porogen from the polymerized monomer.

Embodiment C28. The method of any one of Embodiment C14 to Embodiment C27, wherein a plurality of macropores are formed by removing the porogens, and wherein the plurality of macropores comprise between about 2% and about 30% of a total number of pores of the particle.

Embodiment C29. The method of any one of Embodiment C14 to Embodiment C28, wherein the particle has a porosity between about 80% and about 95% of a volume of the particle.

Embodiment C30. The method of any one of Embodiment C14 to Embodiment C29, wherein a refractive index of the particle is greater than about 1.10, greater than about 1.15, greater than about 1.20, greater than about 1.25, greater than about 1.30, greater than about 1.35, greater than about 1.40, greater than about 1.45, greater than about 1.50, greater than about 1.55, greater than about 1.60, greater than about 1.65, greater than about 1.70, greater than about 1.75, greater than about 1.80, greater than about 1.85, greater than about 1.90, greater than about 1.95, greater than about 2.00, greater than about 2.10, greater than about 2.20, greater than about 2.30, greater than about 2.40, greater than about 2.50, greater than about 2.60, greater than about 2.70, greater than about 2.80, or greater than about 2.90.

Embodiment C31. The method of any one of Embodiment C14 to Embodiment C30, wherein the particle exhibits increased side scatter compared to an otherwise identical particle lacking macropores.

Embodiment C32. The method of any one of Embodiment C14 to Embodiment C31, wherein the particle exhibits increased forward scatter compared to an otherwise identical particle lacking macropores.

Embodiment C33. The method of any one of Embodiment C14 to Embodiment C32, wherein the particle exhibits a Young's modulus of between about 0.2 kPa and about 400 kPa.

Embodiment C34. The method of any one of Embodiment C14 to Embodiment C33, further comprising curing the particle.

Embodiment C35. The method of Embodiment C34, wherein curing comprises thermal curing.

Embodiment C36. The method of any one of Embodiment C14 to Embodiment C35, wherein the one or more antibodies or antibody fragments are attached to surfaces of the particle via a linker.

Embodiment C37. The method of Embodiment C36, wherein the surfaces of the particle are an internal surface or an external surface.

Embodiment C38. The method of Embodiment C37, wherein the linker is streptavidin.

Embodiment C39. The method of any one of Embodiment C14 to Embodiment C38, wherein the one or more antibodies or antibody fragments are biotinylated.

Embodiment C40. The method of any one of Embodiment C14 to Embodiment C39, wherein the polymerized monomer comprises one or more monomers selected from the group consisting of: hydroxyethyl methacrylate; ethyl methacrylate; 2-hydroxyethyl methacrylate (HEMA); propylene glycol methacrylate; acrylamide; N-vinylpyrrolidone (NVP); methyl methacrylate; glycidyl methacrylate; glycerol methacrylate (GMA); glycol methacrylate; ethylene glycol; fumaric acid; 2-hydroxyethyl methacrylate; hydroxyethoxyethyl methacrylate; hydroxydiethoxyethyl methacrylate; methoxyethyl methacrylate; methoxyethoxyethyl methacrylate; methoxydiethoxyethyl methacrylate; poly(ethylene glycol) methacrylate; methoxy-poly(ethylene glycol) methacrylate; methacrylic acid, sodium methacrylate; glycerol methacrylate; hydroxypropyl methacrylate; hydroxybutyl methacrylate; phenyl acrylate; phenyl methacrylate; benzyl acrylate; benzyl methacrylate; 2-phenylethyl acrylate; 2-phenylethyl methacrylate; 2-phenoxyethyl acrylate; 2-phenoxyethyl methacrylate; phenylthioethyl acrylate; phenylthioethyl methacrylate; 2,4,6-tribromophenyl acrylate, 2,4,6-tribromophenyl methacrylate; pentabromophenyl acrylate; pentabromophenyl methacrylate; pentachlorophenyl acrylate; pentachlorophenyl methacrylate, 2,3-dibromopropyl acrylate; 2,3-dibromopropyl methacrylate; 2-naphthyl acrylate; 2-naphthyl methacrylate, 4-methoxybenzyl acrylate; 4-methoxybenzyl methacrylate; 2-benzyloxyethyl acrylate; 2-benzyloxyethyl methacrylate; 4-chlorophenoxyethyl acrylate; 4-chlorophenoxyethyl methacrylate; 2-phenoxyethoxyethyl acrylate; 2-phenoxyethoxyethyl methacrylate; N-phenyl acrylamide; N-phenyl methacrylamide; N-benzyl acrylamide; N-benzyl methacrylamide; N,N-dibenzyl acrylamide; N,N-dibenzyl methacrylamide; N-diphenylmethyl acrylamide N-(4-methylphenyl)methyl acrylamide; N-1-naphthyl acrylamide; N-4-nitrophenyl acrylamide; N-(2-phenylethyl)acrylamide; N-triphenylmethyl acrylamide; N-(4-hydroxyphenyl)acrylamide; N,N-methylphenyl acrylamide; N,N-phenyl phenylethyl acrylamide; N-diphenylmethyl methacrylamide; N-(4-methyl phenyl)methyl methacrylamide; N-1-naphthyl methacrylamide; N-4-nitrophenyl methacrylamide; N-(2-phenylethyl)methacrylamide; N-triphenylmethyl methacrylamide; N-(4-hydroxyphenyl)methacrylamide; N,N-methylphenyl methacrylamide; N,N'-phenyl phenylethyl methacrylamide; N-vinyl carbazole; 4-vinylpyridine; and 2-vinylpyridine.

Embodiment C41. The method of any one of Embodiment C14 to Embodiment C40, further comprising attaching at least one fluorophore to the particle.

Embodiment C42. The method of any one of Embodiment C14 to Embodiment C41, further comprising attaching at least one fluorophore to surfaces of the particle.

Embodiment C43. The method of Embodiment C42 or Embodiment C42, wherein the at least one fluorophore is one or more selected from the group consisting of: peridinin chlorophyll protein-cyanine 5.5 dye (PerCP-Cy5.5); phycoerythrin-cyanine7 (PE Cy7); allophycocyanin-cyanine 7 (APC-Cy7); fluorescein isothiocyanate (FITC); phycoerythrin (PE); allophyscocyanin (APC); 6-carboxy-4', 5'-dichloro-2', 7-dimethoxyfluorescein succinimidylester; 5-(and-6)-carboxyeosin; 5-carboxyfluorescein; 6 carboxyfluorescein; 5-(and-6)-carboxyfluorescein; S-carboxyfluorescein-bis-(5-carboxymethoxy-2-nitrobenzyl)ether,-alanine-carboxamide, or succinimidyl ester; 5-carboxy fluorescein succinimidyl ester; 6-carboxyfluorescein succinimidyl ester; 5-(and-6)-carboxyfluorescein succinimidyl ester; 5-(4,6-dichlorotriazinyl) amino fluorescein; 2', 7-difluoro fluorescein; eosin-5-isothiocyanate; erythrosin5-isothiocyanate; 6-(fluorescein-5-carboxamido) hexanoic acid or succinimidyl ester; 6-(fluorescein-5-(and-6)-carboxamido) hexanoic acid or succinimidylester; fluorescein-S-EX succinimidyl ester; fluorescein-5-isothiocyanate; fluorescein-6-isothiocyanate; OregonGreen® 488 carboxylic acid, or succinimidyl ester; Oregon Green® 488 isothiocyanate; Oregon Green® 488-X succinimidyl ester; Oregon Green® 500 carboxylic acid; Oregon Green® 500 carboxylic acid, succinimidylester or triethylammonium salt; Oregon Green® 514 carboxylic acid; Oregon Green® 514 carboxylic acid or succinimidyl ester; Rhodamine-Green™ carboxylic acid, succinimidyl ester or hydrochloride; Rhodamine Green™ carboxylic acid, trifluoroacetamide or succinimidylester; Rhodamine Green™-X succinimidyl ester or hydrochloride; RhodolGreen™ carboxylic acid, N,O-bis-(trifluoroacetyl) or succinimidylester; bis-(4-carboxypiperidinyl) sulfonerhodamine or di(succinimidylester); 5-(and-6) carboxynaphtho fluorescein, 5-(and-6)carboxynaphthofluorescein succinimidyl ester; 5-carboxyrhodamine 6G hydrochloride; 6-carboxyrhodamine6Ghydrochloride, 5-carboxyrhodamine 6G succinimidyl ester; 6-carboxyrhodamine 6G succinimidyl ester; 5-(and-6)-carboxyrhodamine6G succinimidyl ester; 5-carboxy-2',4',5',7'-tetrabromosulfonefluorescein succinimidyl esteror bis-(diisopropylethylammonium) salt; 5-carboxytetramethylrhodamine; 6-carboxytetramethylrhodamine; 5-(and-6)-carboxytetramethylrhodamine; 5-carboxytetramethylrhodamine succinimidyl ester; 6-carboxytetramethylrhodaminesuccinimidyl ester; 5-(and-6)-carboxytetramethylrhodamine succinimidyl ester; 6-carboxy-X-rhodamine; 5-carboxy-X-rhodamine succinimidyl ester; 6-carboxy-X-rhodamine succinimidyl ester; 5-(and-6)-carboxy-X-rhodamine succinimidyl ester; 5-carboxy-X-rhodamine triethylammonium salt; Lissamine™ rhodamine B sulfonyl chloride; malachite green; isothiocyanate; NANOGOLD® mono(sulfosuccinimidyl ester); QSY® 21carboxylic acid or succinimidyl ester; QSY® 7 carboxylic acid or succinimidyl ester; Rhodamine Red™-X succinimidyl ester; 6-(tetramethylrhodamine-5-(and-6)-carboxamido) hexanoic acid; succinimidyl ester; tetramethylrhodamine-5-isothiocyanate; tetramethylrhodamine-6-isothiocyanate; tetramethylrhodamine-5-(and-6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; X-rhodamine-5-(and-6) isothiocyanate, BODIPY® FL; BODIPY® TMR STP ester; BODIPY® TR-X STP ester; BODIPY® 630/650-X STPester; BODIPY® 650/665-X STP ester; 6-dibromo-4, 4-difluoro-5, 7-dimethyl-4-bora-3 a, 4a-diaza-s-indacene-3-propionic acid succinimidyl ester; 4,4-difluoro-4-bora-3a,4a-diaza-s-indacene-3,5-dipropionic acid; 4,4-difluoro-5,7-dimethyl-4-bora-3a,4a-diaza-s-indacene-3-pentanoicacid; 4,4-difluoro-5,7-dimethyl-4-bora3a,4a-diaza-s-indacene-3-pentanoicacid succinimidyl ester; 4,4-difluoro-5,7-dimethyl-4-bora-3 a, 4a-diaza-s-indacene-3propionicacid; 4, 4-difluoro-5, 7-dimethyl-4-bora-3 a, 4adiaza-s-indacene-3-propionicacid succinimidyl ester; 4, 4-difluoro-5, 7-dimethyl-4-bora-3a,4a-diaza-s-indacene-3propionic acid; sulfosuccinimidyl ester or sodium salt; 6-((4,4-difluoro-5, 7-dimethyl-4-bora-3a, 4a-diaza-s-indacene-3propionyl)amino)hexanoicacid; 6-((4,4-difluoro-5, 7 dimethyl-4-bora-3a,4a-diaza-s-indacene-3-propionyl)amino)hexanoic acid or succinimidyl ester; N-(4, 4-difluoro 5, 7-dimethyl-4-bora-3 a, 4a-diaza-s-indacene-3-propionyl) cysteic acid, succinimidyl ester or triethylammonium salt; 6-4,4-difluoro-1,3-dimethyl-5-(4-methoxyphenyl)-4-bora3a, 4a4, 4-difluoro-5, 7-diphenyl-4-bora-3a,4a-diaza-sindacene-3-propionicacid; 4, 4-difluoro-5, 7-diphenyl-4-bora3 a, 4a-diaza-s-indacene-3-propionicacid succinimidyl ester; 4, 4-difluoro-5-phenyl-4-bora-3 a, 4a-diaza-s-indacene-3-propionic acid; succinimidyl ester; 6-((4, 4-difluoro-5-phenyl-4 bora-3 a, 4a-diaza-s-indacene-3-propionyl)amino) hexanoicacid or succinimidyl ester; 4,4-difluoro-5-(4-phenyl-1,3butadienyl)-4-bora-3 a, 4a-diaza-s-indacene-3-propionicacid succinimidyl ester; 4, 4-difluoro-5-(2-pyrrolyl)-4-bora-3a,4a-diaza-s-indacene-3-propionic acid succinimidyl ester; 6-(((4,4-difluoro-5-(2-pyrrolyl)-4-bora-3a,4a-diaza-s-indacene-3-yl)styryloxy)acetyl)amino-hexanoicacid or succinimidyl ester; 4,4-difluoro-5-styryl-4-bora-3a, 4a-diaza-s-indacene-3-propionic acid; 4, 4-difluoro-5-styryl-4-bora-3 a, 4a-diaza-sindacene-3-propionic acid; succinimidyl ester; 4,4-difluoro-1,3,5,7-tetramethyl-4-bora-3a,4adiaza-s-indacene-8-propionicacid; 4,4-difluoro-1,3,5,7-tetramethyl-4bora-3a,4a-diaza-sindacene-8-propionic acid succinimidyl ester; 4,4-difluoro-5-(2-thienyl)-4-bora-3a,4a-diaza-sindacene-3-propionic acid succinimidyl ester; 6-(((4-(4, 4-difluoro-5-(2-thienyl)-4-bora-3 a, 4adiazas-indacene-3-yl)phenoxy)acetyl)amino) hexanoic acid or succinimidyl ester; and 6-(((4,4-difluoro-5-(2-thienyl)-4-bora-3a,4a-diaza-s-indacene-3-yl)styryloxy)acetyl) aminohexanoic acid or succinimidyl ester, Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 64 7 carboxylic acid; Alexa Fluor® 660 carboxylic acid; Alexa Fluor® 680 carboxylic acid, Cy3 NHS ester; Cy 5 NHS ester; Cy5.5 NHSester; and Cy7 NHS ester.

The invention claimed is:

1. A particle for inducing an immune cell response, the particle comprising:
    a matrix comprising a polymerized monomer having a plurality of micropores and a plurality of macropores; and
    one or more immunostimulatory or co-stimulatory biomolecules,
    wherein the plurality of macropores comprise an average diameter between about 200 nm and about 2 μm, wherein the particle is capable of inducing the immune cell response when contacted with an immune cell, and wherein the immune cell response comprises activation and/or expansion of the immune cell.

2. The particle of claim 1, wherein an average diameter of the plurality of micropores is between about 1 nm and about 20 nm.

3. The particle of claim 1, wherein the average diameter of the plurality of micropores is between about 2 nm and about 4 nm.

4. The particle of claim 1, wherein the immune cell response from contacting the immune cell with the particle is higher than the immune cell response from a control immune cell contacted with an otherwise identical particle lacking the plurality of macropores.

5. The particle of claim 4, wherein the immune cell response is determined by IL-2 secretion, CD25 expression, or CD69 expression, from the immune cell.

6. The particle of claim 1, wherein the immune cell is a T cell.

7. The particle of claim 1, wherein the immune cell is a cytotoxic T cell.

8. The particle of claim 1, wherein the immune cell is a chimeric antigen receptor (CAR) T cell.

9. The particle of claim 1, wherein the particle has a porosity of about 5% to about 95% of a volume of the particle.

10. The particle of claim 1, wherein the one or more immunostimulatory or co-stimulatory biomolecules are attached to a surface of the matrix via a linker.

11. The particle of claim 10, wherein the linker comprises streptavidin.

12. The particle of claim 1, wherein the one or more immunostimulatory or co-stimulatory biomolecules are biotinylated.

13. The particle of claim 1, wherein the matrix comprises a bifunctional monomer and wherein the one or more immunostimulatory or co-stimulatory biomolecules are attached to the bifunctional monomer.

14. The particle of claim 1, wherein the one or more immunostimulatory or co-stimulatory biomolecules are selected from the group consisting of an anti-CD3 antibody or antigen-binding fragment thereof, an anti-CD28 antibody or antigen-binding fragment thereof, an anti-CD19 antibody or antigen-binding fragment, an anti-41BBL antibody or antigen-binding fragment, an anti-OX40L antibody or anti-gen-binding fragment, an anti-CD2 antibody or antigen-binding fragment, an anti-CD335 antibody or antigen-binding fragment, an anti-CD16 antibody or antigen-binding fragment, an anti-CD56 antibody or antigen-binding fragment, an anti-CD20 antibody or antigen-binding fragment, an anti-CD80 antibody or antigen-binding fragment, an anti-CD86 antibody or antigen-binding fragment, an anti-CD69 antibody or antigen-binding fragment, an anti-CD154 antibody or antigen-binding fragment, an anti-CD137 antibody or antigen-binding fragment, an IgM antibody or antigen-binding fragment, an IgG antibody or antigen-binding fragment, an IgE antibody or antigen-binding fragment, an IgA antibody or antigen-binding fragment, an IgD antibody or antigen-binding fragment, a toll-like receptor, and any combination thereof.

15. The particle of claim 1, wherein the one or more immunostimulatory or co-stimulatory biomolecules are selected from the group consisting of anti-CD19, anti-41BBL, anti-OX40L, anti-CD2, anti-CD335, anti-CD16, anti-CD56, anti-CD20, anti-CD80, anti-CD86, anti-CD69, anti-CD154, anti-CD137, and any combination thereof.

16. The particle of claim 1, wherein the one or more immunostimulatory or co-stimulatory biomolecules comprise:
    an anti-CD3 antibody or an antigen-binding fragment thereof; and/or
    an anti-CD28 antibody or an antigen-binding fragment thereof.

17. The particle of claim 1, wherein the plurality of micropores are formed during monomer polymerization.

18. The particle of claim 1, wherein the plurality of macropores comprise between about 2% and about 30% of a total number of pores of the particle, the total number of pores of the particle being a combination of the plurality of micropores and the plurality of macropores.

19. The particle of claim 1, wherein the particle comprises the plurality of macropores at a concentration of at least about 2.25% v/v.

20. The particle of claim 1, wherein the particle has a diameter between about 1 μm and about 25 μm.

21. The particle of claim 20, wherein the particle has a diameter between about 2 μm and about 5 μm.

22. A particle for inducing an immune cell response, the particle comprising:

a matrix comprising a polymerized monomer having a plurality of micropores and a plurality of macropores; and one or more immunostimulatory or co-stimulatory biomolecules, wherein the particle is capable of inducing the immune cell response when contacted with an immune cell, wherein the immune cell response comprises activation and/or expansion of the immune cell, and wherein the immune cell response from contacting the immune cell with the particle is higher than the immune cell response from a control immune cell contacted with an otherwise identical particle lacking the plurality of macropores.

23. The particle of claim 22, wherein an average diameter of the plurality of micropores is between about 1 nm and about 20 nm.

24. The particle of claim 22, wherein the average diameter of the plurality of micropores is between about 2 nm and about 4 nm.

25. The particle of claim 22, wherein the immune cell response is determined by IL-2 secretion, CD25 expression, or CD69 expression, from the immune cell.

26. The particle of claim 22, wherein the immune cell is a T cell.

27. The particle of claim 22, wherein the immune cell is a cytotoxic T cell.

28. The particle of claim 22, wherein the immune cell is a chimeric antigen receptor (CAR) T cell.

29. The particle of claim 22, wherein the particle has a porosity of about 5% to about 95% of a volume of the particle.

30. The particle of claim 22, wherein the one or more immunostimulatory or co-stimulatory biomolecules are attached to a surface of the matrix via a linker.

31. The particle of claim 30, wherein the linker comprises streptavidin.

32. The particle of claim 22, wherein the one or more immunostimulatory or co-stimulatory biomolecules are biotinylated.

33. The particle of claim 22, wherein the matrix comprises a bifunctional monomer and wherein the one or more immunostimulatory or co-stimulatory biomolecules are attached to the bifunctional monomer.

34. The particle of claim 22, wherein the one or more immunostimulatory or co-stimulatory biomolecules are selected from the group consisting of an anti-CD3 antibody or antigen-binding fragment thereof, an anti-CD28 antibody or antigen-binding fragment thereof, an anti-CD19 antibody or antigen-binding fragment, an anti-41BBL antibody or antigen-binding fragment, an anti-OX40L antibody or antigen-binding fragment, an anti-CD2 antibody or antigen-binding fragment, an anti-CD335 antibody or antigen-binding fragment, an anti-CD16 antibody or antigen-binding fragment, an anti-CD56 antibody or antigen-binding fragment, an anti-CD20 antibody or antigen-binding fragment, an anti-CD80 antibody or antigen-binding fragment, an anti-CD86 antibody or antigen-binding fragment, an anti-CD69 antibody or antigen-binding fragment, an anti-CD154 antibody or antigen-binding fragment, an anti-CD137 antibody or antigen-binding fragment, an IgM antibody or antigen-binding fragment, an IgG antibody or antigen-binding fragment, an IgE antibody or antigen-binding fragment, an IgA antibody or antigen-binding fragment, an IgD antibody or antigen-binding fragment, a toll-like receptor, and any combination thereof.

35. The particle of claim 22, wherein the one or more immunostimulatory or co-stimulatory biomolecules are selected from the group consisting of anti-CD19, anti-41BBL, anti-OX40L, anti-CD2, anti-CD335, anti-CD16, anti-CD56, anti-CD20, anti-CD80, anti-CD86, anti-CD69, anti-CD154, anti-CD137, and any combination thereof.

36. The particle of claim 22, wherein the one or more immunostimulatory or co-stimulatory biomolecules comprise:

an anti-CD3 antibody or an antigen-binding fragment thereof; and/or an anti-CD28 antibody or an antigen-binding fragment thereof.

37. The particle of claim 22, wherein the plurality of micropores are formed during monomer polymerization.

38. The particle of claim 22, wherein the plurality of macropores comprise between about 2% and about 30% of a total number of pores of the particle, the total number of pores of the particle being a combination of the plurality of micropores and the plurality of macropores.

39. The particle of claim 22, wherein the particle comprises the plurality of macropores at a concentration of at least about 2.25% v/v.

40. The particle of claim 22, wherein the particle has a diameter between about 1 μm and about 25 μm.

41. The particle of claim 40, wherein the particle has a diameter between about 2 μm and about 5 μm.

42. A particle for inducing an immune cell response, the particle comprising:

a matrix comprising a polymerized monomer having a plurality of micropores and a plurality of macropores; and one or more immunostimulatory or co-stimulatory biomolecules, wherein the particle is capable of inducing the immune cell response when contacted with an immune cell, wherein the immune cell response comprises activation and/or expansion of the immune cell, and wherein the plurality of micropores are formed during monomer polymerization.

43. The particle of claim 42, wherein an average diameter of the plurality of micropores is between about 1 nm and about 20 nm.

44. The particle of claim 42, wherein the average diameter of the plurality of micropores is between about 2 nm and about 4 nm.

45. The particle of claim 42, wherein the immune cell response from contacting the immune cell with the particle is higher than the immune cell response from a control immune cell contacted with an otherwise identical particle lacking the plurality of macropores, and wherein the immune cell response is determined by IL-2 secretion, CD25 expression, or CD69 expression, from the immune cell.

46. The particle of claim 42, wherein the immune cell is a T cell.

47. The particle of claim 42, wherein the immune cell is a cytotoxic T cell.

48. The particle of claim 42, wherein the immune cell is a chimeric antigen receptor (CAR) T cell.

49. The particle of claim 42, wherein the particle has a porosity of about 5% to about 95% of a volume of the particle.

50. The particle of claim 42, wherein the one or more immunostimulatory or co-stimulatory biomolecules are attached to a surface of the matrix via a linker.

51. The particle of claim 50, wherein the linker comprises streptavidin.

52. The particle of claim 42, wherein the one or more immunostimulatory or co-stimulatory biomolecules are biotinylated.

53. The particle of claim 42, wherein the matrix comprises a bifunctional monomer and wherein the one or more immunostimulatory or co-stimulatory biomolecules are attached to the bifunctional monomer.

54. The particle of claim 42, wherein the one or more immunostimulatory or co-stimulatory biomolecules are selected from the group consisting of an anti-CD3 antibody or antigen-binding fragment thereof, an anti-CD28 antibody or antigen-binding fragment thereof, an anti-CD19 antibody or antigen-binding fragment, an anti-41BBL antibody or antigen-binding fragment, an anti-OX40L antibody or antigen-binding fragment, an anti-CD2 antibody or antigen-binding fragment, an anti-CD335 antibody or antigen-binding fragment, an anti-CD16 antibody or antigen-binding fragment, an anti-CD56 antibody or antigen-binding fragment, an anti-CD20 antibody or antigen-binding fragment, an anti-CD80 antibody or antigen-binding fragment, an anti-CD86 antibody or antigen-binding fragment, an anti-CD69 antibody or antigen-binding fragment, an anti-CD154 antibody or antigen-binding fragment, an anti-CD137 antibody or antigen-binding fragment, an IgM antibody or antigen-binding fragment, an IgG antibody or antigen-binding fragment, an IgE antibody or antigen-binding fragment, an IgA antibody or antigen-binding fragment, an IgD antibody or antigen-binding fragment, a toll-like receptor, and any combination thereof.

55. The particle of claim 42, wherein the one or more immunostimulatory or co-stimulatory biomolecules are selected from the group consisting of anti-CD19, anti-41BBL, anti-OX40L, anti-CD2, anti-CD335, anti-CD16, anti-CD56, anti-CD20, anti-CD80, anti-CD86, anti-CD69, anti-CD154, anti-CD137, and any combination thereof.

56. The particle of claim 42, wherein the one or more immunostimulatory or co-stimulatory biomolecules comprise:

an anti-CD3 antibody or an antigen-binding fragment thereof; and/or an anti-CD28 antibody or an antigen-binding fragment thereof.

57. The particle of claim 42, wherein the plurality of macropores comprise between about 2% and about 30% of a total number of pores of the particle, the total number of pores of the particle being a combination of the plurality of micropores and the plurality of macropores.

58. The particle of claim 42, wherein the particle comprises the plurality of macropores at a concentration of at least about 2.25% v/v.

59. The particle of claim 42, wherein the particle has a diameter between about 1 μm and about 25 μm.

60. The particle of claim 59, wherein the particle has a diameter between about 2 μm and about 5 μm.

61. A particle for inducing an immune cell response, the particle comprising:

a matrix comprising a polymerized monomer having a plurality of micropores and a plurality of macropores; and one or more immunostimulatory or co-stimulatory biomolecules, wherein the particle is capable of inducing the immune cell response when contacted with an immune cell, wherein the immune cell response comprises activation and/or expansion of the immune cell, and wherein the particle has a diameter of between about 1 μm and about 25 μm.

62. The particle of claim 61, wherein an average diameter of the plurality of micropores is between about 1 nm and about 20 nm.

63. The particle of claim 61, wherein the average diameter of the plurality of micropores is between about 2 nm and about 4 nm.

64. The particle of claim 61, wherein the immune cell response from contacting the immune cell with the particle is higher than the immune cell response from a control immune cell contacted with an otherwise identical particle lacking the plurality of macropores, and wherein the immune cell response is determined by IL-2 secretion, CD25 expression, or CD69 expression, from the immune cell.

65. The particle of claim 61, wherein the immune cell is a T cell.

66. The particle of claim 61, wherein the immune cell is a cytotoxic T cell.

67. The particle of claim 61, wherein the immune cell is a chimeric antigen receptor (CAR) T cell.

68. The particle of claim 61, wherein the particle has a porosity of about 5% to about 95% of a volume of the particle.

69. The particle of claim 61, wherein the one or more immunostimulatory or co-stimulatory biomolecules are attached to a surface of the matrix via a linker.

70. The particle of claim 69, wherein the linker comprises streptavidin.

71. The particle of claim 61, wherein the one or more immunostimulatory or co-stimulatory biomolecules are biotinylated.

72. The particle of claim 61, wherein the matrix comprises a bifunctional monomer and wherein the one or more immunostimulatory or co-stimulatory biomolecules are attached to the bifunctional monomer.

73. The particle of claim 61, wherein the one or more immunostimulatory or co-stimulatory biomolecules are selected from the group consisting of an anti-CD3 antibody or antigen-binding fragment thereof, an anti-CD28 antibody or antigen-binding fragment thereof, an anti-CD19 antibody or antigen-binding fragment, an anti-41BBL antibody or antigen-binding fragment, an anti-OX40L antibody or antigen-binding fragment, an anti-CD2 antibody or antigen-binding fragment, an anti-CD335 antibody or antigen-binding fragment, an anti-CD16 antibody or antigen-binding fragment, an anti-CD56 antibody or antigen-binding fragment, an anti-CD20 antibody or antigen-binding fragment, an anti-CD80 antibody or antigen-binding fragment, an anti-CD86 antibody or antigen-binding fragment, an anti-CD69 antibody or antigen-binding fragment, an anti-CD154 antibody or antigen-binding fragment, an anti-CD137 antibody or antigen-binding fragment, an IgM antibody or antigen-binding fragment, an IgG antibody or antigen-binding fragment, an IgE antibody or antigen-binding fragment, an IgA antibody or antigen-binding fragment, an IgD antibody or antigen-binding fragment, a toll-like receptor, and any combination thereof.

74. The particle of claim 61, wherein the one or more immunostimulatory or co-stimulatory biomolecules are selected from the group consisting of anti-CD19, anti-41BBL, anti-OX40L, anti-CD2, anti-CD335, anti-CD16, anti-CD56, anti-CD20, anti-CD80, anti-CD86, anti-CD69, anti-CD154, anti-CD137, and any combination thereof.

75. The particle of claim 61, wherein the one or more immunostimulatory or co-stimulatory biomolecules comprise:

an anti-CD3 antibody or an antigen-binding fragment thereof; and/or an anti-CD28 antibody or an antigen-binding fragment thereof.

76. The particle of claim 61, wherein the plurality of macropores comprise between about 2% and about 30% of a total number of pores of the particle, the total number of pores of the particle being a combination of the plurality of micropores and the plurality of macropores.

77. The particle of claim 61, wherein the particle comprises the plurality of macropores at a concentration of at least 2.25% v/v, at least 3.4% v/v, and/or at least 4.5% v/v.

78. The particle of claim 61, wherein the particle has a diameter of between about 2 μm and about 5 μm.

\* \* \* \* \*